US012655447B2

(12) United States Patent
Krishnan et al.

(10) Patent No.: US 12,655,447 B2
(45) Date of Patent: Jun. 16, 2026

(54) COMPOSITIONS AND METHODS FOR THE TREATMENT OF SKIN DISEASES

(71) Applicant: Krystal Biotech, Inc., Pittsburgh, PA (US)

(72) Inventors: Suma Krishnan, San Francisco, CA (US); Pooja Agarwal, Mars, PA (US); Trevor Parry, San Diego, CA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 768 days.

(21) Appl. No.: 17/279,501

(22) PCT Filed: Sep. 25, 2019

(86) PCT No.: PCT/US2019/053005
§ 371 (c)(1),
(2) Date: Mar. 24, 2021

(87) PCT Pub. No.: WO2020/069018
PCT Pub. Date: Apr. 2, 2020

(65) Prior Publication Data
US 2021/0395775 A1      Dec. 23, 2021

Related U.S. Application Data

(60) Provisional application No. 62/744,531, filed on Oct. 11, 2018, provisional application No. 62/737,009, filed on Sep. 26, 2018.

(51) Int. Cl.
| | |
|---|---|
| *C12N 15/86* | (2006.01) |
| *A61K 9/00* | (2006.01) |
| *A61K 38/00* | (2006.01) |
| *A61K 47/02* | (2006.01) |
| *A61K 47/26* | (2006.01) |
| *A61K 47/38* | (2006.01) |
| *A61P 17/02* | (2006.01) |
| *C07K 14/78* | (2006.01) |
| *C12N 7/00* | (2006.01) |

(52) U.S. Cl.
CPC ............ *C12N 15/86* (2013.01); *A61K 9/0019* (2013.01); *A61K 47/02* (2013.01); *A61K 47/26* (2013.01); *A61K 47/38* (2013.01); *A61P 17/02* (2018.01); *C07K 14/78* (2013.01); *C12N 7/00* (2013.01); *A61K 38/00* (2013.01); *C12N 2710/16021* (2013.01); *C12N 2710/16043* (2013.01); *C12N 2710/16062* (2013.01); *C12N 2710/16071* (2013.01)

(58) Field of Classification Search
CPC ..................... C12N 15/86; C12N 7/00; C12N 2710/16021; C12N 2710/16043; C12N 2710/16062; C12N 2710/16071; C12N 15/8695; C12N 2799/04; A61K 9/0019; A61K 47/02; A61K 47/26; A61K 47/38; A61K 38/00; A61P 17/02; A61P 17/00; C07K 14/78
See application file for complete search history.

(56) References Cited

U.S. PATENT DOCUMENTS

| | | | |
|---|---|---|---|
| 5,658,724 | A | 8/1997 | Deluca et al. |
| 5,672,344 | A | 9/1997 | Kelley et al. |
| 5,753,234 | A | 5/1998 | Lee et al. |
| 5,998,174 | A | 12/1999 | Glorioso et al. |
| 6,106,826 | A | 8/2000 | Brandt et al. |
| 6,719,982 | B1 | 4/2004 | Coffin et al. |
| 6,846,670 | B2 | 1/2005 | Schwartz et al. |
| 6,887,490 | B1 | 5/2005 | Jahoda et al. |
| 7,081,483 | B2 | 7/2006 | Cahiko |
| 7,531,167 | B2 | 5/2009 | Glorioso et al. |
| 9,314,505 | B2 | 4/2016 | Wise et al. |
| 9,770,489 | B2 | 9/2017 | Angel et al. |
| 9,877,990 | B2 | 1/2018 | Krishnan et al. |
| 10,155,016 | B2 | 12/2018 | Krishnan et al. |
| 10,174,341 | B2 | 1/2019 | Glorioso et al. |
| 10,441,614 | B2 | 10/2019 | Krishnan et al. |
| 10,525,090 | B2 | 1/2020 | Krishnan et al. |
| 10,786,438 | B2 | 9/2020 | Krishnan et al. |
| 11,185,564 | B2 | 11/2021 | Krishnan et al. |
| 2002/0037575 | A1 | 3/2002 | Speck |
| 2002/0187163 | A1 | 12/2002 | Johnson et al. |
| 2003/0082142 | A1 | 5/2003 | Coffin et al. |
| 2003/0190637 | A1 | 10/2003 | Hovnanian et al. |
| 2004/0005663 | A1 | 1/2004 | Bell et al. |

(Continued)

FOREIGN PATENT DOCUMENTS

| | | |
|---|---|---|
| CN | 102 212 559 | 4/2014 |
| JP | 2008-174459 | 7/2008 |

(Continued)

OTHER PUBLICATIONS

Kallunki P, et. al. Laminin, gamma 2 isoform b precursor [*Homo sapiens*]. NCBI Reference Sequence: NP_061486.2; Updated Sep. 21, 2007. (Year: 2007).*

(Continued)

*Primary Examiner* — Rachel B Gill
(74) *Attorney, Agent, or Firm* — The Webb Law Firm

(57)      ABSTRACT

Provided herein are recombinant nucleic acids comprising one or more polynucleotides encoding a laminin polypeptide and/or a filaggrin polypeptide; viruses comprising the recombinant nucleic acids; compositions and formulations comprising the recombinant nucleic acids and/or viruses; methods of their use; and articles of manufacture or kits thereof.

10 Claims, 14 Drawing Sheets
Specification includes a Sequence Listing.

(56) References Cited

U.S. PATENT DOCUMENTS

| | | | |
|---|---|---|---|
| 2004/0018592 A1 | 1/2004 | Bell et al. | |
| 2004/0253606 A1 | 12/2004 | Aziz et al. | |
| 2005/0255085 A1 | 11/2005 | Fong et al. | |
| 2006/0246139 A1 | 11/2006 | Miyaji et al. | |
| 2007/0066552 A1 | 3/2007 | Clarke et al. | |
| 2007/0092575 A1 | 4/2007 | Balaban et al. | |
| 2007/0148074 A1 | 6/2007 | Sadoqi et al. | |
| 2008/0039397 A1 | 2/2008 | Weiss | |
| 2008/0095819 A1 | 4/2008 | Gourdie et al. | |
| 2008/0299182 A1 | 12/2008 | Zhang | |
| 2010/0081707 A1 | 4/2010 | Ali et al. | |
| 2010/0330112 A1 | 12/2010 | Long et al. | |
| 2011/0212530 A1 | 9/2011 | Baltimore et al. | |
| 2011/0218234 A1* | 9/2011 | Annoni | A61P 37/08 |
| | | | 435/325 |
| 2011/0245592 A1 | 10/2011 | Schoolcraft et al. | |
| 2012/0148627 A1 | 6/2012 | Terman | |
| 2013/0034586 A1 | 2/2013 | Mohr et al. | |
| 2013/0259923 A1 | 10/2013 | Bancel et al. | |
| 2013/0295076 A1 | 11/2013 | Kolattukudy et al. | |
| 2013/0331547 A1 | 12/2013 | Hall et al. | |
| 2014/0256798 A1 | 9/2014 | Osborn et al. | |
| 2014/0288155 A1 | 9/2014 | Hovnanian et al. | |
| 2014/0341877 A1 | 11/2014 | Kolattukudy | |
| 2015/0038556 A1 | 2/2015 | Heartlein et al. | |
| 2015/0265688 A1 | 9/2015 | Cigarini et al. | |
| 2015/0352191 A1 | 12/2015 | South et al. | |
| 2016/0153000 A1 | 6/2016 | Glorioso et al. | |
| 2016/0158343 A1 | 6/2016 | Jacobs et al. | |
| 2016/0250267 A1 | 9/2016 | Uchida et al. | |
| 2016/0324934 A1* | 11/2016 | Angel | A61K 38/44 |
| 2017/0096684 A1 | 4/2017 | Alton et al. | |
| 2017/0290866 A1 | 10/2017 | Krishnan et al. | |
| 2017/0319693 A1 | 11/2017 | Koizumi et al. | |
| 2018/0256748 A1* | 9/2018 | Angel | A61M 37/00 |
| 2018/0339004 A1 | 11/2018 | Greenberg et al. | |
| 2018/0353614 A1 | 12/2018 | Peters | |
| 2019/0328644 A1 | 10/2019 | Krishnan et al. | |
| 2020/0061209 A1 | 2/2020 | Bennett et al. | |
| 2020/0071703 A1 | 3/2020 | Giuliano et al. | |
| 2020/0101123 A1 | 4/2020 | Krishnan et al. | |
| 2020/0199618 A1 | 6/2020 | Krisky et al. | |
| 2021/0040172 A1 | 2/2021 | Cascio et al. | |
| 2021/0045988 A1 | 2/2021 | Krishnan et al. | |
| 2022/0273737 A1 | 9/2022 | Krishnan et al. | |
| 2023/0149486 A1 | 5/2023 | Krishnan | |

FOREIGN PATENT DOCUMENTS

| | | | |
|---|---|---|---|
| JP | 2015-221759 | 12/2015 | |
| JP | 2017518370 A | 7/2017 | |
| WO | WO 1999/064094 | 12/1999 | |
| WO | WO 2000/040734 | 7/2000 | |
| WO | 2005103237 A1 | 3/2005 | |
| WO | WO 2006/052285 | 5/2006 | |
| WO | WO 2007/136428 | 11/2007 | |
| WO | 2010021738 A2 | 2/2010 | |
| WO | 2011063320 A2 | 5/2011 | |
| WO | WO 2012/001170 | 1/2012 | |
| WO | WO 2013/119880 | 8/2013 | |
| WO | WO 2013/121202 | 8/2013 | |
| WO | WO 2014/043189 | 3/2014 | |
| WO | WO 2015/009952 | 1/2015 | |
| WO | WO 2015/117021 | 8/2015 | |
| WO | 2015184134 A1 | 12/2015 | |
| WO | WO 2015/181211 | 12/2015 | |
| WO | WO 2016/128374 | 8/2016 | |
| WO | WO 2016/128783 | 8/2016 | |
| WO | WO 2016/141315 | 9/2016 | |
| WO | WO 2016/191684 | 12/2016 | |
| WO | WO 2017/165806 | 9/2017 | |
| WO | WO 2017/165813 | 9/2017 | |
| WO | 2017180587 A2 | 10/2017 | |
| WO | WO 2017/176336 | 10/2017 | |
| WO | 2017191274 A2 | 11/2017 | |
| WO | WO 2017/191315 | 11/2017 | |
| WO | WO-2018154412 A1 * | 8/2018 | A61K 35/34 |
| WO | WO 2019/210219 | 10/2019 | |
| WO | WO 2020/069018 | 4/2020 | |

OTHER PUBLICATIONS

Sybert VP, et. al. Filaggrin [*Homo sapiens*]. NCBI Reference Sequence: NP_002007.1, Submitted Feb. 20, 2005. (Year: 2005).*

Xu X, Ma Q, Lin M, et al. A loss of function mutation in the filaggrin gene associated with ichthyosis vulgaris and rheumatoid arthritis. European Journal of Inflammation. 2021;19. (Year: 2021).*

"Rheumatoid arthritis." Mayo Foundation for Medical Education and Research (MFMER). 2024; Accessed Jan. 10, 2024. https://www.mayoclinic.org/diseases-conditions/rheumatoid-arthritis/symptoms-causes/syc-20353648?p=1. (Year: 2024).*

Parente MG, et. al. Collagen alpha-1(VII) chain precursor [*Homo sapiens*]. NCBI Reference Sequence: NP_000085.1, First Dep. Mar. 24, 1999. (Year: 1999).*

Agrawal et al., "Skin Barrier Defects in Atopic Dermatitis," Curr Allergy Asthma Rep (2014) 14(5): 433 pp. 1-11.

Aldawsari et al., "Progress in Topical siRNA Delivery Approaches for Skin Disorders," Curr Pharm Des. (2015) 21(31): 4594-4605.

Andtbacka et. al., "Talimogene Laherparepvec Improves Durable Response Rate in Patients With Advanced Melanoma," J Clin Oncol. (2015) 33(25): 2780-2788.

Anonymous, "Public summary of opinion on orphan designation Genetically modified replication-incompetent herpes simplex virus-1 expressing collagen VII for treatment of epidermolysis bullosa", May 15, 2018 (May 15, 2018), p. 1-5, Retrieved from the Internet: URL:https://www.ema.europa.eu/en/documents/orphan-designation/eu/3/18/2012-public-summary-opinion-orphan-designation-genetically-modified-replication-incompetent-herpes_en.pdf. XP055652122 [retrieved on Dec. 12, 2019].

Anonymous, "First two patients enrolled in Phase 1/2 clinical study of KB103, a first-in-class topical gene therapy for the treatment of dystrophic epidermolysis bullosa.", Aug. 6, 2018 (Aug. 6, 2018), p. 1-10, Retrieved from the Internet: URL:https://www.krystalbio.com/blog/XP055652520 [retrieved on Dec. 12, 2019].

Anonymous, "Krystal Biotech Announces FDA Clearance of IND on KB103 to Begin Enrolling Patients for the Treatment of Dystrophic Epidermolysis Bullosa", Apr. 26, 2018 (Apr. 26, 2018), p. 1-2, Retrieved from the Internet: URL:http://ir.krystalbio.com/node/6546/pdfXP055652524 [retrieved on Dec. 12, 2019].

Antonov et al., "Methods for the Assessment of Barrier Function," Curr Probl Dermatol. (2016) 49:61-70.

Armstrong, M. "Krystal gets more skin in the epidermolysis bullosa game." Vantage. Mar. 5, 2019.

Armstrong, M. "Krystal gets a flying start in epidermolysis bullosa gene therapy" Vantage. Oct. 17, 2018.

Asgari et al., "In vitro fibrillogenesis of tropocollagen type III in collagen type I affects its relative fibrillar topology and mechanics," Scientific Reports (2017) 7 Article ID:1392.

Bastian et al., "Herpes simplex virus type 1 immediate-early protein ICP22 is required for VICE domain formation during productive viral infection." J Virol. Mar. 2010;84(5):2384-94. doi: 10.1128/JVI.01686-09. Epub Dec. 23, 2009.

Baumann et al., "Comparison of smooth-gel hyaluronic acid dermal fillers with cross-linked bovine collagen: a multicenter, double-masked, randomized, within-subject study," Dermatol Surg (2007) 33 Suppl 2:s128-135.

Berkers et al., "Rectal Organoids Enable Personalized Treatment of Cystic Fibrosis," Cell Rep (2019) 26(7): 1701-1708.e3.

Birket et al., "Development of an airway mucus defect in the cystic fibrosis rat," JCI Insight (2018) 3(1): e97199.

Bowen et al., Comparison of Herpes Simplex Virus 1 Strains Circulating in Finland Demonstrates the Uncoupling of Whole-Genome Relatedness and Phenotypic Outcomes of Viral Infection, J Virol. (2019) 93(8):e01824-18.

(56) References Cited

OTHER PUBLICATIONS

Brehm et al., "Immunogenicity of herpes simplex virus type 1 mutants containing deletions in one or more alpha-genes: ICP4, ICP27, ICP22, and ICP0," Virology (1999) 256(2): 258-69.

Brown et al., "Subject global evaluation and subject satisfaction using injectable poly-L-lactic acid versus human collagen for the correction of nasolabial fold wrinkles," Plast Reconstr Surg (2011) 127(4):1684-1692.

Burton et al., "Gene delivery using herpes simplex virus vectors." DNA Cell Biol. Dec. 2002;21(12):915-936.

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.

Cheng et al., "The content and ratio of type I and III collagen in skin differ with age and injury," African Journal of Biotechnology (2011) 10(13):2524-2529.

Christiano AM. Collagen, type VII, alpha 1 (epidermolysis bullosa, dystrophic, dominant and recessive) [*Homo sapiens*]. NCBI Reference Sequence: NP_000085.1. Dep. Mar. 19, 1999.

Clancy et al., "Personalized Medicine in Cystic Fibrosis: Dawning of a New Era," Am J Respir Crit Care Med (2012) 186(7): 593-597.

Clancy et al., "CFTR Modulator Theratyping: Current Status, Gaps and Future Directions," J Cyst Fibros (2019) 18(1): 22-34.

Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Clinicaltrials.gov. NCT04047732: Topical KB105 Gene Therapy for the Treatment of TGM1-deficient Autosonnal Recessive Congenital Ichthyosis (ARCI). Aug. 7, 2019.

Clinicaltrials.gov. NCT04214002: The Natural History of Wounds in Patients with Dystrophic Epidermolysis Bullosa (DEB). Dec. 30, 2019.

Cole et al., "Extracellular matrix regulation of fibroblast function: redefining our perspective on skin aging," Journal of Cell Communication and Signaliing (2018) 12:35-43.

Collawn et al., "CFTR and Lung Homeostasis," Am J Physiol Lung Cell Mol Physiol (2014) 307(12): L917-923.

Communication pursuant to Article 94(3) EPC for EP 16826873.8, dated Apr. 17, 2019, 7 pages.

Cooney et al., "Cystic Fibrosis Gene Therapy: Looking Back, Looking Forward," Genes (Basel) (2018) 9(11): 538.

Cutting, G. "Cystic Fibrosis Genetics: From Molecular Understanding to Clinical Application," Nat Rev Genet (2015) 16(1): 45-56.

De Silva et al., "Herpes Virus Amplicon Vectors," Viruses. (2009) 1(3):594-629.

Dekkers et al., "A Functional CFTR Assay Using Primary Cystic Fibrosis Intestinal Organoids," Nat Med (2013) 19(7): 939-945.

Deluca et al., "Isolation and Characterization of Deletion Mutants of Herpes Simplex Virus Type 1 in the Gene Encoding Immediate-Early Regulatory Protein ICP4", Journal Of Virology, (1985) 56(2): 558-570.

Derichs et al., "Hyperviscous Airway Periciliary and Mucous Liquid Layers in Cystic Fibrosis Measured by Confocal Fluorescence Photobleaching," FASEB J (2011) 25(7): 2325-2332.

Dingwell et al., "The Herpes Simplex Virus gE-gI Complex Facilitates Cell-to-Cell Spread and Binds to Components of Cell Junctions," J Virol. (1998) 72(11): 8933-8942.

Eming SA, Krieg T, Davidson JM. Gene therapy and wound healing. Clin Dermatol. Jan.-Feb. 2007;25(1):79-92.

Eming et al., "Gene transfer in tissue repair: status, challenges and future directions," Exp Opin Biol Ther (2004) 4(9):1373-1386.

Estrada-Veras et al., "Palliative Care for Patients With Cystic Fibrosis #265," J Palliat Med (2013) 16(4): 446-447.

European Medicines Agency, "Assessment Report on Imlygic," Published Oct. 22, 2015.

Examination Report No. 1 received for Australian Patent Application No. 2016401692, , mailed on Jul. 12, 2019, 4 pages.

Fath et al., "Multiparameter RNA and codon optimization: a standardized tool to assess and enhance autologous mammalian gene expression," PLoS One. (2011) 6(3): e17596.

FDA Briefing Document, "Cellular, Tissue, and Gene Therpies Advisory Committee and Oncologic Drugs Advisory Committee Meeting," Dated Apr. 29, 2015.

Final Office Action received for U.S. Appl. No. 15/393,151, mailed on Aug. 31, 2017, 13 pages.

Fink et al., "Gene therapy for pain: Results of a Phase I clinical trial," Ann Neurol (2011) 70(2):207-212.

Fink, "Gene transfer to the peripheral nervous system: Treatments for polyneuropathy and for pain," (2011).

Fisher et al., "Pathophysiology of Premature Skin Aging Induced by Ultraviolet Light," N Engl J Med (1997) 337:1419-1429.

Ganceviciene et al., "Skin anti-aging strategies," Dermatoendocrinology (2012) 4:308-319.

Geller et al., "An efficient deletion mutant packaging system for defective herpes simplex virus vectors: potential applications to human gene therapy and neuronal physiology," Proc Natl Acad Sci U S A. (1990) 87(22): 8950-8954.

Georgiadis et al., "Lentiviral Engineered Fibroblasts Expressing Codon-Optimized COL7A1 Restore Anchoring Fibrils in RDEB", Journal of Investigative Dermatology, (2016) 136: 284-292.

Gill et al., "Delivery of Genes Into the CF Airway," Thorax (2014) 69(10): 962-964.

Glorioso JC. "Herpes simplex viral vectors: late bloomers with big potential." Hum Gene Ther. (2014) 25(2): 83-91.

Goins et al. "Engineering HSV-1 Vectors for Gene Therapy," Methods Mol Biol (2014) 1144: 63-79.

Goldsmith et al., "Infected cell protein (ICP)47 enhances herpes simplex virus neurovirulence by blocking the CD8+ T cell response," J Exp Med. (1998) 187(3): 341-8.

Gorell et al., "Gene therapy for skin diseases," Cold Spring Harb Perspect Med (2014) 4:a015149.

Gorouchi et al., "Role of topical peptides in preventing or treating aged skin," International Journal of Cosmetic Science (2009) 31:327-345.

Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.

Grant, Kyle, "Production and Purification of Highly Replication Defective Hsv-1 Based Gene Therapy Vectors", Doctoral Dissertation, University of Pittsburgh, 2008, 137 pages.

Gurevich et. al. 759 "Successful in vivo COL7A1 gene delivery and correction of recessive dystrophic epidermolysis bullosa (RDEB) skin using an off the shelf HSV-1 vector (KB103)." J Invest Derm. vol. 138, Iss. 5 Supp. May 2018, p. S129. Available online Apr. 19, 2018.

Harrington et al., "Efficacy and safety of talimogene laherparepvec versus granulocyte-macrophage colony-stimulating factor in patients with stage IIB/C and IVMla melanoma: subanalysis of the Phase III OPTiM trial," Onco Targets and Therapy (2016) 9:7081-7093.

Harrow et al., "HSV1716 injection into the brain adjacent to tumour following surgical resection of high-grade glioma: safety data and long-term survival," Gene Therapy (2004) 11:1648-1658.

Heikkinen et al., "Diremerization of human lysyl hydroxylase 3 (LH3) is mediated by the amino acids 541 547," Matrix Biology (2010) 30(1):27-33.

Hennig et al., "HEK293-based production platform for y-retroviral (self-inactivating) vectors: application for safe and efficient transfer of COL7A1 cDNA". Hum Gene Ther Clin Dev. Dec. 2014;25(4):218-28.

Humbert et al., "In the shadow of the wrinkle: experimental models," Journal of Cosmetic Dermatology (2011) 11:79-83.

Hyde et al., "Repeat Administration of DNA/liposomes to the Nasal Epithelium of Patients With Cystic Fibrosis," Gene Ther (2000) 7(13): 1156-1165.

International Preliminary Report on Patentability received for PCT Patent Application No. PCT/US2016/068974, mailed on Oct. 18, 2018, 11 pages.

International Preliminary Report on Patentability for PCT/US2019/029422, dated Oct. 27, 2020, 5 pages.

(56) References Cited

OTHER PUBLICATIONS

International Search Report and Written Opinion for PCT/US2019/29422, dated Jul. 10, 2019, 13 pages.

International Search Report and Written Opinion received for PCT Patent Application No. PCT/US2016/068974, mailed on May 18, 2017, 18 pages.

Invitation to Pay Additional Fee received for PCT Patent Application No. PCT/US2016/068974, mailed on Mar. 27, 2017, 8 pages.

Kerem et al., "Identification of the Cystic Fibrosis Gene: Genetic Analysis," Science (1989) 245(4922): 1073-1080.

Kim et al., "Microneedles for Drug and Vaccine Delivery", Advanced Drug Delivery Reviews, vol. 64, 2012, pp. 1547-1568.

Kim et al., "Barriers to Inhaled Gene Therapy of Obstructive Lung Diseases: A Review," J Control Release (2016) 240: 465-488.

Knowles et al., "A Controlled Study of Adenoviral-Vector-Mediated Gene Transfer in the Nasal Epithelium of Patients With Cystic Fibrosis," N Engl J Med (1995) 333(13): 823-831.

Kohlhapp et al., Molecular Pathways: Mechanism of Action for Talimogene Laherparepvec, a New Oncolytic Virus Immunotherapy, Clinical Cancer Research (2015) 22(5):1048-1054.

Kopecki et al., "Commentary: New advances in the development of therapies for treating inherited skin fragility disorders," Wound Practice and Research (2015) 23(4): 184, Dec. 5, 2015.

Krisky et al., "Deletion of multiple immediate-early genes from herpes simplex virus reduces cytotoxicity and permits long-term gene expression in neurons," Gene Ther. (1998) 5(12):1593-603.

Krisky et al., "Development of herpes simplex virus replication-defective multigene vectors for combination gene therapy applications," Gene Ther (1998) 5(110):1517-1530.

Lachmann, R. "Herpes simplex virus-based vectors," Int J Exp Pathol. (2004) 85(4): 177-190.

Lemperle et al., "A classification of facial wrinkles," Plastic and Reconstructive Surgery (2001) 1735-1750.

Lewin et al., "Gene therapy for autosomal dominant disorders of keratin," J Investig Dermatol Symp Proc. (2005) 10(1): 47-61.

Liou et al., "Year-to-year Changes in Lung Function in Individuals With Cystic Fibrosis," J Cyst Fibros (2010) 9(4): 250-256.

Liu et al., "The Use of Type I and Type III Injectable Human Collagen for Dermal Fill: 10 Years of Clinical Experience in China," Semin Plast Surg (2005) 19(3):241-250.

Liu et al., "Type III collagen is crucial for collagen I fibrillogenesis and for normal cardiovascular development," Proc Natl Acad Sci USA (1997) 94:1852-1856.

Lommatzsch et al., "The Combination of Tezacaftor and Ivacaftor in the Treatment of Patients With Cystic Fibrosis: Clinical Evidence and Future Prospects in Cystic Fibrosis Therapy," Ther Adv Respir Dis (2019) 13: 1-13. https://doi.org/10.1177/1753466619844424.

Lu et al., "Topical Application of Viral Vectors for Epidermal Gene Transfer", J Invest Dermatol. (1997) 108(5): 803-808.

Ma et al., "Efficacy of Herpes Simplex Virus Vector Encoding V the Human Preproenkephalin Gene for Treatment of Facial Pain in Mice," J aral Facial Pain Headachce (2016) 30(1):42-50.

Manservigi et al., "HSV Recombinant Vectors for Gene Therapy," Open Virol J. (2010) 4:123-56.

Marconi et al., "HSV as a Vector in Vaccine Development and Gene Therapy." In: Madame Curie Bioscience Database [Internet]. Austin (TX): Landes Bioscience; 2000-2013. 30 pages.

Marconi et al., "Replication-defective herpes simplex virus vectors for gene transfer in vivo," Proc Natl Acad Sci USA (1996) 93:11319-11320.

Markert et al., "Conditionally replicating herpes simplex virus mutant, G207 for the treatment of malignant glioma: results of a phase I trial," Gene Ther (2000) 7:867-874.

Mavilio et al., "Correction of junctional epidermolysis bullosa by transplantation of genetically modified epidermal stem cells," Nat Med. (2006) 12(12): 1397-1402.

Mayr et al., "Gene Therapy for the COL7A1 Gene", Chapter 23, Intech, 2013, pp. 561-589.

Melo et al., "Somatic correction of junctional epidermolysis bullosa by a highly recombinogenic AAV variant," Mol Ther. (2014) 22(4):725-33.

Miezeiewski et al., "Role of adherens junction proteins in differential herpes simplex virus type 2 infectivity in communication-competent and -deficient cell lines," Intervirology. (2012) 55(6): 465-474.

Miyagawa et al., "Herpes simplex viral-vector design for efficient transfuction of nonneuronal cells without cytotoxcity," Proc Natl Acad Sci USA (2015) 112(13):E1632-E1641.

Miyagawa et al., "Deletion of the Virion Host Shut-off Gene Enhances Neuronal-Selective Transgene Expression from an HSV Vector Lacking Functional IE Genes," Mol Ther Methods Clin Dev. (2017) 6: 79-90.

Mokrejs et al., "IRESite: the database of experimentally verified IRES structures (www.iresite.org)," Nucleic Acids Res. (2006) 34(Database issue):D125-30.

Nakao et al., "Intratumoral injection of herpes simplex virus HF10 in recurrent breast cancer," Ann Oncol (2004) 15(6):988-989.

Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.

Non-Final Office Action received for U.S. Appl. No. 15/393,151, mailed on Apr. 14, 2017, 13 pages.

Non-Final Office Action received for U.S. Appl. No. 15/851,488, mailed on May 14, 2018, 10 pages.

Non-Final Office Action received for U.S. Appl. No. 16/177,153, mailed on May 9, 2019, 13 pages.

Notice of Allowance received for U.S. Appl. No. 15/393,151, mailed on Dec. 6, 2017, 11 pages.

Notice of Allowance received for U.S. Appl. No. 15/851,488, mailed on Oct. 29, 2018, 11 pages.

Notice of Allowance received for U.S. Appl. No. 16/177,153, mailed on Aug. 30, 2019, 10 pages.

Nuutila et al., "Recombinant human collagen III gel for transplantation of autologous skin cells in porcine full-thickness wounds," J Tissue Eng Regen Med (2015) 9:1386-1393.

Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.

Papanastassiou et al., "The potential for efficacy of the modified (ICP 34.5-) herpes simplex virus HSV1716 following intratumoural injection into human malignant glioma: a proof of principle study," Gene Ther (2002) 9:398-406.

Periphagen, Krystal Biotech Inc., Answer and Counterclaim in *PeriphaGen* v. *Krystal Biotech*, Filed Jun. 6, 2020 in the Western District of Pennsylvania (60 pgs).

Qin et al., "Rapamycin Protects Skin Fibroblasts from Ultraviolet B-Induced Photoaging by Suppressing the Production of Reactive Oxygen Species," Cell Physiol Biochem (2018) 46:1849-1860.

Quan et al., "Role of Age-Associated Alterations of the Dermal Extracellular Matrix Microenvironment in Human Skin Aging," Gerontology (2015) 61(5):427-434.

Rahn et al., "Invasion of Herpes Simplex Virus Type 1 into Murine Epidermis: An Ex Vivo Infection Study," J Invest Dermatol. (2015) 135(12): 3009-3016.

Rampling et al., "Toxicity evaluation of replication-competent herpes simplex virus (ICP 34.5 null mutant 1716) in patients with recurrent malignant glioma," Gene Ther (2000) 7:859-866.

Rayess et al., "A Cross-sectional Analysis of Adverse Events and Litigation for Injectable Fillers," JAMA Facial Plast Surg (2018) 20(3):207-214.

Ricard-Blum, "The Collagen Family," Cold Spring Harb Perspect Biol (2011) 3:a004978.

Rittie et al., "Natural and Sun-Induced Aging of Human Skin," Cold Spring Harb Perspect Med (2015) 5:a015370.

Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.

(56)　　　　　　References Cited

OTHER PUBLICATIONS

Salameh et al., "Early events in herpes simplex virus lifecycle with implications for an infection of lifetime," Open Virol J. (2012) 6:1-6.

Salmon-Ehr et al., "Implication of Interleukin-4 in Wound Healing", Laboratory Investigation, vol. 80, No. 8, Aug. 2000, pp. 1337-1343.

Samaniego et al., "Persistence and Expression of the Herpes Simplex Virus Genome in the Absence of Immediate-Early Proteins", Journal of Virology, (1998) 72(4); 3307-3320.

Samaniego et al., "The herpes simplex virus immediate-early protein ICP0 affects transcription from the viral genome and infected-cell survival in the absence of ICP4 and ICP27," J Virol. (1997) 71(6): 4614-4625.

Sankar et al., "A novel role for keratin 17 in coordinating oncogenic transformation and cellular adhersion in eqing sarcoma," Molecular and Cellular Biology (2013) 33(22):4448-4460.

Shen et al., "Herpes simplex virus 1 (HSV-1) for cancer treatment," Cancer Gene Therapy (2006) 13: 975-992.

Silva et al., "Herpes Virus Amplicon Vectors", Viruses, vol. 1, 2009, pp. 594-629.

Siprashvili et al., "Long-term type VII collagen restoration to human epidermolysis bullosa skin tissue," Hum Gene Ther. Oct. 2010;21(10):1299-310.

Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.

Sufiawati et al., "HIV-associated disruption of tight and adherens junctions of oral epithelial cells facilitates HSV-1 infection and spread," PLoS One. (2014) 9(2): e88803.

Sufiawati et al., "HIV-induced matrix metalloproteinase-9 activation through mitogen-activated protein kinase signalling promotes HSV-1 cell-to-cell spread in oral epithelial cells," J Gen Virol. (2018) 99(7): 937-947.

Summary of safety and effectiveness data of CosmoDerm™ 1 Human-Based collagen. Approval date to applicant Mar. 11, 2003.

Thangapazham et al., "Alteration of Skin Properties with Autologous Dermal Fibroblasts," Int J Mol Sci (2014) 15:8407-8427.

Theopold et al., "A novel replication-defective HSV-1 vector for regulatable gene delivery to wounds," Journal of the American College of Surgeons (2004) 199(3):57-58.

Uitto et al., "Progress toward Treatment and Cure of Epidermolysis Bullosa: Summary of the DEBRA International Research Symposium EB2015", Journal of Investigative Dermatology, vol. 136, 2016, pp. 352-358.

Volk et al., "Diminished Type III Collagen Promotes Myofibroblast Differentiation and Increases Scar Deposition in Cutaneous Wound Healing," Cells Tissues Organs (2011) 194:25-37.

Von Heijne, G., "Patterns of amino acids near signal-sequence cleavage sites," Eur J Biochem. Jun. 1, 1983;133(1):17-21.

Wang et al., "Comparative Effectiveness of Antinociceptive Gene Therapies in Animal Models of Diabetic Neuropathic Pain", Gene Therapy, vol. 20, 2013, pp. 742-750.

Wang et al., "Wound healing," J Chin Med Assoc (2018) 81:94-101.

Watanabe et al., "Properties of a Herpes Simplex Virus Multiple Immediate-early Gene-Deleted Recombinant as a Vaccine Vector", Virology, vol. 357, 2007, pp. 186-198.

Watson et al., "Autologous Fibroblasts for Treatment of Facial Rhytids and Dermal Depressions," Arch Facial Plast Surg (1999) 1:165-170.

Watt et al., "Lysyl Hydroxylase 3 Localizes to Epidermal Basement Membrane and Is Reduced in Patients with Recessive Dystrophic Epidermolysis Bullosa", Plos One, (2015) 10(9): e0137639.

Weiss et al., "The Role of Interleukin 10 in the Pathogenesis and Potential Treatment of Skin Diseases", Journal of the American Academy of Dermatology, vol. 50, No. 5, May 2004, pp. 657-675.

White et al., "Evaluation and optimization of the administration of a selectively replicating herpes simplex viral vector to the brain by convection-enhanced delivery," Cancer Gene Ther. May 2011;18(5):358-69. doi: 10.1038/ cgt.2011.2. Epub Mar. 4, 2011.

Wikipedia, "Collagen, type VII, alpha 1," Edited on Apr. 17, 2020. Retrieved from https://en.wikipedia.org/wiki/Collagen,_type_VII,_alpha_1&oldid=951427836 on Jul. 22, 2020.

Wikipedia, "Collagen," p. 1-10. Retrieved Aug. 20, 2019.

Wolfe et al., "Engineering Herpes Simplex Viral Vectors for Therapeutic Gene Transfer", Chapter 6, Gene and Cell Therapy, 2004, pp. 103-129.

Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.

Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.

Wu et al., "Prolonged gene expression and cell survival after infection by a herpes simplex virus mutant defective in the immediate-early genes encoding ICP4, ICP27, and ICP22," J Virol. (1996) 70(9): 6358-6369.

Yano et al., "Regulatory approval for autologous human cells and tissue products in the United States, the European Union, and Japan," Regenerative Therapy (2015) 1:45-56.

Yoon et al., "Anti-wrinkle effect of bone morphogenetic protein receptor 1a-extracellular domain (BMPR1a-ECD)," BMB Rep (2013) 46(9):465-470.

Zeng et al., "Preclinical Safety Studies on Autologous Cultured Human Skin Fibroblast Transplantation," Cell Transplant (2014) 23:39-49.

Zhao et al., "Preliminary Survival Studies on Autologous Cultured Skin Fibroblasts Transplantation by Injection," Cell Transplant (2008) 17:775-783.

Unpublished U.S. Appl. No. 18/342,284, filed Jun. 27, 2023, by Krishnan et al. titled "Compositions and Methods for the Treatment of Wounds, Disorders, and Diseases of the Skin" (Copy not submitted herewith pursuant to the waiver of 37 C.F. R. § 1.98(a)(2)(iii) issued by the Office on Sep. 21, 2004).

Acland et al., "Gene therapy restores vision in a canine model of childhood blindness," Nat Genet. (2001) 28(1):92-5.

Ali et al., "Gene therapy for inherited retinal degeneration," Br J Ophthalmol. (1997) 81(9):795-801.

Boehmer et al., "Herpes Virus Replication," IUBMB Life (2003) 55(1):13-22.

Boettiger, D., "Quantitative measurements of integrin-mediated adhesion to extracellular matrix," Methods Enzymol. (2007) 426:1-25. Abstract only.

Choate et al., "Transglutaminase 1 delivery to lamellar ichthyosis keratinocytes," Human Gene Therapy (1996) 7:2247-2253.

Di et al., "Phase I study protocol for ex vivo lentiviral gene therapy for the inherited skin disease, Netherton syndrome," Hum Gene Ther Clin Dev. (2013) 24(4):182-190.

Farasat et al., "Novel transglutaminase-1 mutations and genotype-phenotype investigations of 104 patients with autosomal recessive congenital ichthyosis in the USA," J Med Genet (2009) 46(2):103-111.

Fraefel et al., "In vivo gene transfer to the rat retina using herpes simplex virus type 1 (HSV-1)-based amplicon vectors," Gene Ther. (2005) 12(16):1283-8.

Goins et al. "Generation of replication-competent and -defective HSV vectors," Cold Spring Harb Protoc. May 1, 2011;2011(5): 512-519; pdb.prot5615.

Hegde et al., "The surprising complexity of signal sequences," Trends Biochem Sci. (2006) 31(10): 563-571.

Hill et al., "Herpes simplex virus turns off the TAP to evade host immunity," Nature. (1995) 375(6530): 411-415.

Krystal Biotech, Inc. "Krystal Biotech Announces Settlement with PeriphaGen, Inc." Mar. 15, 2022, https://ir.krystalbio.com/node/8481/pdf. (Year: 2022).

Liu et al., "Herpes simplex virus mediated gene transfer to primate ocular tissues," Exp Eye Res. (1999) 69(4):385-95.

Martoglio et al., "Signal sequences: more than just greasy peptides," Trends Cell Biol. (1998) 8(10): 410-415.

Mcgowan et al., "Keratin 17 n ull mice exhibit age- and strain-dependent alopecia," Genes & Dev (2002) 16:1412-1422.

(56) References Cited

OTHER PUBLICATIONS

Messmer et al., "Ocular manifestations of keratitis-ichthyosis-deafness (KID) syndrome," Ophthalmology. (2005) 112(2):e1-6.

Peek et al., "Herpes simplex virus infection of the human eye induces a compartmentalized virus-specific B cell response," J Infect Dis. (2002) 186(11):1539-46.

Pepose et al., "Herpes simplex viral vectors for therapeutic gene delivery to ocular tissues. Recent breakthroughs in the molecular genetics of ocular diseases," Invest Ophthalmol Vis Sci. (1994) 35(6):2662-6.

Robbins et al., "In vivo restoration of laminin 5 beta 3 expression and function in junctional epidermolysis bullosa," Proc Natl Acad Sci USA (2001) 98(9):5193-5198.

Sabater et al., "Topical beremagene geperpavec (B-VEC) for the treatment of recurrent cicatrizing conjunctivitis in a patient with dystrophic epidermolysis bullosa," ARVO Annual Meeting, New Orleans, LA, USA, Apr. 23-27, 2023. (2023).

Shtessel et al., "Reliability of allergy skin testing," Ann Allergy Asthma Immunol. (2018) 120(1): 80-83. Abstract only.

Siegle et al., "Intradermal Implantation of Bovine Collagen: Humoral Immune Responses Associated with Clinical Reactions," Arch Dermatol (1984) 120:183-187.

Smith et al., "A Randomized, Bilateral, Prospective Comparison of Calcium Hydroxylapatite Microspheres versus Human-Based Collagen for the Correction of Nasolabial Folds," Dermatol Surg (2007) 33:S112-S121.

Spencer et al., "HSV-1 vector-delivered FGF2 to the retina is neuroprotective but does not preserve functional responses," Mol Ther. (2001) 3(5 Pt 1):746-56.

Vauthier et al., "Poly(alkylcyanoacrylates) as biodegradable materials for biomedical applications," Adv Drug Del Rev. (2003) 55: 519-48.

Wang et al., "Updates on Gene Therapy for Diabetic Retinopathy," Curr Diab Rep. (2020) 20(7):22.

Yutskovskaya et al., "A Randomized, Split-Face, Histomorphological Study Comparing a Volumetric Calcium Hydroxylapatite and a Hyaluornic Acid-Based Dermal Filler," J Drugs Dermatol (2014) 13(9):47-52.

Goins, et al., "Herpes Simplex Virus Type 1 Vector-Mediated Expression of Nerve Growth Factor Protects Dorsal Root Ganglion Neurons from Peroxide Toxicity," Journal of Virology, Jan. 1999, pp. 519-532, vol. 73, No. 1.

Office Action for U.S. Appl. No. 18/342,284 dated Aug. 15, 2024.

Ivanov et al., "A Tobamovirus Genome That Contains an Internal Ribosome Entry Site Functional in Vitro." Virology, vol. 232, 1997, pp. 32-43.

Sadikoglou et al., "Comparative analysis of internal ribosomal entry sites as molecular tools for bicistronic expression." Journal of Biotechnology, vol. 181, 2014, pp. 31-34.

Wang et al., "Neurological Complications of herpes zoster," Zhejiang Medical Journal, Issue 6, pp. 26-28, 1985.

Office Action for related Application No. CN 201980028654.6 dated Dec. 22, 2023.

Office Action for related Application No. AE P6001497/2020 dated Dec. 4, 2023.

Saeki et al., "Improved Helper Virus-Free Packaging System for HSV Amplicon Vectors Using an ICP27-Deleted, Oversized HSV-1 DNA in a Bacterial Artificial Chromosome." Molecular Therapy. 2001. vol. 3, No. 4, pp. 591-601.

Titeux et al., "Gene therapeutics strategies for blistering skin diseases." Drug Discovery Today: Therapeutic Strategies. 2006. vol. 3, No. 1, pp. 87-92.

Office Action from related Application KR 10-2018-7030112, dated Jan. 24, 2024.

Office Action or Application No. NC 2023/0017711 dated Jan. 9, 2025.

Office Action in Related Application No. CO NC20230017712 dated Nov. 19, 2024.

Office Action in Application No. CN 201980028654.6 dated Aug. 30, 2024.

Office Action in Related Application No. JP2024-027283, dated Feb. 20, 2025.

Ain et al., "Gene Delivery to the Skin—How Far Have We Come?", Trends in Biotechnology, 2020, pp. 474-487, 39 (5).

Di et al., "Ex-vivo gene therapy restores LEKT1 activity and corrects the architecture of Netherton syndrome-derived skin grafts" Mol. Ther. 2011, pp. 408-416, 19(2).

Ghazizadeh et al., "In vivo transduction of mouse epidermis with recombinant retroviral vectors: implications for cutaneous gene therapy" Gene Ther., 1999, pp. 1267-1275, vol. 6, No. 7.

Perkins, "Targeting apoptosis in neurological diseasae using the herpes simplex virus", Journal of Cellular and Molecular Medicine, 2002, pp. 341-356, 6(3).

Roedl et al., "rAAV2-mediated restoration of LEKTI in LEKTI-deficient cells from Netherton patients" J. Dermatol. Sci., 2011, pp. 194-198, vol. 61, No. 3.

Whitley et al., "Pathogenesis and disease," In: Arvin A, Campadelli-Fiume G, Mocarski E, et al., eds. Human Herpesviruses: Biology, Therapy, and Immunoprophylaxis, 2007, Cambridge: Cambridge Univ. Press; 2007. Chapter 32.

Office Action in related CA application 3,112,633 dated dated Apr. 16, 2024.

Office Action for CO Application No. NC2023/0017711 dated May 6, 2025.

* cited by examiner

= heterologous promoter

= wild-type coding sequence of human *LAMB3*

= codon-optimized coding sequence of human *LAMB3*

= regulatory elements

Figures 1D, 1E:
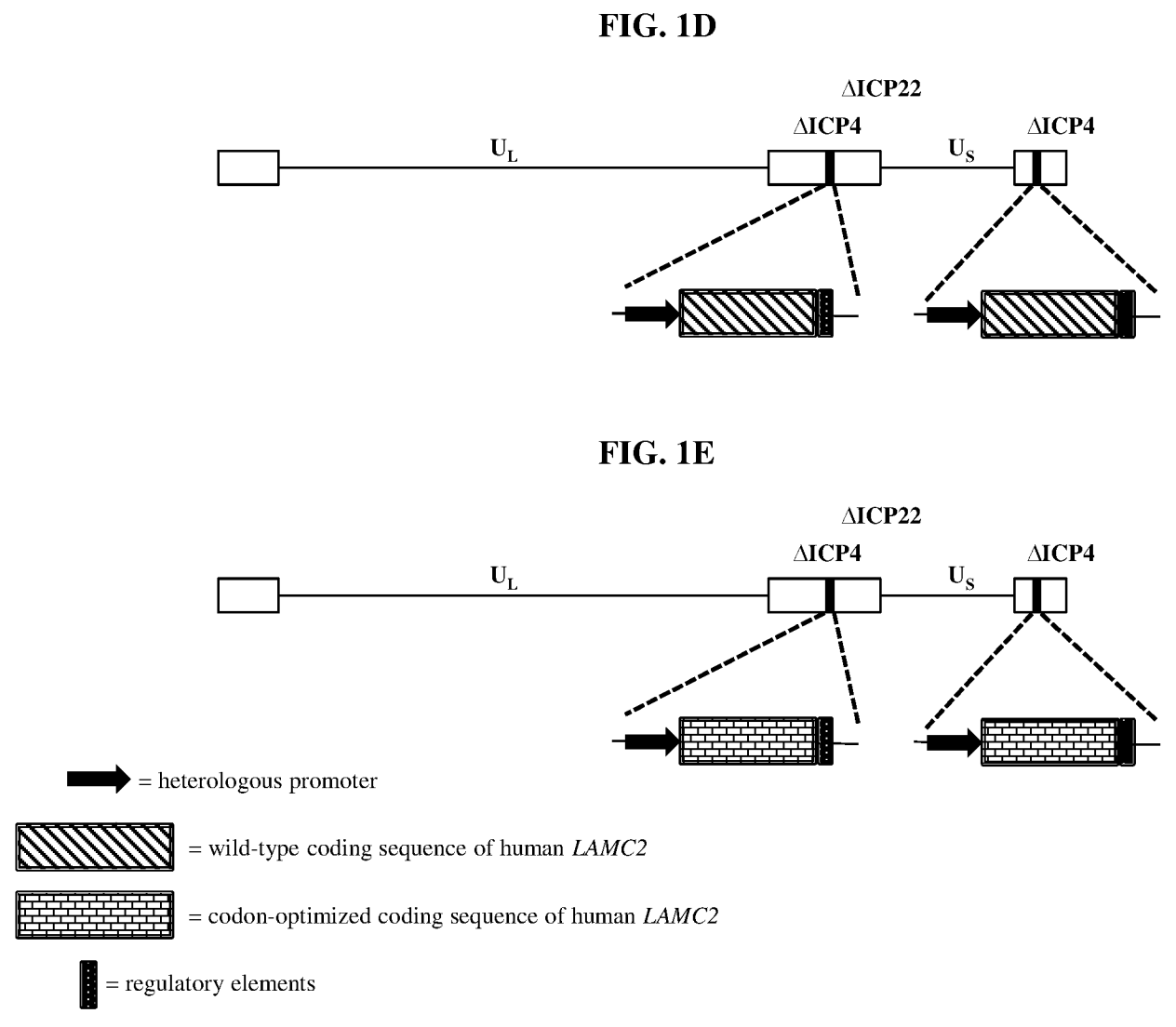

= heterologous promoter

= wild-type coding sequence of human *LAMC2*

= codon-optimized coding sequence of human *LAMC2*

= regulatory elements

FIG. 2A

LAMB3 WT - Transcript

FIG. 2B

LAMC2 DNA

LAMC2 transcript

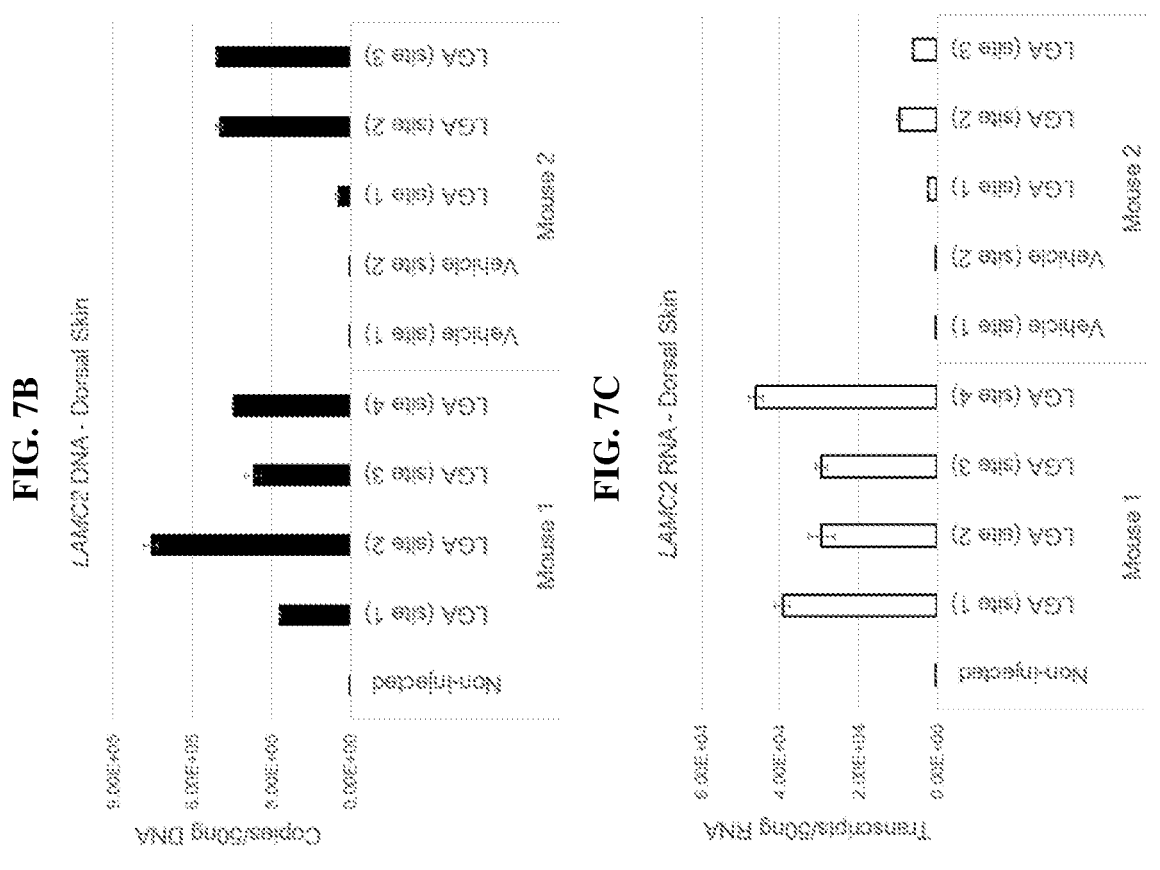

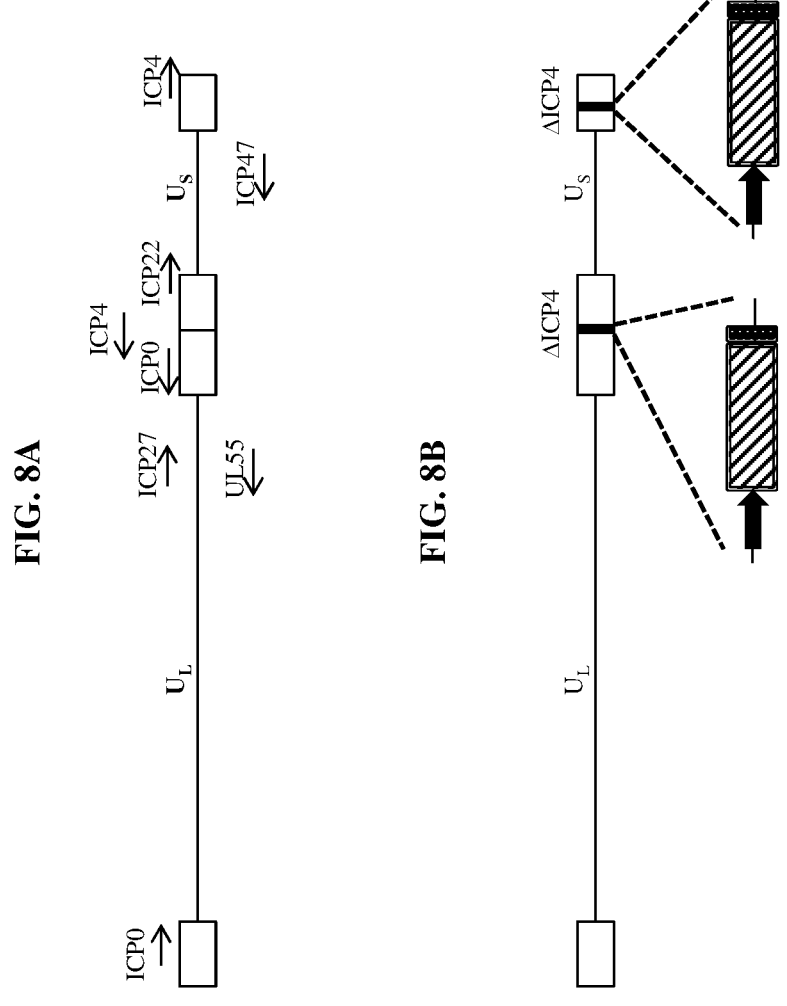
FIG. 8A
FIG. 8B
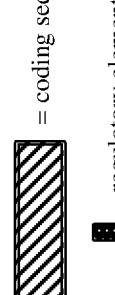
= heterologous promoter
= coding sequence of human filaggrin
= regulatory elements = heterologous promoter = coding sequence of human filaggrin = regulatory elements

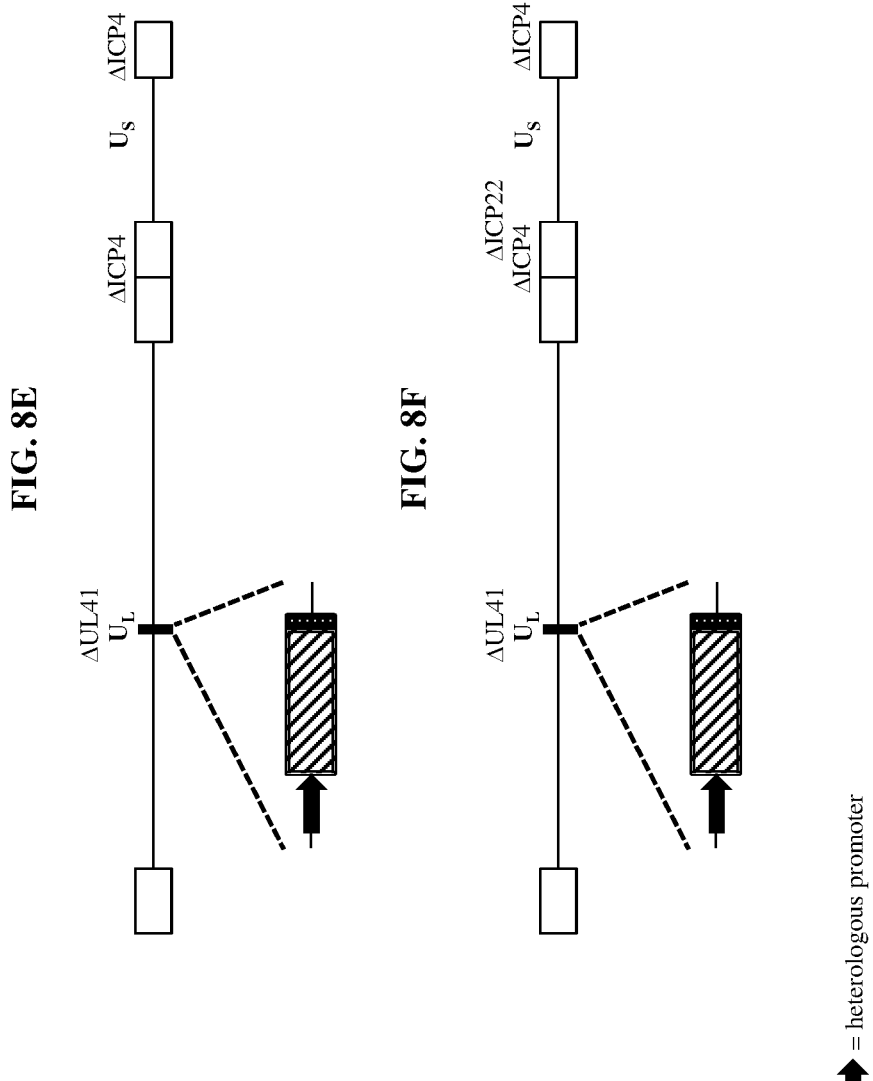
FIG. 8E
FIG. 8F
= heterologous promoter
= coding sequence of human filaggrin
= regulatory elements

SEQUENCE LISTING

<160> NUMBER OF SEQ ID NOS: 50

<210> SEQ ID NO 1
<211> LENGTH: 5175
<212> TYPE: DNA
<213> ORGANISM: Homo sapiens

<400> SEQUENCE: 1

```
atgcctccag cagtgaggcg gtcagcctgc agcatgggat ggctgtggat ctttggggca      60
gccctggggc agtgtctggg ctacagttca cagcagcaaa gggtgccatt tcttcagcct     120
cccggtcaaa gtcaactgca agcgagttat gtggagttta gacccagcca gggttgtagc     180
cctggatact atcgggatca taaaggcttg tataccggac ggtgtgttcc ctgcaattgc     240
aacggacatt caaatcaatg ccaggatggc tcaggcatat gtgttaactg tcagcacaac     300
accgcgggag agcactgtga acgctgccag gagggctact atggcaacgc cgtccacgga     360
tcctgcaggg cctgcccatg tcctcacact aacagctttg ccactggctg tgtggtgaat     420
gggggagacg tgcggtgctc ctgcaaagct gggtacacag aacacagtg tgaaaggtgt     480 gcaccgggat atttcgggaa tccccagaaa ttcggaggta gctgccaacc atgcagttgt     540
aacagcaatg gccagctggg cagctgtcat cccctgactg gagactgcat aaaccaagaa     600
cccaaagata gcagccctgc agaagaatgt gatgattgcg acagctgtgt gatgaccctc     660
ctgaacgacc tggccaccat gggcgagcag ctccgcctgg tcaagtctca gctgcagggc     720
ctgagtgcca gcgcagggct tctggagcag atgaggcaca tggagaccca ggccaaggac     780
ctgaggaatc agttgctcaa ctaccgttct gccatttcaa atcatggatc aaaaatagaa     840
ggcctggaaa gagaactgac tgatttgaat caagaatttg agactttgca agaaaaggct     900
caagtaaatt ccagaaaagc acaaacatta aacaacaatg ttaatcgggc aacacaaagc     960 gcaaagaac tggatgtgaa gattaaaaat gtcatccgga atgtgcacat tcttttaaag    1020
cagatctctg ggacagatgg agagggaaac aacgtgcctt caggtgactt ttccagagag    1080
tgggctgaag cccagcgcat gatgagggaa ctgcggaaca ggaactttgg aaagcacctc    1140
agagaagcag aagctgataa aagggagtcg cagctcttgc tgaaccggat aaggacctgg    1200 cagaaaccc accaggggga gaacaatggg cttgctaaca gtatccggga ttctttaaat    1260
gaatacgaag ccaaactcag tgaccttcgt gctcggctgc aggaggcagc tgcccaagcc    1320
aagcaggcaa atggcttgaa ccaagaaaac gagagagctt tgggagccat tcagagacaa    1380
gtgaaagaaa taaattccct gcagagtgat ttcaccaagt atctaaccac tgcagactca    1440
tctttgttgc aaaccaacat tgcgctgcag ctgatggaga aaagccagaa ggaatatgaa    1500
aaattagctg ccagtttaaa tgaagcaaga caagaactaa gtgacaaagt aagagaactt    1560
tccagatctg ctggcaaaac atcccttgtg gaggaggcag aaaagcacgc gcggtcctta    1620
caagagctgg caaagcagct ggaagagatc aagagaaacg ccagcgggga tgagctggtg    1680
cgctgtgctg tggatgccgc caccgcctac gagaacatcc tcaatgccat caaagcggcc    1740
gaggacgcag ccaacagggc tgccagtgca tctgaatctg ccctccagac agtgataaag    1800
gaagatctgc caagaaaagc taaaaccctg agttccaaca gtgataaact gttaaatgaa    1860
gccaagatga cacaaaagaa gctaaagcaa gaagtcagtc agctctcaa caacctacag    1920 caaacccctga atattgtgac agttcagaaa gaagtgatag acaccaatct cacaactctc    1980
cgagatggtc ttcatgggat acagagaggt gatattgatg ctatgatcag tagtgcaaag    2040
agcatggtca gaaaggccaa cgacatcaca gatgaggttc tggatgggct caaccccatc    2100
```

-continued

```
cagacagatg tggaaagaat taaggacacc tatgggagga cacagaacga agacttcaaa    2160
aaggctctga ctgatgcaga taactcggtg aataagttaa ccaacaaact acctgatctt    2220
tggcgcaaga ttgaaagtat caaccaacag ctgttgccct tgggaaacat ctctgacaac    2280
atggacagaa tacgagaact aattcagcag gccagagatg ctgccagtaa ggttgctgtc    2340
cccatgaggt tcaatggtaa atctggagtc gaagtccgac tgccaaatga cctggaagat    2400
ttgaaaggat atacatctct gtccttgttt ctccaaaggc ccaactcaag agaaaatggg    2460
ggtactgaga atatgtttgt gatgtacctt ggaaataaag atgcctcccg ggactacatc    2520
ggcatggcag ttgtggatgg ccagctcacc tgtgtctaca acctggggga ccgtgaggct    2580
gaactccaag tggaccagat cttgaccaag agtgagacta aggaggcagt tatggatcgg    2640
gtgaaatttc agagaattta tcagtttgca aggcttaatt acaccaaagg agccacatcc    2700
agtaaaccag aaacacccgg agtctatgac atggatggta gaaatagcaa tacactcctt    2760
aatttggatc ctgaaaatgt tgtattttat gttggaggtt acccacctga tttttaaactt    2820 cccagtcgac taagtttccc tccatacaaa ggttgtattg aattagatga cctcaatgaa    2880
aatgttctga gcttgtacaa cttcaaaaaa acattcaatc tcaacacaac tgaagtggag    2940
ccttgtagaa ggaggaagga agagtcagac aaaaattatt ttgaaggtac gggctatgct    3000
cgagttccaa ctcaaccaca tgctcccatc ccaacctttg gacagacaat tcagaccacc    3060
gtggatagag gcttgctgtt cttttgcagaa aacgggatc gcttcatatc tctaaatata    3120
gaagatggca agctcatggt gagatacaaa ctgaattcag agctaccaaa agagagagga    3180
gttggagacg ccataaacaa cggcagagac cattcgattc agatcaaaat tggaaaactc    3240
caaaagcgta tgtggataaa tgtggacgtt caaaacacta taattgatgg tgaagtattt    3300
gatttcagca catattatct gggaggaatt ccaattgcaa tcaggaaag atttaacatt    3360 tctacgcctg ctttccgagg ctgcatgaaa aatttgaaga aaaccagtgg tgtcgttaga    3420
ttgaatgata ctgtgggagt aaccaaaaag tgctcggaag actggaagct tgtgcgatct    3480
gcctcattct ccagaggagg acaattgagt ttcactgatt tgggcttacc acctactgac    3540
cacctccagg cctcatttgg atttcagacc tttcaaccca gtggcatatt attagatcat    3600
cagacatgga caaggaacct gcaggtcact ctggaagatg gttacattga attgagcacc    3660
agcgatagcg gcggcccaat ttttaaatct ccacagacgt atatggatgg tttactgcat    3720
tatgtatctg taataagcga caactctgga ctacggcttc tcatcgatga ccagcttctg    3780
agaaatagca aaaggctaaa acacatttca agttcccggc agtctctgcg tctgggcggg    3840
agcaattttg agggttgtat tagcaatgtt tttgtccaga ggttatcact gagtcctgaa    3900
gtcctagatt tgaccagtaa ctctctcaag agagatgtgt ccctgggagg ctgcagttta    3960
aacaaaccac cttttctaat gttgcttaaa ggttctacca ggtttaacaa gaccaagact    4020
tttcgtatca accagctgtt gcaggacaca ccagtggcct ccccaaggag cgtgaaggtg    4080
tggcaagatg cttgctcacc acttcccaag acccaggcca atcatggagc cctccagttt    4140
ggggacattc ccaccagcca cttgctattc aagcttcctc aggagctgct gaaacccagg    4200
tcacagtttg ctgtggacat gcagacaaca tcctccagag gactggtgtt tcacacgggc    4260
actaagaact cctttatggc tctttatctt tcaaaaggac gtctggtctt tgcactgggg    4320
acagatggga aaaaattgag gatcaaaagc aaggagaaat gcaatgatgg gaaatggcac    4380
acggtggtgt ttggccatga tggggaaaag gggcgcttgg ttgtggatgg actgagggcc    4440
```

-continued

```
cgggagggaa gtttgcctgg aaactccacc atcagcatca gagcgccagt ttacctggga    4500
tcacctccat cagggaaacc aaagagcctc cccacaaaca gctttgtggg atgcctgaag    4560
aactttcagc tggattcaaa acccttgtat accccttctt caagcttcgg ggtgtcttcc    4620
tgcttgggtg gtcctttgga gaaaggcatt tatttctctg aagaaggagg tcatgtcgtc    4680
ttggctcact ctgtattgtt ggggccagaa tttaagcttg ttttcagcat ccgcccaaga    4740
agtctcactg ggatcctaat acacatcgga agtcagcccg ggaagcactt atgtgtttac    4800
ctggaggcag gaaaggtcac ggcctctatg gacagtgggg caggtgggac ctcaacgtcg    4860
gtcacaccaa agcagtctct gtgtgatgga cagtggcact cggtggcagt caccataaaa    4920
caacacatcc tgcacctgga actggacaca gacagtagct acacagctgg acagatcccc    4980
ttcccacctg ccagcactca agagccacta caccttggag gtgctccagc caatttgacg    5040
acactgagga tccctgtgtg gaaatcattc tttggctgtc tgaggaatat tcatgtcaat    5100
cacatccctg tccctgtcac tgaagccttg gaagtccagg ggcctgtcag tctgaatggt    5160
tgtcctgacc agtaa                                                     5175
```

```
<210> SEQ ID NO 2
<211> LENGTH: 5175
<212> TYPE: DNA
<213> ORGANISM: Artificial Sequence
<220> FEATURE:
<223> OTHER INFORMATION: Synthetic Construct

<400> SEQUENCE: 2
```

```
atgcctcctg ctgtgcggag aagcgcctgt tctatgggat ggctgtggat ctttggcgcc      60
gctctgggac agtgtctggg ctactcttct cagcagcagc gggtgccatt tctgcagcca     120
cctggacagt ctcagctgca ggccagctac gtggaattca acctagcca gggctgtagc      180 cccggctact acagagatca aagggcctg tacaccggca gatgcgtgcc ctgcaactgt      240
aacggccaca gcaaccagtg tcaggacggc tctggcatct cgtgaactg ccagcataat      300 actgccggcg agcactgcga gagatgccaa gagggctact acggcaatgc cgtgcatggc      360
agctgtcggg cttgtccttg tcctcacacc aacagctttg ccaccggctg cgttgtgaac      420
ggcggagatg ttcggtgttc ttgcaaggcc ggctacacag gcacacagtg cgaaagatgt      480
gcccctggct actttggcaa ccctcagaag tttggcggct cctgccagcc ttgctcctgc      540
aattctaatg ccagctgggc tcttgtcac cctctgaccg gcgactgcat caatcaagag      600
cctaaggaca gcagccctgc cgaggaatgc gacgattgcg atagctgcgt gatgaccctg      660
ctgaacgacc tggccacaat gggagaacag ctgcggctgg ttaagagcca gctccaggga      720
ctgtctgcct ctgctggact gctggaacag atgcggcaca tggaaaccca ggccaaggac      780
ctgagaaacc agctgctgaa ctacagaagc gccatctcca accacggcag caagatcgaa      840
ggcctggaaa gagagctgac cgacctgaat caagagttcg agacactgca gagaaggcc      900 caagtgaaca gccggaaggc ccagactctg aacaacaacg tgaaccgggc cacacagtcc      960
gccaaagaac tggacgtgaa gatcaagaac gtgatccgga acgtgcacat cctgctgaag     1020
cagatcagcg gcacagatgg cgagggcaac aatgtgccta cgggcgactt agcagagag     1080 tgggccgaag ctcagcggat gatgagagag ctgcggaacc ggaacttcgg caagcacctg     1140
agagaagccg aggccgacaa agagagagag caactgctgc tcaaccggat cagaacctgg     1200
cagaaaaccc accagggcga gaacaacggc ctggccaaca gcatcagaga cagcctgaat     1260
gagtacgagg ccaagctgag cgatctgcgg gccagacttc aagaagctgc cgctcaggcc     1320
```

-continued

```
aagcaggcca acggccttaa tcaagagaac gagagagccc tgggcgccat ccagagacaa    1380
gtgaaagaga tcaacagcct gcagagcgac ttcaccaagt acctgaccac cgccgatagc    1440
agcctgctgc agacaaatat cgccctgcag ctcatggaaa agagccagaa agagtacgaa    1500
aagctggccg ccagcctgaa cgaggccagg caagaactgt ctgacaaagt gcgcgagctg    1560
agcagatccg ccggcaagac atctctggtg gaagaggccg agaagcacgc cagatctctg    1620
caagagctgg ccaaacagct ggaagagatt aagcggaacg ccagcggcga cgaactcgtc    1680
agatgtgcag tggatgccgc caccgcctac gagaacatcc tgaatgccat caaggccgcc    1740
gaggacgccg ctaatagagc cgcttctgct tctgagtctg ccctgcagac cgtgatcaaa    1800
gaggacctgc ctagaaaggc caagacactg agcagcaaca gcgacaaact gctgaatgag    1860
gccaagatga cccagaagaa actgaagcaa gaggtgtccc ctgcactgaa caacctgcag    1920
cagaccctga acatcgtgac cgtgcagaaa gaagtgatcg acaccaacct gacaacccctg    1980 agagatggcc tgcacggaat ccagagaggc gacatcgacg ccatgatcag cagcgccaag    2040
agcatggttc gaaaagccaa cgacatcacc gacgaggtgc tggacggcct gaatcctatc    2100
cagaccgacg tggaacggat caaggacacc tacggcagaa cccagaacga ggatttcaag    2160
aaggccctga ccgacgccga caactccgtg aacaagctga ccaacaagct gcccgatctg    2220
tggcggaaga tcgagagcat caaccagcaa ctgctccctc tgggcaacat cagcgacaac    2280
atggacagaa tccgggaact gatccagcag gccagagatg ccgcctccaa agtggctgtg    2340
cccatgagat tcaacggcaa gagcggagtg gaagtgcggc tgcccaacga tctggaagat    2400
ctgaagggct ataccagcct gagcctgttc ctgcagaggc ccaacagcag agagaatggc    2460
ggcaccgaga atatgttcgt gatgtacctg ggaaacaagg acgccagccg ggactatatc    2520
ggaatggccg ttgtggacgg ccagctgacc tgcgtgtaca acctgggaga cagagaagct    2580
gaactgcagg tcgaccagat cctgaccaag agcgagacaa aagaggccgt gatggacaga    2640
gtgaagttcc agcggatcta ccagttcgcc cggctgaatt acaccaaggg cgccacaagc    2700
agcaagcccg aaacacctgg cgtgtacgac atggacggcc ggaactctaa cactctgctg    2760
aatctggacc ccgagaacgt ggtgtttac gtcggcggct accctcctga cttcaagctg    2820
cctagcagac tgagcttccc accttacaag ggctgcatcg agctggatga cctgaacgaa    2880
aacgtgctgt ccctgtacaa cttcaaaaag accttcaacc tgaacaccac cgaggtggaa    2940
ccctgcaggc gcagaaaaga ggaatccgac aagaactact tcgaaggcac cggctacgcc    3000
agagtgccta cacaacctca cgctcccatt cctaccttcg gccagaccat ccagacaacc    3060
gtggatagag gcctgctgtt cttcgccgag aacggcgaca gattcatctc cctgaatatc    3120
gaggatggca agctgatggt ccgatacaag ctgaatagcg agctgcccaa agaaagaggc    3180
gtgggcgacg ccatcaacaa cggcagggat cacagcatcc agatcaagat cggcaaactg    3240
cagaaacgga tgtggatcaa cgtggacgtg cagaacacca tcatcgacgg cgaggtgttc    3300
gacttcagca cctactatct cggcggaatc cctatcgcca tcagagagcg gttcaatatc    3360
agcacccctg ccttccgggg ctgcatgaag aacctgaaaa agaccagcgg cgtcgtgcgg    3420
ctgaatgata cagtgggcgt gaccaagaag tgcagcgagg actggaagct tgtgcggagc    3480
gccagttttt ctagaggcgg acagctgagc tttaccgacc tgggactgcc tcctaccgat    3540
catctgcagg caagcttcgg attccagacc ttccagccaa gcggaatcct gctgaccac    3600 cagacctgga ccagaaaacct gcaagtgacc ctggaagatg gctacatcga actgagcacc    3660
```

-continued

```
agcgactctg gcggccctat ctttaagagc cctcagacct acatggatgg gctgctgcac    3720
tacgtgtccg tgatcagcga taacagcggc ctgagactgc tgatcgacga ccagctcctg    3780
cggaacagca agcggctgaa gcacatctcc agcagcagac agagtctgag actcggcggc    3840
agcaatttcg agggctgtat cagcaacgtg ttcgtgcagc gcctgagtct gtctccagaa    3900
gtgctggacc tgaccagcaa tagcctgaag agggatgtgt ctctcggcgg ctgctccctg    3960
aacaaacctc ctttcctgat gctgctgaag ggcagcaccc ggttcaacaa gaccaagacc    4020
tttcggatca atcagctgct ccaggacacc cctgtggcta gccctagaag cgtgaaagtg    4080
tggcaggacg cctgcagtcc cctgcctaaa acacaggcca atcacggggc tctgcagttc    4140
ggcgatatcc ccacaagcca tctgctgttt aagctgcccc aagagctgct caagcctcgg    4200
agccagttcg ctgtggatat gcagaccacc tcctccagag gactggtgtt tcacaccggc    4260
accaagaaca gcttcatggc cctgtacctg agcaaaggca ggctggtgtt tgccctgggc    4320
accgacggaa agaaactgcg gatcaagagc aaagagaagt gcaacgacgg caagtggcac    4380
accgtggtgt tcggacacga tggcgagaaa ggcagactcg tggtggatgg cctgagagcc    4440
agagagggat ctctgcctgg caactccacc atctccatca gagcccctgt gtatctgggc    4500
agccctccta gcgcgaaagcc taagagcctg cctaccaact ccttcgtggg ctgtctgaag    4560
aactttcagc tggacagcaa gcctctgtac accccctagca gcagctttgg cgtgtcctcc    4620
tgtctcggag gccctctgga aaagggcatc tacttctctg aggaaggcgg ccacgttgtc    4680
ctggctcatt ctgttctgct gggccccgag ttcaagctgg tgttctctat ccggcctaga    4740
agcctgaccg gcatcctgat tcacatcggc agccagcctg ggaagcacct gtgtgtgtat    4800
ctcgaggccg gcaaagtgac cgccagcatg gattctggtg ctggcggcac aagcacctcc    4860
gtgacaccta agcagagcct gtgtgatggc cagtggcaca gtgtggccgt gacaatcaag    4920
cagcacattc tgcacctgga actggacacc gacagcagct ataccgccgg acagatccca    4980
tttcctccag ccagcacaca agagcctctg caccttggag gcgcccctgc caatctgacc    5040
acactgagaa tccccgtgtg gaagtccttc ttcggctgcc tgcggaatat ccatgtgaac    5100
cacattccag tgcctgtgac agaggccctg gaagtgcagg acccgtgtc tctgaatgga    5160 tgccccgatc agtga                                                     5175
```

<210> SEQ ID NO 3
<211> LENGTH: 3519
<212> TYPE: DNA
<213> ORGANISM: Homo sapiens

<400> SEQUENCE: 3

```
atgagaccat tcttcctctt gtgttttgcc ctgcctggcc tcctgcatgc ccaacaagcc      60
tgctcccgtg gggcctgcta tccacctgtt ggggacctgc ttgttgggag gacccggttt     120
ctccgagctt catctacctg tggactgacc aagcctgaga cctactgcac ccagtatggc     180
gagtggcaga tgaaatgctg caagtgtgac tccaggcagc ctcacaacta ctacagtcac     240
cgagtagaga atgtggcttc atcctccggc cccatgcgct ggtggcagtc acagaatgat     300
gtgaaccctg tctctctgca gctggacctg gacaggagat tccagcttca agaagtcatg     360
atggagttcc aggggcccat gcccgccggc atgctgattg agcgctcctc agacttcggt     420
aagacctggc gagtgtacca gtacctggct gccgactgca cctccaccctt ccctcgggtc     480 cgccagggtc ggcctcagag ctggcaggat gttcggtgcc agtccctgcc tcagaggcct     540
aatgcacgcc taaatggggg gaaggtccaa cttaacctta tggatttagt gtctgggatt     600
```

```
ccagcaactc aaagtcaaaa aattcaagag gtgggggaga tcacaaactt gagagtcaat      660
ttcaccaggc tggcccctgt gccccaaagg ggctaccacc ctcccagcgc ctactatgct      720
gtgtcccagc tccgtctgca ggggagctgc ttctgtcacg gccatgctga tcgctgcgca      780
cccaagcctg gggcctctgc aggcccctcc accgctgtgc aggtccacga tgtctgtgtc      840
tgccagcaca acactgccgg cccaaattgt gagcgctgtg cacccttcta caacaaccgg      900
ccctggagac cggcggaggg ccaggacgcc catgaatgcc aaaggtgcga ctgcaatggg      960
cactcagaga catgtcactt tgaccccgct gtgtttgccg ccagccaggg ggcatatgga     1020
ggtgtgtgtg acaattgccg ggaccacacc gaaggcaaga actgtgagcg gtgtcagctg     1080
cactatttcc ggaaccggcg cccgggagct tccattcagg agacctgcat ctcctgcgag     1140
tgtgatccgg atggggcagt gccaggggct ccctgtgacc cagtgaccgg gcagtgtgtg     1200
tgcaaggagc atgtgcaggg agagcgctgt gacctatgca agccgggctt cactggactc     1260
acctacgcca acccgcaggg ctgccaccgc tgtgactgca acatcctggg gtcccggagg     1320
gacatgccgt gtgacgagga gagtgggcgc tgcctttgtc tgcccaacgt ggtgggtccc     1380
aaatgtgacc agtgtgctcc ctaccactgg aagctggcca gtggccaggg ctgtgaaccg     1440
tgtgcctgcg acccgcacaa ctccctcagc ccacagtgca accagttcac agggcagtgc     1500
ccctgtcggg aaggctttgg tggcctgatg tgcagcgctg cagccatccg ccagtgtcca     1560
gaccggacct atggagacgt ggccacagga tgccgagcct gtgactgtga tttccgggga     1620
acagagggcc cgggctgcga caaggcatca ggccgctgcc tctgccgccc tggcttgacc     1680
gggccccgct gtgaccagtg ccagcgaggc tactgtaatc gctacccggt gtgcgtggcc     1740
tgccaccctt gcttccagac ctatgatgcg gacctccggg agcaggccct gcgctttggt     1800
agactccgca atgccaccgc cagcctgtgg tcagggcctg ggctggagga ccgtggcctg     1860
gcctcccgga tcctagatgc aaagagtaag attgagcaga tccgagcagt tctcagcagc     1920
cccgcagtca cagagcagga ggtggctcag gtggccagtg ccatcctctc cctcaggcga     1980
actctccagg gcctgcagct ggatctgccc ctggaggagg agacgttgtc ccttccgaga     2040
gacctggaga gtcttgacag aagcttcaat ggtctcctta ctatgtatca gaggaagagg     2100
gagcagtttg aaaaaataag cagtgctgat ccttcaggag ccttccggat gctgagcaca     2160
gcctacgagc agtcagccca ggctgctcag caggtctccg acagctcgcg ccttttggac     2220
cagctcaggg acagccggag agaggcagag aggctggtgc ggcaggcggg aggaggagga     2280
ggcaccggca gccccaagct tgtggccctg aggctggaga tgtcttcgtt gcctgacctg     2340
acacccacct tcaacaagct ctgtggcaac tccaggcaga tggcttgcac cccaatatca     2400
tgccctggta gctatgtcc ccaagacaat ggcacagcct gtggctcccg ctgcaggggt     2460
gtccttccca gggccggtgg ggccttcttg atggcggggc aggtggctga gcagctgcgg     2520
ggcttcaatg cccagctcca gcggaccagg cagatgatta gggcagccga ggaatctgcc     2580
tcacagattc aatccagtgc ccagcgcttg agacccagg tgagcgccag ccgctcccag     2640
atggaggaag atgtcagacg cacacggctc ctaatccagc aggtccggga cttcctaaca     2700
gaccccgaca ctgatgcagc cactatccag gaggtcagcg aggccgtgct ggccctgtgg     2760
ctgcccacag actcagctac tgttctgcag aagatgaatg agatccaggc cattgcagcc     2820 aggctccccca acgtggactt ggtgctgtcc cagaccaagc aggacattgc gcgtgcccgc     2880
cggttgcagg ctgaggctga ggaagccagg agccgagccc atgcagtgga gggccaggtg     2940
```

```
gaagatgtgg ttgggaacct gcggcagggg acagtggcac tgcaggaagc tcaggacacc   3000
atgcaaggca ccagccgctc ccttcggctt atccaggaca gggttgctga ggttcagcag   3060
gtactgcggc cagcagaaaa gctggtgaca agcatgacca agcagctggg tgacttctgg   3120
acacggatgg aggagctccg ccaccaagcc cggcagcagg gggcagaggc agtccaggcc   3180
cagcagcttg cggaaggtgc cagcgagcag gcattgagtg cccaagaggg atttgagaga   3240
ataaaacaaa agtatgctga gttgaaggac cggttgggtc agagttccat gctgggtgag   3300
cagggtgccc ggatccagag tgtgaagaca gaggcagagg agctgtttgg ggagaccatg   3360
gagatgatgg acaggatgaa agacatggag ttggagctgc tgcggggcag ccaggccatc   3420
atgctgcgct cagcggacct gacaggactg gagaagcgtg tggagcagat ccgtgaccac   3480
atcaatgggc gcgtgctcta ctatgccacc tgcaagtga                          3519
```

<210> SEQ ID NO 4
<211> LENGTH: 3519
<212> TYPE: DNA
<213> ORGANISM: Artificial Sequence
<220> FEATURE:
<223> OTHER INFORMATION: Synthetic Construct

<400> SEQUENCE: 4

```
atgaggccct tcttcctgct gtgctttgcc ctgcctggac tgctgcatgc tcagcaggct     60
tgtagcagag gcgcctgcta tcctcctgtg ggcgatctgc ttgtgggcag aaccagattc    120
ctgcgggcca gctctacatg cggcctgaca aagcctgaga catactgcac ccagtacggc    180
gagtggcaga tgaagtgctg caagtgcgac agcagacagc cccacaacta ctacagccac    240
agagtggaaa acgtggccag cagcagcggc cctatgagat ggtggcagag ccagaacgac    300
gtgaaccccg ttagcctgca gctggacctg gacgacacgg ttcagctgca agaagtgatg    360
atggaatttc agggccccat gcctgccggc atgctgatcg agagaagcag cgatttcggc    420
aagacctggc gggtgtacca gtatctggcc gccgattgca ccagcacatt ccccagagtt    480
agacagggca gaccccagag ctggcaggat gttcgttgtc agtctctgcc ccagcggcct    540
aacgctagac tgaatggcgg aaaggtgcag ctcaacctga tggacctggt gtctggcatc    600
cctgccacac agtcccagaa aatccaagaa gtgggcgaga tcaccaacct gagagtgaac    660
ttcacccggc tggctcccgt tcctcagaga ggatatcatc ctcctagcgc ctactacgcc    720
gtgtctcagc ttagactgca gggcagctgc ttctgtcacg gccacgctga tagatgcgcc    780
cctaaacctg gtgcctctgc cggaccttct acagccgtgc aagtgcacga tgtgtgcgtg    840
tgccagcaca ataccgccgg acctaactgc gagagatgtg ccccttttcta caacaaccgg    900 ccttggaggc ctgccgaagg acaggatgct cacgagtgcc agagatgcga ctgcaacggc    960
cacagcgaga catgccactt tgaccctgcc gtgtttgccg cttctcaggg cgcttatggc   1020
ggcgtgtgtg acaactgcag agatcacacc gagggcaaga actgcgagcg ctgtcagctg   1080
cactacttcc ggaatagaag gccaggcgcc agcatccaag agacatgcat cagctgcgag   1140
tgcgatcccg atggtgctgt tcctggcgct ccttgtgatc ctgtgacagg ccagtgcgtg   1200
tgtaaagaac acgtgcaggg cgaaagatgc gacctgtgca agcctggctt taccggcctg   1260
acctacgcca tcctcaaggg ctgccacaga tgtgattgca acatcctggg cagcagacgg   1320
gacatgccct gtgatgaaga gtctggcaga tgcctgtgcc tgcctaatgt cgtgggcccc   1380
aagtgcgatc agtgtgcccc atatcactgg aagctggcct ctggccaggg atgcgaacct   1440
tgtgcctgcg atccccacaa cagcctgtct ccacagtgca accagttcac cggccagtgt   1500
```

-continued

```
ccttgcagag aaggctttgg cggcctgatg tgttctgccg ccgctatcag acagtgcccc      1560
gatagaacat atggcgacgt ggccacaggc tgcagagcct gcgattgtga cttccgggga      1620
acagaaggac ccggctgcga taaggccagc ggaagatgtc tgtgtcggcc tggactcaca      1680
ggccccagat gtgaccagtg tcagcggggc tactgcaaca gataccctgt gtgtgtggcc      1740
tgccatcctt gcttccagac ctacgacgcc gacctgagag aacaggccct gagattcggc      1800
agactgagaa atgccaccgc cagcctttgg agcggacctg gccttgaaga tagaggcctg      1860
gcctccagaa tcctggacgc caagtctaag atcgagcaga tcagagccgt gctgtctagc      1920
ccagccgtga ccgaacaaga ggtggcccaa gtggctagcg ccatcctgag cctgagaaga      1980
actctgcagg gactgcagct cgatctgccc ctggaagagg aaacactgag cctgcctaga      2040
gatctggaaa gcctggatcg gagcttcaac ggcctgctga caatgtacca gagaaagaga      2100
gagcagttcg agaagatcag cagcgccgat cctagcggcg ccttcagaat gctgagcaca      2160
gcctatgagc agagcgccca ggctgctcag caagtgtccg atagcagcag actgctggac      2220
cagctgcggg actctagaag agaagccgaa agacttgtgc ggcaggcagg cggcggaggt      2280
ggaacaggat ctcctaaact ggtggccctg cggctggaaa tgtcctctct gcctgatctg      2340
acccctacct tcaacaagct gtgcggcaac agccggcaga tggcctgcac acctattagc      2400
tgtcctggcg agctgtgccc tcaggataat ggaaccgcct cgggctccag atgtagaggc      2460
gttttgccaa gagccggcgg agcctttctg atggctggac aagttgccga gcagctgaga      2520
ggcttcaacg ctcagctgca gcggaccaga cagatgatta gagccgccga ggaaagcgcc      2580
agccagattc aatctagcgc ccagagactg gaaacccagg tgtccgccag cagatcccag      2640
atggaagaag atgtgcggcg gacaagactg ctgatccagc aagtgcggga cttcctgacc      2700
gatcctgata ccgatgccgc cacaatccaa gaggtgtccg aagctgttct ggcactgtgg      2760
ctgcctaccg atagcgctac agtgctgcag aagatgaacg agatccaggc aatcgccgcc      2820
agactgccca atgtggatct ggtgctgagc cagaccaagc aggatatcgc cagagctaga      2880
aggctgcagg ccgaggccga agaggcaaga tctagagccc atgccgtgga aggccaagtc      2940
gaggacgttg tgggcaatct gagacaggga accgtggctc tgcaagaggc ccaggataca      3000
atgcagggca ccagcagaag cctgcgcctg atccaggata gagtggccga agtgcagcag      3060
gtcctgaggc cagccgaaaa gctggtcacc agcatgacca aacagctggg cgatttctgg      3120
acgcgcatgg aagaactgag gcatcaggca agacagcagg gcgctgaagc agtgcaggct      3180
caacaacttg ccgagggcgc ttctgaacag gctctgtctg cccaagaggg cttcgagcgg      3240
atcaagcaga gtacgccga gctgaaggac agactgggcc agagttctat gctgggcgaa      3300
cagggcgcca gaattcagag cgtgaaaaca gaggccgagg aactgttcgg cgagacaatg      3360
gaaatgatgg accggatgaa ggacatggaa ctggaactgc tgagggggcag ccaggccatc      3420 atgctgagaa gtgccgatct gacaggcctg gaaaagagag tggaacagat ccgggaccac      3480
atcaacggcc gggtgctgta ctacgccaca tgcaagtaa                              3519
```

```
<210> SEQ ID NO 5
<211> LENGTH: 3582
<212> TYPE: DNA
<213> ORGANISM: Homo sapiens

<400> SEQUENCE: 5
atgcctgcgc tctggctggg ctgctgcctc tgcttctcgc tcctcctgcc cgcagcccgg       60
```

```
gccacctcca ggagggaagt ctgtgattgc aatgggaagt ccaggcagtg tatctttgat     120
cgggaacttc acagacaaac tggtaatgga ttccgctgcc tcaactgcaa tgacaacact     180
gatggcattc actgcgagaa gtgcaagaat ggcttttacc ggcacagaga aagggaccgc     240
tgtttgccct gcaattgtaa ctccaaaggt tctcttagtg ctcgatgtga caactccgga     300
cggtgcagct gtaaaccagg tgtgacagga gccagatgcg accgatgtct gccaggcttc     360
cacatgctca cggatgcggg gtgcacccaa gaccagagac tgctagactc caagtgtgac     420
tgtgacccag ctggcatcgc agggccctgt gacgcgggcc gctgtgtctg caagccagct     480
gtcactggag aacgctgtga taggtgtcga tcaggttact ataatctgga tggggggaac     540
cctgagggct gtacccagtg tttctgctat gggcattcag ccagctgccg cagctctgca     600
gaatacagtg tccataagat cacctctacc tttcatcaag atgttgatgg ctggaaggct     660
gtccaacgaa atgggtctcc tgcaaagctc caatggtcac agcgccatca agatgtgttt     720
agctcagccc aacgactaga ccctgtctat tttgtggctc ctgccaaatt tcttgggaat     780
caacaggtga gctatggtca aagcctgtcc tttgactacc gtgtggacag aggaggcaga     840
cacccatctg cccatgatgt gattctggaa ggtgctggtc tacggatcac agctcccttg     900
atgccacttg gcaagacact gccttgtggg ctcaccaaga cttacacatt caggttaaat     960
gagcatccaa gcaataattg gagcccccag ctgagttact ttgagtatcg aaggttactg    1020
cggaatctca cagccctccg catccgagct acatatggag aatacagtac tgggtacatt    1080
gacaatgtga ccctgatttc agcccgccct gtctctggag ccccagcacc ctgggttgaa    1140
cagtgtatat gtcctgttgg gtacaagggg caattctgcc aggattgtgc ttctggctac    1200
aagagagatt cagcgagact ggggcctttt ggcacctgta ttccttgtaa ctgtcaaggg    1260
ggaggggcct gtgatccaga cacaggagat tgttattcag gggatgagaa tcctgacatt    1320
gagtgtgctg actgcccaat tggtttctac aacgatccgc acgaccccg cagctgcaag    1380 ccatgtccct gtcataacgg gttcagctgc tcagtgatgc cggagacgga ggaggtggtg    1440
tgcaataact gccctcccgg ggtcaccggt gcccgctgtg agctctgtgc tgatggctac    1500 tttgggggacc cctttggtga acatggccca gtgaggcctt gtcagccctg tcaatgcaac    1560
aacaatgtgg accccagtgc ctctgggaat tgtgaccggc tgacaggcag gtgtttgaag    1620
tgtatccaca acacagccgg catctactgc gaccagtgca agcaggcta cttcggggac    1680 ccattggctc ccaacccagc agacaagtgt cgagcttgca actgtaaccc catgggctca    1740
gagcctgtag gatgtcgaag tgatggcacc tgtgtttgca agccaggatt tggtggcccc    1800
aactgtgagc atggagcatt cagctgtcca gcttgctata atcaagtgaa gattcagatg    1860
gatcagttta tgcagcagct tcagagaatg gaggccctga tttcaaaggc tcagggtggt    1920
gatggagtag tacctgatac agagctggaa ggcaggatgc agcaggctga gcaggccctt    1980
caggacattc tgagagatgc ccagatttca gaaggtgcta gcagatccct tggtctccag    2040
ttggccaagg tgaggagcca agagaacagc taccagagcc gcctggatga cctcaagatg    2100
actgtggaaa gagttcgggc tctgggaagt cagtaccaga accgagttcg ggatactcac    2160
aggctcatca ctcagatgca gctgagcctg cagaaagtg aagcttcctt gggaaacact    2220
aacattcctg cctcagacca ctacgtgggg ccaaatggct ttaaagtct ggctcaggag    2280 gccacaagat tagcagaaag ccacgttgag tcagccagta catggagca actgacaagg    2340 gaaactgagg actattccaa acaagccctc tcactggtgc gcaaggccct gcatgaagga    2400
gtcggaagcg gaagcggtag cccggacggt gctgtggtgc aagggcttgt ggaaaaattg    2460
```

-continued

```
gagaaaacca agtccctggc ccagcagttg acaagggagg ccactcaagc ggaaattgaa      2520
gcagataggt cttatcagca cagtctccgc ctcctggatt cagtgtctcg gcttcaggga      2580
gtcagtgatc agtcctttca ggtggaagaa gcaagagga tcaaacaaaa agcggattca       2640
ctctcaagcc tggtaaccag gcatatggat gagttcaagc gtacacagaa gaatctggga      2700
aactggaaag aagaagcaca gcagctctta cagaatggaa aaagtgggag agagaaatca      2760
gatcagctgc tttcccgtgc caatcttgct aaaagcagag cacaagaagc actgagtatg      2820
ggcaatgcca cttttttatga agttgagagc atccttaaaa acctcagaga gtttgacctg     2880
caggtggaca acagaaaagc agaagctgaa gaagccatga agagactctc ctacatcagc      2940
cagaaggttt cagatgccag tgacaagacc cagcaagcag aaagagcctt ggggagcgct       3000
gctgctgatg cacagagggc aaagaatggg gccggggagg ccctggaaat ctccagtgag       3060
attgaacagg agattgggag tctgaacttg gaagccaatg tgacagcaga tggagccttg       3120
gccatggaaa agggactggc ctctctgaag agtgagatga gggaagtgga aggagagctg       3180
gaaaggaagg agctggagtt tgacacgaat atggatgcag tacagatggt gattacagaa       3240
gcccagaagg ttgataccag agccaagaac gctgggggtta caatccaaga cacactcaac      3300
acattagacg gcctcctgca tctgatggac cagcctctca gtgtagatga agaggggctg       3360
gtcttactgg agcagaagct ttcccgagcc aagacccaga tcaacagcca actgcggccc       3420
atgatgtcag agctggaaga gagggcacgt cagcagaggg gccacctcca tttgctggag       3480
acaagcatag atgggattct ggctgatgtg aagaacttgg agaacattag ggacaacctg       3540
cccccaggct gctacaatac ccaggctctt gagcaacagt ga                         3582
```

```
<210> SEQ ID NO 6
<211> LENGTH: 3582
<212> TYPE: DNA
<213> ORGANISM: Artificial Sequence
<220> FEATURE:
<223> OTHER INFORMATION: Synthetic Construct

<400> SEQUENCE: 6
```

```
atgcctgctc tgtggctggg ctgctgcctg tgttttagtc tgctgctgcc agccgccaga         60 gcccacatcta gaagagaagt gtgcgactgc aacggcaaga gccggcagtg catcttcgac        120
agagagctgc acagacagac cggcaacggc ttcagatgcc tgaactgcaa cgacaacacc        180
gacggcatcc actgcgagaa gtgcaagaac ggcttctacc ggcaccgcga gagggatgaga       240 tgcctgcctt gcaactgcaa ctccaagggc agcctgagcg ccagatgcga caatagcggc        300
agatgtagct gcaagcctgg cgtgacaggc gctagatgcg atagatgtct ccccggcttc         360
cacatgctga ccgatgccgg atgtacccag accagagac tgctggacag caagtgcgat          420
tgcgaccctg ccggaattgc cggaccttgt gatgccggaa gatgcgtgtg taaacctgcc         480
gtgaccggcg agagatgtga cagatgtaga agcggctact acaacctgga cggcggcaat        540
cctgaaggct gcacccagtg cttttgctac ggccacagcg ccagctgtag aagcagcgcc         600
gaatactccg tgcacaagat caccagcacc ttccaccagg atgtggacgg atggaaggcc        660
gtgcagagaa atggctctcc tgccaagctg cagtggtccc agagacacca ggacgtgttc        720
agcagcgctc agagactgga ccccgtgtac tttgtggccc ctgccaagtt cctgggcaac        780
cagcaagtgt cttacggcca gagcctgagc ttcgactaca gagtggatag aggcggcaga       840 cacccccagcg ctcacgatgt gattcttgaa ggcgccggac tgcggatcac agcccctctt        900
```

-continued

```
atgcctctgg gcaagaccct gccttgtggc ctgaccaaga cctacacctt ccggctgaat      960
gagcacccca gcaacaactg gtccccacag ctgagctact tcgagtacag acggctgctg     1020
cggaacctga cagccctgag aatcagagcc acctacggcg agtacagcac cggctacatc     1080
gacaacgtga ccctgatcag cgccagacct gtttctggtg ctcctgctcc ttgggtcgag     1140
cagtgtatct gtcccgtggg ctacaagggc cagttctgcc aggattgtgc cagcggctac     1200
aagagagact ctgccagact gggcccccttc ggcacatgca tcccttgtaa ttgtcaaggc     1260
ggcggagcct gcgatcccga tacaggcgat tgctacagcg gcgacgagaa ccccgatatc     1320
gagtgcgccg attgtcccat cggctttttac aacgaccctc acgaccccag atcctgcaag     1380
ccatgtcctt gccacaatgg cttcagctgc agcgtgatgc ccgaaaccga agaggtcgtg     1440
tgcaacaatt gccccaccagg cgttacaggg gccagatgtg aactgtgtgc cgacggctac     1500
ttcggcgatc cttttggaga acacggaccc gtgcgacctt gccagccttg tcagtgcaac     1560
aacaacgtgg acccaagcgc cagcggcaac tgcgatagac tgacaggcag atgtctgaag     1620
tgcatccaca ataccgccgg gatctactgt gaccagtgca aggccggcta ttttggcgac     1680
cctctggctc ccaatcctgc cgataagtgc agagcctgca actgtaaccc tatgggctct     1740
gagcctgtgg gctgcagatc tgatggaacc tgcgtgtgca agccaggctt tggcggacct     1800
aattgtgaac acggcgcctt tagctgcccc gcctgctaca atcaagtgaa gatccagatg     1860
gaccagttca tgcagcagct gcagaggatg gaagccctga tctctaaagc ccaaggcgga     1920
gatggcgtgg tgcctgatac agagctggaa ggcagaatgc agcaggccga acaggccctg     1980
caggacattc tgagagatgc ccagattagc gagggcgcct ctagaagtct gggactgcag     2040
ctggctaaag tgcggagcca agagaacagc taccagagca gactggacga cctgaagatg     2100
accgtggaaa gagtcagagc cctgggcagc cagtaccaga acagagtgcg ggatacccac     2160
cggctgatca cccagatgca actgtctctg ccgagagcg aagccagcct gggcaatacc     2220
aatattcccg ccagcgacca ctacgtgggc cccaacggtt ttaagagcct ggctcaagag     2280
gccaccagac tggccgaaag ccatgtggaa agcgcctcca acatggaaca gctgacccgg     2340
gaaaccgagg actactctaa gcaggccctg agcctcgtca gaaaagccct gcatgaaggc     2400
gtcggcagcg gctctggatc tcctgatggt gctgtggtgc agggactcgt ggaaaagctg     2460
gaaaagacca aatctctggc ccagcagctg accagagaag ccacacaggc cgagatcgag     2520
gccgacagaa gctaccagca ctcactgagg ctgctggact ccgtgtctag actgcagggc     2580
gtgtccgacc agagcttcca ggtggaagag gccaagcgga tcaagcagaa ggccgatagc     2640
ctgagcagcc tggtcaccag acacatggac gagttcaagc ggacccagaa gaacctcggc     2700
aactggaaag aggaagccca gcaactgctg cagaacggca gtctggaag agagaagtct     2760 gaccagctgc tgagcagagc caacctggcc aagtctagag cccaagaggc cctgtctatg     2820
ggcaacgcca ccttctacga ggtggaatcc atcctgaaga acctgcgcga gttcgacctg     2880
caagtggaca acagaaaggc cgaggccgag gaagccatga gagactgag ctacatcagc     2940 cagaaagtgt ccgacgcctc cgacaagaca cagcaggcag aaagagcact gggatctgcc     3000
gcagccgatg ctcagagagc taaaaacggc gctggcgagg ccctggaaat cagctctgag     3060
atcgagcaag agatcggctc cctgaatctg gaagccaatg tgacagccga tggcgccctg     3120
gccatggaaa aaggactggc ctctctgaag tccgagatga gagaggtgga aggcgagctg     3180
gaacggaaag aactggaatt cgacaccaat atggacgctg tgcagatggt catcacagag     3240
gcccagaagg tggacaccag agccaaaaat gccggcgtga ccatccagga caccctgaat     3300
```

```
actctggacg gactgctgca cctgatggat cagcctctga gcgtggacga ggaaggactg    3360
gttctgctgg aacagaagct gagccgggcc aagactcaga tcaacagcca gctgaggccc    3420
atgatgagcg aactggaaga cgggccaga cagcagaggg gccatctgca tctgctcgaa     3480
accagcatcg atggcatcct ggccgacgtg aagaatctcg agaacatccg ggacaacctg    3540
ccacctggct gctacaacac acaggcactg gaacagcagt ga                       3582
```

<210> SEQ ID NO 7
<211> LENGTH: 1724
<212> TYPE: PRT
<213> ORGANISM: Homo sapiens

<400> SEQUENCE: 7

```
Met Pro Pro Ala Val Arg Arg Ser Ala Cys Ser Met Gly Trp Leu Trp
1               5                   10                  15

Ile Phe Gly Ala Ala Leu Gly Gln Cys Leu Gly Tyr Ser Ser Gln Gln
            20                  25                  30

Gln Arg Val Pro Phe Leu Gln Pro Pro Gly Gln Ser Gln Leu Gln Ala
        35                  40                  45

Ser Tyr Val Glu Phe Arg Pro Ser Gln Gly Cys Ser Pro Gly Tyr Tyr
    50                  55                  60

Arg Asp His Lys Gly Leu Tyr Thr Gly Arg Cys Val Pro Cys Asn Cys
65                  70                  75                  80

Asn Gly His Ser Asn Gln Cys Gln Asp Gly Ser Gly Ile Cys Val Asn
                85                  90                  95

Cys Gln His Asn Thr Ala Gly Glu His Cys Glu Arg Cys Gln Glu Gly
            100                 105                 110

Tyr Tyr Gly Asn Ala Val His Gly Ser Cys Arg Ala Cys Pro Cys Pro
        115                 120                 125

His Thr Asn Ser Phe Ala Thr Gly Cys Val Val Asn Gly Gly Asp Val
    130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Gly Ser Cys Gln
                165                 170                 175

Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Ser Pro Ala Glu
        195                 200                 205

Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
        275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320
```

-continued

```
Ala Lys Glu Leu Asp Val Lys Ile Lys Asn Val Ile Arg Asn Val His
            325                 330                 335

Ile Leu Leu Lys Gln Ile Ser Gly Thr Asp Gly Glu Gly Asn Asn Val
            340                 345                 350

Pro Ser Gly Asp Phe Ser Arg Glu Trp Ala Glu Ala Gln Arg Met Met
            355                 360                 365

Arg Glu Leu Arg Asn Arg Asn Phe Gly Lys His Leu Arg Glu Ala Glu
        370                 375                 380

Ala Asp Lys Arg Glu Ser Gln Leu Leu Leu Asn Arg Ile Arg Thr Trp
385                 390                 395                 400

Gln Lys Thr His Gln Gly Glu Asn Asn Gly Leu Ala Asn Ser Ile Arg
                405                 410                 415

Asp Ser Leu Asn Glu Tyr Glu Ala Lys Leu Ser Asp Leu Arg Ala Arg
            420                 425                 430

Leu Gln Glu Ala Ala Ala Gln Ala Lys Gln Ala Asn Gly Leu Asn Gln
            435                 440                 445

Glu Asn Glu Arg Ala Leu Gly Ala Ile Gln Arg Gln Val Lys Glu Ile
        450                 455                 460

Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
            485                 490                 495

Lys Glu Tyr Glu Lys Leu Ala Ala Ser Leu Asn Glu Ala Arg Gln Glu
            500                 505                 510

Leu Ser Asp Lys Val Arg Glu Leu Ser Arg Ser Ala Gly Lys Thr Ser
            515                 520                 525

Leu Val Glu Glu Ala Glu Lys His Ala Arg Ser Leu Gln Glu Leu Ala
        530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
            565                 570                 575

Ile Lys Ala Ala Glu Asp Ala Ala Asn Arg Ala Ala Ser Ala Ser Glu
            580                 585                 590

Ser Ala Leu Gln Thr Val Ile Lys Glu Asp Leu Pro Arg Lys Ala Lys
            595                 600                 605

Thr Leu Ser Ser Asn Ser Asp Lys Leu Leu Asn Glu Ala Lys Met Thr
        610                 615                 620

Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
            645                 650                 655

Leu Thr Thr Leu Arg Asp Gly Leu His Gly Ile Gln Arg Gly Asp Ile
            660                 665                 670

Asp Ala Met Ile Ser Ser Ala Lys Ser Met Val Arg Lys Ala Asn Asp
            675                 680                 685

Ile Thr Asp Glu Val Leu Asp Gly Leu Asn Pro Ile Gln Thr Asp Val
        690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
            725                 730                 735

Leu Pro Asp Leu Trp Arg Lys Ile Glu Ser Ile Asn Gln Gln Leu Leu
```

```
              740              745              750

Pro Leu Gly Asn Ile Ser Asp Asn Met Asp Arg Ile Arg Glu Leu Ile
        755              760              765

Gln Gln Ala Arg Asp Ala Ala Ser Lys Val Ala Val Pro Met Arg Phe
        770              775              780

Asn Gly Lys Ser Gly Val Glu Val Arg Leu Pro Asn Asp Leu Glu Asp
785              790              795              800

Leu Lys Gly Tyr Thr Ser Leu Ser Leu Phe Leu Gln Arg Pro Asn Ser
                805              810              815

Arg Glu Asn Gly Gly Thr Glu Asn Met Phe Val Met Tyr Leu Gly Asn
                820              825              830

Lys Asp Ala Ser Arg Asp Tyr Ile Gly Met Ala Val Val Asp Gly Gln
        835              840              845

Leu Thr Cys Val Tyr Asn Leu Gly Asp Arg Glu Ala Glu Leu Gln Val
        850              855              860

Asp Gln Ile Leu Thr Lys Ser Glu Thr Lys Glu Ala Val Met Asp Arg
865              870              875              880

Val Lys Phe Gln Arg Ile Tyr Gln Phe Ala Arg Leu Asn Tyr Thr Lys
                885              890              895

Gly Ala Thr Ser Ser Lys Pro Glu Thr Pro Gly Val Tyr Asp Met Asp
                900              905              910

Gly Arg Asn Ser Asn Thr Leu Leu Asn Leu Asp Pro Glu Asn Val Val
                915              920              925

Phe Tyr Val Gly Gly Tyr Pro Pro Asp Phe Lys Leu Pro Ser Arg Leu
        930              935              940

Ser Phe Pro Pro Tyr Lys Gly Cys Ile Glu Leu Asp Asp Leu Asn Glu
945              950              955              960

Asn Val Leu Ser Leu Tyr Asn Phe Lys Lys Thr Phe Asn Leu Asn Thr
                965              970              975

Thr Glu Val Glu Pro Cys Arg Arg Arg Lys Glu Glu Ser Asp Lys Asn
                980              985              990

Tyr Phe Glu Gly Thr Gly Tyr Ala Arg Val Pro Thr Gln Pro His Ala
        995              1000             1005

Pro Ile Pro Thr Phe Gly Gln Thr Ile Gln Thr Thr Val Asp Arg Gly
        1010             1015             1020

Leu Leu Phe Phe Ala Glu Asn Gly Asp Arg Phe Ile Ser Leu Asn Ile
1025             1030             1035             1040

Glu Asp Gly Lys Leu Met Val Arg Tyr Lys Leu Asn Ser Glu Leu Pro
                1045             1050             1055

Lys Glu Arg Gly Val Gly Asp Ala Ile Asn Asn Gly Arg Asp His Ser
                1060             1065             1070

Ile Gln Ile Lys Ile Gly Lys Leu Gln Lys Arg Met Trp Ile Asn Val
        1075             1080             1085

Asp Val Gln Asn Thr Ile Ile Asp Gly Glu Val Phe Asp Phe Ser Thr
        1090             1095             1100

Tyr Tyr Leu Gly Gly Ile Pro Ile Ala Ile Arg Glu Arg Phe Asn Ile
1105             1110             1115             1120

Ser Thr Pro Ala Phe Arg Gly Cys Met Lys Asn Leu Lys Lys Thr Ser
                1125             1130             1135

Gly Val Val Arg Leu Asn Asp Thr Val Gly Val Thr Lys Lys Cys Ser
                1140             1145             1150

Glu Asp Trp Lys Leu Val Arg Ser Ala Ser Phe Ser Arg Gly Gly Gln
                1155             1160             1165
```

```
Leu Ser Phe Thr Asp Leu Gly Leu Pro Pro Thr Asp His Leu Gln Ala
    1170             1175             1180

Ser Phe Gly Phe Gln Thr Phe Gln Pro Ser Gly Ile Leu Leu Asp His
1185             1190             1195             1200

Gln Thr Trp Thr Arg Asn Leu Gln Val Thr Leu Glu Asp Gly Tyr Ile
            1205             1210             1215

Glu Leu Ser Thr Ser Asp Ser Gly Gly Pro Ile Phe Lys Ser Pro Gln
            1220             1225             1230

Thr Tyr Met Asp Gly Leu Leu His Tyr Val Ser Val Ile Ser Asp Asn
        1235             1240             1245

Ser Gly Leu Arg Leu Leu Ile Asp Asp Gln Leu Leu Arg Asn Ser Lys
    1250             1255             1260

Arg Leu Lys His Ile Ser Ser Ser Arg Gln Ser Leu Arg Leu Gly Gly
1265             1270             1275             1280

Ser Asn Phe Glu Gly Cys Ile Ser Asn Val Phe Val Gln Arg Leu Ser
            1285             1290             1295

Leu Ser Pro Glu Val Leu Asp Leu Thr Ser Asn Ser Leu Lys Arg Asp
        1300             1305             1310

Val Ser Leu Gly Gly Cys Ser Leu Asn Lys Pro Pro Phe Leu Met Leu
        1315             1320             1325

Leu Lys Gly Ser Thr Arg Phe Asn Lys Thr Lys Thr Phe Arg Ile Asn
    1330             1335             1340

Gln Leu Leu Gln Asp Thr Pro Val Ala Ser Pro Arg Ser Val Lys Val
1345             1350             1355             1360

Trp Gln Asp Ala Cys Ser Pro Leu Pro Lys Thr Gln Ala Asn His Gly
            1365             1370             1375

Ala Leu Gln Phe Gly Asp Ile Pro Thr Ser His Leu Leu Phe Lys Leu
        1380             1385             1390

Pro Gln Glu Leu Leu Lys Pro Arg Ser Gln Phe Ala Val Asp Met Gln
        1395             1400             1405

Thr Thr Ser Ser Arg Gly Leu Val Phe His Thr Gly Thr Lys Asn Ser
    1410             1415             1420

Phe Met Ala Leu Tyr Leu Ser Lys Gly Arg Leu Val Phe Ala Leu Gly
1425             1430             1435             1440

Thr Asp Gly Lys Lys Leu Arg Ile Lys Ser Lys Glu Lys Cys Asn Asp
            1445             1450             1455

Gly Lys Trp His Thr Val Val Phe Gly His Asp Gly Glu Lys Gly Arg
            1460             1465             1470

Leu Val Val Asp Gly Leu Arg Ala Arg Glu Gly Ser Leu Pro Gly Asn
        1475             1480             1485

Ser Thr Ile Ser Ile Arg Ala Pro Val Tyr Leu Gly Ser Pro Pro Ser
    1490             1495             1500

Gly Lys Pro Lys Ser Leu Pro Thr Asn Ser Phe Val Gly Cys Leu Lys
1505             1510             1515             1520

Asn Phe Gln Leu Asp Ser Lys Pro Leu Tyr Thr Pro Ser Ser Ser Phe
            1525             1530             1535

Gly Val Ser Ser Cys Leu Gly Gly Pro Leu Glu Lys Gly Ile Tyr Phe
        1540             1545             1550

Ser Glu Glu Gly Gly His Val Val Leu Ala His Ser Val Leu Leu Gly
    1555             1560             1565

Pro Glu Phe Lys Leu Val Phe Ser Ile Arg Pro Arg Ser Leu Thr Gly
    1570             1575             1580
```

-continued

```
Ile Leu Ile His Ile Gly Ser Gln Pro Gly Lys His Leu Cys Val Tyr
1585                1590                1595                1600

Leu Glu Ala Gly Lys Val Thr Ala Ser Met Asp Ser Gly Ala Gly Gly
                1605                1610                1615

Thr Ser Thr Ser Val Thr Pro Lys Gln Ser Leu Cys Asp Gly Gln Trp
                1620                1625                1630

His Ser Val Ala Val Thr Ile Lys Gln His Ile Leu His Leu Glu Leu
            1635                1640                1645

Asp Thr Asp Ser Ser Tyr Thr Ala Gly Gln Ile Pro Phe Pro Pro Ala
    1650                1655                1660

Ser Thr Gln Glu Pro Leu His Leu Gly Gly Ala Pro Ala Asn Leu Thr
1665                1670                1675                1680

Thr Leu Arg Ile Pro Val Trp Lys Ser Phe Phe Gly Cys Leu Arg Asn
                1685                1690                1695

Ile His Val Asn His Ile Pro Val Pro Val Thr Glu Ala Leu Glu Val
                1700                1705                1710

Gln Gly Pro Val Ser Leu Asn Gly Cys Pro Asp Gln
        1715                1720

<210> SEQ ID NO 8
<211> LENGTH: 1172
<212> TYPE: PRT
<213> ORGANISM: Homo sapiens

<400> SEQUENCE: 8

Met Arg Pro Phe Phe Leu Leu Cys Phe Ala Leu Pro Gly Leu Leu His
1                5                10                15

Ala Gln Gln Ala Cys Ser Arg Gly Ala Cys Tyr Pro Pro Val Gly Asp
                20                25                30

Leu Leu Val Gly Arg Thr Arg Phe Leu Arg Ala Ser Ser Thr Cys Gly
            35                40                45

Leu Thr Lys Pro Glu Thr Tyr Cys Thr Gln Tyr Gly Glu Trp Gln Met
    50                55                60

Lys Cys Cys Lys Cys Asp Ser Arg Gln Pro His Asn Tyr Tyr Ser His
65                70                75                80

Arg Val Glu Asn Val Ala Ser Ser Ser Gly Pro Met Arg Trp Trp Gln
                85                90                95

Ser Gln Asn Asp Val Asn Pro Val Ser Leu Gln Leu Asp Leu Asp Arg
                100                105                110

Arg Phe Gln Leu Gln Glu Val Met Met Glu Phe Gln Gly Pro Met Pro
            115                120                125

Ala Gly Met Leu Ile Glu Arg Ser Ser Asp Phe Gly Lys Thr Trp Arg
    130                135                140

Val Tyr Gln Tyr Leu Ala Ala Asp Cys Thr Ser Thr Phe Pro Arg Val
145                150                155                160

Arg Gln Gly Arg Pro Gln Ser Trp Gln Asp Val Arg Cys Gln Ser Leu
                165                170                175

Pro Gln Arg Pro Asn Ala Arg Leu Asn Gly Gly Lys Val Gln Leu Asn
                180                185                190

Leu Met Asp Leu Val Ser Gly Ile Pro Ala Thr Gln Ser Gln Lys Ile
            195                200                205

Gln Glu Val Gly Glu Ile Thr Asn Leu Arg Val Asn Phe Thr Arg Leu
    210                215                220

Ala Pro Val Pro Gln Arg Gly Tyr His Pro Pro Ser Ala Tyr Tyr Ala
225                230                235                240
```

-continued

```
Val Ser Gln Leu Arg Leu Gln Gly Ser Cys Phe Cys His Gly His Ala
            245             250             255

Asp Arg Cys Ala Pro Lys Pro Gly Ala Ser Ala Gly Pro Ser Thr Ala
            260             265             270

Val Gln Val His Asp Val Cys Val Cys Gln His Asn Thr Ala Gly Pro
            275             280             285

Asn Cys Glu Arg Cys Ala Pro Phe Tyr Asn Asn Arg Pro Trp Arg Pro
    290             295             300

Ala Glu Gly Gln Asp Ala His Glu Cys Gln Arg Cys Asp Cys Asn Gly
305             310             315             320

His Ser Glu Thr Cys His Phe Asp Pro Ala Val Phe Ala Ala Ser Gln
            325             330             335

Gly Ala Tyr Gly Gly Val Cys Asp Asn Cys Arg Asp His Thr Glu Gly
            340             345             350

Lys Asn Cys Glu Arg Cys Gln Leu His Tyr Phe Arg Asn Arg Arg Pro
            355             360             365

Gly Ala Ser Ile Gln Glu Thr Cys Ile Ser Cys Glu Cys Asp Pro Asp
    370             375             380

Gly Ala Val Pro Gly Ala Pro Cys Asp Pro Val Thr Gly Gln Cys Val
385             390             395             400

Cys Lys Glu His Val Gln Gly Glu Arg Cys Asp Leu Cys Lys Pro Gly
            405             410             415

Phe Thr Gly Leu Thr Tyr Ala Asn Pro Gln Gly Cys His Arg Cys Asp
            420             425             430

Cys Asn Ile Leu Gly Ser Arg Arg Asp Met Pro Cys Asp Glu Glu Ser
            435             440             445

Gly Arg Cys Leu Cys Leu Pro Asn Val Val Gly Pro Lys Cys Asp Gln
    450             455             460

Cys Ala Pro Tyr His Trp Lys Leu Ala Ser Gly Gln Gly Cys Glu Pro
465             470             475             480

Cys Ala Cys Asp Pro His Asn Ser Leu Ser Pro Gln Cys Asn Gln Phe
            485             490             495

Thr Gly Gln Cys Pro Cys Arg Glu Gly Phe Gly Gly Leu Met Cys Ser
            500             505             510

Ala Ala Ala Ile Arg Gln Cys Pro Asp Arg Thr Tyr Gly Asp Val Ala
            515             520             525

Thr Gly Cys Arg Ala Cys Asp Cys Asp Phe Arg Gly Thr Glu Gly Pro
    530             535             540

Gly Cys Asp Lys Ala Ser Gly Arg Cys Leu Cys Arg Pro Gly Leu Thr
545             550             555             560

Gly Pro Arg Cys Asp Gln Cys Gln Arg Gly Tyr Cys Asn Arg Tyr Pro
            565             570             575

Val Cys Val Ala Cys His Pro Cys Phe Gln Thr Tyr Asp Ala Asp Leu
            580             585             590

Arg Glu Gln Ala Leu Arg Phe Gly Arg Leu Arg Asn Ala Thr Ala Ser
            595             600             605

Leu Trp Ser Gly Pro Gly Leu Glu Asp Arg Gly Leu Ala Ser Arg Ile
    610             615             620

Leu Asp Ala Lys Ser Lys Ile Glu Gln Ile Arg Ala Val Leu Ser Ser
625             630             635             640

Pro Ala Val Thr Glu Gln Glu Val Ala Gln Val Ala Ser Ala Ile Leu
            645             650             655
```

-continued

```
Ser Leu Arg Arg Thr Leu Gln Gly Leu Gln Leu Asp Leu Pro Leu Glu
            660             665             670

Glu Glu Thr Leu Ser Leu Pro Arg Asp Leu Glu Ser Leu Asp Arg Ser
            675             680             685

Phe Asn Gly Leu Leu Thr Met Tyr Gln Arg Lys Arg Glu Gln Phe Glu
            690             695             700

Lys Ile Ser Ser Ala Asp Pro Ser Gly Ala Phe Arg Met Leu Ser Thr
705             710             715             720

Ala Tyr Glu Gln Ser Ala Gln Ala Gln Gln Val Ser Asp Ser Ser
            725             730             735

Arg Leu Leu Asp Gln Leu Arg Asp Ser Arg Arg Glu Ala Glu Arg Leu
            740             745             750

Val Arg Gln Ala Gly Gly Gly Gly Thr Gly Ser Pro Lys Leu Val
            755             760             765

Ala Leu Arg Leu Glu Met Ser Ser Leu Pro Asp Leu Thr Pro Thr Phe
            770             775             780

Asn Lys Leu Cys Gly Asn Ser Arg Gln Met Ala Cys Thr Pro Ile Ser
785             790             795             800

Cys Pro Gly Glu Leu Cys Pro Gln Asp Asn Gly Thr Ala Cys Gly Ser
            805             810             815

Arg Cys Arg Gly Val Leu Pro Arg Ala Gly Gly Ala Phe Leu Met Ala
            820             825             830

Gly Gln Val Ala Glu Gln Leu Arg Gly Phe Asn Ala Gln Leu Gln Arg
            835             840             845

Thr Arg Gln Met Ile Arg Ala Ala Glu Glu Ser Ala Ser Gln Ile Gln
            850             855             860

Ser Ser Ala Gln Arg Leu Glu Thr Gln Val Ser Ala Ser Arg Ser Gln
865             870             875             880

Met Glu Glu Asp Val Arg Arg Thr Arg Leu Leu Ile Gln Gln Val Arg
            885             890             895

Asp Phe Leu Thr Asp Pro Asp Thr Asp Ala Ala Thr Ile Gln Glu Val
            900             905             910

Ser Glu Ala Val Leu Ala Leu Trp Leu Pro Thr Asp Ser Ala Thr Val
            915             920             925

Leu Gln Lys Met Asn Glu Ile Gln Ala Ile Ala Ala Arg Leu Pro Asn
            930             935             940

Val Asp Leu Val Leu Ser Gln Thr Lys Gln Asp Ile Ala Arg Ala Arg
945             950             955             960

Arg Leu Gln Ala Glu Ala Glu Glu Ala Arg Ser Arg Ala His Ala Val
            965             970             975

Glu Gly Gln Val Glu Asp Val Val Gly Asn Leu Arg Gln Gly Thr Val
            980             985             990

Ala Leu Gln Glu Ala Gln Asp Thr Met Gln Gly Thr Ser Arg Ser Leu
            995             1000            1005

Arg Leu Ile Gln Asp Arg Val Ala Glu Val Gln Gln Val Leu Arg Pro
    1010            1015            1020

Ala Glu Lys Leu Val Thr Ser Met Thr Lys Gln Leu Gly Asp Phe Trp
1025            1030            1035            1040

Thr Arg Met Glu Glu Leu Arg His Gln Ala Arg Gln Gln Gly Ala Glu
            1045            1050            1055

Ala Val Gln Ala Gln Gln Leu Ala Glu Gly Ala Ser Glu Gln Ala Leu
            1060            1065            1070

Ser Ala Gln Glu Gly Phe Glu Arg Ile Lys Gln Lys Tyr Ala Glu Leu
```

```
              1075                1080                1085

Lys Asp Arg Leu Gly Gln Ser Ser Met Leu Gly Glu Gln Gly Ala Arg
   1090                1095                1100

Ile Gln Ser Val Lys Thr Glu Ala Glu Glu Leu Phe Gly Glu Thr Met
1105                1110                1115                1120

Glu Met Met Asp Arg Met Lys Asp Met Glu Leu Glu Leu Leu Arg Gly
                1125                1130                1135

Ser Gln Ala Ile Met Leu Arg Ser Ala Asp Leu Thr Gly Leu Glu Lys
            1140                1145                1150

Arg Val Glu Gln Ile Arg Asp His Ile Asn Gly Arg Val Leu Tyr Tyr
            1155                1160                1165

Ala Thr Cys Lys
   1170

<210> SEQ ID NO 9
<211> LENGTH: 1193
<212> TYPE: PRT
<213> ORGANISM: Homo sapiens

<400> SEQUENCE: 9

Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270
```

```
Tyr Arg Val Asp Arg Gly Gly Arg His Pro Ser Ala His Asp Val Ile
    275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
                340                 345                 350

Gly Glu Tyr Ser Thr Gly Tyr Ile Asp Asn Val Thr Leu Ile Ser Ala
                355                 360                 365

Arg Pro Val Ser Gly Ala Pro Ala Pro Trp Val Glu Gln Cys Ile Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
                435                 440                 445

Phe Tyr Asn Asp Pro His Asp Pro Arg Ser Cys Lys Pro Cys Pro Cys
    450                 455                 460

His Asn Gly Phe Ser Cys Ser Val Met Pro Glu Thr Glu Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
                500                 505                 510

Pro Cys Gln Pro Cys Gln Cys Asn Asn Asn Val Asp Pro Ser Ala Ser
                515                 520                 525

Gly Asn Cys Asp Arg Leu Thr Gly Arg Cys Leu Lys Cys Ile His Asn
    530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
    595                 600                 605

Cys Pro Ala Cys Tyr Asn Gln Val Lys Ile Gln Met Asp Gln Phe Met
    610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
                660                 665                 670

Ala Ser Arg Ser Leu Gly Leu Gln Leu Ala Lys Val Arg Ser Gln Glu
                675                 680                 685

Asn Ser Tyr Gln Ser Arg Leu Asp Asp Leu Lys Met Thr Val Glu Arg
```

-continued

```
                690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
                755                 760                 765

Val Glu Ser Ala Ser Asn Met Glu Gln Leu Thr Arg Glu Thr Glu Asp
                770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
                820                 825                 830

Glu Ala Thr Gln Ala Glu Ile Glu Ala Asp Arg Ser Tyr Gln His Ser
                835                 840                 845

Leu Arg Leu Leu Asp Ser Val Ser Arg Leu Gln Gly Val Ser Asp Gln
                850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
                900                 905                 910

Gly Lys Ser Gly Arg Glu Lys Ser Asp Gln Leu Leu Ser Arg Ala Asn
                915                 920                 925

Leu Ala Lys Ser Arg Ala Gln Glu Ala Leu Ser Met Gly Asn Ala Thr
                930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
                965                 970                 975

Ser Tyr Ile Ser Gln Lys Val Ser Asp Ala Ser Asp Lys Thr Gln Gln
                980                 985                 990

Ala Glu Arg Ala Leu Gly Ser Ala Ala Ala Asp Ala Gln Arg Ala Lys
                995                 1000                1005

Asn Gly Ala Gly Glu Ala Leu Glu Ile Ser Ser Glu Ile Glu Gln Glu
    1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
                1060                1065                1070

Ala Val Gln Met Val Ile Thr Glu Ala Gln Lys Val Asp Thr Arg Ala
                1075                1080                1085

Lys Asn Ala Gly Val Thr Ile Gln Asp Thr Leu Asn Thr Leu Asp Gly
    1090                1095                1100

Leu Leu His Leu Met Asp Gln Pro Leu Ser Val Asp Glu Glu Gly Leu
1105                1110                1115                1120
```

-continued

```
Val Leu Leu Glu Gln Lys Leu Ser Arg Ala Lys Thr Gln Ile Asn Ser
              1125                1130                1135

Gln Leu Arg Pro Met Met Ser Glu Leu Glu Glu Arg Ala Arg Gln Gln
              1140                1145                1150

Arg Gly His Leu His Leu Leu Glu Thr Ser Ile Asp Gly Ile Leu Ala
         1155                1160                1165

Asp Val Lys Asn Leu Glu Asn Ile Arg Asp Asn Leu Pro Pro Gly Cys
      1170                1175                1180

Tyr Asn Thr Gln Ala Leu Glu Gln Gln
1185                1190
```

```
<210> SEQ ID NO 10
<211> LENGTH: 148
<212> TYPE: DNA
<213> ORGANISM: Artificial Sequence
<220> FEATURE:
<223> OTHER INFORMATION: Synthetic Construct

<400> SEQUENCE: 10
gaattcgtcg attcggttgc agcatttaaa gcggttgaca actttaaaag aaggaaaaag      60
aaggttgaag aaaagggtgt agtaagtaag tataagtaca gaccggagaa gtacgccggt     120
cctgattcgt ttaatttgaa agaagaaa                                        148

<210> SEQ ID NO 11
<211> LENGTH: 491
<212> TYPE: DNA
<213> ORGANISM: Artificial Sequence
<220> FEATURE:
<223> OTHER INFORMATION: Synthetic Construct

<400> SEQUENCE: 11
gttattttcc accatattgc cgtcttttgg caatgtgagg gcccggaaac ctggccctgt      60
cttcttgacg agcattccta ggggtctttc ccctctcgcc aaaggaatgc aaggtctgtt     120
gaatgtcgtg aaggaagcag ttcctctgga agcttcttga agacaaacaa cgtctgtagc     180 gacccttttgc aggcagcgga acccccacc tggcgacagg tgcctctgcg gccaaaagcc     240
acgtgtataa gatacacctg caaaggcggc acaacccccag tgccacgttg tgagttggat     300
agttgtggaa agagtcaaat ggctcacctc aagcgtattc aacaagggggc tgaaggatgc     360 ccagaaggta ccccattgta tgggatctga tctggggcct cggtgcacat gctttacatg     420
tgtttagtcg aggttaaaaa gcgtctaggc cccccgaacc acggggacgt ggttttcctt     480
tgaaaaacac g                                                          491

<210> SEQ ID NO 12
<211> LENGTH: 8842
<212> TYPE: DNA
<213> ORGANISM: Artificial Sequence
<220> FEATURE:
<223> OTHER INFORMATION: Synthetic Construct

<400> SEQUENCE: 12
atgcctcctg ctgtgcggag aagcgcctgt tctatgggat ggctgtggat ctttggcgcc      60
gctctgggac agtgtctggg ctactcttct cagcagcagc gggtgccatt tctgcagcca     120
cctggacagt ctcagctgca ggccagctac gtggaattca gacctagcca gggctgtagc     180
cccggctact acagagatca aagggcctg tacaccggca gatgcgtgcc ctgcaactgt     240
aacggccaca gcaaccagtg tcaggacggc tctggcatct gcgtgaactg ccagcataat     300
```

```
actgccggcg agcactgcga gagatgccaa gagggctact acggcaatgc cgtgcatggc    360
agctgtcggg cttgtccttg tcctcacacc aacagctttg ccaccggctg cgttgtgaac    420
ggcggagatg ttcggtgttc ttgcaaggcc ggctacacag gcacacagtg cgaaagatgt    480 gccctggct actttggcaa ccctcagaag tttggcggct cctgccagcc ttgctcctgc      540
aattctaatg gccagctggg ctcttgtcac cctctgaccg gcgactgcat caatcaagag    600
cctaaggaca gcagccctgc cgaggaatgc gacgattgcg atagctgcgt gatgaccctg    660
ctgaacgacc tggccacaat gggagaacag ctgcggctgg ttaagagcca gctccaggga    720
ctgtctgcct ctgctggact gctggaacag atgcggcaca tggaaaccca ggccaaggac    780
ctgagaaacc agctgctgaa ctacagaagc gccatctcca accacggcag caagatcgaa    840
ggcctggaaa gagagctgac cgacctgaat caagagttcg agacactgca agagaaggcc    900
caagtgaaca gccggaaggc ccagactctg aacaacaacg tgaaccgggc cacacagtcc    960 gccaagaac tggacgtgaa gatcaagaac gtgatccgga acgtgcacat cctgctgaag    1020
cagatcagcg gcacagatgg cgagggcaac aatgtgccta gcggcgactt tagcagagag    1080
tgggccgaag ctcagcggat gatgagagag ctgcggaacc ggaacttcgg caagcacctg    1140
agagaagccg aggccgacaa gagagagagc caactgctgc tcaaccggat cagaacctgg    1200
cagaaaaccc accagggcga gaacaacggc ctggccaaca gcatcagaga cagcctgaat    1260
gagtacgagg ccaagctgag cgatctgcgg gccagacttc aagaagctgc cgctcaggcc    1320
aagcaggcca acggccttaa tcaagagaac gagagagccc tgggcgccat ccagagacaa    1380
gtgaaagaga tcaacagcct gcagagcgac ttcaccaagt acctgaccac cgccgatagc    1440
agcctgctgc agacaaatat cgccctgcag ctcatggaaa agagccagaa agagtacgaa    1500
aagctggccg ccagcctgaa cgaggccagg caagaactgt ctgacaaagt gcgcgagctg    1560
agcagatccg ccggcaagac atctctggtg aagaggccg agaagcacgc cagatctctg    1620
caagagctgg ccaaacagct ggaagagatt aagcggaacg ccagcggcga cgaactcgtc    1680
agatgtgcag tggatgccgc caccgcctac gagaacatcc tgaatgccat caaggccgcc    1740
gaggacgccg ctaatagagc cgcttctgct tctgagtctg ccctgcagac cgtgatcaaa    1800
gaggacctgc ctagaaaggc caagacactg agcagcaaca gcgacaaact gctgaatgag    1860
gccaagatga cccagaagaa actgaagcaa gaggtgtccc ctgcactgaa caacctgcag    1920
cagaccctga acatcgtgac cgtgcagaaa gaagtgatcg acaccaacct gacaaccctg    1980
agagatggcc tgcacggaat ccagagaggc gacatcgacg ccatgatcag cagcgccaag    2040
agcatggttc gaaaagccaa cgacatcacc gacgaggtgc tggacggcct gaatcctatc    2100
cagaccgacg tggaacggat caaggacacc tacggcagaa cccagaacga ggatttcaag    2160
aaggccctga ccgacgccga caactccgtg aacaagctga ccaacaagct gcccgatctg    2220
tggcggaaga tcgagagcat caaccagcaa ctgctccctc tgggcaacat cagcgacaac    2280
atggacagaa tccgggaact gatccagcag gccagagatg ccgcctccaa agtggctgtg    2340
cccatgagat tcaacggcaa gagcggagtg gaagtgcggc tgcccaacga tctggaagat    2400
ctgaagggct ataccagcct gagcctgttc ctgcagaggc ccaacagcag agagaatggc    2460
ggcaccgaga atatgttcgt gatgtacctg ggaaacaagg acgccagccg ggactatatc    2520
ggaatggcct tgtggacgg ccagctgacc tgcgtgtaca acctgggaga cagagaagct    2580
gaactgcagg tcgaccagat cctgaccaag agcgagacaa aagaggccgt gatggacaga    2640
```

```
gtgaagttcc agcggatcta ccagttcgcc cggctgaatt acaccaaggg cgccacaagc   2700
agcaagcccg aaacacctgg cgtgtacgac atggacggcc ggaactctaa cactctgctg   2760
aatctggacc ccgagaacgt ggtgtttac gtcggcggct accctcctga cttcaagctg     2820
cctagcagac tgagcttccc accttacaag ggctgcatcg agctggatga cctgaacgaa   2880
aacgtgctgt ccctgtacaa cttcaaaaag accttcaacc tgaacaccac cgaggtggaa   2940
ccctgcaggc gcagaaaaga ggaatccgac aagaactact tcgaaggcac cggctacgcc   3000
agagtgccta cacaacctca cgctcccatt cctaccttcg gccagaccat ccagacaacc   3060
gtggatagag gcctgctgtt cttcgccgag aacggcgaca gattcatctc cctgaatatc   3120
gaggatggca agctgatggt ccgatacaag ctgaatagcg agctgcccaa agaaagaggc   3180
gtgggcgacg ccatcaacaa cggcagggat cacagcatcc agatcaagat cggcaaactg   3240
cagaaacgga tgtggatcaa cgtggacgtg cagaacacca tcatcgacgg cgaggtgttc   3300
gacttcagca cctactatct cggcggaatc cctatcgcca tcagagagcg gttcaatatc   3360
agcacccctg ccttccgggg ctgcatgaag aacctgaaaa agaccagcgg cgtcgtgcgg   3420
ctgaatgata cagtgggcgt gaccaagaag tgcagcgagg actggaagct tgtgcggagc   3480
gccagttttt ctagaggcgg acagctgagc tttaccgacc tgggactgcc tcctaccgat   3540
catctgcagg caagcttcgg attccagacc ttccagccaa gcggaatcct gctggaccac   3600
cagacctgga ccagaaacct gcaagtgacc ctggaagatg ctacatcga actgagcacc   3660 agcgactctg cggccctat ctttaagagc cctcagacct acatggatgg gctgctgcac   3720
tacgtgtccg tgatcagcga taacagcggc ctgagactgc tgatcgacga ccagctcctg   3780
cggaacagca agcggctgaa gcacatctcc agcagcagac agagtctgag actcggcggc   3840
agcaatttcg agggctgtat cagcaacgtg ttcgtgcagc gcctgagtct gtctccagaa   3900
gtgctggacc tgaccagcaa tagcctgaag agggatgtgt ctctcggcgg ctgctccctg   3960
aacaaacctc ctttcctgat gctgctgaag ggcagcaccc ggttcaacaa gaccaagacc   4020
tttcggatca atcagctgct ccaggacacc cctgtggcta gccctagaag cgtgaaagtg   4080
tggcaggacg cctgcagtcc cctgcctaaa acacaggcca atcacggggc tctgcagttc   4140
ggcgatatcc ccacaagcca tctgctgttt aagctgcccc aagagctgct caagcctcgg   4200
agccagttcg ctgtggatat gcagaccacc tcctccagag gactggtgtt tcacaccggc   4260
accaagaaca gcttcatggc cctgtacctg agcaaaggca ggctggtgtt tgccctgggc   4320
accgacggaa agaaactgcg gatcaagagc aaagagaagt gcaacgacgg caagtggcac   4380
accgtggtgt tcggacacga tggcgagaaa ggcagactcg tggtggatgg cctgagagcc   4440
agagagggat ctctgcctgg caactccacc atctccatca gagcccctgt gtatctgggc   4500
agccctccta gcgggaaagcc taagagcctg cctaccaact ccttcgtggg ctgtctgaag   4560
aactttcagc tggacagcaa gcctctgtac accccctagca gcagctttgg cgtgtcctcc   4620
tgtctcggag gccctctgga aaagggcatc tacttctctg aggaaggcgg ccacgttgtc   4680
ctggctcatt ctgttctgct gggccccgag ttcaagctgg tgttctctat ccggcctaga   4740
agcctgaccg gcatcctgat tcacatcggc agccagcctg gaagcacct gtgtgtgtat   4800 ctcgaggccg gcaaagtgac cgccagcatg gattctggtg ctggcggcac aagcacctcc   4860
gtgacaccta agcagagcct gtgtgatggc cagtggcaca gtgtggccgt gacaatcaag   4920
cagcacattc tgcacctgga actggacacc gacagcagct ataccgccgg acagatccca   4980
tttcctccag ccagcacaca agagcctctg caccttggag gcgcccctgc caatctgacc   5040
```

```
acactgagaa tccccgtgtg gaagtccttc ttcggctgcc tgcggaatat ccatgtgaac    5100
cacattccag tgcctgtgac agaggccctg gaagtgcagg gacccgtgtc tctgaatgga    5160
tgccccgatc agtgagaatt cgtcgattcg gttgcagcat ttaaagcggt tgacaacttt    5220
aaaagaagga aaaagaaggt tgaagaaaag ggtgtagtaa gtaagtataa gtacagaccg    5280
gagaagtacg ccggtcctga ttcgtttaat ttgaaagaag aaaatgaggc ccttcttcct    5340
gctgtgcttt gccctgcctg gactgctgca tgctcagcag gcttgtagca gaggcgcctg    5400
ctatcctcct gtgggcgatc tgcttgtggg cagaaccaga ttcctgcggg ccagctctac    5460
atgcggcctg acaaagcctg agacatactg cacccagtac ggcgagtggc agatgaagtg    5520
ctgcaagtgc gacagcagac agccccacaa ctactacagc cacagagtgg aaaacgtggc    5580
cagcagcagc ggccctatga gatggtggca gagccagaac gacgtgaacc ccgttagcct    5640
gcagctggac ctggacagac ggtttcagct gcaagaagtg atgatggaat ttcagggccc    5700
catgcctgcc ggcatgctga tcgagagaag cagcgatttc ggcaagacct ggcgggtgta    5760
ccagtatctg gccgccgatt gcaccagcac attccccaga gttagacagg cagacccca    5820 gagctggcag gatgttcgtt gtcagtctct gccccagcgg cctaacgcta gactgaatgg    5880
cggaaaggtg cagctcaacc tgatggacct ggtgtctggc atccctgcca cacagtccca    5940
gaaaatccaa gaagtgggcg agatcaccaa cctgagagtg aacttcaccc ggctggctcc    6000
cgttcctcag agaggatatc atcctcctag cgcctactac gccgtgtctc agcttagact    6060
gcagggcagc tgcttctgtc acggccacgc tgatagatgc gcccctaaac ctggtgcctc    6120
tgccggacct tctacagccg tgcaagtgca cgatgtgtgc gtgtgccagc acaataccgc    6180
cggacctaac tgcgagagat gtgccccttt ctacaacaac cggccttgga ggcctgccga    6240
aggacaggat gctcacgagt gccagagatg cgactgcaac ggccacagcg agacatgcca    6300
ctttgaccct gccgtgtttg ccgcttctca gggcgcttat ggcggcgtgt gtgacaactg    6360
cagagatcac accgagggca agaactgcga gcgctgtcag ctgcactact tccggaatag    6420
aaggccaggc gccagcatcc aagagacatg catcagctgc gagtgcgatc ccgatggtgc    6480
tgttcctggc gctccttgtg atcctgtgac aggccagtgc gtgtgtaaag aacacgtgca    6540
gggcgaaaga tgcgacctgt gcaagcctgg ctttaccggc ctgacctacg ccaatcctca    6600
gggctgccac agatgtgatt gcaacatcct gggcagcaga cgggacatgc cctgtgatga    6660
agagtctggc agatgcctgt gcctgcctaa tgtcgtgggc cccaagtgcg atcagtgtgc    6720
cccatatcac tggaagctgg cctctggcca gggatgcgaa ccttgtgcct gcgatccca    6780 caacagcctg tctccacagt gcaaccagtt caccggccag tgtccttgca gagaaggctt    6840
tggcggcctg atgtgttctg ccgccgctat cagacagtgc cccgatagaa catatggcga    6900
cgtggccaca ggctgcagag cctgcgattg tgacttccgg ggaacagaag acccggctg    6960 cgataaggcc agcggaagat gtctgtgtcg gcctggactc acaggcccca gatgtgacca    7020
gtgtcagcgg ggctactgca acagataccc tgtgtgtgtg gcctgccatc cttgcttcca    7080
gacctacgac gccgacctga gagaacaggc cctgagattc ggcagactga gaaatgccac    7140
cgccagcctt tggagcggac ctggccttga agatagaggc ctggcctcca gaatcctgga    7200
cgccaagtct aagatcgagc agatcagagc cgtgctgtct agcccagccg tgaccgaaca    7260
agaggtggcc caagtggcta gcgccatcct gagcctgaga gaactctgc agggactgca    7320 gctcgatctg cccctggaag aggaaacact gagcctgcct agagatctgg aaagcctgga    7380
```

```
tcggagcttc aacggcctgc tgacaatgta ccagagaaag agagagcagt tcgagaagat    7440
cagcagcgcc gatcctagcg gcgccttcag aatgctgagc acagcctatg agcagagcgc    7500
ccaggctgct cagcaagtgt ccgatagcag cagactgctg gaccagctgc gggactctag    7560
aagagaagcc gaaagacttg tgcggcaggc aggcggcgga ggtggaacag gatctcctaa    7620
actggtggcc ctgcggctgg aaatgtcctc tctgcctgat ctgaccccta ccttcaacaa    7680
gctgtgcggc aacagccggc agatggcctg cacacctatt agctgtcctg gcgagctgtg    7740
ccctcaggat aatggaaccg cctgcggctc cagatgtaga ggcgttttgc caagagccgg    7800
cggagccttt ctgatggctg acaagttgc cgagcagctg agaggcttca acgctcagct      7860
gcagcggacc agacagatga ttagagccgc cgaggaaagc gccagccaga ttcaatctag    7920
cgcccagaga ctggaaaccc aggtgtccgc cagcagatcc cagatggaag aagatgtgcg    7980
gcggacaaga ctgctgatcc agcaagtgcg ggacttcctg accgatcctg ataccgatgc    8040
cgccacaatc caagaggtgt ccgaagctgt tctggcactg tggctgccta ccgatagcgc    8100
tacagtgctg cagaagatga cgagatcca ggcaatcgcc gccagactgc ccaatgtgga     8160
tctggtgctg agccagacca agcaggatat cgccagagct agaaggctgc aggccgaggc    8220
cgaagaggca agatctagag cccatgccgt ggaaggccaa gtcgaggacg ttgtgggcaa    8280
tctgagacag ggaaccgtgg ctctgcaaga ggcccaggat acaatgcagg gcaccagcag    8340
aagcctgcgc ctgatccagg atagagtggc cgaagtgcag caggtcctga ggccagccga    8400
aaagctggtc accagcatga ccaaacagct gggcgatttc tggacgcgca tggaagaact    8460
gaggcatcag gcaagacagc agggcgctga agcagtgcag gctcaacaac ttgccgaggg    8520
cgcttctgaa caggctctgt ctgcccaaga gggcttcgag cggatcaagc agaagtacgc    8580
cgagctgaag gacagactgg gccagagttc tatgctgggc gaacagggcg ccagaattca    8640
gagcgtgaaa acagaggccg aggaactgtt cggcgagaca atggaaatga tggaccggat    8700
gaaggacatg gaactggaac tgctgagggg cagccaggcc atcatgctga gaagtgccga    8760
tctgacaggc ctggaaaaga gagtggaaca gatccgggac cacatcaacg gccgggtgct    8820
gtactacgcc acatgcaagt aa                                            8842
```

<210> SEQ ID NO 13
<211> LENGTH: 12572
<212> TYPE: DNA
<213> ORGANISM: Artificial Sequence
<220> FEATURE:
<223> OTHER INFORMATION: Synthetic Construct

<400> SEQUENCE: 13

```
atgcctcctg ctgtgcggag aagcgcctgt tctatgggat ggctgtggat ctttggcgcc      60
gctctgggac agtgtctggg ctactcttct cagcagcagc gggtgccatt tctgcagcca     120
cctggacagt ctcagctgca ggccagctac gtggaattca gacctagcca gggctgtagc     180
cccggctact acagagatca caaggggctg tacaccggca gatgcgtgcc ctgcaactgt     240
aacggccaca gcaaccagtg tcaggacggc tctggcatct gcgtgaactg ccagcataat     300
actgccggcg agcactgcga gagatgccaa gagggctact acggcaatgc cgtgcatggc     360
agctgtcggg cttgtccttg tcctcacacc aacagctttg ccaccggctg cgttgtgaac     420
ggcggagatg ttcggtgttc ttgcaaggcc ggctacacag gcacacagtg cgaaagatgt     480 gccctggct actttggcaa ccctcagaag tttggcggct cctgccagcc ttgctcctgc     540
aattctaatg gccagctggg ctcttgtcac cctctgaccg gcgactgcat caatcaagag    600
```

-continued

```
cctaaggaca gcagccctgc cgaggaatgc gacgattgcg atagctgcgt gatgaccctg        660
ctgaacgacc tggccacaat gggagaacag ctgcggctgg ttaagagcca gctccaggga        720
ctgtctgcct ctgctggact gctggaacag atgcggcaca tggaaaccca ggccaaggac        780
ctgagaaacc agctgctgaa ctacagaagc gccatctcca accacggcag caagatcgaa        840
ggcctggaaa gagagctgac cgacctgaat caagagttcg agacactgca agagaaggcc        900
caagtgaaca gccggaaggc ccagactctg aacaacaacg tgaaccgggc cacacagtcc        960
gccaaagaac tggacgtgaa gatcaagaac gtgatccgga acgtgcacat cctgctgaag       1020
cagatcagcg gcacagatgg cgagggcaac aatgtgccta gcggcgactt tagcagagag       1080
tgggccgaag ctcagcggat gatgagagag ctgcggaacc ggaacttcgg caagcacctg       1140
agagaagccg aggccgacaa gagagagagc caactgctgc tcaaccggat cagaacctgg       1200
cagaaaaccc accagggcga gaacaacggc ctggccaaca gcatcagaga cagcctgaat       1260
gagtacgagc ccaagctgag cgatctgcgg gccagacttc aagaagctgc cgctcaggcc       1320
aagcaggcca acggccttaa tcaagagaac gagagagccc tgggcgccat ccagagacaa       1380
gtgaaagaga tcaacagcct gcagagcgac ttcaccaagt acctgaccac cgccgatagc       1440
agcctgctgc agacaaatat cgccctgcag ctcatggaaa agagccagaa agagtacgaa       1500
aagctggccg ccagcctgaa cgaggccagg caagaactgt ctgacaaagt gcgcgagctg       1560
agcagatccg ccggcaagac atctctggtg aagaggccg agaagcacgc cagatctctg        1620
caagagctgg ccaaacagct ggaagagatt aagcggaacg ccagcggcga cgaactcgtc       1680
agatgtgcag tggatgccgc caccgcctac gagaacatcc tgaatgccat caaggccgcc       1740
gaggacgccg ctaatagagc cgcttctgct tctgagtctg ccctgcagac cgtgatcaaa       1800
gaggacctgc ctagaaaggc caagacactg agcagcaaca gcgacaaact gctgaatgag       1860
gccaagatga cccagaagaa actgaagcaa gaggtgtccc ctgcactgaa caacctgcag       1920
cagaccctga acatcgtgac cgtgcagaaa gaagtgatcg acaccaacct gacaaccctg       1980
agagatggcc tgcacggaat ccagagaggc gacatcgacg ccatgatcag cagcgccaag       2040
agcatggttc gaaaagccaa cgacatcacc gacgaggtgc tggacggcct gaatcctatc       2100
cagaccgacg tggaacggat caaggacacc tacggcagaa cccagaacga ggatttcaag       2160
aaggccctga ccgacgccga caactccgtg aacaagctga ccaacaagct gcccgatctg       2220
tggcggaaga tcgagagcat caaccagcaa ctgctccctc tgggcaacat cagcgacaac       2280
atggacagaa tccgggaact gatccagcag gccagagatg ccgcctccaa agtggctgtg       2340
cccatgagat tcaacggcaa gagcggagtg gaagtgcggc tgcccaacga tctggaagat       2400
ctgaagggct ataccagcct gagcctgttc ctgcagaggc ccaacagcag agagaatggc       2460
ggcaccgaga atatgttcgt gatgtacctg ggaaacaagg acgccagccg ggactatatc       2520
ggaatggccg ttgtggacgg ccagctgacc tgcgtgtaca acctgggaga cagagaagct       2580
gaactgcagg tcgaccagat cctgaccaag agcgagacaa agaggccgt gatggacaga        2640 gtgaagttcc agcggatcta ccagttcgcc cggctgaatt acaccaaggg cgccacaagc       2700
agcaagcccg aaacacctgg cgtgtacgac atggacggcc ggaactctaa cactctgctg       2760
aatctggacc ccgagaacgt ggtgtttttac gtcggcggct accctcctga cttcaagctg       2820
cctagcagac tgagcttccc accttacaag ggctgcatcg agctggatga cctgaacgaa       2880
aacgtgctgt ccctgtacaa cttcaaaaag accttcaacc tgaacaccac cgaggtggaa       2940
```

-continued

```
ccctgcaggc gcagaaaaga ggaatccgac aagaactact tcgaaggcac cggctacgcc   3000
agagtgccta cacaacctca cgctcccatt cctaccttcg gccagaccat ccagacaacc   3060
gtggatagag gcctgctgtt cttcgccgag aacggcgaca gattcatctc cctgaatatc   3120
gaggatggca agctgatggt ccgatacaag ctgaatagcg agctgcccaa agaaagaggc   3180
gtgggcgacg ccatcaacaa cggcagggat cacagcatcc agatcaagat cggcaaactg   3240
cagaaacgga tgtggatcaa cgtggacgtg cagaacacca tcatcgacgg cgaggtgttc   3300
gacttcagca cctactatct cggcggaatc cctatcgcca tcagagagcg gttcaatatc   3360
agcacccctg ccttccgggg ctgcatgaag aacctgaaaa agaccagcgg cgtcgtgcgg   3420
ctgaatgata cagtgggcgt gaccaagaag tgcagcgagg actggaagct tgtgcggagc   3480
gccagttttt ctagaggcgg acagctgagc tttaccgacc tgggactgcc tcctaccgat   3540
catctgcagg caagcttcgg attccagacc ttccagccaa gcggaatcct gctggaccac   3600
cagacctgga ccagaaacct gcaagtgacc ctggaagatg gctacatcga actgagcacc   3660
agcgactctg gcggccctat ctttaagagc cctcagacct acatggatgg gctgctgcac   3720
tacgtgtccg tgatcagcga taacagcggc ctgagactgc tgatcgacga ccagctcctg   3780
cggaacagca agcggctgaa gcacatctcc agcagcagac agagtctgag actcggcggc   3840
agcaatttcg agggctgtat cagcaacgtg ttcgtgcagc gcctgagtct gtctccagaa   3900
gtgctggacc tgaccagcaa tagcctgaag agggatgtgt ctctcggcgg ctgctccctg   3960
aacaaacctc ctttcctgat gctgctgaag ggcagcaccc ggttcaacaa gaccaagacc   4020
tttcggatca atcagctgct ccaggacacc cctgtggcta gccctagaag cgtgaaagtg   4080
tggcaggacg cctgcagtcc cctgcctaaa acacaggcca atcacggggc tctgcagttc   4140
ggcgatatcc ccacaagcca tctgctgttt aagctgcccc aagagctgct caagcctcgg   4200
agccagttcg ctgtggatat gcagaccacc tcctccagag gactggtgtt tcacaccggc   4260
accaagaaca gcttcatggc cctgtacctg agcaaaggca ggctggtgtt tgccctgggc   4320
accgacggaa agaaactgcg gatcaagagc aaagagaagt gcaacgacgg caagtggcac   4380
accgtggtgt tcggacacga tggcgagaaa ggcagactcg tggtggatgg cctgagagcc   4440
agagagggat ctctgcctgg caactccacc atctccatca gagcccctgt gtatctgggc   4500
agccctccta gcggaaagcc taagagcctg cctaccaact ccttcgtggg ctgtctgaag   4560
aactttcagc tggacagcaa gcctctgtac accccctagca gcagctttgg cgtgtcctcc   4620
tgtctcggag gccctctgga aaagggcatc tacttctctg aggaaggcgg ccacgttgtc   4680
ctggctcatt ctgttctgct gggccccgag ttcaagctgg tgttctctat ccggcctaga   4740
agcctgaccg gcatcctgat tcacatcggc agccagcctg ggaagcacct gtgtgtgtat   4800
ctcgaggccg gcaaagtgac cgccagcatg gattctggtg ctggcggcac aagcacctcc   4860
gtgacaccta agcagagcct gtgtgatggc agtggcaca gtgtggccgt gacaatcaag   4920
cagcacattc tgcacctgga actggacacc gacagcagct ataccgccgg acagatccca   4980
tttcctccag ccagcacaca agagcctctg caccttggag gcgcccctgc caatctgacc   5040
acactgagaa tccccgtgtg gaagtccttc ttcggctgcc tgcggaatat ccatgtgaac   5100
cacattccag tgcctgtgac agaggccctg gaagtgcagg acccgtgtc tctgaatgga   5160 tgcccccgatc agtgagaatt cgtcgattcg gttgcagcat ttaaagcggt tgacaacttt   5220
aaaagaagga aaaagaaggt tgaagaaaag ggtgtagtaa gtaagtataa gtacagaccg   5280
gagaagtacg ccggtcctga ttcgtttaat ttgaaagaag aaaatgaggc ccttcttcct   5340
```

```
gctgtgcttt gccctgcctg gactgctgca tgctcagcag gcttgtagca gaggcgcctg     5400
ctatcctcct gtgggcgatc tgcttgtggg cagaaccaga ttcctgcggg ccagctctac     5460
atgcggcctg acaaagcctg agacatactg cacccagtac ggcgagtggc agatgaagtg     5520
ctgcaagtgc gacagcagac agccccacaa ctactacagc cacagagtgg aaaacgtggc     5580
cagcagcagc ggccctatga gatggtggca gagccagaac gacgtgaacc ccgttagcct     5640
gcagctggac ctggacagac ggtttcagct gcaagaagtg atgatggaat ttcagggccc     5700
catgcctgcc ggcatgctga tcgagagaag cagcgatttc ggcaagacct ggcgggtgta     5760
ccagtatctg gccgccgatt gcaccagcac attccccaga gttagacagg cagaccccca     5820
gagctggcag gatgttcgtt gtcagtctct gccccagcgg cctaacgcta gactgaatgg     5880
cggaaaggtg cagctcaacc tgatggacct ggtgtctggc atccctgcca cacagtccca     5940
gaaaatccaa gaagtgggcg agatcaccaa cctgagagtg aacttcaccc ggctggctcc     6000
cgttcctcag agaggatatc atcctcctag cgcctactac gccgtgtctc agcttagact     6060
gcagggcagc tgcttctgtc acggccacgc tgatagatgc gcccctaaac ctggtgcctc     6120
tgccggacct tctacagccg tgcaagtgca cgatgtgtgc gtgtgccagc acaataccgc     6180
cggacctaac tgcgagagat gtgccccttt ctacaacaac cggccttgga ggcctgccga     6240
aggacaggat gctcacgagt gccagagatg cgactgcaac ggccacagcg agacatgcca     6300
ctttgaccct gccgtgtttg ccgcttctca gggcgcttat ggcggcgtgt gtgacaactg     6360
cagagatcac accgagggca agaactgcga gcgctgtcag ctgcactact ccggaatag     6420 aaggccaggc gccagcatcc aagagacatg catcagctgc gagtgcgatc ccgatggtgc     6480
tgttcctggc gctccttgtg atcctgtgac aggccagtgc gtgtgtaaag aacacgtgca     6540
gggcgaaaga tgcgacctgt gcaagcctgg ctttaccggc ctgacctacg ccaatcctca     6600
gggctgccac agatgtgatt gcaacatcct gggcagcaga cgggacatgc cctgtgatga     6660
agagtctggc agatgcctgt gcctgcctaa tgtcgtgggc cccaagtgcg atcagtgtgc     6720
cccatatcac tggaagctgg cctctggcca gggatgcgaa ccttgtgcct gcgatcccca     6780
caacagcctg tctccacagt gcaaccagtt caccggccag tgtccttgca gagaaggctt     6840
tggcggcctg atgtgttctg ccgccgctat cagacagtgc cccgatagaa catatggcga     6900
cgtggccaca ggctgcagag cctgcgattg tgacttccgg ggaacagaag acccggctg     6960 cgataaggcc agcggaagat gtctgtgtcg gcctggactc acaggcccca gatgtgacca     7020
gtgtcagcgg ggctactgca acagataccc tgtgtgtgtg gcctgccatc cttgcttcca     7080
gacctacgac gccgacctga gagaacaggc cctgagattc ggcagactga gaaatgccac     7140
cgccagcctt tggagcggac ctggccttga agatagaggc ctggcctcca gaatcctgga     7200
cgccaagtct aagatcgagc agatcagagc cgtgctgtct agcccagccg tgaccgaaca     7260
agaggtggcc caagtggcta cgccatcct gagcctgaga gaactctgc agggactgca     7320 gctcgatctg cccctggaag aggaaacact gagcctgcct agagatctgg aaagcctgga     7380
tcggagcttc aacggcctgc tgacaatgta ccagagaaag agagagcagt tcgagaagat     7440
cagcagcgcc gatcctagcg cgccttcag aatgctgagc acagcctatg agcagagcgc     7500
ccaggctgct cagcaagtgt ccgatagcag cagactgctg gaccagctgc gggactctag     7560
aagagaagcc gaaagacttg tgcggcaggc aggcggcgga ggtggaacag gatctcctaa     7620
actggtggcc ctgcggctgg aaatgtcctc tctgcctgat ctgacccta ccttcaacaa     7680
```

-continued

```
gctgtgcggc aacagccggc agatggcctg cacacctatt agctgtcctg gcgagctgtg   7740
ccctcaggat aatggaaccg cctgcggctc cagatgtaga ggcgttttgc caagagccgg   7800
cggagccttt ctgatggctg gacaagttgc cgagcagctg agaggcttca acgctcagct   7860
gcagcggacc agacagatga ttagagccgc cgaggaaagc gccagccaga ttcaatctag   7920
cgcccagaga ctggaaaccc aggtgtccgc cagcagatcc cagatggaag aagatgtgcg   7980
gcggacaaga ctgctgatcc agcaagtgcg ggacttcctg accgatcctg ataccgatgc   8040
cgccacaatc caagaggtgt ccgaagctgt tctggcactg tggctgccta ccgatagcgc   8100
tacagtgctg cagaagatga acgagatcca ggcaatcgcc gccagactgc ccaatgtgga   8160
tctggtgctg agccagacca agcaggatat cgccagagct agaaggctgc aggccgaggc   8220
cgaagaggca agatctagag cccatgccgt ggaaggccaa gtcgaggacg ttgtgggcaa   8280
tctgagacag ggaaccgtgg ctctgcaaga ggcccaggat acaatgcagg gcaccagcag   8340
aagcctgcgc ctgatccagg atagagtggc cgaagtgcag caggtcctga ggccagccga   8400
aaagctggtc accagcatga ccaaacagct gggcgatttc tggacgcgca tggaagaact   8460
gaggcatcag gcaagacagc agggcgctga agcagtgcag gctcaacaac ttgccgaggg   8520
cgcttctgaa caggctctgt ctgcccaaga gggcttcgag cggatcaagc agaagtacgc   8580
cgagctgaag gacagactgg gccagagttc tatgctgggc gaacagggcg ccagaattca   8640
gagcgtgaaa acagaggccg aggaactgtt cggcgagaca atggaaatga tggaccggat   8700
gaaggacatg gaactggaac tgctgagggg cagccaggcc atcatgctga gaagtgccga   8760
tctgacaggc ctggaaaaga gagtggaaca gatccgggac cacatcaacg gccgggtgct   8820
gtactacgcc acatgcaagt aagaattcgt cgattcggtt gcagcattta aagcggttga   8880
caactttaaa agaaggaaaa agaaggttga agaaaagggt gtagtaagta agtataagta   8940
cagaccggag aagtacgccg gtcctgattc gtttaatttg aaagaagaaa atgcctgctc   9000
tgtggctggg ctgctgcctg tgtttttagtc tgctgctgcc agccgccaga gccacatcta   9060
gaagagaagt gtgcgactgc aacggcaaga gccggcagtg catcttcgac agagagctgc   9120
acagacagac cggcaacggc ttcagatgcc tgaactgcaa cgacaacacc gacggcatcc   9180
actgcgagaa gtgcaagaac ggcttctacc ggcaccgcga gagggataga tgcctgcctt   9240
gcaactgcaa ctccaagggc agcctgagcg ccagatgcga caatagcggc agatgtagct   9300
gcaagcctgg cgtgacaggc gctagatgcg atagatgtct ccccggcttc cacatgctga   9360
ccgatgccgg atgtacccag gaccagagac tgctggacag caagtgcgat tgcgaccctg   9420
ccggaattgc cggaccttgt gatgccggaa gatgcgtgtg taaacctgcc gtgaccggcg   9480
agagatgtga cagatgtaga agcggctact acaacctgga cggcggcaat cctgaaggct   9540
gcacccagtg cttttgctac ggccacagcg ccagctgtag aagcagcgcc gaatactccg   9600
tgcacaagat caccagcacc ttccaccagg atgtggacgg atggaaggcc gtgcagagaa   9660
atggctctcc tgccaagctg cagtggtccc agagacacca ggacgtgttc agcagcgctc   9720
agagactgga ccccgtgtac tttgtggccc ctgccaagtt cctgggcaac agcaagtgt    9780 cttacgccca gagcctgagc ttcgactaca gagtggatag aggcggcaga cacccccagcg   9840 ctcacgatgt gattcttgaa ggcgccggac tgcggatcac agcccctctt atgcctctgg   9900
gcaagaccct gccttgtggc ctgaccaaga cctacacctt ccggctgaat gagcacccca   9960
gcaacaactg gtcccacagc ctgagctact tcgagtacac acggctgctg cggaacctga   10020
cagccctgag aatcagagcc acctacggcg agtacagcac cggctacatc gacaacgtga   10080
```

-continued

```
ccctgatcag cgccagacct gtttctggtg ctcctgctcc ttgggtcgag cagtgtatct   10140
gtcccgtggg ctacaagggc cagttctgcc aggattgtgc cagcggctac aagagagact   10200
ctgccagact gggccccttc ggcacatgca tcccttgtaa ttgtcaaggc ggcggagcct   10260
gcgatcccga tacaggcgat tgctacacgc gcgacgagaa ccccgatatc gagtgcgccg   10320
attgtcccat cggcttttac aacgaccctc acgaccccag atcctgcaag ccatgtcctt   10380
gccacaatgg cttcagctgc agcgtgatgc ccgaaaccga gaggtcgtg tgcaacaatt    10440 gcccaccagg cgttacaggg gccagatgtg aactgtgtgc cgacggctac ttcggcgatc   10500
cttttggaga acacggaccc gtgcgacctt gccagcttg tcagtgcaac aacaacgtgg     10560
acccaagcgc cagcggcaac tgcgatagac tgacaggcag atgtctgaag tgcatccaca   10620
ataccgccgg gatctactgt gaccagtgca aggccggcta ttttggcgac cctctggctc   10680
ccaatcctgc cgataagtgc agagcctgca actgtaaccc tatgggctct gagcctgtgg   10740
gctgcagatc tgatggaacc tgcgtgtgca agccaggctt tggcggacct aattgtgaac   10800
acggcgcctt tagctgcccc gcctgctaca atcaagtgaa gatccagatg gaccagttca   10860
tgcagcagct gcagaggatg gaagccctga tctctaaagc ccaaggcgga gatggcgtgg   10920
tgcctgatac agagctggaa ggcagaatgc agcaggccga acaggccctg caggacattc   10980
tgagagatgc ccagattagc gagggcgcct ctagaagtct gggactgcag ctggctaaag   11040
tgcggagcca agagaacagc taccagagca gactggacga cctgaagatg accgtggaaa   11100
gagtcagagc cctgggcagc cagtaccaga acagagtgcg ggatacccac cggctgatca   11160
cccagatgca actgtctctg gccgagagcg aagccagcct gggcaatacc aatattcccg   11220
ccagcgacca ctacgtgggc cccaacggtt ttaagagcct ggctcaagag gccaccagac   11280
tggccgaaag ccatgtggaa agcgcctcca acatggaaca gctgacccgg gaaaccgagg   11340
actactctaa gcaggccctg agcctcgtca gaaaagccct gcatgaaggc gtcggcagcg   11400
gctctggatc tcctgatggt gctgtggtgc agggactcgt ggaaaagctg gaaaagacca   11460
aatctctggc ccagcagctg accagagaag ccacacaggc cgagatcgag gccgacagaa   11520
gctaccagca ctcactgagg ctgctggact ccgtgtctag actgcagggc gtgtccgacc   11580
agagcttcca ggtggaagag gccaagcgga tcaagcagaa ggccgatagc ctgagcagcc   11640
tggtcaccag acacatggac gagttcaagc ggacccagaa gaacctcggc aactggaaag   11700
aggaagccca gcaactgctg cagaacggca gtctggaag agagaagtct gaccagctgc     11760
tgagcagagc caacctggcc aagtctagag cccaagaggc cctgtctatg ggcaacgcca   11820
ccttctacga ggtggaatcc atcctgaaga acctgcgcga gttcgacctg caagtggaca   11880
acagaaaggc cgaggccgag gaagccatga gagactgag ctacatcagc cagaaagtgt    11940
ccgacgcctc cgacaagaca cagcaggcag aaagagcact gggatctgcc gcagccgatg   12000
ctcagagagc taaaaacggc gctggcgagg ccctggaaat cagctctgag atcgagcaag   12060
agatcggctc cctgaatctg gaagccaatg tgacagccga tggcgccctg gccatggaaa   12120
aaggactggc ctctctgaag tccgagatga gagaggtgga aggcgagctg gaacggaaag   12180
aactggaatt cgacaccaat atggacgctg tgcagatggt catcacagag gcccagaagg   12240
tggacaccag agccaaaaat gccggcgtga ccatccagga caccctgaat actctggacg   12300
gactgctgca cctgatggat cagcctctga gcgtggacgg ggaaggactg gttctgctgg   12360
aacagaagct gagccgggcc aagactcaga tcaacagcca gctgaggccc atgatgagcg   12420
```

-continued

```
aactggaaga acgggccaga cagcagaggg gccatctgca tctgctcgaa accagcatcg   12480
atggcatcct ggccgacgtg aagaatctcg agaacatccg ggacaacctg ccacctggct   12540
gctacaacac acaggcactg gaacagcagt ga                                 12572
```

<210> SEQ ID NO 14
<211> LENGTH: 75
<212> TYPE: DNA
<213> ORGANISM: Artificial Sequence
<220> FEATURE:
<223> OTHER INFORMATION: Synthetic Construct

<400> SEQUENCE: 14

```
agggccaaga ggggcagcgg cgagggcagg ggcagcctgc tgacctgcgg cgacgtggag   60
gagaaccccg gcccc                                                    75
```

<210> SEQ ID NO 15
<211> LENGTH: 66
<212> TYPE: DNA
<213> ORGANISM: Artificial Sequence
<220> FEATURE:
<223> OTHER INFORMATION: Synthetic Construct

<400> SEQUENCE: 15

```
ggaagcggag ctactaactt cagcctgctg aagcaggctg agacgtgga ggagaaccct    60 ggacct                                                              66
```

<210> SEQ ID NO 16
<211> LENGTH: 69
<212> TYPE: DNA
<213> ORGANISM: Artificial Sequence
<220> FEATURE:
<223> OTHER INFORMATION: Synthetic Construct

<400> SEQUENCE: 16

```
ggaagcggac agtgtactaa ttatgctctc ttgaaattgg ctggagatgt tgagagcaac   60
cctggacct                                                           69
```

<210> SEQ ID NO 17
<211> LENGTH: 75
<212> TYPE: DNA
<213> ORGANISM: Artificial Sequence
<220> FEATURE:
<223> OTHER INFORMATION: Synthetic Construct

<400> SEQUENCE: 17

```
ggaagcggag tgaaacagac tttgaatttt gaccttctca agttggcggg agacgtggag   60
tccaaccctg gacct                                                    75
```

<210> SEQ ID NO 18
<211> LENGTH: 25
<212> TYPE: PRT
<213> ORGANISM: Artificial Sequence
<220> FEATURE:
<223> OTHER INFORMATION: Synthetic Construct

<400> SEQUENCE: 18

```
Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25
```

<210> SEQ ID NO 19
<211> LENGTH: 22
<212> TYPE: PRT
<213> ORGANISM: Artificial Sequence
<220> FEATURE:
<223> OTHER INFORMATION: Synthetic Construct

<400> SEQUENCE: 19

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic Construct

<400> SEQUENCE: 20

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 21
<211> LENGTH: 25
<212> TYPE: PRT
<213> ORGANISM: Artificial Sequence
<220> FEATURE:
<223> OTHER INFORMATION: Synthetic Construct

<400> SEQUENCE: 21

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 22
<211> LENGTH: 8766
<212> TYPE: DNA
<213> ORGANISM: Artificial Sequence
<220> FEATURE:
<223> OTHER INFORMATION: Synthetic Construct

<400> SEQUENCE: 22
atgcctcctg ctgtgcggag aagcgcctgt tctatgggat ggctgtggat ctttggcgcc        60
gctctgggac agtgtctggg ctactcttct cagcagcagc gggtgccatt tctgcagcca       120
cctggacagt ctcagctgca ggccagctac gtggaattca gacctagcca gggctgtagc       180
cccggctact acagagatca caagggcctg tacaccggca gatgcgtgcc ctgcaactgt       240
aacggccaca gcaaccagtg tcaggacggc tctggcatct gcgtgaactg ccagcataat       300
actgccggcg agcactgcga gagatgccaa gagggctact acggcaatgc cgtgcatggc       360
agctgtcggg cttgtccttg tcctcacacc aacagctttg ccaccggctg cgttgtgaac       420
ggcggagatg ttcggtgttc ttgcaaggcc ggctacacag cacacagtg cgaaagatgt       480 gcccctggct actttggcaa ccctcagaag tttggcggct cctgccagcc ttgctcctgc       540
aattctaatg ccagctgggc ctcttgtcac cctctgaccg gcgactgcat caatcaagag       600
cctaaggaca gcagccctgc cgaggaatgc gacgattgcg atagctgcgt gatgaccctg       660

-continued

```
ctgaacgacc tggccacaat gggagaacag ctgcggctgg ttaagagcca gctccaggga      720
ctgtctgcct ctgctggact gctggaacag atgcggcaca tggaaaccca ggccaaggac      780
ctgagaaacc agctgctgaa ctacagaagc gccatctcca accacggcag caagatcgaa      840
ggcctggaaa gagagctgac cgacctgaat caagagttcg agacactgca agagaaggcc      900
caagtgaaca gccggaaggc ccagactctg aacaacaacg tgaaccgggc cacacagtcc      960
gccaaagaac tggacgtgaa gatcaagaac gtgatccgga acgtgcacat cctgctgaag      1020
cagatcagcg gcacagatgg cgagggcaac aatgtgccta gcggcgactt tagcagagag      1080
tgggccgaag ctcagcggat gatgagagag ctgcggaacc ggaacttcgg caagcacctg      1140
agagaagccg aggccgacaa gagagagagc caactgctgc tcaaccggat cagaacctgg      1200
cagaaaaccc accagggcga gaacaacggc ctggccaaca gcatcagaga cagcctgaat      1260
gagtacgagg ccaagctgag cgatctgcgg gccagacttc aagaagctgc cgctcaggcc      1320
aagcaggcca acggccttaa tcaagagaac gagagagccc tgggcgccat ccagagacaa      1380
gtgaaagaga tcaacagcct gcagagcgac ttcaccaagt acctgaccac cgccgatagc      1440
agcctgctgc agacaaatat cgccctgcag ctcatggaaa agagccagaa agagtacgaa      1500
aagctggccc cagcctgaa cgaggccagg caagaactgt ctgacaaagt gcgcgagctg      1560
agcagatccg ccggcaagac atctctggtg gaagaggccg agaagcacgc cagatctctg      1620
caagagctgg ccaaacagct ggaagagatt aagcggaacg ccagcggcga cgaactcgtc      1680
agatgtgcag tggatgccgc caccgcctac gagaacatcc tgaatgccat caaggccgcc      1740
gaggacgccg ctaatagagc cgcttctgct tctgagtctg ccctgcagac cgtgatcaaa      1800
gaggacctgc ctagaaaggc caagacactg agcagcaaca gcgacaaact gctgaatgag      1860
gccaagatga cccagaagaa actgaagcaa gaggtgtccc ctgcactgaa caacctgcag      1920
cagaccctga acatcgtgac cgtgcagaaa gaagtgatcg acaccaacct gacaaccctg      1980
agagatggcc tgcacggaat ccagagaggc gacatcgacg ccatgatcag cagcgccaag      2040
agcatggttc gaaaagccaa cgacatcacc gacgaggtgc tggacggcct gaatcctatc      2100
cagaccgacg tggaacggat caaggacacc tacggcagaa cccagaacga ggatttcaag      2160
aaggccctga ccgacgccga caactccgtg aacaagctga ccaacaagct gcccgatctg      2220
tggcggaaga tcgagagcat caaccagcaa ctgctccctc tgggcaacat cagcgacaac      2280
atggacagaa tccgggaact gatccagcag gccagagatg ccgcctccaa agtggctgtg      2340
cccatgagat tcaacggcaa gagcggagtg gaagtgcggc tgcccaacga tctggaagat      2400
ctgaagggct ataccagcct gagcctgttc ctgcagaggc ccaacagcag agagaatggc      2460
ggcaccgaga atatgttcgt gatgtacctg ggaaacaagg acgccagccg ggactatatc      2520
ggaatggccg ttgtggacgg ccagctgacc tgcgtgtaca acctgggaga cagagaagct      2580
gaactgcagg tcgaccagat cctgaccaag agcgagacaa agaggccgt gatggacaga      2640 gtgaagttcc agcggatcta ccagttcgcc cggctgaatt acaccaaggg cgccacaagc      2700
agcaagcccg aaacacctgg cgtgtacgac atggacggcc ggaactctaa cactctgctg      2760
aatctggacc ccgagaacgt ggtgtttttac gtcggcggct accctcctga cttcaagctg      2820
cctagcagac tgagcttccc accttacaag ggctgcatcg agctggatga cctgaacgaa      2880
aacgtgctgt ccctgtacaa cttcaaaaag accttcaacc tgaacaccac cgaggtggaa      2940
ccctgcaggc gcagaaaaga ggaatccgac aagaactact cgaaggcac cggctacgcc      3000 agagtgccta cacaacctca cgctcccatt cctaccttcg gccagaccat ccagacaacc      3060
```

-continued

```
gtggatagag gcctgctgtt cttcgccgag aacggcgaca gattcatctc cctgaatatc    3120
gaggatggca agctgatggt ccgatacaag ctgaatagcg agctgcccaa agaaagaggc    3180
gtgggcgacg ccatcaacaa cggcagggat cacagcatcc agatcaagat cggcaaactg    3240
cagaaacgga tgtggatcaa cgtggacgtg cagaacacca tcatcgacgg cgaggtgttc    3300
gacttcagca cctactatct cggcggaatc cctatcgcca tcagagagcg gttcaatatc    3360
agcacccctg ccttccgggg ctgcatgaag aacctgaaaa agaccagcgg cgtcgtgcgg    3420
ctgaatgata cagtgggcgt gaccaagaag tgcagcgagg actggaagct tgtgcggagc    3480
gccagttttt ctagaggcgg acagctgagc tttaccgacc tgggactgcc tcctaccgat    3540
catctgcagg caagcttcgg attccagacc ttccagccaa gcggaatcct gctggaccac    3600
cagacctgga ccagaaacct gcaagtgacc ctggaagatg ctacatcga actgagcacc    3660 agcgactctg gcggccctat ctttaagagc cctcagacct acatggatgg gctgctgcac    3720
tacgtgtccg tgatcagcga taacagcggc ctgagactgc tgatcgacga ccagctcctg    3780
cggaacagca agcggctgaa gcacatctcc agcagcagac agagtctgag actcggcggc    3840
agcaatttcg agggctgtat cagcaacgtg ttcgtgcagc gcctgagtct gtctccagaa    3900
gtgctggacc tgaccagcaa tagcctgaag agggatgtgt ctctcggcgg ctgctccctg    3960
aacaaacctc ctttcctgat gctgctgaag ggcagcaccc ggttcaacaa gaccaagacc    4020
tttcggatca atcagctgct ccaggacacc cctgtggcta gccctagaag cgtgaaagtg    4080
tggcaggacg cctgcagtcc cctgcctaaa acacaggcca atcacggggc tctgcagttc    4140
ggcgatatcc ccacaagcca tctgctgttt aagctgcccc aagagctgct caagcctcgg    4200
agccagttcg ctgtggatat gcagaccacc tcctccagag gactggtgtt tcacaccggc    4260
accaagaaca gcttcatggc cctgtacctg agcaaaggca ggctggtgtt tgccctgggc    4320
accgacggaa agaaactgcg gatcaagagc aaagagaagt gcaacgacgg caagtggcac    4380
accgtggtgt tcggacacga tggcgagaaa ggcagactcg tggtggatgg cctgagagcc    4440
agagagggat ctctgcctgg caactccacc atctccatca gagcccctgt gtatctgggc    4500
agccctccta gcgggaaagcc taagagcctg cctaccaact ccttcgtggg ctgtctgaag    4560
aactttcagc tggacagcaa gcctctgtac accccctagca gcagctttgg cgtgtcctcc    4620
tgtctcggag gccctctgga aaagggcatc tacttctctg aggaaggcgg ccacgttgtc    4680
ctggctcatt ctgttctgct gggccccgag ttcaagctgg tgttctctat ccggcctaga    4740
agcctgaccg gcatcctgat tcacatcggc agccagcctg ggaagcacct gtgtgtgtat    4800
ctcgaggccg gcaaagtgac cgccagcatg gattctggtg ctggcggcac aagcacctcc    4860
gtgacaccta agcagagcct gtgtgatggc cagtggcaca gtgtggccgt gacaatcaag    4920
cagcacattc tgcacctgga actggacacc gacagcagct ataccgccgg acagatccca    4980
tttcctccag ccagcacaca agagcctctg caccttggag gcgcccctgc caatctgacc    5040
acactgagaa tccccgtgtg gaagtccttc ttcggctgcc tgcggaatat ccatgtgaac    5100
cacattccag tgcctgtgac agaggccctg gaagtgcagg acccgtgtc tctgaatgga    5160 tgccccgatc agagggccaa gaggggcagc ggcgagggca gggcagcct gctgacctgc    5220 ggcgacgtgg aggagaaccc cggccccatg aggcccttct tcctgctgtg ctttgccctg    5280
cctggactgc tgcatgctca gcaggcttgt agcagaggcg cctgctatcc tcctgtgggc    5340
gatctgcttg tgggcagaac cagattcctg cgggccagct ctacatgcgg cctgacaaag    5400
```

```
cctgagacat actgcaccca gtacggcgag tggcagatga agtgctgcaa gtgcgacagc    5460
agacagcccc acaactacta cagccacaga gtggaaaacg tggccagcag cagcggccct    5520
atgagatggt ggcagagcca gaacgacgtg aaccccgtta gcctgcagct ggacctggac    5580
agacggtttc agctgcaaga agtgatgatg gaatttcagg gccccatgcc tgccggcatg    5640
ctgatcgaga gaagcagcga tttcggcaag acctggcggg tgtaccagta tctggccgcc    5700
gattgcacca gcacattccc cagagttaga caggcagac cccagagctg gcaggatgtt      5760
cgttgtcagt ctctgcccca gcggcctaac gctagactga atggcggaaa ggtgcagctc     5820
aacctgatgg acctggtgtc tggcatccct gccacacagt cccagaaaat ccaagaagtg    5880
ggcgagatca ccaacctgag agtgaacttc acccggctgg ctcccgttcc tcagagagga    5940
tatcatcctc ctagcgccta ctacgccgtg tctcagctta gactgcaggg cagctgcttc    6000
tgtcacggcc acgctgatag atgcgcccct aaacctggtg cctctgccgg accttctaca    6060
gccgtgcaag tgcacgatgt gtgcgtgtgc cagcacaata ccgccggacc taactgcgag    6120
agatgtgccc ctttctacaa caaccggcct tggaggcctg ccgaaggaca ggatgctcac    6180
gagtgccaga gatgcgactg caacggccac agcgagacat gccactttga ccctgccgtg    6240
tttgccgctt ctcagggcgc ttatggcggc gtgtgtgaca actgcagaga tcacaccgag    6300
ggcaagaact gcgagcgctg tcagctgcac tacttccgga atagaaggcc aggcgccagc    6360
atccaagaga catgcatcag ctgcgagtgc gatcccgatg gtgctgttcc tggcgctcct    6420
tgtgatcctg tgacaggcca gtgcgtgtgt aaagaacacg tgcagggcga aagatgcgac    6480
ctgtgcaagc ctggctttac cggcctgacc tacgccaatc ctcagggctg ccacagatgt    6540
gattgcaaca tcctgggcag cagacgggac atgccctgtg atgaagagtc tggcagatgc    6600
ctgtgcctgc ctaatgtcgt gggccccaag tgcgatcagt gtgccccata tcactggaag    6660
ctggcctctg gccagggatg cgaaccttgt gcctgcgatc cccacaacag cctgtctcca    6720
cagtgcaacc agttcaccgg ccagtgtcct tgcagagaag gctttggcgg cctgatgtgt    6780
tctgccgccg ctatcagaca gtgccccgat agaacatatg gcgacgtggc cacaggctgc    6840
agagcctgcg attgtgactt ccggggaaca gaaggacccg gctgcgataa ggccagcgga    6900
agatgtctgt gtcggcctgg actcacaggc cccagatgtg accagtgtca gcggggctac    6960
tgcaacagat accctgtgtg tgtggcctgc catccttgct tccagaccta cgacgccgac    7020
ctgagagaac aggccctgag attcggcaga ctgagaaatg ccaccgccag cctttggagc    7080
ggacctggcc ttgaagatag aggcctggcc tccagaatcc tggacgccaa gtctaagatc    7140
gagcagatca gagccgtgct gtctagccca gccgtgaccg aacaagaggt ggcccaagtg    7200
gctagcgcca tcctgagcct gagaagaact ctgcagggac tgcagctcga tctgccctg    7260 gaagaggaaa cactgagcct gcctagagat ctggaaagcc tggatcggag cttcaacggc    7320
ctgctgacaa tgtaccagag aaagagagag cagttcgaga agatcagcag cgccgatcct    7380
agcggcgcct tcagaatgct gagcacagcc tatgagcaga gcgcccaggc tgctcagcaa    7440
gtgtccgata gcagcagact gctggaccag ctgcgggact ctagaagaga agccgaaaga    7500
cttgtgcggc aggcaggcgg cggaggtgga acaggatctc ctaaactggt ggccctgcgg    7560
ctggaaatgt cctctctgcc tgatctgacc cctaccttca caagctgtg cggcaacagc    7620 cggcagatgg cctgcacacc tattagctgt cctggcgagc tgtgccctca ggataatgga    7680
accgcctgcg gctccagatg tagaggcgtt ttgccaagag ccggcggagc ctttctgatg    7740
gctggacaag ttgccgagca gctgagaggc ttcaacgctc agctgcagcg gaccagacag    7800
```

```
atgattagag ccgccgagga aagcgccagc cagattcaat ctagcgccca gagactggaa    7860
acccaggtgt ccgccagcag atcccagatg gaagaagatg tgcggcggac aagactgctg    7920
atccagcaag tgcgggactt cctgaccgat cctgataccg atgccgccac aatccaagag    7980
gtgtccgaag ctgttctggc actgtggctg cctaccgata cgctacagt gctgcagaag      8040 atgaacgaga tccaggcaat cgccgccaga ctgcccaatg tggatctggt gctgagccag    8100
accaagcagg atatcgccag agctagaagg ctgcaggccg aggccgaaga ggcaagatct    8160
agagcccatg ccgtggaagg ccaagtcgag gacgttgtgg gcaatctgag acagggaacc    8220
gtggctctgc aagaggccca ggatacaatg cagggcacca gcagaagcct gcgcctgatc    8280
caggatagag tggccgaagt gcagcaggtc ctgaggccag ccgaaaagct ggtcaccagc    8340
atgaccaaac agctgggcga tttctggacg cgcatggaag aactgaggca tcaggcaaga    8400
cagcagggcg ctgaagcagt gcaggctcaa caacttgccg agggcgcttc tgaacaggct    8460
ctgtctgccc aagagggctt cgagcggatc aagcagaagt acgccgagct gaaggacaga    8520
ctgggccaga gttctatgct gggcgaacag ggcgccagaa ttcagagcgt gaaaacagag    8580
gccgaggaac tgttcggcga gacaatggaa atgatggacc ggatgaagga catggaactg    8640
gaactgctga ggggcagcca ggccatcatg ctgagaagtg ccgatctgac aggcctggaa    8700
aagagagtgg aacagatccg ggaccacatc aacggccggg tgctgtacta cgccacatgc    8760
aagtaa                                                                8766
```

<210> SEQ ID NO 23
<211> LENGTH: 12420
<212> TYPE: DNA
<213> ORGANISM: Artificial Sequence
<220> FEATURE:
<223> OTHER INFORMATION: Synthetic Construct

<400> SEQUENCE: 23

```
atgcctcctg ctgtgcggag aagcgcctgt tctatgggat ggctgtggat ctttggcgcc      60
gctctgggac agtgtctggg ctactcttct cagcagcagc gggtgccatt tctgcagcca     120
cctggacagt ctcagctgca ggccagctac gtggaattca gacctagcca gggctgtagc     180
cccggctact acagagatca caagggcctg tacaccggca gatgcgtgcc ctgcaactgt     240
aacggccaca gcaaccagtg tcaggacggc tctggcatct gcgtgaactg ccagcataat     300
actgccggcg agcactgcga gagatgccaa gagggctact acggcaatgc cgtgcatggc     360
agctgtcggg cttgtccttg tcctcacacc aacagctttg ccaccggctg cgttgtgaac     420
ggcggagatg ttcggtgttc ttgcaaggcc ggctacacag gcacacagtg cgaaagatgt     480
gcccctggct actttggcaa ccctcagaag tttggcggct cctgccagcc ttgctcctgc     540
aattctaatg gccagctggg ctcttgtcac cctctgaccg gcgactgcat caatcaagag     600
cctaaggaca gcagccctgc cgaggaatgc gacgattgcg atagctgcgt gatgaccctg     660
ctgaacgacc tggccacaat gggagaacag ctgcggctgg ttaagagcca gctccaggga     720
ctgtctgcct ctgctggact gctggaacag atgcggcaca tggaaaccca ggccaaggac     780
ctgagaaacc agctgctgaa ctacagaagc gccatctcca ccacggcag caagatcgaa      840 ggcctggaaa gagagctgac cgacctgaat caagagttcg agacactgca agagaaggcc     900
caagtgaaca gccggaaggc cagactctg aacaacacg tgaaccgggc cacacagtcc       960 gccaagaac tggacgtgaa gatcaagaac gtgatccgga acgtgcacat cctgctgaag     1020
```

-continued

```
cagatcagcg gcacagatgg cgagggcaac aatgtgccta gcggcgactt tagcagagag    1080
tgggccgaag ctcagcggat gatgagagag ctgcggaacc ggaacttcgg caagcacctg    1140
agagaagccg aggccgacaa gagagagagc caactgctgc tcaaccggat cagaacctgg    1200
cagaaaaccc accagggcga gaacaacggc ctggccaaca gcatcagaga cagcctgaat    1260
gagtacgagg ccaagctgag cgatctgcgg gccagacttc aagaagctgc cgctcaggcc    1320
aagcaggcca acggccttaa tcaagagaac gagagagccc tgggcgccat ccagagacaa    1380
gtgaaagaga tcaacagcct gcagagcgac ttcaccaagt acctgaccac cgccgatagc    1440
agcctgctgc agacaaatat cgccctgcag ctcatggaaa agagccagaa agagtacgaa    1500
aagctggccg ccagcctgaa cgaggccagg caagaactgt ctgacaaagt gcgcgagctg    1560
agcagatccg ccggcaagac atctctggtg gaagaggccg agaagcacgc cagatctctg    1620
caagagctgg ccaaacagct ggaagagatt aagcggaacg ccagcggcga cgaactcgtc    1680
agatgtgcag tggatgccgc caccgcctac gagaacatcc tgaatgccat caaggccgcc    1740
gaggacgccg ctaatagagc cgcttctgct tctgagtctg ccctgcagac cgtgatcaaa    1800
gaggacctgc ctagaaaggc caagacactg agcagcaaca gcgacaaact gctgaatgag    1860
gccaagatga cccagaagaa actgaagcaa gaggtgtccc ctgcactgaa caacctgcag    1920
cagaccctga acatcgtgac cgtgcagaaa gaagtgatcg acaccaacct gacaaccctg    1980
agagatggcc tgcacggaat ccagagaggc gacatcgacg ccatgatcag cagcgccaag    2040
agcatggttc gaaaagccaa cgacatcacc gacgaggtgc tggacggcct gaatcctatc    2100
cagaccgacg tggaacggat caaggacacc tacggcagaa cccagaacga ggatttcaag    2160
aaggccctga ccgacgccga caactccgtg aacaagctga ccaacaagct gcccgatctg    2220
tggcggaaga tcgagagcat caaccagcaa ctgctccctc tgggcaacat cagcgacaac    2280
atggacagaa tccgggaact gatccagcag gccagagatg ccgcctccaa agtggctgtg    2340
cccatgagat tcaacggcaa gagcggagtg gaagtgcggc tgcccaacga tctggaagat    2400
ctgaagggct ataccagcct gagcctgttc ctgcagaggc ccaacagcag agagaatggc    2460
ggcaccgaga atatgttcgt gatgtacctg ggaaacaagg acgccagccg ggactatatc    2520
ggaatggccg ttgtggacgg ccagctgacc tgcgtgtaca acctgggaga cagagaagct    2580
gaactgcagg tcgaccagat cctgaccaag agcgagacaa aagaggccgt gatggacaga    2640
gtgaagttcc agcggatcta ccagttcgcc cggctgaatt acaccaaggg cgccacaagc    2700
agcaagcccg aaacacctgg cgtgtacgac atggacggcc ggaactctaa cactctgctg    2760
aatctggacc ccgagaacgt ggtgtttttac gtcggcggct accctcctga cttcaagctg    2820
cctagcagac tgagcttccc accttacaag ggctgcatcg agctggatga cctgaacgaa    2880
aacgtgctgt ccctgtacaa cttcaaaaag accttcaacc tgaacaccac cgaggtggaa    2940
ccctgcaggc gcagaaaaga ggaatccgac aagaactact cgaaggcac cggctacgcc    3000 agagtgccta cacaacctca cgctcccatt cctaccttcg gccagaccat ccagacaacc    3060
gtggatagag gcctgctgtt cttcgccgag aacggcgaca gattcatctc cctgaatatc    3120
gaggatggca agctgatggt ccgatacaag ctgaatagcg agctgcccaa agaaagaggc    3180
gtgggcgacg ccatcaacaa cggcagggat cacagcatcc agatcaagat cggcaaactg    3240
cagaaacgga tgtggatcaa cgtggacgtg cagaacacca tcatcgacgg cgaggtgttc    3300
gacttcagca cctactatct cggcggaatc cctatcgcca tcagagagcg gttcaatatc    3360
agcacccctg ccttccgggg ctgcatgaag aacctgaaaa agaccagcgg cgtcgtgcgg    3420
```

```
ctgaatgata cagtgggcgt gaccaagaag tgcagcgagg actggaagct tgtgcggagc      3480
gccagttttt ctagaggcgg acagctgagc tttaccgacc tgggactgcc tcctaccgat      3540
catctgcagg caagcttcgg attccagacc ttccagccaa gcggaatcct gctggaccac      3600
cagacctgga ccagaaacct gcaagtgacc ctggaagatg gctacatcga actgagcacc      3660
agcgactctg gcggccctat ctttaagagc cctcagacct acatggatgg gctgctgcac      3720
tacgtgtccg tgatcagcga taacagcggc ctgagactgc tgatcgacga ccagctcctg      3780
cggaacagca agcggctgaa gcacatctcc agcagcagac agagtctgag actcggcggc      3840
agcaatttcg agggctgtat cagcaacgtg ttcgtgcagc gcctgagtct gtctccagaa      3900
gtgctggacc tgaccagcaa tagcctgaag agggatgtgt ctctcggcgg ctgctccctg      3960
aacaaacctc ctttcctgat gctgctgaag ggcagcaccc ggttcaacaa gaccaagacc      4020
tttcggatca atcagctgct ccaggacacc cctgtggcta gccctagaag cgtgaaagtg      4080
tggcaggacg cctgcagtcc cctgcctaaa acacaggcca atcacggggc tctgcagttc      4140
ggcgatatcc ccacaagcca tctgctgttt aagctgcccc aagagctgct caagcctcgg      4200
agccagttcg ctgtggatat gcagaccacc tcctccagag gactggtgtt tcacaccggc      4260
accaagaaca gcttcatggc cctgtacctg agcaaaggca ggctggtgtt tgccctgggc      4320
accgacggaa agaaactgcg gatcaagagc aaagagaagt gcaacgacgg caagtggcac      4380
accgtggtgt tcggacacga tggcgagaaa ggcagactcg tggtggatgg cctgagagcc      4440
agagagggat ctctgcctgg caactccacc atctccatca gagcccctgt gtatctgggc      4500
agccctccta gcggaaagcc taagagcctg cctaccaact ccttcgtggg ctgtctgaag      4560
aactttcagc tggacagcaa gcctctgtac acccctagca gcagctttgg cgtgtcctcc      4620
tgtctcggag gccctctgga aaagggcatc tacttctctg aggaaggcgg ccacgttgtc      4680
ctggctcatt ctgttctgct gggccccgag ttcaagctgg tgttctctat ccggcctaga      4740
agcctgaccg gcatcctgat tcacatcggc agccagcctg ggaagcacct gtgtgtgtat      4800
ctcgaggccg gcaaagtgac cgccagcatg gattctggtg ctggcggcac aagcacctcc      4860
gtgacaccta agcagagcct gtgtgatggc cagtggcaca gtgtggccgt gacaatcaag      4920
cagcacattc tgcacctgga actggacacc gacagcagct ataccgccgg acagatccca      4980
tttcctccag ccagcacaca agagcctctg caccttggag gcgccctgc caatctgacc      5040 acactgagaa tccccgtgtg gaagtccttc ttcggctgcc tgcggaatat ccatgtgaac      5100
cacattccag tgcctgtgac agaggccctg gaagtgcagg acccgtgtc tctgaatgga      5160 tgccccgatc agagggccaa gaggggcagc ggcgagggca ggggcagcct gctgacctgc      5220
ggcgacgtgg aggagaaccc cggccccatg aggcccttct tcctgctgtg ctttgccctg      5280
cctggactgc tgcatgctca gcaggcttgt agcagaggcg cctgctatcc tcctgtgggc      5340
gatctgcttg tgggcagaac cagattcctg cgggccagct ctacatgcgg cctgacaaag      5400
cctgagacat actgcaccca gtacggcgag tggcagatga agtgctgcaa gtgcgacagc      5460
agacagcccc acaactacta cagccacaga gtggaaaacg tggccagcag cagcggccct      5520
atgagatggt ggcagagcca gaacgacgtg aaccccgtta gcctgcagct ggacctggac      5580
agacggtttc agctgcaaga agtgatgatg gaatttcagg gccccatgcc tgccggcatg      5640
ctgatcgaga gaagcagcga tttcggcaag acctggcggg tgtaccagta tctgccgcc      5700 gattgcacca gcacattccc cagagttaga cagggcagac cccagagctg gcaggatgtt      5760
```

-continued

```
cgttgtcagt ctctgcccca gcggcctaac gctagactga atggcggaaa ggtgcagctc     5820
aacctgatgg acctggtgtc tggcatccct gccacacagt cccagaaaat ccaagaagtg     5880
ggcgagatca ccaacctgag agtgaacttc acccggctgg ctcccgttcc tcagagagga     5940
tatcatcctc ctagcgccta ctacgccgtg tctcagctta gactgcaggg cagctgcttc     6000
tgtcacggcc acgctgatag atgcgcccct aaacctggtg cctctgccgg accttctaca     6060
gccgtgcaag tgcacgatgt gtgcgtgtgc cagcacaata ccgccggacc taactgcgag     6120
agatgtgccc ctttctacaa caaccggcct tggaggcctg ccgaaggaca ggatgctcac     6180
gagtgccaga gatgcgactg caacggccac agcgagacat gccactttga ccctgccgtg     6240
tttgccgctt ctcagggcgc ttatggcggc gtgtgtgaca actgcagaga tcacaccgag     6300
ggcaagaact gcgagcgctg tcagctgcac tacttccgga atagaaggcc aggcgccagc     6360
atccaagaga catgcatcag ctgcgagtgc gatcccgatg gtgctgttcc tggcgctcct     6420
tgtgatcctg tgacaggcca gtgcgtgtgt aaagaacacg tgcagggcga aagatgcgac     6480
ctgtgcaagc ctggctttac cggcctgacc tacgccaatc ctcagggctg ccacagatgt     6540
gattgcaaca tcctgggcag cagacgggac atgccctgtg atgaagagtc tggcagatgc     6600
ctgtgcctgc ctaatgtcgt gggccccaag tgcgatcagt gtgccccata tcactggaag     6660
ctggcctctg ccagggatg cgaaccttgt gcctgcgatc cccacaacag cctgtctcca     6720
cagtgcaacc agttcaccgg ccagtgtcct tgcagagaag gctttggcgg cctgatgtgt     6780
tctgccgccg ctatcagaca gtgccccgat agaacatatg cgacgtggc cacaggctgc     6840 agagcctgcg attgtgactt ccggggaaca gaaggacccg gctgcgataa ggccagcgga     6900
agatgtctgt gtcggcctgg actcacaggc cccagatgtg accagtgtca gcggggctac     6960
tgcaacagat accctgtgtg tgtggcctgc catccttgct tccagaccta cgacgccgac     7020
ctgagagaac aggccctgag attcggcaga ctgagaaatg ccaccgccag cctttggagc     7080
ggacctggcc ttgaagatag aggcctggcc tccagaatcc tggacgccaa gtctaagatc     7140
gagcagatca gagccgtgct gtctagccca gccgtgaccg aacaagaggt ggcccaagtg     7200
gctagcgcca tcctgagcct gagaagaact ctgcagggac tgcagctcga tctgcccctg     7260
gaagaggaaa cactgagcct gcctagagat ctggaaagcc tggatcggag cttcaacggc     7320
ctgctgacaa tgtaccagag aaagagagag cagttcgaga agatcagcag cgccgatcct     7380
agcggcgcct tcagaatgct gagcacagcc tatgagcaga gcgcccaggc tgctcagcaa     7440
gtgtccgata gcagcagact gctggaccag ctgcgggact ctagaagaga gccgaaaga     7500 cttgtgcggc aggcaggcgg cggaggtgga acaggatctc ctaaactggt ggccctgcgg     7560
ctggaaatgt cctctctgcc tgatctgacc cctaccttca acaagctgtg cggcaacagc     7620
cggcagatgg cctgcacacc tattagctgt cctggcgagc tgtgccctca ggataatgga     7680
accgcctgcg gctccagatg tagaggcgtt ttgccaagag ccggcggagc ctttctgatg     7740
gctggacaag ttgccgagca gctgagaggc ttcaacgctc agctgcagcg gaccagacag     7800
atgattagag ccgccgagga aagcgccagc cagattcaat ctagcgccca gagactggaa     7860
acccaggtgt ccgccagcag atcccagatg aagaagatg tgcggcggac aagactgctg     7920
atccagcaag tgcgggactt cctgaccgat cctgataccg atgccgccac aatccaagag     7980
gtgtccgaag ctgttctggc actgtggctg cctaccgata cgctacagt gctgcagaag     8040 atgaacgaga tccaggcaat cgccgccaga ctgcccaatg tggatctggt gctgagccag     8100
accaagcagg atatcgccag agctagaagg ctgcaggccg aggccgaaga ggcaagatct     8160
```

-continued

```
agagcccatg ccgtggaagg ccaagtcgag gacgttgtgg gcaatctgag acagggaacc   8220
gtggctctgc aagaggccca ggatacaatg cagggcacca gcagaagcct gcgcctgatc   8280
caggatagag tggccgaagt gcagcaggtc ctgaggccag ccgaaaagct ggtcaccagc   8340
atgaccaaac agctgggcga tttctggacg cgcatggaag aactgaggca tcaggcaaga   8400
cagcagggcg ctgaagcagt gcaggctcaa caacttgccg agggcgcttc tgaacaggct   8460
ctgtctgccc aagagggctt cgagcggatc aagcagaagt acgccgagct gaaggacaga   8520
ctgggccaga gttctatgct gggcgaacag ggcgccagaa ttcagagcgt gaaaacagag   8580
gccgaggaac tgttcggcga gacaatggaa atgatggacc ggatgaagga catggaactg   8640
gaactgctga ggggcagcca ggccatcatg ctgagaagtg ccgatctgac aggcctggaa   8700
aagagagtgg aacagatccg ggaccacatc aacggccggg tgctgtacta cgccacatgc   8760
aagagggcca agaggggcag cggcgagggc aggggcagcc tgctgacctg cggcgacgtg   8820
gaggagaacc ccggccccat gcctgctctg tggctgggct gctgcctgtg ttttagtctg   8880
ctgctgccag ccgccagagc cacatctaga agagaagtgt gcgactgcaa cggcaagagc   8940
cggcagtgca tcttcgacag agagctgcac agacagaccg gcaacggctt cagatgcctg   9000
aactgcaacg acaacaccga cggcatccac tgcgagaagt gcaagaacgg cttctaccgg   9060
caccgcgaga gggatagatg cctgccttgc aactgcaact ccaagggcag cctgagcgcc   9120
agatgcgaca atagcggcag atgtagctgc aagcctggcg tgacaggcgc tagatgcgat   9180
agatgtctcc ccggcttcca catgctgacc gatgccggat gtacccagga ccagagactg   9240
ctggacagca agtgcgattg cgaccctgcc ggaattgccg gaccttgtga tgccggaaga   9300
tgcgtgtgta aacctgccgt gaccggcgag agatgtgaca gatgtagaag cggctactac   9360
aacctggacg gcggcaatcc tgaaggctgc acccagtgct tttgctacgg ccacagcgcc   9420
agctgtagaa gcagcgccga atactccgtg cacaagatca ccagcacctt ccaccaggat   9480
gtggacggat ggaaggccgt gcagagaaat ggctctcctg ccaagctgca gtggtcccag   9540
agacaccagg acgtgttcag cagcgctcag agactggacc ccgtgtactt tgtggcccct   9600
gccaagttcc tgggcaacca gcaagtgtct tacggccaga gcctgagctt cgactacaga   9660
gtggatagag gcggcagaca ccccagcgct cacgatgtga ttcttgaagg cgccggactg   9720
cggatcacag cccctcttat gcctctgggc aagaccctgc cttgtggcct gaccaagacc   9780
tacaccttcc ggctgaatga gcaccccagc aacaactggt ccccacagct gagctacttc   9840 gagtacgac ggctgctgcg gaacctgaca gccctgagaa tcagagccac ctacggcgag   9900
tacagcaccg gctacatcga caacgtgacc ctgatcagcg ccagacctgt ttctggtgct   9960
cctgctcctt gggtcgagca gtgtatctgt cccgtgggct acaagggcca gttctgccag  10020
gattgtgcca gcggctacaa gagagactct gccagactgg gcccctttcgg cacatgcatc  10080 ccttgtaatt gtcaaggcgg cggagcctgc gatcccgata caggcgattg ctacagcggc  10140
gacgagaacc ccgatatcga gtgcgccgat tgtcccatcg gcttttacaa cgaccctcac  10200
gaccccagat cctgcaagcc atgtccttgc cacaatggct tcagctgcag cgtgatgccc  10260
gaaaccgaag aggtcgtgtg caacaattgc ccaccaggcg ttacaggggc cagatgtgaa  10320
ctgtgtgccg acggctactt cggcgatcct tttggagaac acggacccgt gcgaccttgc  10380
cagccttgtc agtgcaacaa caacgtggac ccaagcgcca gcggcaactg cgatagactg  10440
acaggcagat gtctgaagtg catccacaat accgccggga tctactgtga ccagtgcaag  10500
```

-continued

```
gccggctatt ttggcgaccc tctggctccc aatcctgccg ataagtgcag agcctgcaac    10560
tgtaacccta tgggctctga gcctgtgggc tgcagatctg atggaacctg cgtgtgcaag    10620
ccaggctttg gcggacctaa ttgtgaacac ggcgccttta gctgccccgc ctgctacaat    10680
caagtgaaga tccagatgga ccagttcatg cagcagctgc agaggatgga agccctgatc    10740
tctaaagccc aaggcggaga tggcgtggtg cctgatacag agctggaagg cagaatgcag    10800
caggccgaac aggccctgca ggacattctg agagatgccc agattagcga gggcgcctct    10860
agaagtctgg gactgcagct ggctaaagtg cggagccaag agaacagcta ccagagcaga    10920
ctggacgacc tgaagatgac cgtggaaaga gtcagagccc tgggcagcca gtaccagaac    10980
agagtgcggg atacccaccg gctgatcacc cagatgcaac tgtctctggc cgagagcgaa    11040
gccagcctgg gcaataccaa tattcccgcc agcgaccact acgtgggccc caacggtttt    11100
aagagcctgg ctcaagaggc caccagactg gccgaaagcc atgtggaaag cgcctccaac    11160
atggaacagc tgacccggga aaccgaggac tactctaagc aggccctgag cctcgtcaga    11220
aaagccctgc atgaaggcgt cggcagcggc tctggatctc ctgatggtgc tgtggtgcag    11280
ggactcgtgg aaaagctgga aaagaccaaa tctctggccc agcagctgac cagagaagcc    11340
acacaggccg agatcgaggc cgacagaagc taccagcact cactgaggct gctggactcc    11400
gtgtctagac tgcagggcgt gtccgaccag agcttccagg tggaagaggc caagcggatc    11460
aagcagaagg ccgatagcct gagcagcctg gtcaccagac acatggacga gttcaagcgg    11520
acccagaaga acctcggcaa ctggaaagag gaagcccagc aactgctgca gaacggcaag    11580
tctggaagag agaagtctga ccagctgctg agcagagcca acctggccaa gtctagagcc    11640
caagaggccc tgtctatggg caacgccacc ttctacgagg tggaatccat cctgaagaac    11700
ctgcgcgagt cgacctgca agtggacaac agaaaggccg aggccgagga agccatgaag    11760
agactgagct acatcagcca gaaagtgtcc gacgcctccg acaagacaca gcaggcagaa    11820
agagcactgg gatctgccgc agccgatgct cagagagcta aaaacggcgc tggcgaggcc    11880
ctggaaatca gctctgagat cgagcaagag atcggctccc tgaatctgga agccaatgtg    11940
acagccgatg gcgccctggc catggaaaaa ggactggcct ctctgaagtc cgagatgaga    12000
gaggtggaag gcgagctgga acggaaagaa ctggaattcg acaccaatat ggacgctgtg    12060
cagatggtca tcacagaggc ccagaaggtg gacaccagag ccaaaaatgc cggcgtgacc    12120
atccaggaca ccctgaatac tctggacgga ctgctgcacc tgatggatca gcctctgagc    12180
gtggacgagg aaggactggt tctgctggaa cagaagctga gccgggccaa gactcagatc    12240
aacagccagc tgaggcccat gatgagcgaa ctggaagaac gggccagaca gcagaggggc    12300
catctgcatc tgctcgaaac cagcatcgat ggcatcctgg ccgacgtgaa gaatctcgag    12360
aacatccggg acaacctgcc acctggctgc tacaacacac aggcactgga acagcagtga    12420
```

<210> SEQ ID NO 24
<211> LENGTH: 10002
<212> TYPE: DNA
<213> ORGANISM: Homo sapiens

<400> SEQUENCE: 24

```
atggcggcgg ccgcgcggcc tcggggtcgg gcactggggc cagtactgcc gccgacgccg        60
ctgctcctgc tggtactgcg ggtgctgcca gcctgcgggg cgaccgctcg ggatcccggg       120
gccgcggccg ggctcagcct tcacccgact tacttcaacc tggccgaggc ggcgaggatt       180
tgggccaccg ccacctgcgg ggagagggga cccggcgagg ggaggcccca gcccgagctc       240
```

```
tactgcaagt tggtcggggg ccccaccgcc ccaggcagcg gccacaccat ccagggccag      300
ttctgtgact attgcaattc tgaagacccc aggaaagcac atcctgtcac caatgccatc      360
gatggatctg aacgttggtg gcaaagccct cccctgtcct caggcacaca gtacaacaga      420
gtcaacctca ccttggatct gggggcagctc ttccatgtgg cctatatttt aatcaaattt     480
gcaaattctc ctcgccctga tctttgggtc ttggaaagat ctgtagactt tggaagcacc      540
tactcaccat ggcaatattt tgctcattct aaagtagact gtttaaaaga atttgggcgg      600
gaggcaaata tggctgtcac ccgggatgat gatgtacttt gtgttactga atattcccgt      660
attgtacctt tggaaaatgg tgaggttgtg gtgtccttga taaacggtcg tccaggtgca      720 aaaaattta ctttctctca caccctgagg gagtttacca aggcaacaaa catccgcttg      780
cgttttctta gaaccaatac gcttcttgga cacctcatct ccaaagccca gcgagatcca      840
actgtcactc ggcggtatta ttacagcata aaggacatca gcattggtgg gcagtgtgtt      900
tgcaatggcc atgctgaagt gtgcaatata aacaatcctg aaaaactgtt tcggtgtgaa      960
tgccagcacc acacctgtgg ggagacgtgt gatcgctgct gcacagggta caatcagagg     1020
cgctggcggc ccgccgcttg ggagcagagc cacgagtgtg aagcatgcaa ctgccacggc     1080
catgccagca actgttacta tgatccagat gttgagcggc agcaggcaag cttgaatacc     1140
cagggcatct atgctggtgg aggggtctgc attaactgtc agcacaacac agctggagta     1200
aactgtgaac agtgtgctaa gggctattac cgcccttatg gggttccagt ggatgcccct     1260
gatggctgca tcccctgcag ctgtgaccct gagcatgcgg atggctgtga acagggttca     1320
ggccgctgtc actgcaagcc aaatttccac ggagacaact gtgagaagtg tgcaattgga     1380
tactacaatt tcccattttg cttgagaatt cccattttc ctgtttctac accaagttca      1440
gaagatccag tagctggaga tataaaaggg tgtgactgta atctggaagg tgttctccct     1500
gaaatatgtg atgcccacgg acggtgcctg tgccgccctg gggttgaggg ccctcgatgt     1560
gatacctgcc gctctggttt ctactcattc cctatttgcc aagcctgctg gtgttcagcc     1620
cttggatcct accagatgcc ctgcagctca gtgactggac agtgtgaatg tcggccagga     1680
gttacaggac agcggtgtga caggtgtctc tcaggagctt atgatttccc ccactgccaa     1740
ggttccagca gtgcttgtga cccagctggt accatcaact ccaatttggg gtattgccaa     1800
tgcaagcttc atgttgaagg tcctacttgt agccgctgca aactgttata ttggaatctg     1860
gacaaagaaa accccagtgg atgttcagaa tgcaagtgcc ataaggcggg aacagtgagt     1920
ggaactggag agtgtaggca gggagatggt gactgtcact gcaagtccca tgtgggtggc     1980
gattcctgcg acacctgtga agatggatat tttgctttgg aaaagagcaa ttactttggg     2040
tgtcaagggt gtcagtgtga cattggtggg gcattgtcct ccatgtgcag tgggccctcg     2100
ggagtgtgcc agtgccgaga gcatgtcgtg ggaaaggtgt gccagcggcc tgaaaacaac     2160
tactatttcc cagatttgca tcatatgaag tatgagattg aagacggcag cacacctaat     2220
gggagagacc ttcgatttgg atttgatccg ctggcatttc ctgagtttag ctggagagga     2280
tatgcccaaa tgacctcagt acagaatgat gtaagaataa cattgaatgt agggaagtca     2340
agtggctcct tgtttcgtgt tattctgaga tacgttaacc ctggaactga agcagtatct     2400
ggccatataa ctatttatcc atcctggggt gctgctcaaa gcaaagagat catcttcctg     2460
ccgagtaagg agccagcctt tgtcactgtc cctggaaatg gttttgcaga cccattttca     2520
atcacaccag gaatatgggt tgcttgtatt aaggcagaag gagtccttct ggattacctg     2580
```

-continued

```
gtgctgctcc ccagggacta ctatgaagcc tctgtactgc agctgccagt cacagaacca   2640
tgtgcctacg caggacctcc ccaagaaaat tgcttactct accagcattt gccagtgacc   2700
agattcccct gtaccctggc ttgtgaggcc agacacttcc tgcttgatgg ggagccaaga   2760
cccgtggcag tgaggcagcc cacacctgca caccctgtca tggtggacct cagcgggaga   2820
gaggtggaat tgcatctgcg gctgcgcatc ccacaggttg gccactacgt ggttgtggtc   2880
gagtattcca cggaggcagc tcagctgttt gtggttgatg tgaatgtgaa gagctccggg   2940
tctgttctgg caggccaggt gaacatttac agctgcaact acagtgttct ctgccggagt   3000
gctgtgattg atcacatgag ccgcatcgcc atgtatgagc tattggcaga tgcagacatt   3060
cagctcaagg gacacatggc ccgattcctt ctgcatcaag tttgtatcat acctattgaa   3120
gaattctcag ctgagtatgt gagaccacaa gtccactgca ttgccagtta tgggcgattt   3180
gtcaatcaaa gtgccacctg tgtctccttg gcccatgaaa ctcctccaac agcattaatt   3240
ttggatgttc taagtggcag gccttttccct cacctgcccc agcagtcgtc accttctgtt   3300
gatgttcttc ctggggtcac cttgaaggca ccgcagaatc aagtgaccct gagaggacgt   3360
gtaccacacc tgggccgata cgtctttgtc atccattttt accaagcagc gcacccgacg   3420
tttcccgcgc aggtgtcggt ggatggcggg tggccacggg caggctcctt ccatgcctct   3480
ttttgccccc atgtgcttgg ctgccgggat caagtgattg ccgaaggcca gattgagttt   3540
gacatctcag agcctgaagt ggccgcaact gtgaaggttc cagaaggaaa gtccttggtt   3600
ttggtccgtg ttctagtggt gcctgcagaa aactatgact accaaatact tcacaaaaaa   3660
tccatggaca agtcactcga gtttatcacc aattgtggaa aaaacagctt ttaccttgac   3720
ccccagacag cctccagatt ctgtaagaat tccgccaggt ccctggtggc cttttaccac   3780
aagggcgccc tgccttgtga gtgccacccc actggggcca ccggccctca ctgcagccct   3840
gagggtgggc agtgcccatg ccagcccaac gtcatcgggc ggcagtgcac ccgctgtgca   3900
acaggccact acggattccc acgctgcaag ccgtgcagct gtggtcggcg cctttgtgaa   3960
gagatgacgg ggcagtgccg ctgccctccc cgcacggtca ggccccagtg tgaggtgtgt   4020
gagacacact cattcagctt ccaccccatg gccggctgcg aaggctgcaa ctgttccagg   4080
aggggcacca tcgaggctgc catgccggag tgtgaccggg acagcgggca gtgcagatgc   4140
aagcccagaa tcacagggcg gcagtgtgac cgatgtgctt ccgggtttta ccgctttcct   4200
gagtgtgttc cctgcaattg caacagagat gggactgagc caggagtgtg tgacccaggg   4260
accggggctt gcctctgcaa ggaaaatgta gaaggcacag agtgtaatgt gtgtcgagaa   4320
ggctcattcc atttggaccc agccaatctc aagggttgta ccagctgttt ctgttttgga   4380
gtaaataatc aatgtcacag ctcacataag cgaaggacta gtttgtgga tatgctgggc   4440 tggcacctgg agacagcaga cagagtggac atccctgtct ctttcaaccc aggcagcaac   4500
agtatggtgg cggatctcca ggagctgccc gcaaccatcc acagcgcgtc ctgggtcgca   4560
cccacctcct acctggggga caaggtttct tcatatggtg gttacctcac ttaccaagcc   4620
aagtcctttg gcttgcctgg cgacatggtt cttctggaaa agaagccgga tgtacagctc   4680
actggtcagc acatgtccat catctatgag gagacaaaca ccccacggcc agaccggctg   4740
catcatggac gagtgcacgt ggtcgaggga aacttcagac atgccagcag ccgtgcccca   4800
gtgtctaggg aggagctgat gacagtgctg tctagactgg cagatgtgcg catccaaggc   4860
ctctacttca cagagactca aaggctcacc ctgagcgagg tggggctaga ggaagcctct   4920
gacacaggaa gtgggcgcat agcacttgct gtggaaatct gtgcctgccc ccctgcctac   4980
```

-continued

```
gctggtgact cttgtcaggg ttgtagccct ggatactatc gggatcataa aggcttgtat   5040
accggacggt gtgttccctg caattgcaac ggacattcaa atcaatgcca ggatggctca   5100
ggcatatgtg ttaactgtca gcacaacacc gcgggagagc actgtgaacg ctgccaggag   5160
ggctactatg gcaacgccgt ccacggatcc tgcagggcct gcccatgtcc tcacactaac   5220
agctttgcca ctggctgtgt ggtgaatggg ggagacgtgc ggtgctcctg caaagctggg   5280
tacacaggaa cacagtgtga aaggtgtgca ccgggatatt tcgggaatcc ccagaaattc   5340
ggaggtagct gccaaccatg cagttgtaac agcaatggcc agctgggcag ctgtcatccc   5400
ctgactggag actgcataaa ccaagaaccc aaagatagca gccctgcaga agaatgtgat   5460
gattgcgaca gctgtgtgat gaccctcctg aacgacctgg ccaccatggg cgagcagctc   5520
cgcctggtca agtctcagct gcagggcctg agtgccagcg cagggcttct ggagcagatg   5580
aggcacatgg agacccaggc caaggacctg aggaatcagt tgctcaacta ccgttctgcc   5640
atttcaaatc atggatcaaa aatagaaggc ctggaaagag aactgactga tttgaatcaa   5700
gaatttgaga ctttgcaaga aaaggctcaa gtaaattcca gaaaagcaca aacattaaac   5760
aacaatgtta atcgggcaac acaaagcgca aaagaactgg atgtgaagat taaaaatgtc   5820
atccggaatg tgcacattct tttaaagcag atctctggga cagatggaga gggaaacaac   5880
gtgccttcag gtgacttttc cagagagtgg gctgaagccc agcgcatgat gagggaactg   5940
cggaacagga actttggaaa gcacctcaga gaagcagaag ctgataaaag gggagtcgcag   6000 ctcttgctga accggataag gacctggcag aaaacccacc aggggggagaa caatgggctt   6060 gctaacagta tccgggattc tttaaatgaa tacgaagcca aactcagtga ccttcgtgct   6120
cggctgcagg aggcagctgc ccaagccaag caggcaaatg gcttgaacca agaaaacgag   6180
agagctttgg gagccattca gagacaagtg aaagaaataa attccctgca gagtgatttc   6240
accaagtatc taaccactgc agactcatct ttgttgcaaa ccaacattgc gctgcagctg   6300
atggagaaaa gccagaagga atatgaaaaa ttagctgcca gtttaaatga agcaagacaa   6360
gaactaagtg acaaagtaag agaactttcc agatctgctg gcaaaacatc ccttgtggag   6420
gaggcagaaa agcacgcgcg gtccttacaa gagctggcaa agcagctgga agagatcaag   6480
agaaacgcca gcggggatga gctggtgcgc tgtgctgtgg atgccgccac cgcctacgag   6540
aacatcctca atgccatcaa agcggccgag gacgcagcca acgggctgc cagtgcatct   6600 gaatctgccc tccagacagt gataaaggaa gatctgccaa gaaaagctaa aaccctgagt   6660
tccaacagtg ataaactgtt aaatgaagcc aagatgacac aaaagaagct aaagcaagaa   6720
gtcagtccag ctctcaacaa cctacagcaa accctgaata ttgtgacagt tcagaaagaa   6780
gtgatagaca ccaatctcac aactctccga gatggtcttc atgggataca gagaggtgat   6840
attgatgcta tgatcagtag tgcaaagagc atggtcagaa aggccaacga catcacagat   6900
gaggttctgg atgggctcaa ccccatccag acagatgtgg aaagaattaa ggacacctat   6960
gggaggacac agaacgaaga cttcaaaaag gctctgactg atgcagataa ctcggtgaat   7020
aagttaacca caaaactacc tgatctttgg cgcaagattg aaagtatcaa ccaacagctg   7080
ttgcccttgg aaacatctc tgacaacatg gacagaatac gagaactaat tcagcaggcc   7140
agagatgctg ccagtaaggt tgctgtcccc atgaggttca atggtaaatc tggagtcgaa   7200
gtccgactgc aaatgacct ggaagatttg aaaggatata catctctgtc cttgtttctc   7260
caaaggccca actcaagaga aaatggggggt actgagaata tgtttgtgat gtaccttgga   7320
```

-continued

```
aataaagatg cctcccggga ctacatcggc atggcagttg tggatggcca gctcacctgt   7380
gtctacaacc tggggaccg tgaggctgaa ctccaagtgg accagatctt gaccaagagt   7440
gagactaagg aggcagttat ggatcgggtg aaatttcaga gaatttatca gtttgcaagg   7500
cttaattaca ccaaaggagc cacatccagt aaaccagaaa cacccggagt ctatgacatg   7560
gatggtagaa atagcaatac actccttaat ttggatcctg aaaatgttgt attttatgtt   7620
ggaggttacc cacctgattt taaacttccc agtcgactaa gtttccctcc atacaaaggt   7680
tgtattgaat tagatgacct caatgaaaat gttctgagct tgtacaactt caaaaaaaca   7740
ttcaatctca acacaactga agtggagcct tgtagaagga ggaaggaaga gtcagacaaa   7800
aattattttg aaggtacggg ctatgctcga gttccaactc aaccacatgc tcccatccca   7860
acctttggac agacaattca gaccaccgtg gatagaggct tgctgttctt tgcagaaaac   7920
ggggatcgct tcatatctct aaatatagaa gatggcaagc tcatggtgag atacaaactg   7980
aattcagagc taccaaaaga gagaggagtt ggagacgcca taaacaacgg cagagaccat   8040
tcgattcaga tcaaaattgg aaaactccaa aagcgtatgt ggataaatgt ggacgttcaa   8100
aacactataa ttgatggtga agtatttgat ttcagcacat attatctggg aggaattcca   8160
attgcaatca gggaaagatt taacatttct acgcctgctt tccgaggctg catgaaaaat   8220
ttgaagaaaa ccagtggtgt cgttagattg aatgatactg tgggagtaac caaaaagtgc   8280
tcggaagact ggaagcttgt gcgatctgcc tcattctcca gaggaggaca attgagtttc   8340
actgatttgg gcttaccacc tactgaccac ctccaggcct catttggatt tcagaccttt   8400
caacccagtg gcatattatt agatcatcag acatggacaa ggaacctgca ggtcactctg   8460
gaagatggtt acattgaatt gagcaccagc gatagcggcg gcccaatttt taaatctcca   8520
cagacgtata tggatggttt actgcattat gtatctgtaa taagcgacaa ctctggacta   8580
cggcttctca tcgatgacca gcttctgaga aatagcaaaa ggctaaaaca catttcaagt   8640
tcccggcagt ctctgcgtct gggcgggagc aattttgagg gttgtattag caatgttttt   8700
gtccagaggt tatcactgag tcctgaagtc ctagatttga ccagtaactc tctcaagaga   8760
gatgtgtccc tgggaggctg cagtttaaac aaaccacctt ttctaatgtt gcttaaaggt   8820
tctaccaggt ttaacaagac caagactttt cgtatcaacc agctgttgca ggacacacca   8880
gtggcctccc caaggagcgt gaaggtgtgg caagatgctt gctcaccact tcccaagacc   8940
caggccaatc atggagccct ccagtttggg gacattccca ccagccactt gctattcaag   9000
cttcctcagg agctgctgaa acccaggtca cagtttgctg tggacatgca gacaacatcc   9060
tccagaggac tggtgtttca cacgggcact aagaactcct ttatggctct ttatctttca   9120
aaaggacgtc tggtctttgc actggggaca gatgggaaaa aattgaggat caaaagcaag   9180
gagaaatgca atgatgggaa atggcacacg gtggtgtttg gccatgatgg ggaaaagggg   9240
cgcttggttg tggatggact gagggccgg gagggaagtt tgcctggaaa ctccaccatc   9300
agcatcagag cgccagttta cctgggatca cctccatcag ggaaaccaaa gagcctcccc   9360
acaaacagct ttgtgggatg cctgaagaac tttcagctgg attcaaaacc cttgtatacc   9420
ccttcttcaa gcttcggggt gtcttcctgc ttgggtggtc ctttggagaa aggcatttat   9480
ttctctgaag aaggaggtca tgtcgtcttg gctcactctg tattgttggg gccagaattt   9540
aagcttgttt tcagcatccg cccaagaagt ctcactggga tcctaataca catcggaagt   9600
cagcccggga agcacttatg tgtttacctg gaggcaggaa aggtcacggc ctctatggac   9660
agtggggcag gtgggacctc aacgtcggtc acaccaaagc agtctctgtg tgatggacag   9720
```
tggcactcgg tggcagtcac cataaaacaa cacatcctgc acctggaact ggacacagac      9780
agtagctaca cagctggaca gatcccccttc ccacctgcca gcactcaaga gccactacac      9840
cttggaggtg ctccagccaa tttgacgaca ctgaggatcc ctgtgtggaa atcattcttt      9900
ggctgtctga ggaatattca tgtcaatcac atccctgtcc ctgtcactga agccttggaa      9960
gtccaggggc ctgtcagtct gaatggttgt cctgaccagt aa                         10002

<210> SEQ ID NO 25
<211> LENGTH: 10002
<212> TYPE: DNA
<213> ORGANISM: Artificial Sequence
<220> FEATURE:
<223> OTHER INFORMATION: Synthetic Construct

<400> SEQUENCE: 25
atggctgctg ccgctagacc tagaggtaga gcactgggac ctgtgctgcc tcctacacct        60
ctgctgctgc tggtgctgag agtgcttcct gcttgtggcg ctaccgctag agatcctggt       120
gctgctgcag gactgtctct gcaccccacc tacttcaatc tggccgaggc cgccagaatc       180
tgggccacag ctacatgtgg cgaaagaggc cctggcgaag gcagacctca gcctgagctg       240
tattgcaagc tcgttggcgg ccctacagct cctggatctg acacacaat ccagggccag        300 ttctgcgact actgcaacag cgaggacccc agaaaggccc atcctgtgac caatgccatc       360
gacggctctg agagatggtg gcagtctcct ccactgagca gcggcaccca gtacaacaga       420
gtgaatctga ccctggacct gggccagctg tttcacgtgg cctacatcct gatcaagttc       480
gccaactctc cccggcctga tctgtgggtg ctcgagagat ctgtggactt cggcagcaca       540
tacagcccct ggcagtactt cgcccacagc aaggtggact gcctgaaaga gttcggccgc       600
gaggccaata tggccgtgac cagagatgac gacgtgctgt gcgtgaccga gtacagcaga       660
atcgtgcccc tggaaaacgg cgaggtggtg gtgtccctga tcaatggtag acctggcgcc       720
aagaacttca ccttcagcca cacactgaga gagttcacca aggccaccaa tatccggctg       780
cggttcctgc ggacaaatac cctgctgggc cacctgatct ctaaggccca aagggacccc      840
accgtgacac ggcggtacta ctacagcatc aaggacatca gcatcggcgg ccagtgcgtg       900
tgtaatggac atgccgaagt gtgcaacatc aacaaccccg agaagctgtt cagatgcgag       960
tgccagcacc acacctgtgg cgagacatgc gatagatgct gcaccggcta caaccagaga      1020
agatggcgac ctgccgcctg ggagcagtct catgaatgcg aggcctgcaa ttgccacggc      1080
cacgccagca actgctacta cgaccccgat gtggaaagac agcaggccag cctgaatacc      1140
cagggcatct atgctggtgg cggcgtgtgc atcaactgtc agcataatac tgccggcgtg      1200
aactgcgagc agtgcgccaa gggctactac agaccttatg gcgtgccagt ggatgcccct      1260
gatggctgca tcccttgcag ctgtgatcct gagcatgccg acggctgtga caaggctct       1320 ggcagatgtc actgcaagcc caacttccac ggcgacaatt gcgagaagtg tgctatcggg      1380
tactacaact tcccattctg cctgcgcatc cctatcttcc ccgtgtctac acccagctct      1440
gaagatcctg tggccggcga tatcaagggc tgcgactgta tctggaagg cgtgctgcct       1500 gagatctgcg acgccatggg aagatgcctg tgtagaccag gcgtggaagg ccccagatgc      1560
gatacctgta gatccggctt ctacagcttc cctatctgtc aggcctgctg gtgttctgcc      1620
ctgggcagct atcagatgcc ttgctctagc gtgaccggac agtgcgaatg cagacccggt      1680
gttaccggcc agagatgtga cagatgtctg agcggcgcct acgacttccc cacactgtcag     1740

-continued

```
ggaagcagca gcgcctgtga tccagccggc accatcaata gcaacctggg ctactgccag   1800
tgcaagctgc acgtggaagg acctacctgc tctcggtgca aactgctgta ttggaacctg   1860
gacaaagaga accccagcgg ctgcagcgag tgcaagtgtc acaaagccgg cacagtgtct   1920
ggcaccggcg aatgtagaca aggcgacggc gattgccact gcaagtctca cgttggcgga   1980
gacagctgcg acacatgcga ggatggctac ttcgctctgg aaaagtccaa ctacttcgga   2040
tgccagggct gccagtgtga tattggcgga gccctgagca gcatgtgttc tggacctagc   2100
ggagtgtgcc agtgccggga acacgttgtg ggcaaagtct gtcagcggcc cgagaacaac   2160
tactacttcc ccgacctgca ccacatgaag tacgagatcg aggacggcag caccccctaac  2220 ggcagagatc tgagattcgg cttcgaccct ctggcctttc ctgagttctc ttggagaggc   2280
tacgcccaga tgaccagcgt gcagaacgat gtgcggatca ccctgaacgt gggcaagagc   2340
agcggaagcc tgtttagagt gattctgaga tacgtgaacc ccggcaccga ggccgtgtct   2400
ggccacatca caatctaccc tagctggggc gctgcccaga gcaaagagat catcttcctg   2460
cctagcaaag aacccgcctt cgtgaccgtg cctggcaacg gatttgccga tcctttcagc   2520 atcacccccag gcatctgggt cgcctgtatt aaggccgaag gcgtcctgct ggactacctg   2580
gttctgctcc ccagagacta ctacgaggcc tctgttctgc agctgcccgt gacagagcca   2640
tgtgcctatg ctggacctcc tcaagagaat tgcctgctgt accagcatct gcctgtgaca   2700
agattcccct gcacactggc ctgcgaagcc aggcactttc tgctggatgg cgagcctaga   2760
ccagtggccg ttagacagcc tacaccagct caccccgtga tggtggatct gtctggcaga   2820
gaggtggaac tgcacctgag actgagaatc cctcaagtgg ccactacgt ggtggtggtc    2880 gagtactcta cagaggccgc tcagctgttc gtggtggacg tgaacgtgaa gtccagcggc   2940
tctgtgctgg ccggacaagt gaacatctac tcttgcaact actccgtgct gtgtcggagc   3000
gccgtgatcg accacatgag ccggatcgct atgtacgagc tgctggccga tgccgacatc   3060
cagctgaagg gacacatggc cagatttctg ctgcaccaag tgtgcattat ccccatcgaa   3120
gagttcagcg ccgagtacgt cagaccccag gtgcactgta tcgccagcta cggcagattc   3180
gtgaaccaga gcgccaccctg tgtgtctctg gcccacgaaa cacctccaac cgctctgatc   3240
ctggacgtgt tgagcggcag accatttcct catctgcccc agcagagcag cccttccgtt   3300
gatgttctgc ctggcgtgac cctgaaggca ccccagaatc aagtgacact gaggggcaga   3360 gtgcccccacc tgggcagata tgtgttcgtg atccacttct accaggctgc ccatcctaca   3420
ttccccgctc aagtgtcagt ggatggcgga tggcctagag ccggaagctt tcacgccagc   3480
ttttgccctc acgtgctggg ctgccgcgat caagtgattg ccgagggcca gatcgagttc   3540
gacatcagcg aacctgaagt ggccgccacc gtgaaagtgc ccgagggaaa atctctggtg   3600
ctcgtcagag tgctggtggt gcccgccgag aactacgact atcagatcct gcacaaaaag   3660
agcatggaca agagcctcga gttcatcacc aactgcggca agaactcctt ctatctggac   3720
cctcagaccg ccagccggtt ctgcaagaat agcgctagaa gcctggtggc tttctaccac   3780
aaaggcgccc tgccttgcga gtgtcatcca acaggtgcca ccggacctca ctgtagtcct   3840
gaaggtggcc agtgtccttg ccagcctaac gtgatcggca ggcagtgtac cagatgtgcc   3900
acaggccact atggcttccc tagatgcaag ccctgtagct gcggtagaag gctgtgcgaa   3960
gagatgaccg gccagtgtag gtgccctcct agaaccgtta gaccccagtg tgaagtgtgc   4020
gaaacccaca gcttcagctt tcacccctatg gccggctgcg agggctgtaa ctgtagcaga   4080
agaggcacca tcgaggccgc tatgcccgag tgcgatagag acagcggaca gtgtcggtgc   4140
```

-continued

```
aagcctagaa tcaccggccg tcagtgcgac agatgcgcca gcggctttta cagatttccc      4200
gagtgtgtgc cctgcaactg caatcgcgac ggaacagaac ctggcgtgtg cgatcctgga      4260
acaggcgctt gcctgtgcaa agaaaatgtg gaaggcaccg agtgtaacgt gtgcagagag      4320
ggcagcttcc atctcgaccc cgccaatctg aagggctgta cctcctgctt ctgcttcgga      4380
gtgaacaacc agtgccacag cagccacaag cggcggacca agttcgtgga tatgctcggc      4440
tggcacctgg aaaccgccga cagagtggat atccctgtgt ccttcaatcc cggcagcaac      4500
agcatggtgg ccgatctgca agagctgcca gccacaattc acagcgcctc ttgggtcgcc      4560
cctacaagct atctgggcga caaggtgtcc tcctacggcg gctacctgac ataccaggcc      4620
aagtcctttg gactgcccgg cgacatggtc ctgctcgaga agaaacctga tgtgcagctg      4680
acaggacagc acatgagcat catctacgag gaaacaaaca cccctcggcc tgaccggctg      4740
catcacggaa gagtgcatgt ggtggaaggg aacttccggc acgcctcttc tagagcccct      4800
gtgtctcggg aagaactgat gaccgtgctg agcagactgg ccgacgttcg gattcagggc      4860
ctgtacttca ccgagactca gcggctgacc ctgtctgaag ttggactgga agaggccagc      4920
gataccggca gcggtagaat tgctctggcc gtggaaatct cgcgcctgtcc tccagcttat      4980 gccggcgatt cttgtcaggg atgtagccca ggctactaca gagatcacaa gggcctgtac      5040
accggcagat gcgtgccctg caactgtaac ggccacagca accagtgtca ggacggctct      5100
ggcatctgcg tgaactgcca gcataatact gccggcgagc actgcgagag atgccaagag      5160
ggctactacg gcaatgccgt gcatggcagc tgtcgggctt gtccttgtcc tcacaccaac      5220
agctttgcca ccggctgcgt tgtgaacggc ggagatgttc ggtgttcttg caaggccggc      5280
tacacaggca cacagtgcga aagatgtgcc cctggctact ttggcaaccc tcagaagttt      5340
ggcggctcct gccagccttg ctcctgcaat tctaatggcc agctgggctc ttgtcaccct      5400
ctgaccggcg actgcatcaa tcaagagcct aaggacagca gccctgccga ggaatgcgac      5460
gattgcgata gctgcgtgat gaccctgctg aacgacctgg ccacaatggg cgaacagctg      5520
agactggtca gtcccagct gcagggactg tctgcttctg ccggactgct ggaacagatg      5580
cggcacatgg aaacccaggc caaggacctg agaaaccagc tgctgaacta cagaagcgcc      5640
atctccaacc acggcagcaa gatcgaaggc ctggaaagag agctgaccga cctgaatcaa      5700
gagttcgaga cactgcaaga gaaggcccaa gtgaacagcc ggaaggccca gacactgaac      5760
aacaacgtga accgggccac acagagcgcc aaagaactgg acgtgaagat caagaacgtg      5820
atccggaacg tgcacatcct gctgaagcag atcagcggca cagatggcga gggcaacaat      5880
gtgcctagcg gcgactttag cagagagtgg gccgaagctc agcggatgat gagagagctg      5940
cggaaccgga acttcggcaa gcacctgaga gaagccgagg ccgacaagag agaatctcag      6000
ctgctgctga atcggatcag gacctggcag aaaacccacc agggcgagaa caacggcctg      6060
gccaacagca tcagagacag cctgaatgag tacgaggcca agctgagcga tctgcgggcc      6120
agacttcaag aagctgccgc tcaggccaag caggccaacg gccttaatca agagaacgag      6180
agagccctgg gcgccatcca gagacaagtg aaagagatca acagcctgca gagcgacttc      6240
accaagtacc tgaccaccgc cgatagcagc ctgctgcaga caaatatcgc actgcagctg      6300
atggaaaaga gccagaaaga gtacgaaaag ctggccgcca gcctgaacga ggccaggcaa      6360
gaactgtctg acaaagtgcg cgagctgagc agatccgccg gcaagacatc tctggtggaa      6420
gaggccgaga agcacgccag atctctgcaa gagctggcca aacagctgga agagattaag      6480
```

-continued

```
cggaacgcca gcggcgacga actcgtcaga tgtgctgtgg atgccgccac cgcctacgag    6540
aacatcctga atgccatcaa ggccgccgag gacgccgcta atagagccgc ttctgcctct    6600
gaaagcgccc tgcagaccgt gatcaaagag gacctgccta gaaaggccaa gactctgagc    6660
agcaacagcg acaaactgct gaatgaggcc aagatgaccc agaagaaact gaagcaagag    6720
gtgtcccctg ctctgaacaa cctgcagcag accctgaaca tcgtgaccgt gcagaaagaa    6780
gtgatcgaca ccaacctgac aaccctgaga gatggcctgc acggaatcca gagaggcgac    6840
atcgacgcca tgatcagcag cgccaagagc atggttcgaa aagccaacga catcaccgac    6900
gaggtgctgg acggcctgaa tcctatccag accgacgtgg aacggatcaa ggacacctac    6960
ggcagaaccc agaacgagga tttcaagaag gccctgaccg acgccgacaa ctccgtgaac    7020
aagctgacca caagctgcc cgatctgtgg cggaagatcg agagcatcaa ccagcaactg    7080
ctgcccctgg gcaacatcag cgacaacatg gaccggatca gggaactgat ccagcaggcc    7140
agagatgccg cctccaaagt ggctgtgccc atgagattca acggcaagag cggagtggaa    7200
gtgcggctgc ccaacgatct ggaagatctg aagggctata ccagcctgag cctgttcctg    7260
cagaggccca acagcagaga gaatggcggc accgagaata tgttcgtgat gtacctggga    7320
aacaaggacg ccagccggga ctatatcgga atggccgttg tggacggcca gctgacctgc    7380
gtgtacaacc tgggagacag agaagctgag ctgcaggtcg accagatcct gaccaagagc    7440
gagacaaaag aggccgtgat ggacagagtg aagttccagc ggatctacca gttcgcccgg    7500
ctgaattaca ccaagggcgc cacaagcagc aagcccgaaa cacctggcgt gtacgacatg    7560
gacggccgga actctaacac cctgctcaat ctggaccccg agaacgtggt gttttacgtc    7620
ggcggctacc ctcctgactt caagctgcct agcagactga gcttcccacc ttacaagggc    7680
tgcatcgagc tggatgacct gaacgaaaac gtgctgtccc tgtacaactt caaaaagacc    7740
ttcaacctga acaccaccga ggtggaaccc tgcaggcgca gaaaagagga tccgacaag    7800 aactacttcg aaggcaccgg ctacgccaga gtgcctacac aacctcacgc tcccattcct    7860
accttcggcc agaccatcca gacaaccgtg gatagaggcc tgctgttctt cgccgagaac    7920
ggcgacagat tcatctccct gaatatcgag gatggcaagc tgatggtccg atacaagctg    7980
aactccgagc tgcccaaaga aagaggcgtg ggcgacgcca tcaacaacgg cagggatcac    8040
agcatccaga tcaagatcgg caagctgcag aaacggatgt ggatcaacgt ggacgtgcag    8100
aacaccatca tcgacggcga ggtgttcgac ttcagcacct actatctcgg cggaatccct    8160
atcgccatca gagagcggtt caatatcagc accccctgcct tccggggctg catgaagaac    8220
ctgaaaaaga ccagcggcgt cgtgcggctg aatgatacag tgggcgtgac caagaagtgc    8280
agcgaggact ggaagcttgt gcggagcgcc agttttttcta gaggcgggca gctgagcttt    8340
accgacctgg gattgcctcc taccgaccat ctgcaggcaa gcttcggatt ccagaccttc    8400
cagccaagcg gaatcctgct ggaccaccag acctggacca gaaacctgca agtgaccctg    8460
gaagatggct acatcgaact gagcaccagc gactctggcg ccctatctt taagagccct    8520 cagacctaca tggatgggct gctgcactac gtgtccgtga tcagcgataa cagcggcctg    8580
agactgctga tcgacgacca gcttctgcgg aacagcaagc ggctgaagca catctccagc    8640
agcagacaga gtctgagact cggcggcagc aatttcgagg gctgtatcag caacgtgttc    8700
gtgcagcgcc tgagtctgtc tccagaagtg ctggacctga ccagcaatag cctgaagagg    8760
gatgtgtctc tcggcggctg ctccctgaac aaacctcctt tcctgatgct gctcaagggc    8820
tccaccagat tcaacaagac caagaccttt cggatcaatc agctgctcca ggacacccct    8880
```

-continued

```
gtggctagcc ctagaagcgt gaaagtgtgg caggacgcct gcagtcccct gcctaaaaca      8940
caggccaatc atggggccct gcagttcggc gatatcccca caagccatct gctgtttaag      9000
ctgccccaag agctgctcaa acctcggagc cagtttgccg tggatatgca gaccaccagc      9060
tccagaggac tggtgtttca caccggcacc aagaacagct tcatggccct gtacctgagc      9120
aagggccgcc tggttttttgc cctgggaacc gacggcaaga aactgcggat caagagcaaa      9180
gagaagtgca cgacggaaa gtggcacacc gtggtgttcg acacgatgg cgagaaaggc      9240 agactggtgg tggatggcct gagagccaga gagggatctc tgcctggcaa ctccaccatc      9300
tccatcagag cccctgtgta tctgggcagc cctcctagcg gaaagcctaa gagcctgcct      9360
accaactcct tcgtgggctg tctgaagaac tttcagctgg acagcaagcc tctgtacacc      9420
cctagctcca gctttggcgt gtcctcctgt ctcggaggcc ctctggaaaa gggcatctac      9480
ttctctgagg aaggcggcca cgttgtcctg gctcattctg ttttgctggg ccccgagttc      9540
aagctggtgt tctccattag gcccagaagc ctgaccggca tcctgattca catcggcagc      9600
cagcctggca aacacctgtg tgtgtatctc gaggccggca aagtgaccgc cagcatggat      9660
tctggtgctg gcggcacaag cacctccgtg acacctaagc agagcctgtg tgatggccag      9720
tggcacagtg tggccgtgac aatcaagcag cacattctgc acctggaact ggacaccgac      9780
agcagctata ccgccggaca gatcccattt cctccagcca gcacacaaga gcctctgcac      9840
cttggaggcg ccccagccaa tctgaccaca ctgagaatcc ccgtgtggaa gtccttcttc      9900
ggctgcctgc ggaatatcca tgtgaaccac attccagtgc ctgtgacaga ggccctggaa      9960
gtgcagggac ccgtgtctct gaatggatgc cccgatcagt ga                       10002
```

```
<210> SEQ ID NO 26
<211> LENGTH: 9834
<212> TYPE: DNA
<213> ORGANISM: Homo sapiens

<400> SEQUENCE: 26
atggcggcgg ccgcgcggcc tcggggtcgg gcactggggc cagtactgcc gccgacgccg        60
ctgctcctgc tggtactgcg ggtgctgcca gcctgcgggg cgaccgctcg ggatcccggg       120
gccgcggccg ggctcagcct tcacccgact tacttcaacc tggccgaggc ggcgaggatt       180
tgggccaccg ccacctgcgg ggagaggggga cccggcgagg ggaggcccca gcccgagctc       240
tactgcaagt tggtcggggg ccccaccgcc ccaggcagcg gccacaccat ccagggccag       300
ttctgtgact attgcaattc tgaagacccc aggaaagcac atcctgtcac caatgccatc       360
gatggatctg aacgttggtg gcaaagccct ccctgtcct caggcacaca gtacaacaga       420
gtcaacctca ccttggatct ggggcagctc ttccatgtgg cctatatttt aatcaaattt       480
gcaaattctc ctcgccctga tctttgggtc ttggaaagat ctgtagactt ggaagcacc       540 tactcaccat ggcaatattt tgctcattct aaagtagact gtttaaaaga atttgggcgg       600
gaggcaaata tggctgtcac ccgggatgat gatgtacttt gtgttactga atattcccgt       660
attgtacctt tggaaaatgg tgaggttgtg gtgtccttga taaacggtcg tccaggtgca       720
aaaaatttta ctttctctca caccctgagg gagtttacca aggcaacaaa catccgcttg       780
cgttttctta gaaccaatac gcttcttgga cacctcatct ccaaagccca gcgagatcca       840
actgtcactc ggcggtatta ttacagcata aaggacatca gcattggtgg gcagtgtgtt       900
tgcaatggcc atgctgaagt gtgcaatata aacaatcctg aaaaactgtt tcggtgtgaa       960
```

-continued

```
tgccagcacc acacctgtgg ggagacgtgt gatcgctgct gcacagggta caatcagagg      1020
cgctggcggc ccgccgcttg ggagcagagc cacgagtgtg aagcatgcaa ctgccacggc      1080
catgccagca actgttacta tgatccagat gttgagcggc agcaggcaag cttgaatacc      1140
cagggcatct atgctggtgg aggggtctgc attaactgtc agcacaacac agctggagta      1200
aactgtgaac agtgtgctaa gggctattac cgcccttatg gggttccagt ggatgcccct      1260
gatggctgca tccctgcag ctgtgaccct gagcatgcgg atggctgtga acagggttca      1320
ggccgctgtc actgcaagcc aaatttccac ggagacaact gtgagaagtg tgcaattgga      1380
tactacaatt tcccattttg cttgagaatt cccattttc ctgtttctac accaagttca      1440
gaagatccag tagctggaga tataaaaggg tgtgactgta atctggaagg tgttctccct      1500
gaaatatgtg atgcccacgg acggtgcctg tgccgccctg gggttgaggg ccctcgatgt      1560
gatacctgcc gctctggttt ctactcattc cctatttgcc aagcctgctg gtgttcagcc      1620
cttggatcct accagatgcc ctgcagctca gtgactggac agtgtgaatg tcggccagga      1680
gttacaggac agcggtgtga caggtgtctc tcaggagctt atgatttccc ccactgccaa      1740
ggttccagca gtgcttgtga cccagctggt accatcaact ccaatttggg gtattgccaa      1800
tgcaagcttc atgttgaagg tcctacttgt agccgctgca aactgttata ttggaatctg      1860
gacaaagaaa accccagtgg atgttcagaa tgcaagtgcc ataaggcggg aacagtgagt      1920
ggaactggag agtgtaggca gggagatggt gactgtcact gcaagtccca tgtgggtggc      1980
gattcctgcg acacctgtga agatggatat tttgctttgg aaaagagcaa ttactttggg      2040
tgtcaagggt gtcagtgtga cattggtggg gcattgtcct ccatgtgcag tgggccctcg      2100
ggagtgtgcc agtgccgaga gcatgtcgtg ggaaaggtgt gccagcggcc tgaaaacaac      2160
tactatttcc cagatttgca tcatatgaag tatgagattg aagacggcag cacacctaat      2220
gggagagacc ttcgatttgg atttgatccg ctggcatttc ctgagtttag ctggagagga      2280
tatgcccaaa tgacctcagt acagaatgat gtaagaataa cattgaatgt agggaagtca      2340
agtggctcct tgtttcgtgt tattctgaga tacgttaacc ctggaactga agcagtatct      2400
ggccatataa ctatttatcc atcctggggt gctgctcaaa gcaaagagat catcttcctg      2460
ccgagtaagg agccagcctt tgtcactgtc cctggaaatg gttttgcaga cccattttca      2520
atcacaccag gaatatgggt tgcttgtatt aaggcagaag gagtccttct ggattacctg      2580
gtgctgctcc ccagggacta ctatgaagcc tctgtactgc agctgccagt cacagaacca      2640
tgtgcctacg caggacctcc ccaagaaaat tgcttactct accagcattt gccagtgacc      2700
agattcccct gtaccctggc ttgtgaggcc agacacttcc tgcttgatgg ggagccaaga      2760
cccgtggcag tgaggcagcc cacacctgca caccctgtca tggtggacct cagcgggaga      2820
gaggtggaat tgcatctgcg gctgcgcatc ccacaggttg gccactacgt ggttgtggtc      2880
gagtattcca cggaggcagc tcagctgttt gtggttgatg tgaatgtgaa gagctccggg      2940
tctgttctgg caggccaggt gaacatttac agctgcaact acagtgttct ctgccggagt      3000
gctgtgattg atcacatgag ccgcatcgcc atgtatgagc tattggcaga tgcagacatt      3060
cagctcaagg gacacatggc ccgattcctt ctgcatcaag tttgtatcat acctattgaa      3120
gaattctcag ctgagtatgt gagaccacaa gtccactgca ttgccagtta tgggcgattt      3180
gtcaatcaaa gtgccacctg tgtctccttg gcccatgaaa ctcctccaac agcattaatt      3240
ttggatgttc taagtggcag gccttttcct cacctgcccc agcagtcgtc accttctgtt      3300
gatgttcttc ctggggtcac cttgaaggca ccgcagaatc aagtgaccct gagaggacgt      3360
```

-continued

```
gtaccacacc tgggccgata cgtctttgtc atccattttt accaagcagc gcacccgacg   3420
tttcccgcgc aggtgtcggt ggatggcggg tggccacggg caggctcctt ccatgcctct   3480
tttgcccccc atgtgcttgg ctgccgggat caagtgattg ccgaaggcca gattgagttt   3540
gacatctcag agcctgaagt ggccgcaact gtgaaggttc cagaaggaaa gtccttggtt   3600
ttggtccgtg ttctagtggt gcctgcagaa aactatgact accaaatact tcacaaaaaa   3660
tccatggaca agtcactcga gtttatcacc aattgtggaa aaaacagctt ttaccttgac   3720
ccccagacag cctccagatt ctgtaagaat tccgccaggt ccctggtggc cttttaccac   3780
aagggcgccc tgccttgtga gtgccacccc actggggcca ccggccctca ctgcagccct   3840
gagggtgggc agtgcccatg ccagcccaac gtcatcgggc ggcagtgcac ccgctgtgca   3900
acaggccact acggattccc acgctgcaag ccgtgcagct gtggtcggcg cctttgtgaa   3960
gagatgacgg ggcagtgccg ctgccctccc cgcacggtca ggccccagtg tgaggtgtgt   4020
gagacacact cattcagctt ccaccccatg gccggctgcg aaggctgcaa ctgttccagg   4080
aggggcacca tcgaggctgc catgccggag tgtgaccggg acagcgggca gtgcagatgc   4140
aagcccagaa tcacagggcg gcagtgtgac cgatgtgctt ccgggtttta ccgctttcct   4200
gagtgtgttc cctgcaattg caacagagat gggactgagc caggagtgtg tgacccaggg   4260
accggggctt gcctctgcaa ggaaaatgta gaaggcacag agtgtaatgt gtgtcgagaa   4320
ggctcattcc atttggaccc agccaatctc aagggttgta ccagctgttt ctgttttgga   4380
gtaaataatc aatgtcacag ctcacataag cgaaggacta gtttgtggga tatgctgggc   4440
tggcacctgg agacagcaga cagagtggac atccctgtct ctttcaaccc aggcagcaac   4500
agtatggtgg cggatctcca ggagctgccc gcaaccatcc acagcgcgtc ctgggtcgca   4560
cccacctcct acctggggga caaggtttct tcatatggtg gttacctcac ttaccaagcc   4620
aagtcctttg gcttgcctgg cgacatggtt cttctggaaa agaagccgga tgtacagctc   4680
actggtcagc acatgtccat catctatgag gagacaaaca ccccacggcc agaccggctg   4740
catcatggac gagtgcacgt ggtcgaggga aacttcagac atgccagcag ccgtgcccca   4800
gtgtctaggg aggagctgat gacagtgctg tctagactgg cagatgtgcg catccaaggc   4860
ctctacttca cagagactca aaggctcacc ctgagcgagg tggggctaga ggaagcctct   4920
gacacaggaa gtgggcgcat agcacttgct gtggaaatct gtgcctgccc ccctgcctac   4980
gctggtgact cttgtcaggg ttgtagccct ggatactatc gggatcataa aggcttgtat   5040
accggacggt gtgttccctg caattgcaac ggacattcaa atcaatgcca ggatggctca   5100
ggcatatgtg ttaactgtca gcacaacacc gcgggagagc actgtgaacg ctgccaggag   5160
ggctactatg gcaacgccgt ccacggatcc tgcagggcct gcccatgtcc tcacactaac   5220
agctttgcca ctggctgtgt ggtgaatggg ggagacgtgc ggtgctcctg caaagctggg   5280
tacacaggaa cacagtgtga aaggtgtgca ccgggatatt cgggaatccc cagaaattc   5340 ggaggtagct gccaaccatg cagttgtaac agcaatggcc agctgggcag ctgtcatccc   5400
ctgactggag actgcataaa ccaagaaccc aaagatagca gccctgcaga agaatgtgat   5460
gattgcgaca ctgtgtgat gaccctcctg aacgacctgg ccaccatggg cgagcagctc   5520
cgcctggtca gtctcagct gcagggcctg agtgccagcg cagggcttct ggagcagatg   5580
aggcacatgg agacccaggc caaggacctg aggaatcagt tgctcaacta ccgttctgcc   5640
atttcaaatc atggatcaaa aatagaaggc ctggaaagag aactgactga tttgaatcaa   5700
```

```
gaatttgaga ctttgcaaga aaaggctcaa gtaaattcca gaaaagcaca aacattaaac    5760
aacaatgtta atcgggcaac acaaagcgca aaagaactgg atgtgaagat taaaaatgtc    5820
atccggaatg tgcacatgct gaaccggata aggacctggc agaaaaccca ccagggggag    5880
aacaatgggc ttgctaacag tatccgggat tctttaaatg aatacgaagc caaactcagt    5940
gaccttcgtg ctcggctgca ggaggcagct gcccaagcca agcaggcaaa tggcttgaac    6000
caagaaaacg agagagcttt gggagccatt cagagacaag tgaaagaaat aaattccctg    6060
cagagtgatt tcaccaagta tctaaccact gcagactcat ctttgttgca aaccaacatt    6120
gcgctgcagc tgatggagaa aagccagaag gaatatgaaa aattagctgc cagtttaaat    6180
gaagcaagac aagaactaag tgacaaagta agagaacttt ccagatctgc tggcaaaaca    6240
tcccttgtgg aggaggcaga aaagcacgcg cggtccttac aagagctggc aaagcagctg    6300
gaagagatca agagaaacgc cagcggggat gagctggtgc gctgtgctgt ggatgccgcc    6360
accgcctacg agaacatcct caatgccatc aaagcggccg aggacgcagc caacagggct    6420
gccagtgcat ctgaatctgc cctccagaca gtgataaagg aagatctgcc aagaaaagct    6480
aaaaccctga gttccaacag tgataaactg ttaaatgaag ccaagatgac acaaaagaag    6540
ctaaagcaag aagtcagtcc agctctcaac aacctacagc aaaccctgaa tattgtgaca    6600
gttcagaaag aagtgataga caccaatctc acaactctcc gagatggtct tcatgggata    6660
cagagaggtg atattgatgc tatgatcagt agtgcaaaga gcatggtcag aaaggccaac    6720
gacatcacag atgaggttct ggatgggctc aaccccatcc agacagatgt ggaaagaatt    6780
aaggacacct atgggaggac acagaacgaa gacttcaaaa aggctctgac tgatgcagat    6840
aactcggtga ataagttaac caacaaacta cctgatcttt ggcgcaagat tgaaagtatc    6900
aaccaacagc tgttgccctt gggaaacatc tctgacaaca tggacagaat acgagaacta    6960
attcagcagg ccagagatgc tgccagtaag gttgctgtcc ccatgaggtt caatggtaaa    7020
tctggagtcg aagtccgact gccaaatgac ctggaagatt tgaaaggata tacatctctg    7080
tccttgtttc tccaaaggcc caactcaaga gaaaatgggg gtactgagaa tatgtttgtg    7140
atgtaccttg gaaataaaga tgcctcccgg gactacatcg gcatggcagt tgtggatggc    7200
cagctcacct gtgtctacaa cctgggggac cgtgaggctg aactccaagt ggaccagatc    7260
ttgaccaaga gtgagactaa ggaggcagtt atggatcggg tgaaatttca gagaatttat    7320
cagtttgcaa ggcttaatta caccaaagga gccacatcca gtaaaccaga aacacccgga    7380
gtctatgaca tggatggtag aaatagcaat acactcctta atttggatcc tgaaaatgtt    7440
gtattttatg ttggaggtta cccacctgat tttaaacttc ccagtcgact aagtttccct    7500
ccatacaaag gttgtattga attagatgac ctcaatgaaa atgttctgag cttgtacaac    7560
ttcaaaaaaa cattcaatct caacacaact gaagtggagc cttgtagaag gaggaaggaa    7620
gagtcagaca aaaattattt tgaaggtacg ggctatgctc gagttccaac tcaaccacat    7680
gctcccatcc caacctttgg acagacaatt cagaccaccg tggatagagg cttgctgttc    7740
tttgcagaaa acgggggatcg cttcatatct ctaaatatag aagatggcaa gctcatggtg    7800
agatacaaac tgaattcaga gctaccaaaa gagagaggga ttggagacgc cataaacaac    7860
ggcagagacc attcgattca gatcaaaatt ggaaaactcc aaaagcgtat gtggataaat    7920
gtggacgttc aaaacactat aattgatggt gaagtatttg atttcagcac atattatctg    7980
ggaggaattc caattgcaat cagggaaaga tttaacattt ctacgcctgc tttccgaggc    8040
tgcatgaaaa atttgaagaa aaccagtggt gtcgttagat tgaatgatac tgtgggagta    8100
```

-continued

```
accaaaaagt gctcggaaga ctggaagctt gtgcgatctg cctcattctc cagaggagga    8160
caattgagtt tcactgattt gggcttacca cctactgacc acctccaggc ctcatttgga    8220
tttcagacct ttcaacccag tggcatatta ttagatcatc agacatggac aaggaacctg    8280
caggtcactc tggaagatgg ttacattgaa ttgagcacca gcgatagcgg cggcccaatt    8340
tttaaatctc cacagacgta tatggatggt ttactgcatt atgtatctgt aataagcgac    8400
aactctggac tacggcttct catcgatgac cagcttctga gaaatagcaa aaggctaaaa    8460
cacatttcaa gttcccggca gtctctgcgt ctgggcggga gcaattttga gggttgtatt    8520
agcaatgttt ttgtccagag gttatcactg agtcctgaag tcctagattt gaccagtaac    8580
tctctcaaga gagatgtgtc cctgggaggc tgcagtttaa acaaaccacc ttttctaatg    8640
ttgcttaaag gttctaccag gtttaacaag accaagactt ttcgtatcaa ccagctgttg    8700
caggacacac cagtggcctc cccaaggagc gtgaaggtgt ggcaagatgc ttgctcacca    8760
cttcccaaga cccaggccaa tcatggagcc ctccagtttg gggacattcc caccagccac    8820
ttgctattca agcttcctca ggagctgctg aaacccaggt cacagtttgc tgtggacatg    8880
cagacaacat cctccagagg actggtgttt cacacgggca ctaagaactc ctttatggct    8940
ctttatcttt caaaaggacg tctggtcttt gcactgggga cagatgggaa aaaattgagg    9000
atcaaaagca aggagaaatg caatgatggg aaatggcaca cggtggtgtt tggccatgat    9060
ggggaaaagg ggcgcttggt tgtggatgga ctgagggccc gggagggaag tttgcctgga    9120
aactccacca tcagcatcag agcgccagtt tacctgggat cacctccatc agggaaacca    9180
aagagcctcc ccacaaacag ctttgtggga tgcctgaaga actttcagct ggattcaaaa    9240
cccttgtata cccttcttc aagcttcggg gtgtcttcct gcttgggtgg tcctttggag    9300
aaaggcattt atttctctga agaaggaggt catgtcgtct tggctcactc tgtattgttg    9360
gggccagaat ttaagcttgt tttcagcatc cgcccaagaa gtctcactgg gatcctaata    9420
cacatcggaa gtcagcccgg gaagcactta tgtgtttacc tggaggcagg aaaggtcacg    9480
gcctctatgg acagtggggc aggtgggacc tcaacgtcgg tcacaccaaa gcagtctctg    9540
tgtgatggac agtggcactc ggtggcagtc accataaaac aacacatcct gcacctggaa    9600
ctggacacag acagtagcta cacagctgga cagatcccct tcccacctgc cagcactcaa    9660
gagccactac accttggagg tgctccagcc aatttgacga cactgaggat ccctgtgtgg    9720
aaatcattct ttggctgtct gaggaatatt catgtcaatc acatccctgt ccctgtcact    9780
gaagccttgg aagtccaggg gcctgtcagt ctgaatggtt gtcctgacca gtaa           9834
```

```
<210> SEQ ID NO 27
<211> LENGTH: 9834
<212> TYPE: DNA
<213> ORGANISM: Artificial Sequence
<220> FEATURE:
<223> OTHER INFORMATION: Synthetic Construct

<400> SEQUENCE: 27
atggctgctg ccgctagacc tagaggtaga gcactgggac ctgtgctgcc tcctacacct      60
ctgctgctgc tggtgctgag agtgcttcct gcttgtggcg ctaccgctag agatcctggt     120
gctgctgcag gactgtctct gcaccccacc tacttcaatc tggccgaggc cgccagaatc     180
tgggccacac tacatgtggg cgaaagaggc cctggcgaag cagacctca gcctgagctg     240 tattgcaagc tcgttggcgg ccctacagct cctggatctg acacacaat ccagggccag     300
```

```
ttctgcgact actgcaacag cgaggacccc agaaaggccc atcctgtgac caatgccatc      360
gacggctctg agagatggtg gcagtctcct ccactgagca gcggcaccca gtacaacaga      420
gtgaatctga ccctggacct gggccagctg tttcacgtgg cctacatcct gatcaagttc      480
gccaactctc cccggcctga tctgtgggtg ctcgagagat ctgtggactt cggcagcaca      540
tacagcccct ggcagtactt cgcccacagc aaggtggact gcctgaaaga gttcggccgc      600
gaggccaata tggccgtgac cagagatgac gacgtgctgt gcgtgaccga gtacagcaga      660
atcgtgcccc tggaaaacgg cgaggtggtg gtgtccctga tcaatggtag acctggcgcc      720
aagaacttca ccttcagcca cacactgaga gagttcacca aggccaccaa tatccggctg      780
cggttcctgc ggacaaatac cctgctgggc cacctgatct ctaaggccca aagggacccc      840
accgtgacac ggcggtacta ctacagcatc aaggacatca gcatcggcgg ccagtgcgtg      900
tgtaatggac atgccgaagt gtgcaacatc aacaacccg agaagctgtt cagatgcgag      960
tgccagcacc acacctgtgg cgagacatgc gatagatgct gcaccggcta caaccagaga     1020
agatggcgac ctgccgcctg ggagcagtct catgaatgcg aggcctgcaa ttgccacggc     1080
cacgccagca actgctacta cgaccccgat gtggaaagac agcaggccag cctgaatacc     1140
cagggcatct atgctggtgg cggcgtgtgc atcaactgtc agcataatac tgccggcgtg     1200
aactgcgagc agtgcgccaa gggctactac agaccttatg gcgtgccagt ggatgcccct     1260
gatggctgca tcccttgcag ctgtgatcct gagcatgccg acggctgtga caaggctct      1320 ggcagatgtc actgcaagcc caacttccac ggcgacaatt gcgagaagtg tgctatcggg     1380
tactacaact tcccattctg cctgcgcatc cctatcttcc ccgtgtctac acccagctct     1440
gaagatcctg tggccggcga tatcaagggc tgcgactgta atctggaagg cgtgctgcct     1500
gagatctgcg acgcccatgg aagatgcctg tgtagaccag gcgtggaagg ccccagatgc     1560
gatacctgta gatccggctt ctacagcttc cctatctgtc aggcctgctg gtgttctgcc     1620
ctgggcagct atcagatgcc ttgctctagc gtgaccggac agtgcgaatg cagacccggt     1680
gttaccggcc agagatgtga cagatgtctg agcggcgcct acgacttccc acactgtcag     1740
ggaagcagca gcgcctgtga tccagccggc accatcaata gcaacctggg ctactgccag     1800
tgcaagctgc acgtggaagg acctacctgc tctcggtgca aactgctgta ttggaacctg     1860
gacaaagaga acccagcgg ctgcagcgag tgcaagtgtc acaaagccgg cacagtgtct     1920
ggcaccggcg aatgtagaca aggcgacggc gattgccact gcaagtctca cgttggcgga     1980
gacagctgcg acacatgcga ggatggctac ttcgctctgg aaaagtccaa ctacttcgga     2040
tgccagggct gccagtgtga tattggcgga gccctgagca gcatgtgttc tggacctagc     2100
ggagtgtgcc agtgccggga acacgttgtg ggcaaagtct gtcagcggcc cgagaacaac     2160
tactacttcc ccgacctgca ccacatgaag tacgagatcg aggacggcag caccctaac      2220 ggcagagatc tgagattcgg cttcgaccct ctggcctttc ctgagttctc ttggagaggc     2280
tacgcccaga tgaccagcgt gcagaacgat gtgcggatca ccctgaacgt gggcaagagc     2340
agcggaagcc tgtttagagt gattctgaga tacgtgaacc ccggcaccga ggccgtgtct     2400
ggccacatca caatctaccc tagctggggc gctgcccaga gcaaagagat catcttcctg     2460
cctagcaaag aacccgcctt cgtgaccgtg cctggcaacg gatttgccga tcctttcagc     2520 atcacccag gcatctgggt cgcctgtatt aaggccgaag gcgtcctgct ggactacctg     2580
gttctgctcc ccagagacta ctacgaggcc tctgttctgc agctgcccgt gacagagcca     2640
tgtgcctatg ctggacctcc tcaagagaat tgcctgctgt accagcatct gcctgtgaca     2700
```

-continued

```
agattcccct gcacactggc ctgcgaagcc aggcactttc tgctggatgg cgagcctaga    2760
ccagtggccg ttagacagcc tacaccagct caccccgtga tggtggatct gtctggcaga    2820
gaggtggaac tgcacctgag actgagaatc cctcaagtgg ccactacgt ggtggtggtc     2880 gagtactcta cagaggccgc tcagctgttc gtggtggacg tgaacgtgaa gtccagcggc    2940
tctgtgctgg ccggacaagt gaacatctac tcttgcaact actccgtgct gtgtcggagc    3000
gccgtgatcg accacatgag ccggatcgct atgtacgagc tgctggccga tgccgacatc    3060
cagctgaagg gacacatggc cagatttctg ctgcaccaag tgtgcattat ccccatcgaa    3120
gagttcagcg ccgagtacgt cagaccccag gtgcactgta tcgccagcta cggcagattc    3180
gtgaaccaga gcgccacctg tgtgtctctg gcccacgaaa cacctccaac cgctctgatc    3240
ctggacgtgt tgagcggcag accatttcct catctgcccc agcagagcag cccttccgtt    3300
gatgttctgc ctggcgtgac cctgaaggca ccccagaatc aagtgacact gaggggcaga    3360
gtgccccacc tggcagata tgtgttcgtg atccacttct accaggctgc ccatcctaca     3420
ttccccgctc aagtgtcagt ggatggcgga tggcctagag ccggaagctt tcacgccagc    3480
ttttgccctc acgtgctggg ctgccgcgat caagtgattg ccgagggcca gatcgagttc    3540
gacatcagcg aacctgaagt ggccgccacc gtgaaagtgc ccgagggaaa atctctggtg    3600
ctcgtcagag tgctggtggt gcccgccgag aactacgact atcagatcct gcacaaaaag    3660
agcatggaca agagcctcga gttcatcacc aactgcggca agaactcctt ctatctggac    3720
cctcagaccg ccagccggtt ctgcaagaat agcgctagaa gcctggtggc tttctaccac    3780
aaaggcgccc tgccttgcga gtgtcatcca acaggtgcca ccggacctca ctgtagtcct    3840
gaaggtggcc agtgtccttg ccagcctaac gtgatcggca ggcagtgtac cagatgtgcc    3900
acaggccact atggcttccc tagatgcaag ccctgtagct gcggtagaag gctgtgcgaa    3960
gagatgaccg gccagtgtag gtgccctcct agaaccgtta gacccagtg tgaagtgtgc     4020 gaaacccaca gcttcagctt tcaccctatg gccggctgcg agggctgtaa ctgtagcaga    4080
agaggcacca tcgaggccgc tatgcccgag tgcgatagag acagcggaca gtgtcggtgc    4140
aagcctagaa tcaccggccg tcagtgcgac agatgcgcca gcggctttta cagatttccc    4200
gagtgtgtgc cctgcaactg caatcgcgac ggaacagaac ctggcgtgtg cgatcctgga    4260
acaggcgctt gcctgtgcaa agaaaatgtg gaaggcaccg agtgtaacgt gtgcagagag    4320
ggcagcttcc atctcgaccc cgccaatctg aagggctgta cctcctgctt ctgcttcgga    4380
gtgaacaacc agtgccacag cagccacaag cggcggacca agttcgtgga tatgctcggc    4440
tggcacctgg aaaccgccga cagagtggat atccctgtgt ccttcaatcc cggcagcaac    4500
agcatggtgg ccgatctgca agagctgcca gccacaattc acagcgcctc ttgggtcgcc    4560
cctacaagct atctgggcga caaggtgtcc tcctacggcg gctacctgac ataccaggcc    4620
aagtcctttg gactgcccgg cgacatggtc ctgctcgaga gaaacctga tgtgcagctg     4680 acaggacagc acatgagcat catctacgag gaaacaaaca cccctcggcc tgaccggctg    4740
catcacggaa gagtgcatgt ggtggaaggg aacttccggc acgcctcttc tagagcccct    4800
gtgtctcggg aagaactgat gaccgtgctg agcagactgg ccgacgttcg gattcagggc    4860
ctgtacttca ccgagactca gcggctgacc ctgtctgaag ttggactgga agaggccagc    4920
gataccggca gcggtagaat tgctctggcc gtggaaatct cgcctgtcc tccagcttat     4980 gccggcgatt cttgtcaggg atgtagccca ggctactaca gagatcacaa gggcctgtac    5040
```

-continued

```
accggcagat gcgtgccctg caactgtaac ggccacagca accagtgtca ggacggctct    5100
ggcatctgcg tgaactgcca gcataatact gccggcgagc actgcgagag atgccaagag    5160
ggctactacg gcaatgccgt gcatggcagc tgtcgggctt gtccttgtcc tcacaccaac    5220
agctttgcca ccggctgcgt tgtgaacggc ggagatgttc ggtgttcttg caaggccggc    5280
tacacaggca cacagtgcga aagatgtgcc cctggctact ttggcaaccc tcagaagttt    5340
ggcggctcct gccagccttg ctcctgcaat tctaatggcc agctgggctc ttgtcaccct    5400
ctgaccggcg actgcatcaa tcaagagcct aaggacagca gccctgccga ggaatgcgac    5460
gattgcgata gctgcgtgat gaccctgctg aacgacctgg ccacaatggg cgaacagctg    5520
agactggtca agtcccagct gcagggactg tctgcttctg ccggactgct ggaacagatg    5580
cggcacatgg aaacccaggc caaggacctg agaaaccagc tgctgaacta cagaagcgcc    5640
atctccaacc acggcagcaa gatcgaaggc ctggaaagag agctgaccga cctgaatcaa    5700
gagttcgaga cactgcaaga gaaggcccaa gtgaacagcc ggaaggccca gacactgaac    5760
aacaacgtga accgggccac acagagcgcc aaagaactgg acgtgaagat caagaacgtg    5820
atccggaacg tgcacatgct gaaccggatc agaacctggc agaaaaccca ccagggcgag    5880
aacaacggcc tggccaacag catcagagac agcctgaatg agtacgaggc caagctgagc    5940
gatctgcggg ccagacttca agaagctgcc gctcaggcca agcaggccaa cggccttaat    6000
caagagaacg agagagccct gggcgccatc cagagacaag tgaaagagat caacagcctg    6060
cagagcgact tcaccaagta cctgaccacc gccgatagca gcctgctgca gacaaatatc    6120
gcactgcagc tgatggaaaa gagccagaaa gagtacgaaa agctggccgc cagcctgaac    6180
gaggccagac aagagctgtc tgacaaagtg cgcgagctgt ctagaagcgc cggcaagaca    6240
tctctggtgg aagaggccga gaagcacgcc agatctctgc aagagctggc caaacagctg    6300
gaagagatta gcggaacgc cagcggcgac gaactcgtca gatgtgctgt ggatgccgcc    6360
accgcctacg agaacatcct gaatgccatc aaggccgccg aggacgccgc taatagagcc    6420
gcttctgcct ctgaaagcgc cctgcagacc gtgatcaaag aggacctgcc tagaaaggcc    6480
aagactctga gcagcaacag cgacaaactg ctgaatgagg ccaagatgac ccagaagaaa    6540
ctgaagcaag aggtgtcccc tgctctgaac aacctgcagc agaccctgaa catcgtgacc    6600
gtgcagaaag aagtgatcga caccaacctg acaaccctga gagatggcct gcacggaatc    6660
cagagaggcg acatcgacgc catgatcagc agcgccaaga gcatggttcg aaaagccaac    6720
gacatcaccg acgaggtgct ggacggcctg aatcctatcc agaccgacgt ggaacggatc    6780
aaggacacct acggcagaac ccagaacgag gatttcaaga aggccctgac cgacgccgac    6840
aactccgtga acaagctgac caacaagctg cccgatctgt ggcggaagat cgagagcatc    6900
aaccagcaac tgctgcccct gggcaacatc agcgacaaca tggacagaat ccgcgagctg    6960
atccagcagg ccagagatgc cgcctctaaa gtggccgtgc ctatgcggtt caatggcaag    7020
tctggcgtgg aagtgcggct gcccaacgat ctggaagatc tgaagggcta taccagcctg    7080
agcctgttcc tgcagaggcc caacagcaga gagaatggcg gcaccgagaa tatgttcgtg    7140
atgtacctgg aaacaaggga cgccagccgg gactatatcg gaatggccgt tgtggacggc    7200
cagctgacct gcgtgtacaa cctgggagat agagaagccg agctgcaggt cgaccagatc    7260
ctgaccaaga gcgagacaaa agaggccgtg atggacagag tgaagttcca gcggatctac    7320
cagttcgccc ggctgaatta caccaagggc gccacaagca gcaagcccga aacacctggc    7380
gtgtacgaca tggacggccg gaactctaac actctgctga atctggaccc cgagaacgtg    7440
```

-continued

```
gtgttttacg tcggcggcta ccctcctgac ttcaagctgc ctagcagact gagcttccca    7500
ccttacaagg gctgcatcga gctggatgac ctgaacgaaa acgtgctgtc cctgtacaac    7560
ttcaaaaaga ccttcaacct gaacaccacc gaggtggaac cctgcaggcg cagaaaagag    7620
gaatccgaca agaactactt cgaaggcacc ggctacgcca gagtgcctac acaacctcac    7680
gctcccattc ctaccttcgg ccagaccatc cagacaaccg tggatagagg cctgctgttc    7740
ttcgccgaga acggcgacag attcatctcc ctgaatatcg aggatggcaa gctgatggtc    7800
cgatacaagc tgaactccga gctgcccaaa gaaagaggcg tgggcgacgc catcaacaac    7860
ggcagggatc acagcatcca gatcaagatc ggcaagctgc agaaacggat gtggatcaac    7920
gtggacgtgc agaacaccat catcgacggc gaggtgttcg acttcagcac ctactatctc    7980
ggcggaatcc ctatcgccat cagagagcgg tttaacatca gcacccctgc cttccggggc    8040
tgcatgaaga acctgaaaaa gaccagcggc gtcgtgcggc tgaatgatac agtgggcgtg    8100
accaagaagt gcagcgagga ctggaagctt gtgcggagcg cctctttag cagaggcggg    8160 cagctgagct ttaccgatct gggactgcct cctaccgacc atctgcaggc aagcttcgga    8220
ttccagacct tccagcctag cggcatcctg ctggaccacc agacctggac cagaaacctg    8280
caagtgaccc tggaagatgg ctatatcgag ctgagcacca gcgactctgg cggccctatc    8340
tttaagagcc ctcagaccta catggatggg ctgctgcact acgtgtccgt gatcagcgat    8400
aacagcggcc tgagactgct gatcgacgac cagcttctgc ggaacagcaa gcggctgaag    8460
cacatcagca gcagcaggca gagtctgaga ctcggcggca gcaatttcga gggctgtatc    8520
agcaacgtgt tcgtgcagcg cctgagtctg tctcccgaag tgctggacct gaccagcaat    8580
agcctgaaga gggatgtgtc tctcggcggc tgctccctga acaaacctcc tttcctgatg    8640
ctgctcaagg gctccaccag attcaacaag accaagacct ttcggatcaa tcagctgctc    8700
caggacaccc ctgtggctag ccctagaagc gtgaaagtgt ggcaggacgc ctgcagtccc    8760
ctgcctaaaa cacaggccaa tcatgggggcc ctgcagttcg gcgatatccc cacaagccat    8820
ctgctgttta agctgccccca agagctgctc aaacctcgga gccagtttgc cgtggatatg    8880
cagaccacca gctccagagg actggtgttt cacaccggcc ccaagaacag cttcatggcc    8940
ctgtacctga gcaagggccg cctggtttttt gccctgggca cagacggcaa gaaactgcgg    9000
atcaagagca aagagaagtg caacgacggc aagtggcaca ccgtggtgtt cggacacgat    9060
ggcgagaaag gcagactggt ggtggatggc ctgagagcca gagaggggatc tctgcctggc    9120 aactccacca tctccatcag agcccctgtg tatctgggca gccctcctag cggaaagcct    9180
aagagcctgc ctaccaactc cttcgtgggc tgtctgaaga actttcagct ggacagcaag    9240
cctctgtaca cccctagcag cagctttggc gtgtcctcct gtctcggagg ccctctggaa    9300
aagggcatct acttctctga ggaaggcggc cacgttgtcc tggctcattc tgttttgctg    9360 ggcccccgagt tcaagctggt gttctccatt aggcccagaa gcctgacagg catcctgatt    9420
cacatcggca gccagcctgg caagcacctg tgtgtgtatc tcgaggccgg caaagtgacc    9480
gccagcatgg attctggtgc cggcggaaca agcacaagcg tgacacctaa gcagagcctg    9540
tgcgacggac agtggcatag tgtggccgtg accatcaagc agcacatcct gcacctggaa    9600
ctggacaccg acagcagcta taccgccgga cagatcccat ttcctccagc cagcacacaa    9660
gagcctctgc accttggagg cgcccctgcc aatctgacca cactgagaat ccccgtgtgg    9720
aagtccttct tcggctgcct gcggaatatc catgtgaacc acattccagt gcctgtgaca    9780
```

-continued

```
gaggccctgg aagtgcaggg acccgtgtct ctgaatggat gccccgatca gtga          9834

<210> SEQ ID NO 28
<211> LENGTH: 5007
<212> TYPE: DNA
<213> ORGANISM: Homo sapiens

<400> SEQUENCE: 28
atgcctccag cagtgaggcg gtcagcctgc agcatgggat ggctgtggat ctttggggca      60
gccctggggc agtgtctggg ctacagttca cagcagcaaa gggtgccatt tcttcagcct     120
cccggtcaaa gtcaactgca agcgagttat gtggagttta gacccagcca gggttgtagc     180
cctggatact atcgggatca taaaggcttg tataccggac ggtgtgttcc ctgcaattgc     240
aacggacatt caaatcaatg ccaggatggc tcaggcatat gtgttaactg tcagcacaac     300
accgcgggag agcactgtga acgctgccag gagggctact atggcaacgc cgtccacgga     360
tcctgcaggg cctgcccatg tcctcacact aacagctttg ccactggctg tgtggtgaat     420
gggggagacg tgcggtgctc ctgcaaagct gggtacacag aacacagtg tgaaaggtgt     480 gcaccgggat atttcgggaa tccccagaaa ttcggaggta gctgccaacc atgcagttgt     540
aacagcaatg gccagctggg cagctgtcat cccctgactg gagactgcat aaaccaagaa     600
cccaaagata gcagccctgc agaagaatgt gatgattgcg acagctgtgt gatgaccctc     660
ctgaacgacc tggccaccat gggcgagcag ctccgcctgg tcaagtctca gctgcagggc     720
ctgagtgcca gcgcagggct tctggagcag atgaggcaca tggagaccca ggccaaggac     780
ctgaggaatc agttgctcaa ctaccgttct gccatttcaa atcatggatc aaaaatagaa     840
ggcctggaaa gagaactgac tgatttgaat caagaatttg agactttgca agaaaaggct     900
caagtaaatt ccagaaaagc acaaacatta aacaacaatg ttaatcgggc aacacaaagc     960 gcaaagaac tggatgtgaa gattaaaaat gtcatccgga atgtgcacat gctgaaccgg    1020
ataaggacct ggcagaaaac ccaccagggg gagaacaatg gcttgctaa cagtatccgg    1080 gattctttaa atgaatacga agccaaactc agtgaccttc gtgctcggct gcaggaggca    1140
gctgcccaag ccaagcaggc aaatggcttg aaccaagaaa acgagagagc ttgggagcc    1200 attcagagac aagtgaaaga aataaattcc ctgcagagtg atttcaccaa gtatctaacc    1260
actgcagact catctttgtt gcaaaccaac attgcgctgc agctgatgga gaaaagccag    1320
aaggaatatg aaaaattagc tgccagttta aatgaagcaa gacaagaact aagtgacaaa    1380
gtaagagaac tttccagatc tgctggcaaa acatcccttg tggaggaggc agaaaagcac    1440
gcgcggtcct acaagagct ggcaaagcag ctggaagaga tcaagagaaa cgccagcggg    1500
gatgagctgg tgcgctgtgc cgtggatgcc gccaccgcct acgagaacat cctcaatgcc    1560
atcaaagcgg ccgaggacgc agccaacagg gctgccagtg catctgaatc tgccctccag    1620
acagtgataa aggaagatct gccaagaaaa gctaaacc tgagttccaa cagtgataaa    1680
ctgttaaatg aagccaagat gacacaaaag aagctaaagc aagaagtcag tccagctctc    1740
aacaacctac agcaaaccct gaatattgtg acagttcaga agaagtgat agacaccaat    1800 ctcacaactc tccgagatgg tcttcatggg atacagagag tgatattga tgctatgatc    1860 agtagtgcaa agagcatggt cagaaaggcc aacgacatca cagatgaggt tctggatggg    1920 ctcaaccca tccagacaga tgtggaaaga attaaggaca cctatgggag gacacagaac    1980
gaagacttca aaaaggctct gactgatgca gataactcgg tgaataagtt aaccaacaaa    2040
ctacctgatc tttggcgcaa gattgaaagt atcaaccaac agctgttgcc cttgggaaac    2100
```

-continued

```
atctctgaca acatggacag aaatacgagaa ctaattcagc aggccagaga tgctgccagt    2160
aaggttgctg tccccatgag gttcaatggt aaatctggag tcgaagtccg actgccaaat    2220
gacctggaag atttgaaagg atatacatct ctgtccttgt ttctccaaag gcccaactca    2280
agagaaaatg ggggtactga gaatatgttt gtgatgtacc ttggaaataa agatgcctcc    2340
cgggactaca tcggcatggc agttgtggat ggccagctca cctgtgtcta caacctgggg    2400
gaccgtgagg ctgaactcca agtggaccag atcttgacca agagtgagac taaggaggca    2460
gttatggatc gggtgaaatt tcagagaatt tatcagtttg caaggcttaa ttacaccaaa    2520
ggagccacat ccagtaaacc agaaacaccc ggagtctatg acatggatgg tagaaatagc    2580
aatacactcc ttaatttgga tcctgaaaat gttgtatttt atgttggagg ttacccacct    2640
gattttaaac ttcccagtcg actaagtttc cctccataca aaggttgtat tgaattagat    2700
gacctcaatg aaaatgttct gagcttgtac aacttcaaaa aaacattcaa tctcaacaca    2760
actgaagtgg agccttgtag aaggaggaag gaagagtcag acaaaaatta ttttgaaggt    2820
acgggctatg ctcgagttcc aactcaacca catgctccca tcccaacctt tggacagaca    2880
attcagacca ccgtggatag aggcttgctg ttctttgcag aaaacgggga tcgcttcata    2940
tctctaaata tagaagatgg caagctcatg gtgagataca aactgaattc agagctacca    3000
aaagagagag gagttggaga cgccataaac aacggcagag accattcgat tcagatcaaa    3060
attggaaaac tccaaaagcg tatgtggata aatgtggacg ttcaaaacac tataattgat    3120
ggtgaagtat ttgatttcag cacatattat ctgggaggaa ttccaattgc aatcagggaa    3180
agatttaaca tttctacgcc tgctttccga ggctgcatga aaaatttgaa gaaaaccagt    3240
ggtgtcgtta gattgaatga tactgtggga gtaaccaaaa agtgctcgga agactggaag    3300
cttgtgcgat ctgcctcatt ctccagagga ggacaattga gtttcactga tttgggctta    3360
ccacctactg accacctcca ggcctcattt ggatttcaga cctttcaacc cagtggcata    3420
ttattagatc atcagacatg gacaaggaac ctgcaggtca ctctggaaga tggttacatt    3480
gaattgagca ccagcgatag cggcggccca atttttaaat ctccacagac gtatatggat    3540
ggtttactgc attatgtatc tgtaataagc gacaactctg gactacggct tctcatcgat    3600
gaccagcttc tgagaaatag caaaaggcta aaacacattt caagttcccg gcagtctctg    3660
cgtctgggcg ggagcaattt tgagggttgt attagcaatg tttttgtcca gaggttatca    3720
ctgagtcctg aagtcctaga tttgaccagt aactctctca agagagatgt gtccctggga    3780
ggctgcagtt taaacaaacc accttttcta atgttgctta aaggtctac caggtttaac    3840 aagaccaaga cttttcgtat caaccagctg ttgcaggaca caccagtggc ctccccaagg    3900
agcgtgaagg tgtggcaaga tgcttgctca ccacttccca agacccaggc caatcatgga    3960
gccctccagt ttggggacat tcccaccagc cacttgctat tcaagcttcc tcaggagctg    4020
ctgaaaccca ggtcacagtt tgctgtggac atgcagacaa catcctccag aggactggtg    4080
tttcacacgg gcactaagaa ctcctttatg gctctttatc tttcaaaagg acgtctggtc    4140
tttgcactgg ggacagatgg gaaaaaattg aggatcaaaa gcaaggagaa atgcaatgat    4200
gggaaatggc acacggtggt gtttggccat gatgggggaaa aggggcgctt ggttgtggat    4260
ggactgaggg cccgggaggg aagtttgcct ggaaactcca ccatcagcat cagagcgcca    4320
gtttacctgg gatcacctcc atcagggaaa ccaaagagcc tccccacaaa cagctttgtg    4380
ggatgcctga agaactttca gctggattca aaacccttgt ataccccttc ttcaagcttc    4440
```

```
ggggtgtctt cctgcttggg tggtcctttg gagaaaggca tttatttctc tgaagaagga      4500
ggtcatgtcg tcttggctca ctctgtattg ttggggccag aatttaagct tgttttcagc      4560
atccgcccaa gaagtctcac tgggatccta atacacatcg gaagtcagcc cgggaagcac      4620
ttatgtgttt acctggaggc aggaaaggtc acggcctcta tggacagtgg ggcaggtggg      4680
acctcaacgt cggtcacacc aaagcagtct ctgtgtgatg gacagtggca ctcggtggca      4740
gtcaccataa aacaacacat cctgcacctg gaactggaca cagacagtag ctacacagct      4800
ggacagatcc ccttcccacc tgccagcact caagagccac tacaccttgg aggtgctcca      4860
gccaatttga cgacactgag gatccctgtg tggaaatcat tctttggctg tctgaggaat      4920
attcatgtca atcacatccc tgtccctgtc actgaagcct tggaagtcca ggggcctgtc      4980
agtctgaatg gttgtcctga ccagtaa                                          5007

<210> SEQ ID NO 29
<211> LENGTH: 5007
<212> TYPE: DNA
<213> ORGANISM: Artificial Sequence
<220> FEATURE:
<223> OTHER INFORMATION: Synthetic Construct

<400> SEQUENCE: 29
atgcctcctg ctgtgcggag aagcgcctgt tctatgggat ggctgtggat ctttggcgcc        60
gctctgggac agtgtctggg ctactcttct cagcagcagc gggtgccatt tctgcagcca       120
cctggacagt ctcagctgca ggccagctac gtggaatttc ggcctagcca gggatgcagc       180
ccaggctact acagagatca caagggcctg tacaccggca gatgcgtgcc ctgcaactgt       240
aacggccaca gcaaccagtg tcaggacggc tctggcatct gcgtgaactg ccagcataat       300
actgccggcg agcactgcga gagatgccaa gagggctact acggcaatgc cgtgcatggc       360
agctgtcggg cttgtccttg tcctcacacc aacagctttg ccaccggctg cgttgtgaac       420
ggcggagatg ttcggtgttc ttgcaaggcc ggctacacag gcacacagtg cgaaagatgt       480
gcccctggct actttggcaa ccctcagaag tttggcggct cctgccagcc ttgctcctgc       540
aattctaatg ccagctgggg ctcttgtcac cctctgaccg gcgactgcat caatcaagag       600
cctaaggaca gcagccctgc cgaggaatgc gacgattgcg atagctgcgt gatgaccctg       660
ctgaacgacc tggccacaat gggagaacag ctgcggctgg ttaagagcca gctccaggga       720
ctgtctgcct ctgctggact gctggaacag atgcggcaca tggaaaccca ggccaaggac       780
ctgagaaacc agctgctgaa ctacagaagc gccatctcca ccacggcag caagatcgaa       840 ggcctggaaa gagagctgac cgacctgaat caagagttcg agacactgca agagaaggcc       900
caagtgaaca gccggaaggc cccagactct aacaacaacg tgaaccgggc cacacagtcc       960
gccaaagaac tggacgtgaa gatcaagaac gtgatccgga acgtgcacat gctgaaccgg      1020
atcagaacct ggcagaaaac ccaccagggc gagaacaacg ccctggccaa cagcatcaga      1080
gacagcctga tgagtacga ggccaagctg agcgatctgc gggccagact tcaagaagct      1140
gccgctcagg ccaagcaggc caacggcctt aatcaagaga cgagagagc cctgggcgcc      1200 atccagagac aagtgaaaga gatcaacagc ctgcagagcg acttcaccaa gtacctgacc      1260
accgccgata gcagcctgct gcagacaaat atcgccctgc agctcatgga aaagagccag      1320
aaagagtacg aaaagctggc cgccagcctg aacgaggcca gacaagagct gtctgacaaa      1380
gtgcgcgagc tgtctagaag cgccggcaag acatctctgg tggaagaggc cgagaagcac      1440
gccagatctc tgcaagagct ggccaaacag ctggaagaga ttaagcggaa cgccagcggc      1500
```

-continued

```
gacgaactcg tcagatgtgc agtggatgcc gccaccgcct acgagaacat cctgaatgcc   1560
atcaaggccg ccgaggacgc cgctaataga gccgcttctg cttctgagtc tgccctgcag   1620
accgtgatca aagaggacct gcctagaaag gccaagacac tgagcagcaa cagcgacaaa   1680
ctgctgaatg aggccaagat gacccagaag aaactgaagc aagaggtgtc ccctgcactg   1740
aacaacctgc agcagaccct gaacatcgtg accgtgcaga agaagtgat cgacaccaac   1800 ctgacaaccc tgagagatgg cctgcacgga atccagagag cgacatcga cgccatgatc   1860 agcagcgcca agagcatggt tcgaaaagcc aacgacatca ccgacgaggt gctggacggc   1920
ctgaatccta tccagaccga cgtggaacgg atcaaggaca cctacggcag aacccagaac   1980
gaggatttca agaaggccct gaccgacgcc gacaactccg tgaacaagct gaccaacaag   2040
ctgcccgatc tgtggcggaa gatcgagagc atcaaccagc aactgctgcc cctgggcaac   2100
atcagcgaca acatggacag aatccgcgag ctgatccagc aggccagaga tgccgcctct   2160
aaagtggccg tgcctatgcg gttcaatggc aagtctggcg tggaagtgcg gctgcccaac   2220
gatctggaag atctgaaggg ctataccagc ctgagcctgt tcctgcagag gcccaacagc   2280
agagagaatg gcggcaccga gaatatgttc gtgatgtacc tgggaaacaa ggacgccagc   2340
cgggactata tcggaatggc cgttgtggac ggccagctga cctgcgtgta caacctggga   2400
gatagagaag ccgaactgca ggtcgaccag atcctgacca agagcgagac aaaagaggcc   2460
gtgatggaca gagtgaagtt ccagcggatc taccagttcg cccggctgaa ttacaccaag   2520
ggcgccacaa gcagcaagcc cgaaacacct ggcgtgtacg acatggacgg ccggaactct   2580
aacactctgc tgaatctgga ccccgagaac gtggtgtttt acgtcggcgg ctaccctcct   2640
gacttcaagc tgcctagcag actgagcttc ccaccttaca agggctgtat cgagctggat   2700
gacctgaacg aaaacgtgct gtccctgtac aacttcaaaa agaccttcaa cctgaacacc   2760
accgaggtgg aaccctgcag gcgcagaaaa gaggaatccg acaagaacta cttcgaaggc   2820
accggctacg ccagagtgcc tacacaacct cacgctccca ttcctacctt cggccagacc   2880
atccagacaa ccgtggatag aggcctgctg ttcttcgccg agaacggcga cagattcatc   2940
tccctgaata tcgaggatgg caagctgatg gtccgataca agctgaactc cgagctgccc   3000
aaagaaagag gcgtgggcga cgccatcaac aacggcaggg atcacagcat ccagatcaag   3060
atcggcaaac tgcagaaacg gatgtggatc aacgtggacg tgcagaacac catcatcgac   3120
ggcgaggtgt cgacttcag cacctactat ctcggcggaa tccctatcgc catcagagag   3180
cggtttaaca tcagcacccc tgccttccgg ggctgcatga agaacctgaa aaagaccagc   3240
ggcgtcgtgc ggctgaatga tacagtgggc gtgaccaaga agtgcagcga ggactggaag   3300
cttgtgcgga gcgcctcttt tagtagaggc ggacagctga gcttcaccga cctgggattg   3360
cctccaaccg atcatctgca ggcaagcttc ggattccaga ccttccagcc tagcggcatc   3420
ctgctggacc accagacctg gaccagaaac ctgcaagtga ccctggaaga tggctacatc   3480
gagctgagca ccagcgattc tggcggccct atcttcaaga gccctcagac ctacatggat   3540
gggctgctgc actacgtgtc cgtgatcagc gataacagcg gcctgagact gctgatcgac   3600
gaccagcttc tgcggaacag caagcggctg aagcacatca gctccagcag acagagtctg   3660
agactcggcg gcagcaattt cgagggatgc atcagcaacg tgttcgtgca gcgcctgtct   3720
ctgtctcccg aagtgctgga cctgaccagc aatagcctga gagggatgt gtctctcggc   3780 ggctgctccc tgaacaaacc tccttttcctg atgctgctga agggcagcac ccggttcaac   3840
```

-continued

```
aagaccaaga cctttcggat caatcagctg ctccaggaca cccctgtggc tagccctaga    3900
agcgtgaaag tgtggcagga cgcctgcagt cccctgccta aaacacaggc caatcacggg    3960
gccctccagt tcggcgatat ccctacaagc catctgctgt ttaagctgcc ccaagagctg    4020
ctcaagcctc ggagccagtt cgctgtggat atgcagacca cctcctccag aggactggtg    4080
tttcacaccg gcaccaagaa cagcttcatg gccctgtacc tgagcaaagg caggctggtg    4140
tttgccctgg gcaccgacgg aaagaaactg cggatcaaga gcaaagagaa gtgcaacgac    4200
ggcaagtggc acaccgtggt gttcggacac gatggcgaga aaggcagact cgtggtggat    4260
ggcctgagag ccagagaggg atctctgcct ggcaactcca ccatctccat cagagcccct    4320
gtgtatctgg gcagccctcc tagcggaaag cctaagagcc tgcctaccaa ctccttcgtg    4380
ggctgtctga agaactttca gctggacagc aagcctctgt acacccctag cagcagcttt    4440
ggcgtgtcct cctgtctcgg aggccctctg gaaaagggca tctacttctc tgaggaaggc    4500
ggccacgttg tcctggctca ttctgttttg ctgggccccg agttcaagct ggtgttctcc    4560
attaggccca gaagcctgac aggcatcctg attcacatcg gcagccagcc tggcaagcac    4620
ctgtgtgtgt atctcgaggc cggcaaagtg accgccagca tggatagcgg agctggcggc    4680
acaagcacat ccgtgacacc taagcagagc ctgtgcgacg gacagtggca tagtgtggcc    4740
gtgaccatca gcagcacat tctgcacctg gaactggaca ccgacagcag ctataccgcc    4800
ggacagatcc catttcctcc agccagcaca caagagcctc tgcaccttgg aggcgcccct    4860
gccaatctga ccacactgag aatccccgtg tggaagtcct tcttcggctg cctgcggaat    4920
atccatgtga accacattcc agtgcctgtg acagaggccc tggaagtgca gggacccgtg    4980
tctctgaatg gatgccccga tcagtga                                        5007

<210> SEQ ID NO 30
<211> LENGTH: 3336
<212> TYPE: DNA
<213> ORGANISM: Homo sapiens

<400> SEQUENCE: 30
atgcctgcgc tctggctggg ctgctgcctc tgcttctcgc tcctcctgcc cgcagcccgg      60
gccacctcca ggagggaagt ctgtgattgc aatgggaagt ccaggcagtg tatctttgat     120
cgggaacttc acagacaaac tggtaatgga ttccgctgcc tcaactgcaa tgacaacact     180
gatggcattc actgcgagaa gtgcaagaat ggcttttacc ggcacagaga aagggaccgc     240
tgtttgccct gcaattgtaa ctccaaaggt tctcttagtg ctcgatgtga caactccgga     300
cggtgcagct gtaaaccagg tgtgacagga gccagatgcg accgatgtct gccaggcttc     360
cacatgctca cggatgcggg gtgcacccaa gaccagagac tgctagactc caagtgtgac     420 tgtgaccag ctggcatcgc agggccctgt gacgcgggcc gctgtgtctg caagccagct     480
gtcactggag aacgctgtga taggtgtcga tcaggttact ataatctgga tgggggggaac     540 cctgagggct gtacccagtg tttctgctat gggcattcag ccagctgccg cagctctgca     600
gaatacagtg tccataagat cacctctacc tttcatcaag atgttgatgg ctggaaggct     660
gtccaacgaa atgggtctcc tgcaaagctc caatggtcac agcgccatca agatgtgttt     720
agctcagccc aacgactaga ccctgtctat tttgtggctc ctgccaaatt tcttgggaat     780
caacaggtga gctatggtca aagcctgtcc tttgactacc gtgtggacag aggaggcaga     840
cacccatctg cccatgatgt gattctggaa ggtgctggtc tacggatcac agctcccttg     900
atgccacttg gcaagacact gccttgtggg ctcaccaaga cttacacatt caggttaaat    960
```

-continued

```
gagcatccaa gcaataattg gagcccccag ctgagttact ttgagtatcg aaggttactg   1020
cggaatctca cagccctccg catccgagct acatatggag aatacagtac tgggtacatt   1080
gacaatgtga ccctgatttc agcccgccct gtctctggag ccccagcacc ctgggttgaa   1140
cagtgtatat gtcctgttgg gtacaagggg caattctgcc aggattgtgc ttctggctac   1200
aagagagatt cagcgagact ggggcctttt ggcacctgta ttccttgtaa ctgtcaaggg   1260
ggaggggcct gtgatccaga cacaggagat tgttattcag gggatgagaa tcctgacatt   1320
gagtgtgctg actgcccaat tggtttctac aacgatccgc acgaccccg cagctgcaag    1380 ccatgtccct gtcataacgg gttcagctgc tcagtgatgc cggagacgga ggaggtggtg   1440
tgcaataact gccctcccgg ggtcaccggt gcccgctgtg agctctgtgc tgatggctac   1500
tttggggacc cctttggtga acatggccca gtgaggcctt gtcagccctg tcaatgcaac   1560
aacaatgtgg accccagtgc ctctgggaat tgtgaccggc tgacaggcag gtgtttgaag   1620
tgtatccaca acacagccgg catctactgc gaccagtgca aagcaggcta cttcgggac    1680 ccattggctc ccaacccagc agacaagtgt cgagcttgca actgtaaccc catgggctca   1740
gagcctgtag gatgtcgaag tgatggcacc tgtgtttgca agccaggatt tggtggcccc   1800
aactgtgagc atggagcatt cagctgtcca gcttgctata atcaagtgaa gattcagatg   1860
gatcagttta tgcagcagct tcagagaatg gaggccctga tttcaaaggc tcagggtggt   1920
gatggagtag tacctgatac agagctggaa ggcaggatgc agcaggctga gcaggccctt   1980
caggacattc tgagagatgc ccagatttca gaaggtgcta gcagatccct tggtctccag   2040
ttggccaagg tgaggagcca agagaacagc taccagagcc gcctggatga cctcaagatg   2100
actgtggaaa gagttcgggc tctgggaagt cagtaccaga accgagttcg ggatactcac   2160
aggctcatca ctcagatgca gctgagcctg gcagaaagtg aagcttcctt gggaaacact   2220
aacattcctg cctcagacca ctacgtgggg ccaaatggct ttaaaagtct ggctcaggag   2280
gccacaagat tagcagaaag ccacgttgag tcagccagta catggagca actgacaagg    2340 gaaactgagg actattccaa acaagccctc tcactggtgc gcaaggccct gcatgaagga   2400
gtcggaagcg gaagcggtag cccggacggt gctgtggtgc aagggcttgt ggaaaaattg   2460
gagaaaacca gtccctggc ccagcagttg acaaggagg ccactcaagc ggaaattgaa      2520
gcagataggt cttatcagca cagtctccgc ctcctggatt cagtgtctcg gcttcaggga   2580
gtcagtgatc agtcctttca ggtggaagaa gcaaagagga tcaaacaaa agcggattca    2640 ctctcaagcc tggtaaccag gcatatggat gagttcaagc gtacacagaa gaatctggga   2700
aactggaaag aagaagcaca gcagctctta cagaatggaa aaagtgggag agagaaatca   2760
gatcagctgc tttcccgtgc caatcttgct aaaagcagag cacaagaagc actgagtatg   2820
ggcaatgcca cttttttatga agttgagagc atccttaaaa acctcagaga gtttgacctg   2880
caggtggaca acagaaaagc agaagctgaa gaagccatga gagactctc ctacatcagc     2940 cagaaggttt cagatgccag tgacaagacc cagcaagcag aaagagccct ggggagcgct    3000
gctgctgatg cacagagggc aaagaatggg gccgggggagg ccctggaaat ctccagtgag   3060
attgaacagg agattgggag tctgaacttg gaagccaatg tgacagcaga tggagccttg   3120
gccatggaaa agggactggc ctctctgaag agtgagatga gggaagtgga aggagagctg   3180
gaaaggaagg agctggagtt tgacacgaat atggatgcag tacagatggt gattacagaa   3240
gcccagaagg ttgataccag agccaagaac gctggggtta caatccaaga cacactcaac    3300
```

```
acattagacg gcctcctgca tctgatgggt atgtga                         3336

<210> SEQ ID NO 31
<211> LENGTH: 3336
<212> TYPE: DNA
<213> ORGANISM: Artificial Sequence
<220> FEATURE:
<223> OTHER INFORMATION: Synthetic Construct

<400> SEQUENCE: 31
atgcctgctc tgtggctggg ctgctgcctg tgttttagtc tgctgctgcc agccgccaga      60
gccacatcta gaagagaagt gtgcgactgc aacggcaaga gccggcagtg catcttcgac     120
agagagctgc acagacagac cggcaacggc ttcagatgcc tgaactgcaa cgacaacacc     180
gacggcatcc actgcgagaa gtgcaagaac ggcttctacc ggcaccgcga gagggataga     240
tgcctgcctt gcaactgcaa ctccaagggc agcctgagcg ccagatgcga caatagcggc     300
agatgtagct gcaagcctgg cgtgacaggc gctagatgcg atagatgtct ccccggcttc     360
cacatgctga ccgatgccgg atgtacccag gaccagagac tgctggacag caagtgcgat     420
tgcgaccctg ccggaattgc cggaccttgt gatgccggaa gatgcgtgtg taaacctgcc     480
gtgaccggcg agagatgtga cagatgtaga agcggctact acaacctgga cggcggcaat     540
cctgaaggct gcacccagtg cttttgctac ggccacagcg ccagctgtag aagcagcgcc     600
gaatactccg tgcacaagat caccagcacc ttccaccagg atgtggacgg atggaaggcc     660
gtgcagagaa atggctctcc tgccaagctg cagtggtccc agagacacca ggacgtgttc     720
agcagcgctc agagactgga ccccgtgtac tttgtggccc ctgccaagtt cctgggcaac     780
cagcaagtgt cttacggcca gagcctgagc ttcgactaca gagtggatag aggcggcaga     840 cacccccagcg ctcacgatgt gattcttgaa ggcgccggac tgcggatcac agcccctctt     900
atgcctctgg gcaagaccct gccttgtggc ctgaccaaga cctacacctt ccggctgaat     960
gagcacccca gcaacaactg gtccccacag ctgagctact cgagtacag acggctgctg    1020 cggaacctga cagccctgag aatcagagcc acctacggcg agtacagcac cggctacatc    1080
gacaacgtga ccctgatcag cgccagacct gtttctggtg ctcctgctcc ttgggtcgag    1140
cagtgtatct gtcccgtggg ctacaagggc cagttctgcc aggattgtgc cagcggctac    1200
aagagagact ctgccagact gggccccttc ggcacatgca tcccttgtaa ttgtcaaggc    1260
ggcggagcct gcgatcccga tacaggcgat tgctacagcg gcgacgagaa ccccgatatc    1320
gagtgcgccg attgtcccat cggctttttac aacgaccctc acgaccccag atcctgcaag    1380
ccatgtcctt gccacaatgg cttcagctgc agcgtgatgc ccgaaaccga agaggtcgtg    1440
tgcaacaatt gcccaccagg cgttacaggg ccagatgtg aactgtgtgc cgacggctac    1500
ttcggcgatc ctttttggaga acacggaccc gtgcgacctt gccagccttg tcagtgcaac    1560
aacaacgtgg acccaagcgc cagcggcaac tgcgatagac tgacaggcag atgtctgaag    1620
tgcatccaca ataccgccgg gatctactgt gaccagtgca aggccggcta ttttggcgac    1680
cctctggctc ccaatcctgc cgataagtgc agagcctgca actgtaaccc tatgggctct    1740
gagcctgtgg gctgcagatc tgatggaacc tgcgtgtgca agccaggctt ggcggacct    1800 aattgtgaac acggcgcctt tagctgcccc gcctgctaca tcaagtgaa gatccagatg    1860 gaccagttca tgcagcagct gcagaggatg gaagccctga tctctaaagc ccaaggcgga    1920
gatgcgtgtg tgcctgatac agagctggaa ggcagaatgc agcaggccga acaggccctg    1980
caggacattc tgagagatgc ccagattagc gagggcgcct ctagaagtct gggactgcag    2040
```

```
ctggctaaag tgcggagcca agagaacagc taccagagca gactggacga cctgaagatg    2100
accgtggaaa gagtcagagc cctgggcagc cagtaccaga acagagtgcg ggatacccac    2160
cggctgatca cccagatgca actgtctctg gccgagagcg aagccagcct gggcaatacc    2220
aatattcccg ccagcgacca ctacgtgggc cccaacggtt ttaagagcct ggctcaagag    2280
gccaccagac tggccgaaag ccatgtggaa agcgcctcca acatggaaca gctgacccgg    2340
gaaaccgagg actactctaa gcaggccctg agcctcgtca gaaaagccct gcatgaaggc    2400
gtcggcagcg gctctggatc tcctgatggt gctgtggtgc agggactcgt ggaaaagctg    2460
gaaaagacca aatctctggc ccagcagctg accagagaag ccacacaggc cgagatcgag    2520
gccgacagaa gctaccagca ctcactgagg ctgctggact ccgtgtctag actgcagggc    2580
gtgtccgacc agagcttcca ggtggaagag gccaagcgga tcaagcagaa ggccgatagc    2640
ctgagcagcc tggtcaccag acacatggac gagttcaagc ggacccagaa gaacctcggc    2700
aactggaaag aggaagccca gcaactgctg cagaacggca gtctggaag agagaagtct    2760 gaccagctgc tgagcagagc caacctggcc aagtctagag cccaagaggc cctgtctatg    2820
ggcaacgcca ccttctacga ggtggaatcc atcctgaaga acctgcgcga gttcgacctg    2880
caagtggaca acagaaaggc cgaggccgag gaagccatga agagactgag ctacatcagc    2940
cagaaagtgt ccgacgcctc cgacaagaca cagcaggcag aaagagcact gggatctgcc    3000
gcagccgatg ctcagagagc taaaaacggc gctggcgagg ccctggaaat cagctctgag    3060
atcgagcaag agatcggctc cctgaatctg gaagccaatg tgacagccga tggcgccctg    3120
gccatggaaa aaggactggc ctctctgaag tccgagatga gagaggtgga aggcgagctg    3180
gaacggaaag aactggaatt cgacaccaat atggacgctg tgcagatggt catcacagag    3240
gcccagaagg tggacaccag agccaaaaat gccggcgtga ccatccagga caccctgaat    3300
actctggacg gactgctgca cctgatgggc atgtaa                              3336
```

```
<210> SEQ ID NO 32
<211> LENGTH: 3333
<212> TYPE: PRT
<213> ORGANISM: Homo sapiens

<400> SEQUENCE: 32

Met Ala Ala Ala Ala Arg Pro Arg Gly Arg Ala Leu Gly Pro Val Leu
1               5                   10                  15

Pro Pro Thr Pro Leu Leu Leu Leu Val Leu Arg Val Leu Pro Ala Cys
                20                  25                  30

Gly Ala Thr Ala Arg Asp Pro Gly Ala Ala Ala Gly Leu Ser Leu His
            35                  40                  45

Pro Thr Tyr Phe Asn Leu Ala Glu Ala Ala Arg Ile Trp Ala Thr Ala
        50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
                85                  90                  95

Ile Gln Gly Gln Phe Cys Asp Tyr Cys Asn Ser Glu Asp Pro Arg Lys
            100                 105                 110

Ala His Pro Val Thr Asn Ala Ile Asp Gly Ser Glu Arg Trp Trp Gln
        115                 120                 125

Ser Pro Pro Leu Ser Ser Gly Thr Gln Tyr Asn Arg Val Asn Leu Thr
        130                 135                 140
```

```
Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                165                 170                 175

Phe Gly Ser Thr Tyr Ser Pro Trp Gln Tyr Phe Ala His Ser Lys Val
                180                 185                 190

Asp Cys Leu Lys Glu Phe Gly Arg Glu Ala Asn Met Ala Val Thr Arg
            195                 200                 205

Asp Asp Asp Val Leu Cys Val Thr Glu Tyr Ser Arg Ile Val Pro Leu
        210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
                245                 250                 255

Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Arg Tyr Tyr Tyr
            275                 280                 285

Ser Ile Lys Asp Ile Ser Ile Gly Gly Gln Cys Val Cys Asn Gly His
        290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
                325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
            355                 360                 365

Pro Asp Val Glu Arg Gln Gln Ala Ser Leu Asn Thr Gln Gly Ile Tyr
        370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
                405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
        435                 440                 445

Phe His Gly Asp Asn Cys Glu Lys Cys Ala Ile Gly Tyr Tyr Asn Phe
    450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
                485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
            515                 520                 525

Ser Phe Pro Ile Cys Gln Ala Cys Trp Cys Ser Ala Leu Gly Ser Tyr
        530                 535                 540

Gln Met Pro Cys Ser Ser Val Thr Gly Gln Cys Glu Cys Arg Pro Gly
545                 550                 555                 560
```

-continued

```
Val Thr Gly Gln Arg Cys Asp Arg Cys Leu Ser Gly Ala Tyr Asp Phe
            565             570             575

Pro His Cys Gln Gly Ser Ser Ser Ala Cys Asp Pro Ala Gly Thr Ile
        580             585             590

Asn Ser Asn Leu Gly Tyr Cys Gln Cys Lys Leu His Val Glu Gly Pro
        595             600             605

Thr Cys Ser Arg Cys Lys Leu Leu Tyr Trp Asn Leu Asp Lys Glu Asn
    610             615             620

Pro Ser Gly Cys Ser Glu Cys Lys Cys His Lys Ala Gly Thr Val Ser
625             630             635             640

Gly Thr Gly Glu Cys Arg Gln Gly Asp Gly Asp Cys His Cys Lys Ser
            645             650             655

His Val Gly Gly Asp Ser Cys Asp Thr Cys Glu Asp Gly Tyr Phe Ala
            660             665             670

Leu Glu Lys Ser Asn Tyr Phe Gly Cys Gln Gly Cys Gln Cys Asp Ile
        675             680             685

Gly Gly Ala Leu Ser Ser Met Cys Ser Gly Pro Ser Gly Val Cys Gln
        690             695             700

Cys Arg Glu His Val Val Gly Lys Val Cys Gln Arg Pro Glu Asn Asn
705             710             715             720

Tyr Tyr Phe Pro Asp Leu His His Met Lys Tyr Glu Ile Glu Asp Gly
            725             730             735

Ser Thr Pro Asn Gly Arg Asp Leu Arg Phe Gly Phe Asp Pro Leu Ala
            740             745             750

Phe Pro Glu Phe Ser Trp Arg Gly Tyr Ala Gln Met Thr Ser Val Gln
            755             760             765

Asn Asp Val Arg Ile Thr Leu Asn Val Gly Lys Ser Ser Gly Ser Leu
        770             775             780

Phe Arg Val Ile Leu Arg Tyr Val Asn Pro Gly Thr Glu Ala Val Ser
785             790             795             800

Gly His Ile Thr Ile Tyr Pro Ser Trp Gly Ala Ala Gln Ser Lys Glu
            805             810             815

Ile Ile Phe Leu Pro Ser Lys Glu Pro Ala Phe Val Thr Val Pro Gly
            820             825             830

Asn Gly Phe Ala Asp Pro Phe Ser Ile Thr Pro Gly Ile Trp Val Ala
        835             840             845

Cys Ile Lys Ala Glu Gly Val Leu Leu Asp Tyr Leu Val Leu Leu Pro
    850             855             860

Arg Asp Tyr Tyr Glu Ala Ser Val Leu Gln Leu Pro Val Thr Glu Pro
865             870             875             880

Cys Ala Tyr Ala Gly Pro Pro Gln Glu Asn Cys Leu Leu Tyr Gln His
            885             890             895

Leu Pro Val Thr Arg Phe Pro Cys Thr Leu Ala Cys Glu Ala Arg His
            900             905             910

Phe Leu Leu Asp Gly Glu Pro Arg Pro Val Ala Val Arg Gln Pro Thr
        915             920             925

Pro Ala His Pro Val Met Val Asp Leu Ser Gly Arg Glu Val Glu Leu
    930             935             940

His Leu Arg Leu Arg Ile Pro Gln Val Gly His Tyr Val Val Val Val
945             950             955             960

Glu Tyr Ser Thr Glu Ala Ala Gln Leu Phe Val Val Asp Val Asn Val
            965             970             975

Lys Ser Ser Gly Ser Val Leu Ala Gly Gln Val Asn Ile Tyr Ser Cys
```

-continued

```
                980             985             990
Asn Tyr Ser Val Leu Cys Arg Ser Ala Val Ile Asp His Met Ser Arg
        995             1000            1005

Ile Ala Met Tyr Glu Leu Leu Ala Asp Ala Asp Ile Gln Leu Lys Gly
    1010            1015            1020

His Met Ala Arg Phe Leu Leu His Gln Val Cys Ile Ile Pro Ile Glu
1025            1030            1035            1040

Glu Phe Ser Ala Glu Tyr Val Arg Pro Gln Val His Cys Ile Ala Ser
            1045            1050            1055

Tyr Gly Arg Phe Val Asn Gln Ser Ala Thr Cys Val Ser Leu Ala His
            1060            1065            1070

Glu Thr Pro Pro Thr Ala Leu Ile Leu Asp Val Leu Ser Gly Arg Pro
        1075            1080            1085

Phe Pro His Leu Pro Gln Gln Ser Ser Pro Ser Val Asp Val Leu Pro
    1090            1095            1100

Gly Val Thr Leu Lys Ala Pro Gln Asn Gln Val Thr Leu Arg Gly Arg
1105            1110            1115            1120

Val Pro His Leu Gly Arg Tyr Val Phe Val Ile His Phe Tyr Gln Ala
            1125            1130            1135

Ala His Pro Thr Phe Pro Ala Gln Val Ser Val Asp Gly Gly Trp Pro
            1140            1145            1150

Arg Ala Gly Ser Phe His Ala Ser Phe Cys Pro His Val Leu Gly Cys
        1155            1160            1165

Arg Asp Gln Val Ile Ala Glu Gly Gln Ile Glu Phe Asp Ile Ser Glu
    1170            1175            1180

Pro Glu Val Ala Ala Thr Val Lys Val Pro Glu Gly Lys Ser Leu Val
1185            1190            1195            1200

Leu Val Arg Val Leu Val Val Pro Ala Glu Asn Tyr Asp Tyr Gln Ile
            1205            1210            1215

Leu His Lys Lys Ser Met Asp Lys Ser Leu Glu Phe Ile Thr Asn Cys
        1220            1225            1230

Gly Lys Asn Ser Phe Tyr Leu Asp Pro Gln Thr Ala Ser Arg Phe Cys
        1235            1240            1245

Lys Asn Ser Ala Arg Ser Leu Val Ala Phe Tyr His Lys Gly Ala Leu
    1250            1255            1260

Pro Cys Glu Cys His Pro Thr Gly Ala Thr Gly Pro His Cys Ser Pro
1265            1270            1275            1280

Glu Gly Gly Gln Cys Pro Cys Gln Pro Asn Val Ile Gly Arg Gln Cys
            1285            1290            1295

Thr Arg Cys Ala Thr Gly His Tyr Gly Phe Pro Arg Cys Lys Pro Cys
        1300            1305            1310

Ser Cys Gly Arg Arg Leu Cys Glu Glu Met Thr Gly Gln Cys Arg Cys
        1315            1320            1325

Pro Pro Arg Thr Val Arg Pro Gln Cys Glu Val Cys Glu Thr His Ser
    1330            1335            1340

Phe Ser Phe His Pro Met Ala Gly Cys Glu Gly Cys Asn Cys Ser Arg
1345            1350            1355            1360

Arg Gly Thr Ile Glu Ala Ala Met Pro Glu Cys Asp Arg Asp Ser Gly
            1365            1370            1375

Gln Cys Arg Cys Lys Pro Arg Ile Thr Gly Arg Gln Cys Asp Arg Cys
        1380            1385            1390

Ala Ser Gly Phe Tyr Arg Phe Pro Glu Cys Val Pro Cys Asn Cys Asn
        1395            1400            1405
```

-continued

```
Arg Asp Gly Thr Glu Pro Gly Val Cys Asp Pro Gly Thr Gly Ala Cys
    1410             1415             1420

Leu Cys Lys Glu Asn Val Glu Gly Thr Glu Cys Asn Val Cys Arg Glu
1425             1430             1435             1440

Gly Ser Phe His Leu Asp Pro Ala Asn Leu Lys Gly Cys Thr Ser Cys
                1445             1450             1455

Phe Cys Phe Gly Val Asn Asn Gln Cys His Ser Ser His Lys Arg Arg
                1460             1465             1470

Thr Lys Phe Val Asp Met Leu Gly Trp His Leu Glu Thr Ala Asp Arg
            1475             1480             1485

Val Asp Ile Pro Val Ser Phe Asn Pro Gly Ser Asn Ser Met Val Ala
    1490             1495             1500

Asp Leu Gln Glu Leu Pro Ala Thr Ile His Ser Ala Ser Trp Val Ala
1505             1510             1515             1520

Pro Thr Ser Tyr Leu Gly Asp Lys Val Ser Ser Tyr Gly Gly Tyr Leu
                1525             1530             1535

Thr Tyr Gln Ala Lys Ser Phe Gly Leu Pro Gly Asp Met Val Leu Leu
                1540             1545             1550

Glu Lys Lys Pro Asp Val Gln Leu Thr Gly Gln His Met Ser Ile Ile
            1555             1560             1565

Tyr Glu Glu Thr Asn Thr Pro Arg Pro Asp Arg Leu His His Gly Arg
    1570             1575             1580

Val His Val Val Glu Gly Asn Phe Arg His Ala Ser Ser Arg Ala Pro
1585             1590             1595             1600

Val Ser Arg Glu Glu Leu Met Thr Val Leu Ser Arg Leu Ala Asp Val
                1605             1610             1615

Arg Ile Gln Gly Leu Tyr Phe Thr Glu Thr Gln Arg Leu Thr Leu Ser
                1620             1625             1630

Glu Val Gly Leu Glu Glu Ala Ser Asp Thr Gly Ser Gly Arg Ile Ala
            1635             1640             1645

Leu Ala Val Glu Ile Cys Ala Cys Pro Pro Ala Tyr Ala Gly Asp Ser
    1650             1655             1660

Cys Gln Gly Cys Ser Pro Gly Tyr Tyr Arg Asp His Lys Gly Leu Tyr
1665             1670             1675             1680

Thr Gly Arg Cys Val Pro Cys Asn Cys Asn Gly His Ser Asn Gln Cys
                1685             1690             1695

Gln Asp Gly Ser Gly Ile Cys Val Asn Cys Gln His Asn Thr Ala Gly
            1700             1705             1710

Glu His Cys Glu Arg Cys Gln Glu Gly Tyr Tyr Gly Asn Ala Val His
        1715             1720             1725

Gly Ser Cys Arg Ala Cys Pro Cys Pro His Thr Asn Ser Phe Ala Thr
    1730             1735             1740

Gly Cys Val Val Asn Gly Gly Asp Val Arg Cys Ser Cys Lys Ala Gly
1745             1750             1755             1760

Tyr Thr Gly Thr Gln Cys Glu Arg Cys Ala Pro Gly Tyr Phe Gly Asn
                1765             1770             1775

Pro Gln Lys Phe Gly Gly Ser Cys Gln Pro Cys Ser Cys Asn Ser Asn
                1780             1785             1790

Gly Gln Leu Gly Ser Cys His Pro Leu Thr Gly Asp Cys Ile Asn Gln
        1795             1800             1805

Glu Pro Lys Asp Ser Ser Pro Ala Glu Glu Cys Asp Asp Cys Asp Ser
    1810             1815             1820
```

-continued

```
Cys Val Met Thr Leu Leu Asn Asp Leu Ala Thr Met Gly Glu Gln Leu
1825                1830                1835                1840

Arg Leu Val Lys Ser Gln Leu Gln Gly Leu Ser Ala Ser Ala Gly Leu
            1845                1850                1855

Leu Glu Gln Met Arg His Met Glu Thr Gln Ala Lys Asp Leu Arg Asn
            1860                1865                1870

Gln Leu Leu Asn Tyr Arg Ser Ala Ile Ser Asn His Gly Ser Lys Ile
        1875                1880                1885

Glu Gly Leu Glu Arg Glu Leu Thr Asp Leu Asn Gln Glu Phe Glu Thr
    1890                1895                1900

Leu Gln Glu Lys Ala Gln Val Asn Ser Arg Lys Ala Gln Thr Leu Asn
1905                1910                1915                1920

Asn Asn Val Asn Arg Ala Thr Gln Ser Ala Lys Glu Leu Asp Val Lys
            1925                1930                1935

Ile Lys Asn Val Ile Arg Asn Val His Ile Leu Leu Lys Gln Ile Ser
            1940                1945                1950

Gly Thr Asp Gly Glu Gly Asn Asn Val Pro Ser Gly Asp Phe Ser Arg
        1955                1960                1965

Glu Trp Ala Glu Ala Gln Arg Met Met Arg Glu Leu Arg Asn Arg Asn
    1970                1975                1980

Phe Gly Lys His Leu Arg Glu Ala Glu Ala Asp Lys Arg Glu Ser Gln
1985                1990                1995                2000

Leu Leu Leu Asn Arg Ile Arg Thr Trp Gln Lys Thr His Gln Gly Glu
            2005                2010                2015

Asn Asn Gly Leu Ala Asn Ser Ile Arg Asp Ser Leu Asn Glu Tyr Glu
            2020                2025                2030

Ala Lys Leu Ser Asp Leu Arg Ala Arg Leu Gln Glu Ala Ala Ala Gln
            2035                2040                2045

Ala Lys Gln Ala Asn Gly Leu Asn Gln Glu Asn Glu Arg Ala Leu Gly
    2050                2055                2060

Ala Ile Gln Arg Gln Val Lys Glu Ile Asn Ser Leu Gln Ser Asp Phe
2065                2070                2075                2080

Thr Lys Tyr Leu Thr Thr Ala Asp Ser Ser Leu Leu Gln Thr Asn Ile
            2085                2090                2095

Ala Leu Gln Leu Met Glu Lys Ser Gln Lys Glu Tyr Glu Lys Leu Ala
            2100                2105                2110

Ala Ser Leu Asn Glu Ala Arg Gln Glu Leu Ser Asp Lys Val Arg Glu
        2115                2120                2125

Leu Ser Arg Ser Ala Gly Lys Thr Ser Leu Val Glu Glu Ala Glu Lys
    2130                2135                2140

His Ala Arg Ser Leu Gln Glu Leu Ala Lys Gln Leu Glu Glu Ile Lys
2145                2150                2155                2160

Arg Asn Ala Ser Gly Asp Glu Leu Val Arg Cys Ala Val Asp Ala Ala
            2165                2170                2175

Thr Ala Tyr Glu Asn Ile Leu Asn Ala Ile Lys Ala Ala Glu Asp Ala
        2180                2185                2190

Ala Asn Arg Ala Ala Ser Ala Ser Glu Ser Ala Leu Gln Thr Val Ile
        2195                2200                2205

Lys Glu Asp Leu Pro Arg Lys Ala Lys Thr Leu Ser Ser Asn Ser Asp
    2210                2215                2220

Lys Leu Leu Asn Glu Ala Lys Met Thr Gln Lys Lys Leu Lys Gln Glu
2225                2230                2235                2240

Val Ser Pro Ala Leu Asn Asn Leu Gln Gln Thr Leu Asn Ile Val Thr
```

```
                    2245              2250              2255

Val Gln Lys Glu Val Ile Asp Thr Asn Leu Thr Thr Leu Arg Asp Gly
            2260              2265              2270

Leu His Gly Ile Gln Arg Gly Asp Ile Asp Ala Met Ile Ser Ser Ala
        2275              2280              2285

Lys Ser Met Val Arg Lys Ala Asn Asp Ile Thr Asp Glu Val Leu Asp
    2290              2295              2300

Gly Leu Asn Pro Ile Gln Thr Asp Val Glu Arg Ile Lys Asp Thr Tyr
2305              2310              2315              2320

Gly Arg Thr Gln Asn Glu Asp Phe Lys Lys Ala Leu Thr Asp Ala Asp
            2325              2330              2335

Asn Ser Val Asn Lys Leu Thr Asn Lys Leu Pro Asp Leu Trp Arg Lys
            2340              2345              2350

Ile Glu Ser Ile Asn Gln Gln Leu Leu Pro Leu Gly Asn Ile Ser Asp
        2355              2360              2365

Asn Met Asp Arg Ile Arg Glu Leu Ile Gln Gln Ala Arg Asp Ala Ala
    2370              2375              2380

Ser Lys Val Ala Val Pro Met Arg Phe Asn Gly Lys Ser Gly Val Glu
2385              2390              2395              2400

Val Arg Leu Pro Asn Asp Leu Glu Asp Leu Lys Gly Tyr Thr Ser Leu
            2405              2410              2415

Ser Leu Phe Leu Gln Arg Pro Asn Ser Arg Glu Asn Gly Gly Thr Glu
            2420              2425              2430

Asn Met Phe Val Met Tyr Leu Gly Asn Lys Asp Ala Ser Arg Asp Tyr
        2435              2440              2445

Ile Gly Met Ala Val Val Asp Gly Gln Leu Thr Cys Val Tyr Asn Leu
    2450              2455              2460

Gly Asp Arg Glu Ala Glu Leu Gln Val Asp Gln Ile Leu Thr Lys Ser
2465              2470              2475              2480

Glu Thr Lys Glu Ala Val Met Asp Arg Val Lys Phe Gln Arg Ile Tyr
            2485              2490              2495

Gln Phe Ala Arg Leu Asn Tyr Thr Lys Gly Ala Thr Ser Ser Lys Pro
        2500              2505              2510

Glu Thr Pro Gly Val Tyr Asp Met Asp Gly Arg Asn Ser Asn Thr Leu
        2515              2520              2525

Leu Asn Leu Asp Pro Glu Asn Val Val Phe Tyr Val Gly Gly Tyr Pro
    2530              2535              2540

Pro Asp Phe Lys Leu Pro Ser Arg Leu Ser Phe Pro Pro Tyr Lys Gly
2545              2550              2555              2560

Cys Ile Glu Leu Asp Asp Leu Asn Glu Asn Val Leu Ser Leu Tyr Asn
            2565              2570              2575

Phe Lys Lys Thr Phe Asn Leu Asn Thr Thr Glu Val Glu Pro Cys Arg
            2580              2585              2590

Arg Arg Lys Glu Glu Ser Asp Lys Asn Tyr Phe Glu Gly Thr Gly Tyr
        2595              2600              2605

Ala Arg Val Pro Thr Gln Pro His Ala Pro Ile Pro Thr Phe Gly Gln
    2610              2615              2620

Thr Ile Gln Thr Thr Val Asp Arg Gly Leu Leu Phe Phe Ala Glu Asn
2625              2630              2635              2640

Gly Asp Arg Phe Ile Ser Leu Asn Ile Glu Asp Gly Lys Leu Met Val
            2645              2650              2655

Arg Tyr Lys Leu Asn Ser Glu Leu Pro Lys Glu Arg Gly Val Gly Asp
        2660              2665              2670
```

```
Ala Ile Asn Asn Gly Arg Asp His Ser Ile Gln Ile Lys Ile Gly Lys
        2675                2680                2685

Leu Gln Lys Arg Met Trp Ile Asn Val Asp Val Gln Asn Thr Ile Ile
        2690                2695                2700

Asp Gly Glu Val Phe Asp Phe Ser Thr Tyr Tyr Leu Gly Gly Ile Pro
2705                2710                2715                2720

Ile Ala Ile Arg Glu Arg Phe Asn Ile Ser Thr Pro Ala Phe Arg Gly
                2725                2730                2735

Cys Met Lys Asn Leu Lys Lys Thr Ser Gly Val Val Arg Leu Asn Asp
                2740                2745                2750

Thr Val Gly Val Thr Lys Lys Cys Ser Glu Asp Trp Lys Leu Val Arg
        2755                2760                2765

Ser Ala Ser Phe Ser Arg Gly Gly Gln Leu Ser Phe Thr Asp Leu Gly
        2770                2775                2780

Leu Pro Pro Thr Asp His Leu Gln Ala Ser Phe Gly Phe Gln Thr Phe
2785                2790                2795                2800

Gln Pro Ser Gly Ile Leu Leu Asp His Gln Thr Trp Thr Arg Asn Leu
                2805                2810                2815

Gln Val Thr Leu Glu Asp Gly Tyr Ile Glu Leu Ser Thr Ser Asp Ser
                2820                2825                2830

Gly Gly Pro Ile Phe Lys Ser Pro Gln Thr Tyr Met Asp Gly Leu Leu
        2835                2840                2845

His Tyr Val Ser Val Ile Ser Asp Asn Ser Gly Leu Arg Leu Leu Ile
        2850                2855                2860

Asp Asp Gln Leu Leu Arg Asn Ser Lys Arg Leu Lys His Ile Ser Ser
2865                2870                2875                2880

Ser Arg Gln Ser Leu Arg Leu Gly Gly Ser Asn Phe Glu Gly Cys Ile
                2885                2890                2895

Ser Asn Val Phe Val Gln Arg Leu Ser Leu Ser Pro Glu Val Leu Asp
                2900                2905                2910

Leu Thr Ser Asn Ser Leu Lys Arg Asp Val Ser Leu Gly Gly Cys Ser
        2915                2920                2925

Leu Asn Lys Pro Pro Phe Leu Met Leu Leu Lys Gly Ser Thr Arg Phe
        2930                2935                2940

Asn Lys Thr Lys Thr Phe Arg Ile Asn Gln Leu Leu Gln Asp Thr Pro
2945                2950                2955                2960

Val Ala Ser Pro Arg Ser Val Lys Val Trp Gln Asp Ala Cys Ser Pro
                2965                2970                2975

Leu Pro Lys Thr Gln Ala Asn His Gly Ala Leu Gln Phe Gly Asp Ile
                2980                2985                2990

Pro Thr Ser His Leu Leu Phe Lys Leu Pro Gln Glu Leu Leu Lys Pro
        2995                3000                3005

Arg Ser Gln Phe Ala Val Asp Met Gln Thr Thr Ser Ser Arg Gly Leu
        3010                3015                3020

Val Phe His Thr Gly Thr Lys Asn Ser Phe Met Ala Leu Tyr Leu Ser
3025                3030                3035                3040

Lys Gly Arg Leu Val Phe Ala Leu Gly Thr Asp Gly Lys Lys Leu Arg
                3045                3050                3055

Ile Lys Ser Lys Glu Lys Cys Asn Asp Gly Lys Trp His Thr Val Val
                3060                3065                3070

Phe Gly His Asp Gly Glu Lys Gly Arg Leu Val Val Asp Gly Leu Arg
        3075                3080                3085
```

```
Ala Arg Glu Gly Ser Leu Pro Gly Asn Ser Thr Ile Ser Ile Arg Ala
    3090            3095            3100

Pro Val Tyr Leu Gly Ser Pro Pro Ser Gly Lys Pro Lys Ser Leu Pro
3105            3110            3115            3120

Thr Asn Ser Phe Val Gly Cys Leu Lys Asn Phe Gln Leu Asp Ser Lys
            3125            3130            3135

Pro Leu Tyr Thr Pro Ser Ser Ser Phe Gly Val Ser Ser Cys Leu Gly
            3140            3145            3150

Gly Pro Leu Glu Lys Gly Ile Tyr Phe Ser Glu Glu Gly Gly His Val
            3155            3160            3165

Val Leu Ala His Ser Val Leu Leu Gly Pro Glu Phe Lys Leu Val Phe
    3170            3175            3180

Ser Ile Arg Pro Arg Ser Leu Thr Gly Ile Leu Ile His Ile Gly Ser
3185            3190            3195            3200

Gln Pro Gly Lys His Leu Cys Val Tyr Leu Glu Ala Gly Lys Val Thr
            3205            3210            3215

Ala Ser Met Asp Ser Gly Ala Gly Gly Thr Ser Thr Ser Val Thr Pro
            3220            3225            3230

Lys Gln Ser Leu Cys Asp Gly Gln Trp His Ser Val Ala Val Thr Ile
    3235            3240            3245

Lys Gln His Ile Leu His Leu Glu Leu Asp Thr Asp Ser Ser Tyr Thr
    3250            3255            3260

Ala Gly Gln Ile Pro Phe Pro Pro Ala Ser Thr Gln Glu Pro Leu His
3265            3270            3275            3280

Leu Gly Gly Ala Pro Ala Asn Leu Thr Thr Leu Arg Ile Pro Val Trp
            3285            3290            3295

Lys Ser Phe Phe Gly Cys Leu Arg Asn Ile His Val Asn His Ile Pro
            3300            3305            3310

Val Pro Val Thr Glu Ala Leu Glu Val Gln Gly Pro Val Ser Leu Asn
            3315            3320            3325

Gly Cys Pro Asp Gln
    3330

<210> SEQ ID NO 33
<211> LENGTH: 3277
<212> TYPE: PRT
<213> ORGANISM: Homo sapiens

<400> SEQUENCE: 33

Met Ala Ala Ala Ala Arg Pro Arg Gly Arg Ala Leu Gly Pro Val Leu
1               5               10              15

Pro Pro Thr Pro Leu Leu Leu Leu Val Leu Arg Val Leu Pro Ala Cys
            20              25              30

Gly Ala Thr Ala Arg Asp Pro Gly Ala Ala Ala Gly Leu Ser Leu His
            35              40              45

Pro Thr Tyr Phe Asn Leu Ala Glu Ala Ala Arg Ile Trp Ala Thr Ala
    50              55              60

Thr Cys Gly Glu Arg Gly Pro Gly Glu Gly Arg Pro Gln Pro Glu Leu
65              70              75              80

Tyr Cys Lys Leu Val Gly Gly Pro Thr Ala Pro Gly Ser Gly His Thr
            85              90              95

Ile Gln Gly Gln Phe Cys Asp Tyr Cys Asn Ser Glu Asp Pro Arg Lys
            100             105             110

Ala His Pro Val Thr Asn Ala Ile Asp Gly Ser Glu Arg Trp Trp Gln
            115             120             125
```

```
Ser Pro Pro Leu Ser Ser Gly Thr Gln Tyr Asn Arg Val Asn Leu Thr
    130             135                 140

Leu Asp Leu Gly Gln Leu Phe His Val Ala Tyr Ile Leu Ile Lys Phe
145             150                 155                 160

Ala Asn Ser Pro Arg Pro Asp Leu Trp Val Leu Glu Arg Ser Val Asp
            165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
            195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
            245                 250                 255

Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Arg Tyr Tyr Tyr
            275                 280                 285

Ser Ile Lys Asp Ile Ser Ile Gly Gly Gln Cys Val Cys Asn Gly His
    290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
            325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
            355                 360                 365

Pro Asp Val Glu Arg Gln Gln Ala Ser Leu Asn Thr Gln Gly Ile Tyr
    370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
            405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
            435                 440                 445

Phe His Gly Asp Asn Cys Glu Lys Cys Ala Ile Gly Tyr Tyr Asn Phe
    450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
            485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
            515                 520                 525

Ser Phe Pro Ile Cys Gln Ala Cys Trp Cys Ser Ala Leu Gly Ser Tyr
    530                 535                 540
```

-continued

```
Gln Met Pro Cys Ser Ser Val Thr Gly Gln Cys Glu Cys Arg Pro Gly
545             550                 555                 560

Val Thr Gly Gln Arg Cys Asp Arg Cys Leu Ser Gly Ala Tyr Asp Phe
                565                 570                 575

Pro His Cys Gln Gly Ser Ser Ser Ala Cys Asp Pro Ala Gly Thr Ile
                580                 585                 590

Asn Ser Asn Leu Gly Tyr Cys Gln Cys Lys Leu His Val Glu Gly Pro
            595                 600                 605

Thr Cys Ser Arg Cys Lys Leu Leu Tyr Trp Asn Leu Asp Lys Glu Asn
        610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Asp Cys His Cys Lys Ser
                645                 650                 655

His Val Gly Gly Asp Ser Cys Asp Thr Cys Glu Asp Gly Tyr Phe Ala
            660                 665                 670

Leu Glu Lys Ser Asn Tyr Phe Gly Cys Gln Gly Cys Gln Cys Asp Ile
            675                 680                 685

Gly Gly Ala Leu Ser Ser Met Cys Ser Gly Pro Ser Gly Val Cys Gln
        690                 695                 700

Cys Arg Glu His Val Val Gly Lys Val Cys Gln Arg Pro Glu Asn Asn
705                 710                 715                 720

Tyr Tyr Phe Pro Asp Leu His His Met Lys Tyr Glu Ile Glu Asp Gly
                725                 730                 735

Ser Thr Pro Asn Gly Arg Asp Leu Arg Phe Gly Phe Asp Pro Leu Ala
                740                 745                 750

Phe Pro Glu Phe Ser Trp Arg Gly Tyr Ala Gln Met Thr Ser Val Gln
            755                 760                 765

Asn Asp Val Arg Ile Thr Leu Asn Val Gly Lys Ser Ser Gly Ser Leu
        770                 775                 780

Phe Arg Val Ile Leu Arg Tyr Val Asn Pro Gly Thr Glu Ala Val Ser
785                 790                 795                 800

Gly His Ile Thr Ile Tyr Pro Ser Trp Gly Ala Ala Gln Ser Lys Glu
                805                 810                 815

Ile Ile Phe Leu Pro Ser Lys Glu Pro Ala Phe Val Thr Val Pro Gly
            820                 825                 830

Asn Gly Phe Ala Asp Pro Phe Ser Ile Thr Pro Gly Ile Trp Val Ala
        835                 840                 845

Cys Ile Lys Ala Glu Gly Val Leu Leu Asp Tyr Leu Val Leu Leu Pro
    850                 855                 860

Arg Asp Tyr Tyr Glu Ala Ser Val Leu Gln Leu Pro Val Thr Glu Pro
865                 870                 875                 880

Cys Ala Tyr Ala Gly Pro Pro Gln Glu Asn Cys Leu Leu Tyr Gln His
                885                 890                 895

Leu Pro Val Thr Arg Phe Pro Cys Thr Leu Ala Cys Glu Ala Arg His
            900                 905                 910

Phe Leu Leu Asp Gly Glu Pro Arg Pro Val Ala Val Arg Gln Pro Thr
            915                 920                 925

Pro Ala His Pro Val Met Val Asp Leu Ser Gly Arg Glu Val Glu Leu
        930                 935                 940

His Leu Arg Leu Arg Ile Pro Gln Val Gly His Tyr Val Val Val Val
945                 950                 955                 960

Glu Tyr Ser Thr Glu Ala Ala Gln Leu Phe Val Val Asp Val Asn Val
```

-continued

```
                965                    970                    975

Lys Ser Ser Gly Ser Val Leu Ala Gly Gln Val Asn Ile Tyr Ser Cys
            980                    985                    990

Asn Tyr Ser Val Leu Cys Arg Ser Ala Val Ile Asp His Met Ser Arg
        995                   1000                   1005

Ile Ala Met Tyr Glu Leu Leu Ala Asp Ala Asp Ile Gln Leu Lys Gly
    1010                   1015                   1020

His Met Ala Arg Phe Leu Leu His Gln Val Cys Ile Ile Pro Ile Glu
1025                   1030                   1035                   1040

Glu Phe Ser Ala Glu Tyr Val Arg Pro Gln Val His Cys Ile Ala Ser
                1045                   1050                   1055

Tyr Gly Arg Phe Val Asn Gln Ser Ala Thr Cys Val Ser Leu Ala His
            1060                   1065                   1070

Glu Thr Pro Pro Thr Ala Leu Ile Leu Asp Val Leu Ser Gly Arg Pro
        1075                   1080                   1085

Phe Pro His Leu Pro Gln Gln Ser Ser Pro Ser Val Asp Val Leu Pro
    1090                   1095                   1100

Gly Val Thr Leu Lys Ala Pro Gln Asn Gln Val Thr Leu Arg Gly Arg
1105                   1110                   1115                   1120

Val Pro His Leu Gly Arg Tyr Val Phe Val Ile His Phe Tyr Gln Ala
                1125                   1130                   1135

Ala His Pro Thr Phe Pro Ala Gln Val Ser Val Asp Gly Gly Trp Pro
            1140                   1145                   1150

Arg Ala Gly Ser Phe His Ala Ser Phe Cys Pro His Val Leu Gly Cys
            1155                   1160                   1165

Arg Asp Gln Val Ile Ala Glu Gly Gln Ile Glu Phe Asp Ile Ser Glu
        1170                   1175                   1180

Pro Glu Val Ala Ala Thr Val Lys Val Pro Glu Gly Lys Ser Leu Val
1185                   1190                   1195                   1200

Leu Val Arg Val Leu Val Val Pro Ala Glu Asn Tyr Asp Tyr Gln Ile
                1205                   1210                   1215

Leu His Lys Lys Ser Met Asp Lys Ser Leu Glu Phe Ile Thr Asn Cys
            1220                   1225                   1230

Gly Lys Asn Ser Phe Tyr Leu Asp Pro Gln Thr Ala Ser Arg Phe Cys
            1235                   1240                   1245

Lys Asn Ser Ala Arg Ser Leu Val Ala Phe Tyr His Lys Gly Ala Leu
    1250                   1255                   1260

Pro Cys Glu Cys His Pro Thr Gly Ala Thr Gly Pro His Cys Ser Pro
1265                   1270                   1275                   1280

Glu Gly Gly Gln Cys Pro Cys Gln Pro Asn Val Ile Gly Arg Gln Cys
            1285                   1290                   1295

Thr Arg Cys Ala Thr Gly His Tyr Gly Phe Pro Arg Cys Lys Pro Cys
            1300                   1305                   1310

Ser Cys Gly Arg Arg Leu Cys Glu Glu Met Thr Gly Gln Cys Arg Cys
            1315                   1320                   1325

Pro Pro Arg Thr Val Arg Pro Gln Cys Glu Val Cys Glu Thr His Ser
    1330                   1335                   1340

Phe Ser Phe His Pro Met Ala Gly Cys Glu Gly Cys Asn Cys Ser Arg
1345                   1350                   1355                   1360

Arg Gly Thr Ile Glu Ala Ala Met Pro Glu Cys Asp Arg Asp Ser Gly
            1365                   1370                   1375

Gln Cys Arg Cys Lys Pro Arg Ile Thr Gly Arg Gln Cys Asp Arg Cys
        1380                   1385                   1390
```

Ala Ser Gly Phe Tyr Arg Phe Pro Glu Cys Val Pro Cys Asn Cys Asn
        1395                1400                1405

Arg Asp Gly Thr Glu Pro Gly Val Cys Asp Pro Gly Thr Gly Ala Cys
    1410                1415                1420

Leu Cys Lys Glu Asn Val Glu Gly Thr Glu Cys Asn Val Cys Arg Glu
1425                1430                1435                1440

Gly Ser Phe His Leu Asp Pro Ala Asn Leu Lys Gly Cys Thr Ser Cys
            1445                1450                1455

Phe Cys Phe Gly Val Asn Asn Gln Cys His Ser Ser His Lys Arg Arg
            1460                1465                1470

Thr Lys Phe Val Asp Met Leu Gly Trp His Leu Glu Thr Ala Asp Arg
            1475                1480                1485

Val Asp Ile Pro Val Ser Phe Asn Pro Gly Ser Asn Ser Met Val Ala
    1490                1495                1500

Asp Leu Gln Glu Leu Pro Ala Thr Ile His Ser Ala Ser Trp Val Ala
1505                1510                1515                1520

Pro Thr Ser Tyr Leu Gly Asp Lys Val Ser Ser Tyr Gly Gly Tyr Leu
            1525                1530                1535

Thr Tyr Gln Ala Lys Ser Phe Gly Leu Pro Gly Asp Met Val Leu Leu
            1540                1545                1550

Glu Lys Lys Pro Asp Val Gln Leu Thr Gly Gln His Met Ser Ile Ile
        1555                1560                1565

Tyr Glu Glu Thr Asn Thr Pro Arg Pro Asp Arg Leu His His Gly Arg
    1570                1575                1580

Val His Val Val Glu Gly Asn Phe Arg His Ala Ser Ser Arg Ala Pro
1585                1590                1595                1600

Val Ser Arg Glu Glu Leu Met Thr Val Leu Ser Arg Leu Ala Asp Val
            1605                1610                1615

Arg Ile Gln Gly Leu Tyr Phe Thr Glu Thr Gln Arg Leu Thr Leu Ser
            1620                1625                1630

Glu Val Gly Leu Glu Glu Ala Ser Asp Thr Gly Ser Gly Arg Ile Ala
        1635                1640                1645

Leu Ala Val Glu Ile Cys Ala Cys Pro Pro Ala Tyr Ala Gly Asp Ser
    1650                1655                1660

Cys Gln Gly Cys Ser Pro Gly Tyr Tyr Arg Asp His Lys Gly Leu Tyr
1665                1670                1675                1680

Thr Gly Arg Cys Val Pro Cys Asn Cys Asn Gly His Ser Asn Gln Cys
            1685                1690                1695

Gln Asp Gly Ser Gly Ile Cys Val Asn Cys Gln His Asn Thr Ala Gly
        1700                1705                1710

Glu His Cys Glu Arg Cys Gln Glu Gly Tyr Tyr Gly Asn Ala Val His
        1715                1720                1725

Gly Ser Cys Arg Ala Cys Pro Cys Pro His Thr Asn Ser Phe Ala Thr
    1730                1735                1740

Gly Cys Val Val Asn Gly Gly Asp Val Arg Cys Ser Cys Lys Ala Gly
1745                1750                1755                1760

Tyr Thr Gly Thr Gln Cys Glu Arg Cys Ala Pro Gly Tyr Phe Gly Asn
            1765                1770                1775

Pro Gln Lys Phe Gly Gly Ser Cys Gln Pro Cys Ser Cys Asn Ser Asn
            1780                1785                1790

Gly Gln Leu Gly Ser Cys His Pro Leu Thr Gly Asp Cys Ile Asn Gln
    1795                1800                1805

-continued

```
Glu Pro Lys Asp Ser Ser Pro Ala Glu Glu Cys Asp Asp Cys Asp Ser
    1810            1815            1820

Cys Val Met Thr Leu Leu Asn Asp Leu Ala Thr Met Gly Glu Gln Leu
1825            1830            1835            1840

Arg Leu Val Lys Ser Gln Leu Gln Gly Leu Ser Ala Ser Ala Gly Leu
            1845            1850            1855

Leu Glu Gln Met Arg His Met Glu Thr Gln Ala Lys Asp Leu Arg Asn
            1860            1865            1870

Gln Leu Leu Asn Tyr Arg Ser Ala Ile Ser Asn His Gly Ser Lys Ile
        1875            1880            1885

Glu Gly Leu Glu Arg Glu Leu Thr Asp Leu Asn Gln Glu Phe Glu Thr
    1890            1895            1900

Leu Gln Glu Lys Ala Gln Val Asn Ser Arg Lys Ala Gln Thr Leu Asn
1905            1910            1915            1920

Asn Asn Val Asn Arg Ala Thr Gln Ser Ala Lys Glu Leu Asp Val Lys
            1925            1930            1935

Ile Lys Asn Val Ile Arg Asn Val His Met Leu Asn Arg Ile Arg Thr
            1940            1945            1950

Trp Gln Lys Thr His Gln Gly Glu Asn Asn Gly Leu Ala Asn Ser Ile
        1955            1960            1965

Arg Asp Ser Leu Asn Glu Tyr Glu Ala Lys Leu Ser Asp Leu Arg Ala
    1970            1975            1980

Arg Leu Gln Glu Ala Ala Ala Gln Ala Lys Gln Ala Asn Gly Leu Asn
1985            1990            1995            2000

Gln Glu Asn Glu Arg Ala Leu Gly Ala Ile Gln Arg Gln Val Lys Glu
            2005            2010            2015

Ile Asn Ser Leu Gln Ser Asp Phe Thr Lys Tyr Leu Thr Thr Ala Asp
            2020            2025            2030

Ser Ser Leu Leu Gln Thr Asn Ile Ala Leu Gln Leu Met Glu Lys Ser
        2035            2040            2045

Gln Lys Glu Tyr Glu Lys Leu Ala Ala Ser Leu Asn Glu Ala Arg Gln
    2050            2055            2060

Glu Leu Ser Asp Lys Val Arg Glu Leu Ser Arg Ser Ala Gly Lys Thr
2065            2070            2075            2080

Ser Leu Val Glu Glu Ala Glu Lys His Ala Arg Ser Leu Gln Glu Leu
            2085            2090            2095

Ala Lys Gln Leu Glu Glu Ile Lys Arg Asn Ala Ser Gly Asp Glu Leu
        2100            2105            2110

Val Arg Cys Ala Val Asp Ala Ala Thr Ala Tyr Glu Asn Ile Leu Asn
        2115            2120            2125

Ala Ile Lys Ala Ala Glu Asp Ala Ala Asn Arg Ala Ala Ser Ala Ser
    2130            2135            2140

Glu Ser Ala Leu Gln Thr Val Ile Lys Glu Asp Leu Pro Arg Lys Ala
2145            2150            2155            2160

Lys Thr Leu Ser Ser Asn Ser Asp Lys Leu Leu Asn Glu Ala Lys Met
            2165            2170            2175

Thr Gln Lys Lys Leu Lys Gln Glu Val Ser Pro Ala Leu Asn Asn Leu
        2180            2185            2190

Gln Gln Thr Leu Asn Ile Val Thr Val Gln Lys Glu Val Ile Asp Thr
    2195            2200            2205

Asn Leu Thr Thr Leu Arg Asp Gly Leu His Gly Ile Gln Arg Gly Asp
    2210            2215            2220

Ile Asp Ala Met Ile Ser Ser Ala Lys Ser Met Val Arg Lys Ala Asn
```

```
            2225                2230                2235                2240

Asp Ile Thr Asp Glu Val Leu Asp Gly Leu Asn Pro Ile Gln Thr Asp
                2245                2250                2255

Val Glu Arg Ile Lys Asp Thr Tyr Gly Arg Thr Gln Asn Glu Asp Phe
                2260                2265                2270

Lys Lys Ala Leu Thr Asp Ala Asp Asn Ser Val Asn Lys Leu Thr Asn
                2275                2280                2285

Lys Leu Pro Asp Leu Trp Arg Lys Ile Glu Ser Ile Asn Gln Gln Leu
                2290                2295                2300

Leu Pro Leu Gly Asn Ile Ser Asp Asn Met Asp Arg Ile Arg Glu Leu
2305                2310                2315                2320

Ile Gln Gln Ala Arg Asp Ala Ala Ser Lys Val Ala Val Pro Met Arg
                2325                2330                2335

Phe Asn Gly Lys Ser Gly Val Glu Val Arg Leu Pro Asn Asp Leu Glu
                2340                2345                2350

Asp Leu Lys Gly Tyr Thr Ser Leu Ser Leu Phe Leu Gln Arg Pro Asn
                2355                2360                2365

Ser Arg Glu Asn Gly Gly Thr Glu Asn Met Phe Val Met Tyr Leu Gly
                2370                2375                2380

Asn Lys Asp Ala Ser Arg Asp Tyr Ile Gly Met Ala Val Val Asp Gly
2385                2390                2395                2400

Gln Leu Thr Cys Val Tyr Asn Leu Gly Asp Arg Glu Ala Glu Leu Gln
                2405                2410                2415

Val Asp Gln Ile Leu Thr Lys Ser Glu Thr Lys Glu Ala Val Met Asp
                2420                2425                2430

Arg Val Lys Phe Gln Arg Ile Tyr Gln Phe Ala Arg Leu Asn Tyr Thr
                2435                2440                2445

Lys Gly Ala Thr Ser Ser Lys Pro Glu Thr Pro Gly Val Tyr Asp Met
                2450                2455                2460

Asp Gly Arg Asn Ser Asn Thr Leu Leu Asn Leu Asp Pro Glu Asn Val
2465                2470                2475                2480

Val Phe Tyr Val Gly Gly Tyr Pro Pro Asp Phe Lys Leu Pro Ser Arg
                2485                2490                2495

Leu Ser Phe Pro Pro Tyr Lys Gly Cys Ile Glu Leu Asp Asp Leu Asn
                2500                2505                2510

Glu Asn Val Leu Ser Leu Tyr Asn Phe Lys Lys Thr Phe Asn Leu Asn
                2515                2520                2525

Thr Thr Glu Val Glu Pro Cys Arg Arg Arg Lys Glu Glu Ser Asp Lys
                2530                2535                2540

Asn Tyr Phe Glu Gly Thr Gly Tyr Ala Arg Val Pro Thr Gln Pro His
2545                2550                2555                2560

Ala Pro Ile Pro Thr Phe Gly Gln Thr Ile Gln Thr Thr Val Asp Arg
                2565                2570                2575

Gly Leu Leu Phe Phe Ala Glu Asn Gly Asp Arg Phe Ile Ser Leu Asn
                2580                2585                2590

Ile Glu Asp Gly Lys Leu Met Val Arg Tyr Lys Leu Asn Ser Glu Leu
                2595                2600                2605

Pro Lys Glu Arg Gly Val Gly Asp Ala Ile Asn Asn Gly Arg Asp His
                2610                2615                2620

Ser Ile Gln Ile Lys Ile Gly Lys Leu Gln Lys Arg Met Trp Ile Asn
2625                2630                2635                2640

Val Asp Val Gln Asn Thr Ile Ile Asp Gly Glu Val Phe Asp Phe Ser
                2645                2650                2655
```

-continued

```
Thr Tyr Tyr Leu Gly Gly Ile Pro Ile Ala Ile Arg Glu Arg Phe Asn
            2660                2665                2670

Ile Ser Thr Pro Ala Phe Arg Gly Cys Met Lys Asn Leu Lys Lys Thr
            2675                2680                2685

Ser Gly Val Val Arg Leu Asn Asp Thr Val Gly Val Thr Lys Lys Cys
        2690                2695                2700

Ser Glu Asp Trp Lys Leu Val Arg Ser Ala Ser Phe Ser Arg Gly Gly
    2705                2710                2715                2720

Gln Leu Ser Phe Thr Asp Leu Gly Leu Pro Pro Thr Asp His Leu Gln
            2725                2730                2735

Ala Ser Phe Gly Phe Gln Thr Phe Gln Pro Ser Gly Ile Leu Leu Asp
            2740                2745                2750

His Gln Thr Trp Thr Arg Asn Leu Gln Val Thr Leu Glu Asp Gly Tyr
            2755                2760                2765

Ile Glu Leu Ser Thr Ser Asp Ser Gly Gly Pro Ile Phe Lys Ser Pro
        2770                2775                2780

Gln Thr Tyr Met Asp Gly Leu Leu His Tyr Val Ser Val Ile Ser Asp
2785                2790                2795                2800

Asn Ser Gly Leu Arg Leu Leu Ile Asp Asp Gln Leu Leu Arg Asn Ser
            2805                2810                2815

Lys Arg Leu Lys His Ile Ser Ser Ser Arg Gln Ser Leu Arg Leu Gly
            2820                2825                2830

Gly Ser Asn Phe Glu Gly Cys Ile Ser Asn Val Phe Val Gln Arg Leu
            2835                2840                2845

Ser Leu Ser Pro Glu Val Leu Asp Leu Thr Ser Asn Ser Leu Lys Arg
        2850                2855                2860

Asp Val Ser Leu Gly Gly Cys Ser Leu Asn Lys Pro Pro Phe Leu Met
2865                2870                2875                2880

Leu Leu Lys Gly Ser Thr Arg Phe Asn Lys Thr Lys Thr Phe Arg Ile
            2885                2890                2895

Asn Gln Leu Leu Gln Asp Thr Pro Val Ala Ser Pro Arg Ser Val Lys
            2900                2905                2910

Val Trp Gln Asp Ala Cys Ser Pro Leu Pro Lys Thr Gln Ala Asn His
            2915                2920                2925

Gly Ala Leu Gln Phe Gly Asp Ile Pro Thr Ser His Leu Leu Phe Lys
        2930                2935                2940

Leu Pro Gln Glu Leu Leu Lys Pro Arg Ser Gln Phe Ala Val Asp Met
2945                2950                2955                2960

Gln Thr Thr Ser Ser Arg Gly Leu Val Phe His Thr Gly Thr Lys Asn
            2965                2970                2975

Ser Phe Met Ala Leu Tyr Leu Ser Lys Gly Arg Leu Val Phe Ala Leu
        2980                2985                2990

Gly Thr Asp Gly Lys Lys Leu Arg Ile Lys Ser Lys Glu Lys Cys Asn
        2995                3000                3005

Asp Gly Lys Trp His Thr Val Val Phe Gly His Asp Gly Glu Lys Gly
    3010                3015                3020

Arg Leu Val Val Asp Gly Leu Arg Ala Arg Glu Gly Ser Leu Pro Gly
3025                3030                3035                3040

Asn Ser Thr Ile Ser Ile Arg Ala Pro Val Tyr Leu Gly Ser Pro Pro
            3045                3050                3055

Ser Gly Lys Pro Lys Ser Leu Pro Thr Asn Ser Phe Val Gly Cys Leu
        3060                3065                3070
```

-continued

```
Lys Asn Phe Gln Leu Asp Ser Lys Pro Leu Tyr Thr Pro Ser Ser Ser
        3075            3080            3085

Phe Gly Val Ser Ser Cys Leu Gly Gly Pro Leu Glu Lys Gly Ile Tyr
        3090            3095            3100

Phe Ser Glu Glu Gly Gly His Val Val Leu Ala His Ser Val Leu Leu
3105            3110            3115            3120

Gly Pro Glu Phe Lys Leu Val Phe Ser Ile Arg Pro Arg Ser Leu Thr
                3125            3130            3135

Gly Ile Leu Ile His Ile Gly Ser Gln Pro Gly Lys His Leu Cys Val
            3140            3145            3150

Tyr Leu Glu Ala Gly Lys Val Thr Ala Ser Met Asp Ser Gly Ala Gly
            3155            3160            3165

Gly Thr Ser Thr Ser Val Thr Pro Lys Gln Ser Leu Cys Asp Gly Gln
        3170            3175            3180

Trp His Ser Val Ala Val Thr Ile Lys Gln His Ile Leu His Leu Glu
3185            3190            3195            3200

Leu Asp Thr Asp Ser Ser Tyr Thr Ala Gly Gln Ile Pro Phe Pro Pro
                3205            3210            3215

Ala Ser Thr Gln Glu Pro Leu His Leu Gly Gly Ala Pro Ala Asn Leu
            3220            3225            3230

Thr Thr Leu Arg Ile Pro Val Trp Lys Ser Phe Phe Gly Cys Leu Arg
            3235            3240            3245

Asn Ile His Val Asn His Ile Pro Val Pro Val Thr Glu Ala Leu Glu
        3250            3255            3260

Val Gln Gly Pro Val Ser Leu Asn Gly Cys Pro Asp Gln
3265            3270            3275

<210> SEQ ID NO 34
<211> LENGTH: 1668
<212> TYPE: PRT
<213> ORGANISM: Homo sapiens

<400> SEQUENCE: 34

Met Pro Pro Ala Val Arg Arg Ser Ala Cys Ser Met Gly Trp Leu Trp
1               5               10              15

Ile Phe Gly Ala Ala Leu Gly Gln Cys Leu Gly Tyr Ser Ser Gln Gln
            20              25              30

Gln Arg Val Pro Phe Leu Gln Pro Pro Gly Gln Ser Gln Leu Gln Ala
        35              40              45

Ser Tyr Val Glu Phe Arg Pro Ser Gln Gly Cys Ser Pro Gly Tyr Tyr
    50              55              60

Arg Asp His Lys Gly Leu Tyr Thr Gly Arg Cys Val Pro Cys Asn Cys
65              70              75              80

Asn Gly His Ser Asn Gln Cys Gln Asp Gly Ser Gly Ile Cys Val Asn
            85              90              95

Cys Gln His Asn Thr Ala Gly Glu His Cys Glu Arg Cys Gln Glu Gly
        100             105             110

Tyr Tyr Gly Asn Ala Val His Gly Ser Cys Arg Ala Cys Pro Cys Pro
        115             120             125

His Thr Asn Ser Phe Ala Thr Gly Cys Val Val Asn Gly Gly Asp Val
        130             135             140

Arg Cys Ser Cys Lys Ala Gly Tyr Thr Gly Thr Gln Cys Glu Arg Cys
145             150             155             160

Ala Pro Gly Tyr Phe Gly Asn Pro Gln Lys Phe Gly Gly Ser Cys Gln
            165             170             175
```

```
Pro Cys Ser Cys Asn Ser Asn Gly Gln Leu Gly Ser Cys His Pro Leu
            180                 185                 190

Thr Gly Asp Cys Ile Asn Gln Glu Pro Lys Asp Ser Ser Pro Ala Glu
            195                 200                 205

Glu Cys Asp Asp Cys Asp Ser Cys Val Met Thr Leu Leu Asn Asp Leu
    210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
            275                 280                 285

Leu Asn Gln Glu Phe Glu Thr Leu Gln Glu Lys Ala Gln Val Asn Ser
    290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
                325                 330                 335

Met Leu Asn Arg Ile Arg Thr Trp Gln Lys Thr His Gln Gly Glu Asn
            340                 345                 350

Asn Gly Leu Ala Asn Ser Ile Arg Asp Ser Leu Asn Glu Tyr Glu Ala
            355                 360                 365

Lys Leu Ser Asp Leu Arg Ala Arg Leu Gln Glu Ala Ala Ala Gln Ala
    370                 375                 380

Lys Gln Ala Asn Gly Leu Asn Gln Glu Asn Glu Arg Ala Leu Gly Ala
385                 390                 395                 400

Ile Gln Arg Gln Val Lys Glu Ile Asn Ser Leu Gln Ser Asp Phe Thr
                405                 410                 415

Lys Tyr Leu Thr Thr Ala Asp Ser Ser Leu Leu Gln Thr Asn Ile Ala
            420                 425                 430

Leu Gln Leu Met Glu Lys Ser Gln Lys Glu Tyr Glu Lys Leu Ala Ala
            435                 440                 445

Ser Leu Asn Glu Ala Arg Gln Glu Leu Ser Asp Lys Val Arg Glu Leu
    450                 455                 460

Ser Arg Ser Ala Gly Lys Thr Ser Leu Val Glu Glu Ala Glu Lys His
465                 470                 475                 480

Ala Arg Ser Leu Gln Glu Leu Ala Lys Gln Leu Glu Glu Ile Lys Arg
                485                 490                 495

Asn Ala Ser Gly Asp Glu Leu Val Arg Cys Ala Val Asp Ala Ala Thr
            500                 505                 510

Ala Tyr Glu Asn Ile Leu Asn Ala Ile Lys Ala Ala Glu Asp Ala Ala
            515                 520                 525

Asn Arg Ala Ala Ser Ala Ser Glu Ser Ala Leu Gln Thr Val Ile Lys
    530                 535                 540

Glu Asp Leu Pro Arg Lys Ala Lys Thr Leu Ser Ser Asn Ser Asp Lys
545                 550                 555                 560

Leu Leu Asn Glu Ala Lys Met Thr Gln Lys Lys Leu Lys Gln Glu Val
                565                 570                 575

Ser Pro Ala Leu Asn Asn Leu Gln Gln Thr Leu Asn Ile Val Thr Val
            580                 585                 590
```

-continued

```
Gln Lys Glu Val Ile Asp Thr Asn Leu Thr Thr Leu Arg Asp Gly Leu
        595                 600                 605

His Gly Ile Gln Arg Gly Asp Ile Asp Ala Met Ile Ser Ser Ala Lys
        610                 615                 620

Ser Met Val Arg Lys Ala Asn Asp Ile Thr Asp Glu Val Leu Asp Gly
625                 630                 635                 640

Leu Asn Pro Ile Gln Thr Asp Val Glu Arg Ile Lys Asp Thr Tyr Gly
                645                 650                 655

Arg Thr Gln Asn Glu Asp Phe Lys Lys Ala Leu Thr Asp Ala Asp Asn
                660                 665                 670

Ser Val Asn Lys Leu Thr Asn Lys Leu Pro Asp Leu Trp Arg Lys Ile
                675                 680                 685

Glu Ser Ile Asn Gln Gln Leu Leu Pro Leu Gly Asn Ile Ser Asp Asn
        690                 695                 700

Met Asp Arg Ile Arg Glu Leu Ile Gln Gln Ala Arg Asp Ala Ala Ser
705                 710                 715                 720

Lys Val Ala Val Pro Met Arg Phe Asn Gly Lys Ser Gly Val Glu Val
                725                 730                 735

Arg Leu Pro Asn Asp Leu Glu Asp Leu Lys Gly Tyr Thr Ser Leu Ser
                740                 745                 750

Leu Phe Leu Gln Arg Pro Asn Ser Arg Glu Asn Gly Gly Thr Glu Asn
        755                 760                 765

Met Phe Val Met Tyr Leu Gly Asn Lys Asp Ala Ser Arg Asp Tyr Ile
        770                 775                 780

Gly Met Ala Val Val Asp Gly Gln Leu Thr Cys Val Tyr Asn Leu Gly
785                 790                 795                 800

Asp Arg Glu Ala Glu Leu Gln Val Asp Gln Ile Leu Thr Lys Ser Glu
                805                 810                 815

Thr Lys Glu Ala Val Met Asp Arg Val Lys Phe Gln Arg Ile Tyr Gln
                820                 825                 830

Phe Ala Arg Leu Asn Tyr Thr Lys Gly Ala Thr Ser Ser Lys Pro Glu
        835                 840                 845

Thr Pro Gly Val Tyr Asp Met Asp Gly Arg Asn Ser Asn Thr Leu Leu
        850                 855                 860

Asn Leu Asp Pro Glu Asn Val Val Phe Tyr Val Gly Gly Tyr Pro Pro
865                 870                 875                 880

Asp Phe Lys Leu Pro Ser Arg Leu Ser Phe Pro Pro Tyr Lys Gly Cys
                885                 890                 895

Ile Glu Leu Asp Asp Leu Asn Glu Asn Val Leu Ser Leu Tyr Asn Phe
                900                 905                 910

Lys Lys Thr Phe Asn Leu Asn Thr Thr Glu Val Glu Pro Cys Arg Arg
        915                 920                 925

Arg Lys Glu Glu Ser Asp Lys Asn Tyr Phe Glu Gly Thr Gly Tyr Ala
        930                 935                 940

Arg Val Pro Thr Gln Pro His Ala Pro Ile Pro Thr Phe Gly Gln Thr
945                 950                 955                 960

Ile Gln Thr Thr Val Asp Arg Gly Leu Leu Phe Phe Ala Glu Asn Gly
                965                 970                 975

Asp Arg Phe Ile Ser Leu Asn Ile Glu Asp Gly Lys Leu Met Val Arg
                980                 985                 990

Tyr Lys Leu Asn Ser Glu Leu Pro Lys Glu Arg Gly Val Gly Asp Ala
        995                 1000                1005

Ile Asn Asn Gly Arg Asp His Ser Ile Gln Ile Lys Ile Gly Lys Leu
```

-continued

```
            1010              1015                1020

Gln Lys Arg Met Trp Ile Asn Val Asp Val Gln Asn Thr Ile Ile Asp
1025              1030                1035                1040

Gly Glu Val Phe Asp Phe Ser Thr Tyr Tyr Leu Gly Gly Ile Pro Ile
                 1045                1050                1055

Ala Ile Arg Glu Arg Phe Asn Ile Ser Thr Pro Ala Phe Arg Gly Cys
                 1060                1065                1070

Met Lys Asn Leu Lys Lys Thr Ser Gly Val Val Arg Leu Asn Asp Thr
             1075                1080                1085

Val Gly Val Thr Lys Lys Cys Ser Glu Asp Trp Lys Leu Val Arg Ser
             1090                1095                1100

Ala Ser Phe Ser Arg Gly Gly Gln Leu Ser Phe Thr Asp Leu Gly Leu
1105                1110                1115                1120

Pro Pro Thr Asp His Leu Gln Ala Ser Phe Gly Phe Gln Thr Phe Gln
                 1125                1130                1135

Pro Ser Gly Ile Leu Leu Asp His Gln Thr Trp Thr Arg Asn Leu Gln
                 1140                1145                1150

Val Thr Leu Glu Asp Gly Tyr Ile Glu Leu Ser Thr Ser Asp Ser Gly
             1155                1160                1165

Gly Pro Ile Phe Lys Ser Pro Gln Thr Tyr Met Asp Gly Leu Leu His
             1170                1175                1180

Tyr Val Ser Val Ile Ser Asp Asn Ser Gly Leu Arg Leu Leu Ile Asp
1185                1190                1195                1200

Asp Gln Leu Leu Arg Asn Ser Lys Arg Leu Lys His Ile Ser Ser Ser
                 1205                1210                1215

Arg Gln Ser Leu Arg Leu Gly Gly Ser Asn Phe Glu Gly Cys Ile Ser
                 1220                1225                1230

Asn Val Phe Val Gln Arg Leu Ser Leu Ser Pro Glu Val Leu Asp Leu
             1235                1240                1245

Thr Ser Asn Ser Leu Lys Arg Asp Val Ser Leu Gly Gly Cys Ser Leu
             1250                1255                1260

Asn Lys Pro Pro Phe Leu Met Leu Leu Lys Gly Ser Thr Arg Phe Asn
1265                1270                1275                1280

Lys Thr Lys Thr Phe Arg Ile Asn Gln Leu Leu Gln Asp Thr Pro Val
                 1285                1290                1295

Ala Ser Pro Arg Ser Val Lys Val Trp Gln Asp Ala Cys Ser Pro Leu
             1300                1305                1310

Pro Lys Thr Gln Ala Asn His Gly Ala Leu Gln Phe Gly Asp Ile Pro
             1315                1320                1325

Thr Ser His Leu Leu Phe Lys Leu Pro Gln Glu Leu Leu Lys Pro Arg
             1330                1335                1340

Ser Gln Phe Ala Val Asp Met Gln Thr Thr Ser Ser Arg Gly Leu Val
1345                1350                1355                1360

Phe His Thr Gly Thr Lys Asn Ser Phe Met Ala Leu Tyr Leu Ser Lys
                 1365                1370                1375

Gly Arg Leu Val Phe Ala Leu Gly Thr Asp Gly Lys Lys Leu Arg Ile
                 1380                1385                1390

Lys Ser Lys Glu Lys Cys Asn Asp Gly Lys Trp His Thr Val Val Phe
             1395                1400                1405

Gly His Asp Gly Glu Lys Gly Arg Leu Val Val Asp Gly Leu Arg Ala
             1410                1415                1420

Arg Glu Gly Ser Leu Pro Gly Asn Ser Thr Ile Ser Ile Arg Ala Pro
1425                1430                1435                1440
```

```
Val Tyr Leu Gly Ser Pro Pro Ser Gly Lys Pro Lys Ser Leu Pro Thr
                1445             1450             1455

Asn Ser Phe Val Gly Cys Leu Lys Asn Phe Gln Leu Asp Ser Lys Pro
                1460             1465             1470

Leu Tyr Thr Pro Ser Ser Ser Phe Gly Val Ser Ser Cys Leu Gly Gly
            1475             1480             1485

Pro Leu Glu Lys Gly Ile Tyr Phe Ser Glu Glu Gly Gly His Val Val
            1490             1495             1500

Leu Ala His Ser Val Leu Leu Gly Pro Glu Phe Lys Leu Val Phe Ser
1505             1510             1515             1520

Ile Arg Pro Arg Ser Leu Thr Gly Ile Leu Ile His Ile Gly Ser Gln
                1525             1530             1535

Pro Gly Lys His Leu Cys Val Tyr Leu Glu Ala Gly Lys Val Thr Ala
                1540             1545             1550

Ser Met Asp Ser Gly Ala Gly Gly Thr Ser Thr Ser Val Thr Pro Lys
                1555             1560             1565

Gln Ser Leu Cys Asp Gly Gln Trp His Ser Val Ala Val Thr Ile Lys
            1570             1575             1580

Gln His Ile Leu His Leu Glu Leu Asp Thr Asp Ser Ser Tyr Thr Ala
1585             1590             1595             1600

Gly Gln Ile Pro Phe Pro Pro Ala Ser Thr Gln Glu Pro Leu His Leu
                1605             1610             1615

Gly Gly Ala Pro Ala Asn Leu Thr Thr Leu Arg Ile Pro Val Trp Lys
            1620             1625             1630

Ser Phe Phe Gly Cys Leu Arg Asn Ile His Val Asn His Ile Pro Val
            1635             1640             1645

Pro Val Thr Glu Ala Leu Glu Val Gln Gly Pro Val Ser Leu Asn Gly
            1650             1655             1660

Cys Pro Asp Gln
1665

<210> SEQ ID NO 35
<211> LENGTH: 1111
<212> TYPE: PRT
<213> ORGANISM: Homo sapiens

<400> SEQUENCE: 35

Met Pro Ala Leu Trp Leu Gly Cys Cys Leu Cys Phe Ser Leu Leu Leu
1               5               10              15

Pro Ala Ala Arg Ala Thr Ser Arg Arg Glu Val Cys Asp Cys Asn Gly
                20              25              30

Lys Ser Arg Gln Cys Ile Phe Asp Arg Glu Leu His Arg Gln Thr Gly
            35              40              45

Asn Gly Phe Arg Cys Leu Asn Cys Asn Asp Asn Thr Asp Gly Ile His
        50              55              60

Cys Glu Lys Cys Lys Asn Gly Phe Tyr Arg His Arg Glu Arg Asp Arg
65              70              75              80

Cys Leu Pro Cys Asn Cys Asn Ser Lys Gly Ser Leu Ser Ala Arg Cys
                85              90              95

Asp Asn Ser Gly Arg Cys Ser Cys Lys Pro Gly Val Thr Gly Ala Arg
            100             105             110

Cys Asp Arg Cys Leu Pro Gly Phe His Met Leu Thr Asp Ala Gly Cys
            115             120             125

Thr Gln Asp Gln Arg Leu Leu Asp Ser Lys Cys Asp Cys Asp Pro Ala
```

```
           130               135               140

Gly Ile Ala Gly Pro Cys Asp Ala Gly Arg Cys Val Cys Lys Pro Ala
145               150               155               160

Val Thr Gly Glu Arg Cys Asp Arg Cys Arg Ser Gly Tyr Tyr Asn Leu
                  165               170               175

Asp Gly Gly Asn Pro Glu Gly Cys Thr Gln Cys Phe Cys Tyr Gly His
                  180               185               190

Ser Ala Ser Cys Arg Ser Ser Ala Glu Tyr Ser Val His Lys Ile Thr
                  195               200               205

Ser Thr Phe His Gln Asp Val Asp Gly Trp Lys Ala Val Gln Arg Asn
         210               215               220

Gly Ser Pro Ala Lys Leu Gln Trp Ser Gln Arg His Gln Asp Val Phe
225               230               235               240

Ser Ser Ala Gln Arg Leu Asp Pro Val Tyr Phe Val Ala Pro Ala Lys
                  245               250               255

Phe Leu Gly Asn Gln Gln Val Ser Tyr Gly Gln Ser Leu Ser Phe Asp
                  260               265               270

Tyr Arg Val Asp Arg Gly Gly Arg His Pro Ser Ala His Asp Val Ile
                  275               280               285

Leu Glu Gly Ala Gly Leu Arg Ile Thr Ala Pro Leu Met Pro Leu Gly
         290               295               300

Lys Thr Leu Pro Cys Gly Leu Thr Lys Thr Tyr Thr Phe Arg Leu Asn
305               310               315               320

Glu His Pro Ser Asn Asn Trp Ser Pro Gln Leu Ser Tyr Phe Glu Tyr
                  325               330               335

Arg Arg Leu Leu Arg Asn Leu Thr Ala Leu Arg Ile Arg Ala Thr Tyr
                  340               345               350

Gly Glu Tyr Ser Thr Gly Tyr Ile Asp Asn Val Thr Leu Ile Ser Ala
                  355               360               365

Arg Pro Val Ser Gly Ala Pro Ala Pro Trp Val Glu Gln Cys Ile Cys
         370               375               380

Pro Val Gly Tyr Lys Gly Gln Phe Cys Gln Asp Cys Ala Ser Gly Tyr
385               390               395               400

Lys Arg Asp Ser Ala Arg Leu Gly Pro Phe Gly Thr Cys Ile Pro Cys
                  405               410               415

Asn Cys Gln Gly Gly Gly Ala Cys Asp Pro Asp Thr Gly Asp Cys Tyr
                  420               425               430

Ser Gly Asp Glu Asn Pro Asp Ile Glu Cys Ala Asp Cys Pro Ile Gly
                  435               440               445

Phe Tyr Asn Asp Pro His Asp Pro Arg Ser Cys Lys Pro Cys Pro Cys
         450               455               460

His Asn Gly Phe Ser Cys Ser Val Met Pro Glu Thr Glu Glu Val Val
465               470               475               480

Cys Asn Asn Cys Pro Pro Gly Val Thr Gly Ala Arg Cys Glu Leu Cys
                  485               490               495

Ala Asp Gly Tyr Phe Gly Asp Pro Phe Gly Glu His Gly Pro Val Arg
                  500               505               510

Pro Cys Gln Pro Cys Gln Cys Asn Asn Asn Val Asp Pro Ser Ala Ser
         515               520               525

Gly Asn Cys Asp Arg Leu Thr Gly Arg Cys Leu Lys Cys Ile His Asn
         530               535               540

Thr Ala Gly Ile Tyr Cys Asp Gln Cys Lys Ala Gly Tyr Phe Gly Asp
545               550               555               560
```

-continued

```
Pro Leu Ala Pro Asn Pro Ala Asp Lys Cys Arg Ala Cys Asn Cys Asn
            565             570             575

Pro Met Gly Ser Glu Pro Val Gly Cys Arg Ser Asp Gly Thr Cys Val
            580             585             590

Cys Lys Pro Gly Phe Gly Gly Pro Asn Cys Glu His Gly Ala Phe Ser
            595             600             605

Cys Pro Ala Cys Tyr Asn Gln Val Lys Ile Gln Met Asp Gln Phe Met
            610             615             620

Gln Gln Leu Gln Arg Met Glu Ala Leu Ile Ser Lys Ala Gln Gly Gly
625             630             635             640

Asp Gly Val Val Pro Asp Thr Glu Leu Glu Gly Arg Met Gln Gln Ala
            645             650             655

Glu Gln Ala Leu Gln Asp Ile Leu Arg Asp Ala Gln Ile Ser Glu Gly
            660             665             670

Ala Ser Arg Ser Leu Gly Leu Gln Leu Ala Lys Val Arg Ser Gln Glu
            675             680             685

Asn Ser Tyr Gln Ser Arg Leu Asp Asp Leu Lys Met Thr Val Glu Arg
            690             695             700

Val Arg Ala Leu Gly Ser Gln Tyr Gln Asn Arg Val Arg Asp Thr His
705             710             715             720

Arg Leu Ile Thr Gln Met Gln Leu Ser Leu Ala Glu Ser Glu Ala Ser
            725             730             735

Leu Gly Asn Thr Asn Ile Pro Ala Ser Asp His Tyr Val Gly Pro Asn
            740             745             750

Gly Phe Lys Ser Leu Ala Gln Glu Ala Thr Arg Leu Ala Glu Ser His
            755             760             765

Val Glu Ser Ala Ser Asn Met Glu Gln Leu Thr Arg Glu Thr Glu Asp
            770             775             780

Tyr Ser Lys Gln Ala Leu Ser Leu Val Arg Lys Ala Leu His Glu Gly
785             790             795             800

Val Gly Ser Gly Ser Gly Ser Pro Asp Gly Ala Val Val Gln Gly Leu
            805             810             815

Val Glu Lys Leu Glu Lys Thr Lys Ser Leu Ala Gln Gln Leu Thr Arg
            820             825             830

Glu Ala Thr Gln Ala Glu Ile Glu Ala Asp Arg Ser Tyr Gln His Ser
            835             840             845

Leu Arg Leu Leu Asp Ser Val Ser Arg Leu Gln Gly Val Ser Asp Gln
            850             855             860

Ser Phe Gln Val Glu Glu Ala Lys Arg Ile Lys Gln Lys Ala Asp Ser
865             870             875             880

Leu Ser Ser Leu Val Thr Arg His Met Asp Glu Phe Lys Arg Thr Gln
            885             890             895

Lys Asn Leu Gly Asn Trp Lys Glu Glu Ala Gln Gln Leu Leu Gln Asn
            900             905             910

Gly Lys Ser Gly Arg Glu Lys Ser Asp Gln Leu Leu Ser Arg Ala Asn
            915             920             925

Leu Ala Lys Ser Arg Ala Gln Glu Ala Leu Ser Met Gly Asn Ala Thr
            930             935             940

Phe Tyr Glu Val Glu Ser Ile Leu Lys Asn Leu Arg Glu Phe Asp Leu
945             950             955             960

Gln Val Asp Asn Arg Lys Ala Glu Ala Glu Glu Ala Met Lys Arg Leu
            965             970             975
```

```
Ser Tyr Ile Ser Gln Lys Val Ser Asp Ala Ser Asp Lys Thr Gln Gln
        980                 985                 990

Ala Glu Arg Ala Leu Gly Ser Ala Ala Ala Asp Ala Gln Arg Ala Lys
        995                 1000                1005

Asn Gly Ala Gly Glu Ala Leu Glu Ile Ser Ser Glu Ile Glu Gln Glu
        1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
                1060                1065                1070

Ala Val Gln Met Val Ile Thr Glu Ala Gln Lys Val Asp Thr Arg Ala
                1075                1080                1085

Lys Asn Ala Gly Val Thr Ile Gln Asp Thr Leu Asn Thr Leu Asp Gly
        1090                1095                1100

Leu Leu His Leu Met Gly Met
1105                1110

<210> SEQ ID NO 36
<211> LENGTH: 12186
<212> TYPE: DNA
<213> ORGANISM: Homo sapiens

<400> SEQUENCE: 36
atgtctactc tcctggaaaa catctttgcc ataattaatc ttttcaagca atattcaaaa      60
aaagataaaa acactgacac attgagtaaa aaagagctga aggaacttct ggaaaaggaa     120
tttcggcaaa tcctgaagaa tccagatgac ccagatatgg ttgatgtctt catggatcac     180
ttggatatag accacaacaa gaaaattgac ttcactgagt ttcttctgat ggtattcaag     240
ttggctcaag catattatga gtctaccaga aaagagaatt taccgatatc aggacacaag     300
cacagaaagc acagtcatca tgataaacat gaagataata aacaggaaga aaacaaagaa     360
aacagaaaaa gaccctcaag tctggaaaga agaaacaata gaaaagggaa taagggaaga     420
tccaagagcc caagagaaac aggggggaaa aggcatgaat ctagttctga aaaaaaagaa     480
agaaaaggat attcacctac tcatagagaa gaagaatatg gaaaaaacca tcataactca     540
agtaaaaaag agaaaaacaa gactgaaaat actagattag gagacaatag gaagaggcta     600
agtgaaagac ttgaagagaa agaagacaat gaagaaggag tatatgatta tgaaaataca     660
ggaagaatga ctcaaaaatg gatacaatca ggccatattg ccacatatta cacaatccag     720
gatgaagcct atgacaccac tgatagtcta ttagaagaaa acaaaatata tgaaagatca     780
aggtcatctg atggcaaatc atcatctcaa gtgaacaggt caagacatga aaatacaagc     840
caggtaccat tgcaggagtc caggacaaga aagcgtaggg gatccagagt tagccaggac     900
agggacagtg agggacactc agaagactct gagaggcact ctgggtcggc ttccagaaac     960
catcatggat ctgcgtggga gcagtcaaga gatggctcca gacaccccag gtcccatgat    1020
gaagacagag ccagtcatgg gcactctgca gacagctcca gacaatcagg cactcgtcac    1080
gcagagactt cctctcgtgg acagactgca tcatcccatg aacaggcaag atcaagtcca    1140
ggagaaagac atggatccgg ccaccagcag tcagcagaca gctccagaca ctcagccact    1200
gggcgcgggc aagcttcatc tgcagtcagc gatcgtggac accggggggtc tagcggtagt    1260 caggccagtg acagtgaggg acattcagaa aactcagaca cacaatcagt gtcaggccac    1320
```

```
ggaaaggctg ggctgagaca gcagagccac caagagtcca cacgtggccg gtcaggggaa      1380
cggtctggac gttcagggtc ttccctctac caggtgagca ctcatgaaca gcctgactct      1440
gcccatggac ggaccgggac cagcactgga ggaagacaag gatcgcacca cgagcaggca      1500
cgagacagct ccaggcattc agcgtcccaa gagggtcagg acaccattcg tggacacccg      1560
gggtcaagca gaggaggaag gcagggatcc caccacgagc aatcggtaaa taggtctgga      1620
cactcaggtt cccatcacag ccacaccaca tcccagggaa ggtctgatgc ctcccatggg      1680
cagtcaggat ccagaagtgc aagcagacaa acacgaaatg aggaacaatc aggagacggc      1740
accaggcact cagggtcacg tcatcatgaa gcttcctctc aggctgacag ctctagacac      1800
tcacaggtgg gccagggaca atcatcgggg cccaggacaa gtaggaacca gggatccagt      1860
gttagccagg acagtgacag tcagggcac tcagaagact ctgagaggtg gtctgggtct       1920
gcttccagaa accatcatgg atctgctcag gagcagtcaa gagatggctc cagacacccc      1980
aggtcccatc acgaagacag agctggtcat gggcactctg cagacagctc cagaaaatca      2040
ggcactcgtc acacacagaa ttcctctagt ggacaggctg cgtcatccca tgaacaggca      2100
agatcaagtg caggagaaag acatggatcc cgccaccagc tccagtcagc agacagctcc      2160
agacactcag gcactgggca cggacaagct tcatctgcag tcagagacag tggacaccga      2220
gggtccagtg gtagtcaggc cactgacagt gagggacatt cagaagactc agacacacag      2280
tcagtgtcag gccatggaca ggctggtcac catcagcaga gccaccaaga gtccgcacgt      2340
gaccggtcag gggaaaggtc tcgacgttca gggtctttcc tctaccaggt gagcactcat      2400
aaacagtctg agtcctccca tggatggaca gggcccagca ctggagtaag acaaggatcc      2460
caccatgagc aggcacgaga caactccagg cactcagcat cccaagatgg tcaggacacc      2520
attcgtggac acccggggtc aagcagaaga ggaaggcagg ggtcccacca cgagcaatcg      2580
gtagataggt ctggacactc agggtcccat cacagccaca ccacatccca gggaaggtct      2640
gatgcctccc gtgggcagtc aggatccaga agtgcaagca gaacaacacg taatgaggaa      2700
caatcaagag acggctccag gcactcaggg tcacgtcacc atgaagcttc ctctcatgcc      2760
gacatctcta gacactcaca ggcaggccag ggacaatcag aggggtccag gacaagcagg      2820
cgccagggat ccagtgttag ccaggacagt gacagtgagg gacattcaga agactctgag      2880
aggtggtctg ggtctgcttc cagaaaccat cgtggatctg ctcaggagca gtcaagacat      2940
ggctccagac accccaggtc ccatcacgaa gacagagccg gtcacgggca ctctgcagac      3000
agctccagac aatcaggaac tcctcacgca gagacttcct ctggtggaca ggctgcgtca      3060
tcccatgaac aggcaagatc aagtccagga gaaagacacg gatcccgcca ccagcagtca      3120
gcagacagct ccagacactc aggcattccg cgcagacaag cttcatctgc agtcagagac      3180
agtggacact gggggtccag tggtagtcag gccagtgata gtgagggaca ttcagaggag      3240
tcagacacac agtcagtgtc aggccatgga caggatgggc cccatcagca gagccaccaa      3300
gagtccgcac gtgactggtc aggggggaagg tctggacgtt cagggtcttt catctaccag      3360
gtgagcactc atgaacagtc tgagtctgcc catgggcgga ccaggaccag cactggacga      3420
agacaaggat cccaccacga gcaggcacga gacagctcca ggcactcagc gtcccaagag      3480
ggtcaggaca ccattcgtgc acacccgggg tcaaggagag gaggaaggca gggatcccac      3540
catgagcaat cggtagatag atctggacac tcagggtccc atcacagcca caccacatcc      3600
cagggaaggt ctgatgcctc ccatgggcag tcaggatcca gaagtgcaag cagacaaact      3660
cgtaaggaca aacaatcagg agacggctcc aggcactcag ggtcacgtca ccatgaagct      3720
```

```
gcctcttggg ctgacagctc tagacactca caggtgggac aggaacaatc atcggggtcc    3780
aggacaagca ggcaccaggg atccagtgtt agccaggaca gtgacagtga gagacactca    3840
gacgactccg agaggttgtc tgggtctgct tccagaaacc atcatggatc ttctcgggag    3900
cagtcaagag atggctccag acaccctggg ttccatcaag aagacagagc cagtcacggg    3960
cactctgcag acagctccag acaatcaggc actcatcaca cagagtcttc ctctcatgga    4020
caggctgtgt catcccatga acaggcaaga tcaagtccag gagaaagaca tggatcccgc    4080
caccagcagt cagcagacag ctccagacac tcaggcattg ggcacagaca agcttcatct    4140
gcagtcagag acagtggaca ccgagggtcc agtggtagtc aggtcactaa cagtgaggga    4200
cattcagaag actcagacac acagtcagtg tcagcccacg gacaagctgg gccccatcag    4260
cagagccaca aagagtccgc acgtggccag tcaggggaaa gctctggacg ttcaaggtct    4320
ttcctctacc aggtgagctc tcatgaacag tctgagtcca cacacggaca gactgcaccc    4380
agcactggag gaagacaagg atcccgccat gagcaggcac gaaacagctc taggcactca    4440
gcatcccaag acggtcagga caccattcgt ggacacccgg ggtcaagcag aggaggaagg    4500
cagggatcct accacgagca atcagtagat aggtctggac actcagggta ccatcacagc    4560
cacaccacac cccagggaag gtctgatgcc tcccatgggc agtcaggacc cagaagtgca    4620
agcaggcaaa caagaaatga ggaacaatca ggagacggct ccaggcactc agggtcacgt    4680
caccatgaac cttccactcg ggccggcagc tctagacact cacaggtggg ccagggagaa    4740
tcagcggggt ccaagacaag caggcgccag ggatccagtg ttagtcagga cagggacagt    4800
gagggacact cagaagactc tgagaggcgg tctgagtcgg cttccagaaa ccattatgga    4860
tctgctcggg agcagtcaag acatggctcc aggaacccca ggtcccatca agaagataga    4920
gccagtcatg ggcactctgc agagagctcc agacaatcag gcactcgtca tgcagagact    4980
tcctctggtg gacaggctgc atcatcccag gaacaggcaa ggtcaagtcc aggagaaaga    5040
catggatccc gccaccagca gtcagcagac agctccacag actcaggcac tgggcgcaga    5100
caagattcat ctgtagtcgg agacagtgga aaccgagggt ccagtggtag ccaggccagt    5160
gacagcgagg gacactcaga agagtcagac acacagtcag tgtcagccca cggacaggct    5220
gggccccatc agcagagcca ccaagagtcc acacgtggcc agtcagggga aaggtctgga    5280
cgttcagggt ctttcctcta ccaggtgagc actcatgaac agtctgagtc cgcccatgga    5340
cgcacagggc ccagcactgg aggaagacaa agatcccgcc acgagcaggc acgagacagc    5400
tccaggcact cagcgtccca agagggtcag gacaccattc gtggacaccc agggtcaagc    5460
agaggaggaa ggcagggatc ccactatgag caatcggtag atagttctgg acactcaggg    5520
tctcatcaca gccacaccac gtcccaggaa aggtctgatg tctcccgtgg gcagtcagga    5580
tccagaagtg tcagcagaca aacacgtaat gagaaacaat caggagacgg ctccaggcac    5640
tcagggtcgc gtcaccatga agcttcctct cgggccgaca gctctagaca ctcgcaggtg    5700
ggccagggac aatcatcagg gcccaggaca agcaggaacc agggatccag tgttagccag    5760
gacagtgaca gtcagggaca ctcagaagac tctgagaggt ggtctgggtc tgcttccaga    5820
aaccatcttg gatctgcttg ggagcagtca agagatggct ccagacaccc tgggtcccat    5880
cacgaagaca gagccggtca cgggcactct gcagacagct ccagacaatc aggcactcgt    5940
cacacagagt cttcctctcg tggacaggct gcgtcatccc atgaacaggc aagatcaagt    6000
gcaggagaaa gacatggatc ccaccaccag ctccagtcag cagacagctc cagacactca    6060
```

-continued

```
ggcattgggc atggacaagc ttcatctgca gtcagagaca gtggacaccg agggtacagt    6120
ggtagtcagg ccagtgacag tgagggacat tcagaagact cagacacaca gtcagtgtca    6180
gcacagggaa aagctgggcc ccatcagcag agccacaaag agtccgcacg tggccagtca    6240
ggggaaagct ctggacgttc agggtctttc ctctaccagg tgagcactca tgaacagtct    6300
gagtccaccc atggacagtc tgcgcccagc actggaggaa gacaaggatc ccattatgat    6360
caggcacaag acagctccag gcactcagca tcccaagagg gtcaggacac cattcgtgga    6420
cacccggggc caagcagagg aggaagacag gggtcccacc aagagcaatc ggtagatagg    6480
tctggacact cagggtctca tcacagccac accacatccc agggaaggtc tgatgcctcc    6540
cgtgggcagt caggatccag aagtgcaagc agaaaaacat atgacaagga acaatcagga    6600
gatggctcta ggcactcagg gtcgcatcat catgaagctt cctcttgggc cgacagctct    6660
agacactcac tggtgggcca gggacaatca tcagggccca ggacaagcag ccccggggga    6720
tccagtgtta gccaggacag tgacagtgag ggacactcag aagattctga gaggcggtct    6780
gggtctgcgt ccagaaacca tcatggatct gctcaggagc agtcaagaga tggctccaga    6840 cacccaggt cccatcacga agacagagcc ggtcatgggc actctgcaga gagctccaga    6900
caatcaggca ctcatcatgc agagaattcc tctggtggac aggctgcatc atcccatgaa    6960
caggcaagat caagtgcagg agagagacac ggatcccacc accagcagtc agcagacagc    7020
tccagacact caggcattgg gcacggacaa gcttcatctg cagtcagaga cagtggacac    7080
cgagggtcca gtggtagtca ggccagtgac agtgagggac attcagaaga ctcagacaca    7140
cagtcagtgt cagcccacgg acaggctggg ccccatcagc agagccacca agagtccaca    7200
cgtggccggt cagcaggaag gtctggacgt tcagggtctt tcctctacca ggtgagcact    7260
catgaacagt ctgagtccgc ccatggacgg accgggacca gcactggagg aagacaagga    7320
tcccaccaca agcaggcacg agacagctcc aggcactcaa cgtcccaaga gggtcaggac    7380
accattcatg acacccgggg tcaagcagt ggaggaaggc agggatccca ctacgagcaa    7440
ttggtagata gatctggaca ctcagggtct catcacagcc acaccacatc ccagggaagg    7500
tctgatgcct cccatgggca ctcaggatcc agaagtgcaa gcagacaaac tcgtaacgat    7560
gaacaatcag gagacggctc caggcactca gggtcgcgtc accatgaagc ttcctctcgg    7620
gccgacagct ctggacactc gcaggtgggc caggacaat cagaggggcc caggacaagc    7680
aggaactggg gatccagttt tagccaggac agtgacagtc agggacactc agaagactct    7740
gagaggtggt ctgggtctgc ttccagaaac catcatggat ctgctcagga gcagctaaga    7800
gatggctcca gacaccccag gtcccatcaa gaagacagag ctggtcatgg gcactctgca    7860
gacagctcca gacaatcagg cactcgtcac acacagactt cctctggtgg acaggctgca    7920
tcatcccatg aacaggcaag atcaagtgca ggagaaagac atggatccca ccaccagcag    7980
tcagcagaca gctccagaca ctcaggcatt gggcacggac aagcttcatc tgcagtcaga    8040
gacagtggac accgagggta cagtggtagt caggccagtg acaatgaggg acattcagaa    8100
gactcagaca cacagtcagt gtcagcccac ggacaggctg ggtcccatca gcagagccac    8160
caagagtccg cacgtggccg tcaggggaa acgtctggac attcaggatc tttcctctac    8220
caggtgagca ctcatgaaca gtctgagtcc tcccatggat ggacggggcc cagcactaga    8280
ggaagacaag gatcccgcca tgagcaggca caagacagct ccaggcactc agcatcccaa    8340
gacggtcagg acaccattcg tggacacccg gggtcaagca gaggaggaag gcaggggtac    8400
caccacgagc attcggtaga tagctctgga cactcagggt cccatcacag ccacaccaca    8460
```

-continued

```
tcccagggaa ggtctgatgc ctcccgtggg cagtcaggat ccagaagtgc aagcagaaca    8520
acacgtaatg aggaacaatc aggagacggc tccaggcact cagggtcgcg tcaccatgaa    8580
gcttccactc atgccgacat ctctagacac tcacaggcag tccagggaca atcagagggg    8640
tccaggagaa gcaggcgcca gggatccagt gtgagccagg acagtgacag tgagggacat    8700
tcagaagact ctgagaggtg gtctgggtct gcttccagaa accatcatgg atctgctcag    8760
gagcagctaa gagatggctc cagacacccc aggtcccatc aagaagacag agctggtcat    8820
gggcactctg cagacagctc cagacaatca ggcactcgtc acacacagac ttcctctggt    8880
ggacaggctg catcatccca tgaacaggca agatcaagtg caggagaaag acatggatcc    8940
caccaccagc agtcagcaga cagctccaga cactcaggca ttgggcacgg acaagcttca    9000
tctgcagtca gagacagtgg acaccgaggg tacagtggta gtcaggccag tgacaatgag    9060
ggacattcag aagactcaga cacacagtca gtgtcagccc acggacaggc tgggtcccat    9120
cagcagagcc accaagagtc cgcacgtggc cggtcagggg aaacgtctgg acattcagga    9180
tctttcctct accaggtgag cactcatgaa cagtctgagt cctcccatgg atggacgggg    9240
cccagcacta gaggaagaca aggatcccgc catgagcagg cacaagacag ctccaggcac    9300
tcagcatccc aatacggtca ggacaccatt cgtggacacc cggggtcaag cagaggagga    9360
aggcaggggt accaccacga gcattcggta gatagctctg gacactcagg gtcccatcac    9420
agccacacca catcccaggg aaggtctgat gcctcccgtg ggcagtcagg atccagaagt    9480
gcaagcagaa caacacgtaa tgaggaacaa tcaggagaca gctccaggca ctcagtgtca    9540
cgtcaccatg aagcttccac tcatgccgac atctctagac actcacaggc agtccaggga    9600
caatcagagg ggtccaggag aagcaggcgc cagggatcca gtgtgagcca ggacagtgac    9660
agtgagggac attcagaaga ctctgagagg tggtctgggt ctgcttccag aaaccatcgt    9720
ggatctgttc aggagcagtc aaggcacggc tccagacacc ccaggtccca tcacgaagac    9780
agagccggtc acgggcactc tgcagaccgc tccagacaat caggcactcg tcacgcagag    9840
acttcctctg gtggacaggc tgcatcatcc catgaacagg caagatcaag tccaggagag    9900
agacacggat cccgccacca gcagtcagca gacagctcca gacactcagg cattccgcgt    9960
ggacaagctt catctgcagt cagagacagt agacactggg ggtccagtgg tagtcaggcc   10020
agtgatagtg agggacattc agaagagtca gacacacagt cagtgtcagg ccatggacag   10080
gctgggcccc atcagcagag ccaccaagag tccgcacgtg accggtcagg gggaaggtct   10140
ggacgttcag ggtctttcct ctaccaggtg agcactcatg aacagtctga gtctgcccat   10200
gggcggacca ggaccagcac tggacgaaga caaggatccc accacgagca ggcacgagac   10260
agctccaggc actcagcgtc ccaagagggt caggacacca ttcgtggaca cccgggggtca   10320 agcagaagag gaaggcaggg atcccactac gagcaatcgg tagataggtc tggacactca   10380
gggtcccatc acagccacac cacatcccag ggaaggtctg atgcctcccg tgggcagtca   10440
ggatccagaa gtgccagcag acaaactcgt aatgacgaac aatcaggaga tggctccagg   10500
cactcatggt cgcatcacca tgaagcttcc actcaggcgg acagctctag acactcacag   10560
tccggccagg acaatcagc ggggcccagg acaagcagga accagggatc cagtgttagc   10620
caggacagtg acagtcaggg acactcagaa gactctgaga ggtggtctgg gtctgcttcc   10680
agaaaccatc gtggatctgc tcaggagcag tcaagagatg gctccagaca ccccacgtcc   10740
catcacgaag acagagccgg tcacgggcac tctgcagaga gctccagaca atcaggcact   10800
```

```
catcatgcag agaattcctc tggtggacag gctgcatcat cccatgaaca ggcaagatca  10860
agtgcaggag agagacatgg atcccaccac cagcagtcag cagacagctc cagacactca  10920
ggcattgggc acggacaagc ttcatctgca gtcagagaca gtggacaccg agggtccagt  10980
ggtagtcagg ccagtgacag tgagggacat tcagaagact cagacacaca gtcagtgtca  11040
gcccacggac aggctgggcc ccatcagcag agccaccaag agtccacacg tggccggtca  11100
gcaggaaggt ctggacgttc agggtctttc ctctaccagg tgagcactca tgaacagtct  11160
gagtctgccc atggacgggc tgggcccagt actggaggaa gacaaggatc ccgccacgag  11220
caggcacgag acagctccag gcactcagcg tcccaagagg gtcaggacac cattcgtgga  11280
cacccggggt caaggagagg aggaagacag ggatcctacc acgagcaatc ggtagatagg  11340
tctggacact cagggtccca tcacagccac accacatccc agggaaggtc tgatgcctcc  11400
catgggcagt caggatccag aagtgcaagc agagaaacac gtaatgagga acagtcagga  11460
gacggctcca ggcactcagg gtcgcgtcac catgaagctt ccactcaggc tgacagctct  11520
agacactcac agtccggcca gggtgaatca gcggggtcca ggagaagcag gcgccaggga  11580
tccagtgtta gccaggacag tgacagtgag gcatacccag aggactctga gaggcgatct  11640
gagtctgctt ccagaaacca tcatggatct tctcgggagc agtcaagaga tggctccaga  11700 cacccccggat cctctcaccg cgatacagcc agtcatgtac agtcttcacc tgtacagtca  11760
gactctagta ccgctaagga acatggtcac tttagtagtc tttcacaaga ttctgcgtat  11820
cactcaggaa tacagtcacg tggcagtcct cacagttcta gttcttatca ttatcaatct  11880
gagggcactg aaaggcaaaa aggtcaatca ggtttagttt ggagacatgg cagctatggt  11940
agtgcagatt atgattatgg tgaatccggg tttagacact ctcagcacgg aagtgttagt  12000
tacaattcca atcctgttgt tttcaaggaa agatctgata tctgtaaagc aagtgcgttt  12060
ggtaaagatc atccaaggta ttatgcaacg tatattaata aggacccagg tttatgtggc  12120
cattctagtg atatatcgaa acaactggga tttagtcagt cacagagata ctattactat  12180
gagtaa                                                                 12186
```

<210> SEQ ID NO 37
<211> LENGTH: 12186
<212> TYPE: DNA
<213> ORGANISM: Artificial Sequence
<220> FEATURE:
<223> OTHER INFORMATION: Synthetic Construct

<400> SEQUENCE: 37

```
atgtctacac tgctggaaaa catcttcgcc atcatcaacc tgttcaagca gtacagcaag     60
aaggacaaga acaccgacac actgagcaag aaagagctga agaactgct cgagaaagag     120 ttccggcaga tcctgaagaa ccccgacgat cccgatatgg tggacgtgtt catggaccac     180
ctggacatcg accacaacaa gaagatcgac ttcaccgagt ttctgctgat ggtgttcaag     240
ctggcccagg cctactacga gagcaccaga aaagagaacc tgcctatcag cggccacaag     300
cacagaaagc acagccacca cgacaagcac gaggacaaca gcaagaaga gaacaaagag     360 aatcggaagc ggcccagcag cctggaaaga cggaacaaca gaaagggcaa caagggcaga     420
agcaagagcc ctagagagac aggcggcaag agacacgaga gcagctccga agagaaagag     480
agaaagggct acagcccac acacagagag gaagagtacg gcaagaacca ccacaacagc     540
agcaaaaaag agaagaacaa gaccgagaac acccggctgg gcgacaatag aaagagactg     600
agcgagcggc tggaagagaa agaggacaac gaggaaggcg tgtacgacta cgagaatacc     660
```

-continued

```
ggccggatga cccagaagtg gattcagtct ggccacattg ccacctacta caccatccag       720
gacgaggcct acgacaccac cgatagcctg ctggaagaaa acaagatcta cgagcggagc       780
agaagcagcg acggcaagag cagcagccaa gtgaacagaa gccggcacga gaacacaagc       840
caggtgccac tgcaagagag ccggacaaga aagcggagag gcagcagagt gtcccaggat       900
agagatagcg agggccacag cgaggatagc gagagacatt ctggcagcgc cagcagaaat       960
caccacggat ctgcctggga gcagagcaga gatggctcta gacaccctag aagccacgac      1020
gaggatagag cctctcacgg ccactctgcc gattctagca gacagtctgg caccagacac      1080
gccgagacaa gctctagagg acagacagcc agctctcacg agcaggctag atcttcccca      1140
ggcgaaagac acggctctgg acatcagcag tctgccgata gttctagaca cagcgccaca      1200
ggcagaggac aggcctcttc tgctgtgtcc gatagaggcc acagaggcag ctctggaagc      1260
caggcctctg attctgaggg ccactccgag aacagcgata cccagtctgt gtctggacac      1320
ggcaaagccg gactgagaca gcagagccac caagagagca ctagaggcag aagcggcgag      1380
agaagcggca gatctggcag ctctctgtac caggtgtcca cacacgaaca gcctgatagc      1440
gcccacggca gaactggaac atctactggt ggcagacagg gctctcacca cgaacaggcc      1500
agagattctt ccagacactc cgccagccaa gaaggccagg ataccattag aggacacccc      1560
ggatctagca gaggcggaag gcagggatct catcatgagc agtccgtgaa cagatccggc      1620
catagcggaa gccaccacag ccacacaaca tcccagggaa gatccgatgc cagccacggc      1680
caatctggaa gcagaagcgc ctccagacag accagaaatg aggaacagag cggcgacggc      1740
acaaggcaca gcggatctag acatcacgaa gccagcagcc aggccgatag cagcagacac      1800
tctcaagttg gccagggcca gtctagcggc cccagaacat ctagaaatca gggcagctcc      1860
gtgtctcagg actccgatag tcagggccat tctgaggatt ctgagcgttg gagcggcagc      1920
gcctctagaa accatcatgg ctctgcccaa gagcagtctc gcgacggaag cagacatcca      1980
cgcagccacc atgaagatag agccggccat ggacatagcg ccgacagctc tagaaagagc      2040
ggaaccagac acacccagaa ctcctctagc ggacaggccg catcttcaca tgagcaggca      2100
agaagctctg ccggcgaaag gcatggttcc agacatcagc tgcagagcgc cgactcttct      2160
agacattccg gaacaggaca tggccaggcc agcagcgctg ttagagattc tggccataga      2220
ggctcaagcg gctctcaggc caccgattcc gaaggacact ccgaagattc tgacacccag      2280
agtgtctctg ccacggaca ggcaggacat caccagcagt ctcaccaaga gtccgccaga      2340
gatagatctg cgagagatc cagaagatcc ggcagcttcc tgtatcaagt ctctacccac      2400
aagcagagcg agtctagcca cggctggaca ggaccttcta caggcgttag acagggcagt      2460
caccatgagc aagcccggga caattctagg catagcgcct ctcaggacgg ccaggacact      2520
ataagaggcc atcctggctc tagccgcaga ggtagacagg gaagccatca cgaacagtct      2580
gtggatagaa gcggccattc cggcagccat cactctcaca caactagcca ggggagatct      2640
gacgcatcta gaggccagtc tggatctaga agcgccagcc ggaccactag gaacgaggaa      2700
cagtctagag atggcagcag gcactccggc agtagacatc atgaggcctc tagccatgcc      2760
gacatctcaa gacattctca ggccggacag ggccagagcc aaggctctag aacatctcgg      2820
agacagggat ctagcgtcag ccaggacagc gacagcgagg ggcattctga agatagcgaa      2880
cgttggagtg gctccgcctc tcggaatcat agaggaagcg cccaagaaca gagcagacac      2940
ggatcaaggc accctcgctc acaccatgag gaccgtgctg gtcatggaca ttccgctgat      3000
```

-continued

```
tcctctaggc agagcggcac acctcacgcc gaaacatcta gcggaggaca agccgctagc   3060
agccatgaac aagctagaag ctctcctggg gagagacatg gaagtagaca ccagcagagc   3120
gctgatagca gccggcattc tggaatccct agaaggcagg ctagctccgc cgtcagagat   3180
tccggacatt gggggttctag tggttcccag gctagcgact ctgaagggca cagcgaagag   3240
tccgatacac agagcgttag cggacatgga caggatggac ctcaccaaca aagccatcaa   3300
gaatctgcta gagattggag cggaggaaga tctgggagaa gcggaagctt catctaccaa   3360
gtttcaaccc acgagcaatc cgagtccgct cacggaagaa ccagaacaag caccggcaga   3420
aggcaaggtt cccatcacga gcaagccaga gactctagcc ggcactctgc ctctcaagag   3480
ggccaagata caatcagggc tcaccccggt agtagaagag gcggtcgaca ggggtcacat   3540
catgaacaaa gcgtggacag atctggacac agcggctccc accactctca taccacatct   3600
caaggccgct ccgacgcctc tcatggtcaa tctgggtcta gatctgccag caggcagacc   3660
cggaaagata agcaatctgg cgacggctcc agacatagtg gaagcaggca tcatgaagcc   3720
gccagctggg ctgatagctc taggcattct caagtgggac aagagcaaag ctccggcagc   3780
aggacaagca gacaccaggg aagctctgtg tcccaagaca gcgattccga gcggcattcc   3840
gatgactctg agagactgtc cggaagcgca tcccggaatc accatggaag cagccgggaa   3900
caaagtcgcg acggttcaag acacccaggc ttccatcaag aggatagggc tagtcacggt   3960
cacagcgctg attctagtag gcagtccgga actcaccaca ccgaatctag cagtcacggc   4020
caggctgtgt cctctcatga acaggctcgt tctagccctg gcgaacggca cggatctcga   4080
caccaacaat cagccgactc cagcagacat agcggcattg gacacagaca ggcatcctct   4140
gccgttagag acagcggaca tagagggtcc tctggctccc aagtgacaaa ctcagagggg   4200
cactcagagg attccgacac acagtcagtg tctgcccatg gccaagctgg accacaccag   4260
caatcccaca aagaaagtgc caggggacag agcggagagt ccagcggcag gtctagaagt   4320
ttcctttacc aagtgtccag tcatgagcaa tctgagagca cccacggcca gacagccccc   4380
tctaccggcg gcagacaagg gtctagacac gaacaagccc ggaactcctc aaggcattct   4440
gctagccagc acgacaaga cacaatccgg ggacatcctg gtagttcacg cggaggcagg   4500
caggggtcct accatgaaca atcagtggat cggagcggac acagtggcta ccatcatagc   4560
catacaaccc ctcagggacg ctctgatgct tctcatgggc agtcaggccc aagaagtgct   4620
tcccggcaga ctcggaatga agaacaaagc ggagatggct cccggcacag tggatcacgc   4680
catcatgaac catctaccag agccggcagc tccaggcata gccaagttgg acaaggcgag   4740
agcgccggct ccaaaaccag tcgtagacaa ggctccagcg tttcccagga tcgggacagt   4800
gaaggccact ctgaggactc cgagagaaga agcgagtccg cctcaagaaa tcattacggc   4860
agcgctagag agcagtcccg gcacggttct aggaacccca gaagtcacca agaggacaga   4920
gccagtcatg gccacagtgc tgaaagttct cgccagtccg gcactaggca tgccgaaacc   4980
agtagtggtg gacaggctgc aagtagtcaa gaacaggcaa gatcaagccc aggcgagcgc   5040
catggttcta ggcaccaaca gtctgctgac agcagcacag atagcggaac aggcagacgg   5100
caggatagct ctgttgtcgg cgatagcggc aataggggca gtagtggatc tcaggcttct   5160
gacagcgaag gccatagcga agaaagcgac actcagagcg tgtccgcaca cggtcaagca   5220
ggccctcatc aacaatcaca ccaagaatcc acacggggac agtccgggga acgtagcgga   5280
cgttctggga gttttctcta tcaagtgtca acgcatgaac agtccgagag tgcccatgga   5340
agaaccggac ctagtactgg tggaaggcag aggtccagac atgaacaggc cagggacagc   5400
```

```
agcagacatt cagcctctca agaaggacag gacacgattc gcggccatcc gggaagtagt    5460
cgaggtggac gccaaggctc tcactatgag cagagcgttg acagctccgg gcactctggt    5520
tctcaccatt ctcacactac aagccaagaa agatccgacg tgtccagggg ccaaagtggc    5580
agtagatctg tgtcaaggca gacgagaaac gagaagcagt caggcgacgg atctcggcac    5640
tcaggttcaa ggcaccatga agctagcagc agagccgatt cctccaggca ctcacaagtc    5700
ggacagggac aaagcagcgg ccctaggact tccagaaacc agggatcatc cgttagccaa    5760
gacagtgact cccaggggca tagtgaagat tccgaacgtt ggagcggatc tgcctccaga    5820
aatcacctgg gaagcgcttg ggagcaatca agagatggtt ctcggcatcc cggctctcat    5880
cacgaggaca gagcaggaca tggacactcc gcagatagct ccagacagag cggcactaga    5940
cataccgaga gcagttcaag aggccaggcc gcaagttcac acgaacaggc taggtcctct    6000
gcaggcgaga gacatggcag ccaccatcaa ctgcagtccg ctgactcatc ccgccactct    6060
ggaattggac atggtcaagc ctccagcgca gtccgcgatt ctgggcacag aggatattct    6120
ggctcacaag cctccgactc agagggacat agcgaggact ctgatacaca gtctgtcagc    6180
gcccagggaa aagctgggcc acatcaacag agtcacaaag agtctgctcg cgggcagtct    6240
ggcgaaagta gcggaagaag tgggagcttt ctgtaccaag tttctacaca tgagcagagt    6300
gaaagcacac acggacagtc agctcctagc actggcggtc gtcaaggctc ccattatgat    6360
caggcccagg actcttctcg gcacagcgct tcacaagagg ggcaagacac tattagggga    6420
caccctggac catccagagg tggccggcaa ggatcacatc aagagcaatc agtggacaga    6480
agcgggcact caggcagtca ccacagccat acgacaagcc aaggcagatc tgatgcctcc    6540
agagggcaga gcggctctag aagtgccagc agaaagacct acgacaaaga acagtccggc    6600
gacggtagta gacattcagg ctcacaccac cacgaagcct ctagctgggc cgacagtagt    6660
aggcactctc ttgtcggcca aggacagtcc tccggaccaa gaacctctag accaagaggg    6720
tcaagtgtct cccaagactc tgactccgaa gggcattccg aggacagcga aagaagatct    6780
ggctctgcca gtaggaacca cccacggaagt gcacaagaac aatcccgaga tgggagcaga    6840
caccctcgga gtcatcacga agatcgcgcc ggacacggac attctgccga atcatccagg    6900
caaagtggaa cccaccacgc tgagaatagt tctggcggcc aggcagcaag tagccatgag    6960
caagcaagat ccagtgctgg cgagcgtcac gggtcccatc atcagcaaag tgcagacagc    7020
agtcgtcaca gcggaatcgg acacgggcaa gcaagttcag cagttagaga ctccggccac    7080
cgaggtagta gtggtagcca agctagcgat agtgaaggcc attcagaaga ttcagatacc    7140
caaagcgtca gtgctcatgg acaggccggt ccacatcagc aatctcatca agagagtacc    7200
cggggcagat cagctgggag atccggtcgc tctggatcat tcttgtacca agtctccacg    7260
cacgagcagt cagaaagcgc tcatggcagg acaggcactt caaccggtgg acggcagggc    7320
tcccatcaca aacaagcacg cgatagtagc aggcacagca cgagccaaga gggacaagat    7380
accatccacg gacaccctgg aagctctagc ggaggcagac agggtagcca ttatgagcag    7440
ctggtggatc gctctggtca ctcagggtca caccatagcc acactacttc tcaggggaga    7500
agcgacgctt cccacgggca ttctgggagt agatccgcaa gccgccagac aagaaatgat    7560
gagcaaagtg gcgacggaag tcgccattct ggctcaagac atcacgaggc tagctctagg    7620
gccgatagct ctggacatag tcaagtcggc caggggcaat ccgagggacc tagaacaagc    7680
agaaattggg gcagcagctt cagccaagac tcagattctc agggtcacag cgaggactcc    7740
```

```
gaacgttgga gcggcagtgc cagcagaaat catcatggaa gcgcccaaga gcagctgaga    7800
gatggcagta gacaccccag atcacaccaa gaggatcgcg caggacatgg gcacagtgcc    7860
gattcctcta gacagtccgg gactagacac acacagacat cttcaggcgg ccaagccgca    7920
tcaagtcatg agcaagctag gtctagcgca ggcgagaggc acggttctca tcatcaacag    7980
agcgccgatt caagccggca cagcggtata ggccatggac aggcttctag cgcagtcaga    8040
gatagcggcc acaggggcta ttccggatca caggcaagcg acaatgaggg tcatagcgaa    8100
gatagtgata cccagtccgt ttctgctcac ggacaggctg gaagccacca acagtcccat    8160
caagaaagcg ccagaggaag atcaggcgaa acctctggcc acagcggttc attcctctat    8220
caagtttcca ctcacgaaca aagcgaaagc agccacggat ggactggccc atccacaaga    8280
ggcagacaag gcagcaggca tgagcaggct caggattcaa gcagacacag cgcatcccag    8340
gatggacagg ataccatacg gggccatcca ggctcaagta gaggcggccg tcagggatat    8400
caccacgagc acagtgttga ttcttccggg catagtggct cacatcactc ccatacaact    8460
tcccaaggcc gaagcgacgc cagtagagga caaagtggtt caagatccgc ctccaggacc    8520
acacgcaacg aggaacaatc aggcgacggg tctagacact ccggctctag acaccacgaa    8580
gcttctaccc acgccgacat cagtagacat agtcaggccg tgcagggaca gtctgaaggc    8640
agtagaagat cacgcaggca aggctcctca gttagtcaag attcagacag cgagggacac    8700
agtgaagatt ctgagcgttg gagtggctca gccagccgca atcatcacgg ctccgctcaa    8760
gaacaacttc gagatggtag tcggcacccg agaagtcatc aagaagatag agctggacac    8820
ggccactccg ctgacagtag tagacagtct ggaaacggc acacccagac aagtagtggc     8880
ggacaagcag catcatccca cgagcaagct agaagttcag ccggcgagcg gcatggatca    8940
caccaccagc aatctgctga ctcctcaaga cacagtggaa ttggtcacgg ccaagccagt    9000
agtgccgtcc gagatagtgg acataggga tacagcggta gccaggcatc cgataacgag     9060
ggacactcag aagatagcga cacccaaagc gtttcagccc atggccaggc aggatctcac    9120
caacagagtc accaagaaag cgctcggggc agatctgggg agacatctgg ccattccgga    9180
tcatttctct accaagtgtc tacccacgaa cagtctgaaa gctctcacgg ctggaccggg    9240
ccaagcacaa gaggacgtca aggatcaaga cacgagcagg cccaggatag ctcaagacat    9300
agcgccagcc agtatggcca ggacacaatt cgagggcacc ctggttcctc aagaggcgga    9360
cgacaaggct accaccacga acactctgtc gattccagcg gccactccgg atctcatcac    9420
agccacacca ccagtcaggg gcgatctgat gctagtagag gccaatcagg ctcccgcagc    9480
gcttccagaa ccaccagaaa cgaagaacaa tctggggata gctcacggca cagcgtgtca    9540
agacaccatg aggccagcac acacgccgac atttccagac atagccaggc agttcagggg    9600
caaagcgaag gttccagaag gtctagacga caggggagtt cagttagcca ggattccgat    9660
tcagagggcc attccgagga ctccgaacgt tggagcggaa gcgcctctcg caatcatagg    9720
ggctctgtgc aagaacagtc aaggcatggc tctcggcacc cacgatctca ccatgaggat    9780
agagcaggac acggtcattc agccgacaga agcagacaaa gcggaaccag gcatgccgag    9840
acatcatccg gtggacaggc cgcttcaagc catgaacagg cacgatcttc acctggcgag    9900
cgacatggta gcagacatca acagtccgca gacagctctc gccacagtgg tatccctagg    9960
ggccaagcct cttcagccgt tcgtgacagt aggcattggg gctcatcagg ctctcaagca   10020
agtgatagcg aggggcactc cgaagaatcc gatactcaat ctgttagcgg ccacggccag   10080
gccggtcctc accaacaatc ccaccaagag agcgctcgag atagatccgg cggcagaagt   10140
```

-continued

```
ggacgatctg gttcatttct gtatcaagtc tcaacacacg aacaatcaga atctgcccac   10200
ggccgcacca gaacctcaac tggtcgtcgg caaggcagcc atcatgaaca ggcaagagat   10260
agctcccgcc acagcgctag ccaagaaggc caagacacta tcagagggca ccccggaagt   10320
tccagaagag gaaggcaagg cagtcactac gagcagagtg tggatagatc agggcattca   10380
gggtcccatc actcccacac cacctcacaa ggccgcagtg atgcatctag gggacaatct   10440
ggcagtcgga gtgcatctag acaaacccgg aacgacgagc agagcggaga tggaagcaga   10500
cactcttgga gccaccatca cgaggcctcc acacaggctg actcttcacg ccattctcag   10560
tctggtcaag gccaaagcgc tggccccagg accagtagaa atcaaggttc tagtgtcagt   10620
caggactcag acagccaagg ccactccgag gatagtgaac gttggagcgg ttccgcaagc   10680
agaaatcaca gaggctccgc acaagagcag tccagagatg gctccaggca tcctacctca   10740
caccacgagg atagagctgg tcacgggcat agcgccgaaa gttccagaca atctggaact   10800
catcacgccg agaattccag cggaggccag gctgcatctt cccacgaaca agcaagatca   10860
tccgctggcg agaggcatgg aagtcatcac cagcaatcag cagatagcag tcgccactca   10920
ggcatcggtc acgacaagc ttcatctgcc gtcagagact caggccacag gggatctagc   10980
ggttctcagg caagcgatag cgaaggacat tctgaggact cagacacaca gagcgtttcc   11040
gctcatgggc aagctggtcc ccatcaacag tcacatcaag agtctaccag aggccgcagc   11100
gccggaagaa gtggtagatc tggaagcttt ctttatcaag tgtctactca cgagcaatcc   11160
gaaagtgccc atggcagagc aggaccatca acaggtggtc gccaggggtc tagacatgag   11220
caggctagag actcctctag gcactctgct tcccaagaag gccaggacac aatccgtgga   11280
cacccaggct ctcgaagagg tggtagacaa ggatcttacc acgagcagtc cgtcgataga   11340
tcaggccaca gtggcagtca tcattcccat accaccagcc agggacgtag cgacgctagt   11400
cacggacaaa gtggcagcag aagcgctagc agagagactc gcaacgaaga acagtctggc   11460
gacggctcaa ggcactctgg atcaaggcat cacgaagcct ctactcaggc cgatagctcc   11520
cgacattctc agagcggtca aggcgaatcc gctggatcac gacgatctag acggcaaggg   11580
tccagtgtgt cacaggattc agactctgag gcttaccctg aggacagtga acgcagatcc   11640
gagagcgcaa gtcggaacca ccatggctcc agccgcgagc aaagtcgaga tggatctcgt   11700
cacccaggca gctcccacag agatacagct agccatgtgc agtctagccc cgtgcagagc   11760
gactcttcca cagccaaaga gcacggacac ttctccagtc tgagtcagga ttctgcctac   11820
cacagcggca tccagagtag aggatctccc cacagcagct cctcttatca ctaccagtcc   11880
gagggcactg agcggcagaa aggacaatcc ggacttgtgt ggcggcacgg ctcttatggc   11940
agcgctgact acgattacgg cgagtctggc tttaggcaca gccagcatgg cagcgtgtcc   12000
tacaacagca accccgtggt gtttaaagag cgcagcgata tctgcaaggc ctccgccttt   12060
ggaaaggatc accctcggta ctacgccacc tacatcaaca aggaccctgg actgtgtggc   12120
cactcctccg atatcagcaa gcagctggga ttttcccaga gccagcggta ctactactac   12180
gaatga                                                               12186
```

<210> SEQ ID NO 38
<211> LENGTH: 7176
<212> TYPE: DNA
<213> ORGANISM: Homo sapiens

<400> SEQUENCE: 38

-continued

```
atgaccgacc tcttgagaag tgttgtcacc gtaattgatg ttttctacaa atacaccaag      60
caagatgggg agtgtggcac actgagcaag ggtgaactaa aggaacttct ggagaaagag     120
cttcatccag ttctgaagaa cccagatgat ccagacacag tggatgtcat catgcatatg     180
ctggatcgag atcatgacag aagattggac tttactgagt ttcttttgat gatattcaag     240
ctgactatgg cctgcaacaa ggtcctcagc aaagaatact gcaaagcttc agggtcaaag     300
aagcataggc gtggtcaccg acaccaagaa gaagaaagtg aaacagaaga ggatgaagag     360
gatacaccag gacataaatc aggttacaga cattcaagtt ggagtgaggg agaggagcat     420
ggatatagtt ctgggcactc aaggggaact gtgaaatgta gacatgggtc caactccagg     480
aggctaggaa gacaaggtaa tttatccagc tctgggaacc aagagggatc tcagaaaaga     540
taccacaggt ccagctgtgg tcattcatgg agtggtggca aagacagaca tggttccagc     600
tctgtagaac tgagagaaag aataaacaag tcacacatta gcccttctag ggaatctggg     660
gaggagtatg aatctggatc tggatcaaac agttgggaaa ggaaaggtca tggtggtctg     720
tcatgtggat tggagactag tgggcatgaa tcaaactcta ctcagtcaag aattagagaa     780
caaaagcttg ggtctagctg ttcaggttca ggagacagtg ggaggcgaag tcatgcatgt     840
ggttatagca attcaagtgg gtgtggaagg ccacaaaatg cttcaagttc ttgtcagtca     900
catagatttg gagggcaagg aaatcaattt agctatattc agtcaggctg tcagtcagga     960
attaagggag gacaaggcca tggctgtgtc tcaggaggtc agccctctgg atgtggtcaa    1020
cctgagtcta cccctgtag tcagtcctat agtcagagag gatatggagc tagagaaaat     1080
ggtcaaccac agaactgtgg aggacaatgg agaacaggct caagtcagtc ctcttgctgt     1140
ggacaatatg ggtctggagg tagccagtct tgtagtaatg gtcaacatga atatggttcc    1200
tgtggccgct tttcaaactc ttctagttca aatgaatttt ccaaatgtga tcaatatggg    1260
tctggttcaa gtcagtctac tagctttgaa caacatggaa caggcttgag tcagtcctct    1320
gggttcgaac aacatgtatg tggctcaggt caaacttgtg ccagcatga gtctacatca    1380 agtcaatcct tgggctatga ccagcatggg tctagctcag gtaagacatc tggctttgga    1440
caacatgggc ctggctcagg tcagtcctct ggctttggac aatgtgggtc aggctcaggt    1500
cagtcctctg gctttggaca gcatgggtct gtctcaggac aatcctctgg ttttggacag    1560
catgggtctg tctcaggaca atcctctggt tttggacaac atgagtctag atcacgtcag    1620
tctagctatg gccaacatgg ttctggctca agtcaatcat ctggctatgg ccaatatggg    1680
tctagagaga catctggctt tggacaacat gggttgggct caggtcaatc cactggcttt    1740
ggccaatatg gatcgggctc aggtcagtcc tctggctttg acaacatgg gtctggctca    1800 ggacaatcct ctggctttgg acaacatgag tctagatcag gtcagtctag ttatggccaa    1860
cacagttctg gctcaagtca gtcatctggc tatggccaac atgggtctag acagacatct    1920
ggctttggac aacatgggtc aggctcaagt caatccactg gctttggcca atatggatca    1980
ggctcaggtc agtcctctgg ctttggacaa catgtttctg gctcaggaca atcctctggt    2040
tttggacaac atgagtctag atcaggtcat tctagctatg gccaacatgg ttttggctca    2100
agtcaatcat ctggctatgg tcaacatggg tcaagttcag acagacatc tggatttgga    2160 caacacgagt taagctcagg tcagtcttcc agctttggcc aacatggatc aggctcaggt    2220
cagtcctctg gctttggaca acatgggtct ggctcaggac aatcctctgg ctttggacaa    2280
catgagtcta gatcaggtca gtctagctat ggccaacaca gttctggctc aagtcagtca    2340
tctggctatg gccaacatgg gtctagacag acatctggct ttggacaaca tgggtcaggc    2400
```

-continued

```
tcaagtcaat ccactggctt tggccaatat ggatcaggct caggtcagtc cgctggcttt      2460
ggacaacatg ggtctggctc aggacaatcc tctggctttg gacagcatga gtctagatca      2520
catcagtcca gctatggcca acatggttct ggctcaagtc aatcatctgg ctatggtcaa      2580
catgggtcaa gttcgggaca gacatctggc tttggacaac acaggtcaag ctcaggtcaa      2640
tactctggct ttggacaaca tggatcaggc tcaggtcagt ccagtggctt tggacaacat      2700
gggactggct caggacaata ctctggtttt ggacaacatg agtctagatc acatcagtct      2760
agctatggcc aacatggttc tggctcaagt cagtcatctg gctatggtca acatgggtca      2820
agttcaggac agacttttgg atttggacaa cacaggtcag gctcaggtca atcctctggc      2880
tttggccaac atggatcagg ctcaggtcag tcctctggct ttggacaaca tgagtcaggc      2940
tcaggaaaat cctctggctt tggacagcat gagtctagat caagtcagtc taattatggc      3000
caacatggtt ctggctcaag tcagtcatct ggctatggtc aacatgggtc tagttcagga      3060
cagacaactg gctttggaca acacaggtca agctcaggcc aatactcagg ctttggacaa      3120
catggatcag gctcagatca gtcctctggc tttggacaac atgggactgg ttcaggacaa      3180
tcctctggtt ttggacaata tgagtctaga tcacgtcagt ctagctatgg ccaacatggt      3240
tctggctcaa gtcaatcatc tggctatggt caacatgggt caaattcagg acagacatct      3300
ggatttggac aacacaggcc aggctcaggt cagtcctctg gctttggcca atatggatcg      3360
ggctcaggtc agtcttctgg ctttggacaa catgggtcag gcacaggtaa atcctctggc      3420
tttgcacagc atgagtacag atcaggtcag tctagctatg gccaacatgg tactggctcc      3480
agtcaatcat ctggctgtgg ccaacatgag tctggctcag gtccaaccac aagtttttgga     3540 cagcatgtgt ctggctcaga caatttctct agttctggac aacatatatc tgactcaggt      3600
cagtccactg gatttggcca atatggttca ggctcaggtc aatcaactgg cttgggccag      3660
ggtgaatctc aacaagtaga gtcaggatcc acagttcatg ggagacagga aactactcat      3720
ggtcagacaa taaataccac tagacatagc cagtctggtc aaggacaatc cacacagaca      3780
gggtccaggg taactagaag acgaagatct agccaaagtg agaacagtga cagtgaagtg      3840
cactcaaagg tctcacacag acattcagaa cacattcaca cacaagctgg atctcactac      3900
ccaaagtcag gatccacagt tcgcagaaga caaggaacta ctcatggaca gagaggagat      3960
accactagac atggccattc tggtcatgga cagtctacac agacaggttc cagaacatct      4020
ggaagacaga gatttagcca cagtgatgcc actgacagtg aagtgcactc aggggtctca      4080
catagaccac actcacaaga acaaactcac agccaagctg gatctcaaca tggagagtca      4140
gaatccacag ttcatgagag acatgaaact acttatggac agacaggaga ggccactgga      4200
catggccact ctggtcatgg acagtccaca cagagagggt ccaggacaac tggaagaagg      4260
ggatctggcc atagtgagtc cagtgacagt gaagtgcact caggggggctc acacagacca      4320 caatcacaag aacaaactca tggccaagcc ggatctcaac atggagagtc aggatccaca      4380
gttcatggga gacacggaac tactcatgga cagacaggag ataccactag acatgcccac      4440
tatcatcatg gaaatccac acagagaggg tccagtacaa ctggaagaag gggatctggc      4500
cacagtgagt ccagtgacag tgaagtgcac tcaggggggct cgcacacaca ttcaggacac      4560
actcacggcc aaagtggatc tcaacatgga gagtcagaat ccataattca tgacagacac      4620
agaattactc atggacagac aggagatacc actagacatt cctactctgg tcatgaacaa      4680
accacacaga cagggtccag gacaactgga agacagagaa ctagccacag tgagtccact      4740
```

-continued

```
gacagtgaag tgcactcagg gggctcacac agaccacact cacgagaaca cacttacggc    4800
caagccggat ctcaacatga agagccagaa ttcacagttc atgagagaca cggaactact    4860
catggacaga taggagatac cactggacat tcccactctg gtcatggaca gtccacacag    4920
agagggtcca ggacaactgg aagacagaga tctagccaca gtgagtccag tgacagtgaa    4980
gtgcactcag gggtctcaca cacacataca ggacacactc atggtcaagc tggatctcaa    5040
catggacagt cagaatccat agttcctgag agacatggaa ctactcatgg acagacagga    5100
gataccacta gacatgccca ctatcatcat ggattaacca cacagacagg gtccaggact    5160
actggaagaa ggggatctgg ccacagtgag tacagtgaca gtgaagggta ctcaggagtc    5220
tcacatacac attcaggaca cactcatggc caagccagat ctcaacatgg agagtcagaa    5280
tccatagttc atgagagaca tggaactata catggacaga caggcgatac caccagacat    5340
gcccactctg gtcatggaca gtccacacag acagggtcca ggaccactgg aagaaggtca    5400
tctggccaca gtgagtacag tgacagtgaa gggcactcag ggttctcaca aagaccacac    5460
tcacgaggac acactcacgg ccaggctgga tctcaacatg gagagtcaga atccatagtt    5520
gacgagagac atggaactac tcatggacag acaggagata ccagtggaca ttctcaatct    5580
ggtcatggac agtccacaca gtcaggatcc agtacaactg gaagaaggag atctggccac    5640
agtgagtcca gtgacagtga agtgcactca gggggctcac atacacattc aggacacaca    5700
cacagccaag ccaggtctca acatggagag tcagaatcca cagttcacaa gagacaccaa    5760
actactcatg gacagacagg agataccact gaacatggcc accctagtca tggacaaacc    5820
atacagacag ggtccaggac aactggaaga aggggatctg gccacagtga gtacagtgac    5880
agtgaagggc cctcaggggt ctcacacaca cattcaggac acactcacgg tcaagctgga    5940
tctcactatc cagagtcagg atcctcagtt catgagagac acggaactac tcatggacaa    6000
acagcagata ccactagaca tggccactct ggtcatggac agtccacaca gagagggtcc    6060
aggacaactg gaagaaggc atctggccac agtgagtaca gtgacagtga agggcactca    6120
ggggtctcac acacacattc aggacacgct catggccaag ccggatctca acatggagag    6180
tcaggatcct cagttcatga gagacacgga actactcatg gacagacagg agataccact    6240
agacatgctc actctggtca tggacagtcc acacagagag ggtcaaggac agctggaaga    6300
aggggatctg gccacagtga gtccagtgac agtgaagtgc actcagggt ctcacacaca    6360 cattcaggac acacttatgg ccaagccaga tctcaacatg gagagtcagg atctgccatt    6420
cacgggagac agggaactat acatggacag acaggagata ccactagaca tggccagtct    6480
ggtcatggac agtccacaca gacaggttcc aggacaactg gaagacaaag atctagtcac    6540
agtgagtcca gtgatagtga agtgcactca gaggcctcac ccacacattc aggacacact    6600
cacagccaag ccggatctcg acatggacag tcaggatcct caggtcatgg agacaggga    6660 actactcatg gacagacagg agataccact agacatgccc actatggtta tggacaatcc    6720
acacagagag ggtccaggac aactggaaga aggggatctg gccacagtga gtccagtgac    6780
agtgaagtgc actcatgggg ctcacacaca cattcaggac acattcaggg ccaagctgga    6840
tctcaacaaa gacagccagg atccacagtt catgggagac tggaaactac tcatggacag    6900
acaggagata ccactagaca tggccattct ggttatggac aatccacaca gacaggttcc    6960
agatctagta gagcaagtca tttcagtca catagtagtg aaaggcaaag gcatggatca    7020
agtcaggttt ggaaacatgg cagctatgga cctgcagaat atgactatgg gcacactggg    7080
tatgggcctt ctggtggcag cagaaaaagc atcagtaatt ctcacctttc atggtcaaca    7140
```
gacagcactg caaacaagca actgtctaga cattga                                    7176

<210> SEQ ID NO 39
<211> LENGTH: 4061
<212> TYPE: PRT
<213> ORGANISM: Homo sapiens

<400> SEQUENCE: 39

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
    130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
    290                 295                 300

Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
        355                 360                 365

-continued

Thr Ala Ser Ser His Glu Gln Ala Arg Ser Ser Pro Gly Glu Arg His
    370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
                420                 425                 430

Asp Thr Gln Ser Val Ser Gly His Gly Lys Ala Gly Leu Arg Gln Gln
        435                 440                 445

Ser His Gln Glu Ser Thr Arg Gly Arg Ser Gly Glu Arg Ser Gly Arg
    450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
                500                 505                 510

Gln Asp Thr Ile Arg Gly His Pro Gly Ser Ser Arg Gly Gly Arg Gln
        515                 520                 525

Gly Ser His His Glu Gln Ser Val Asn Arg Ser Gly His Ser Gly Ser
    530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
                580                 585                 590

Ser Gln Ala Asp Ser Ser Arg His Ser Gln Val Gly Gln Gly Gln Ser
        595                 600                 605

Ser Gly Pro Arg Thr Ser Arg Asn Gln Gly Ser Ser Val Ser Gln Asp
    610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
                660                 665                 670

Ser Ala Asp Ser Ser Arg Lys Ser Gly Thr Arg His Thr Gln Asn Ser
        675                 680                 685

Ser Ser Gly Gln Ala Ala Ser Ser His Glu Gln Ala Arg Ser Ser Ala
    690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
        755                 760                 765

Gly His His Gln Gln Ser His Gln Glu Ser Ala Arg Asp Arg Ser Gly
    770                 775                 780

```
Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
                820                 825                 830

Ala Ser Gln Asp Gly Gln Asp Thr Ile Arg Gly His Pro Gly Ser Ser
                835                 840                 845

Arg Arg Gly Arg Gln Gly Ser His His Glu Gln Ser Val Asp Arg Ser
                850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
                900                 905                 910

His His Glu Ala Ser Ser His Ala Asp Ile Ser Arg His Ser Gln Ala
                915                 920                 925

Gly Gln Gly Gln Ser Glu Gly Ser Arg Thr Ser Arg Arg Gln Gly Ser
                930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His His Glu Asp Arg
                980                 985                 990

Ala Gly His Gly His Ser Ala Asp Ser Ser Arg Gln Ser Gly Thr Pro
                995                 1000                1005

His Ala Glu Thr Ser Ser Gly Gly Gln Ala Ala Ser Ser His Glu Gln
        1010                1015                1020

Ala Arg Ser Ser Pro Gly Glu Arg His Gly Ser Arg His Gln Gln Ser
1025                1030                1035                1040

Ala Asp Ser Ser Arg His Ser Gly Ile Pro Arg Arg Gln Ala Ser Ser
                1045                1050                1055

Ala Val Arg Asp Ser Gly His Trp Gly Ser Ser Gly Ser Gln Ala Ser
                1060                1065                1070

Asp Ser Glu Gly His Ser Glu Glu Ser Asp Thr Gln Ser Val Ser Gly
                1075                1080                1085

His Gly Gln Asp Gly Pro His Gln Gln Ser His Gln Glu Ser Ala Arg
        1090                1095                1100

Asp Trp Ser Gly Gly Arg Ser Gly Arg Ser Gly Ser Phe Ile Tyr Gln
1105                1110                1115                1120

Val Ser Thr His Glu Gln Ser Glu Ser Ala His Gly Arg Thr Arg Thr
                1125                1130                1135

Ser Thr Gly Arg Arg Gln Gly Ser His His Glu Gln Ala Arg Asp Ser
                1140                1145                1150

Ser Arg His Ser Ala Ser Gln Glu Gly Gln Asp Thr Ile Arg Ala His
        1155                1160                1165

Pro Gly Ser Arg Arg Gly Gly Arg Gln Gly Ser His His Glu Gln Ser
        1170                1175                1180

Val Asp Arg Ser Gly His Ser Gly Ser His His Ser His Thr Thr Ser
1185                1190                1195                1200

Gln Gly Arg Ser Asp Ala Ser His Gly Gln Ser Gly Ser Arg Ser Ala
```

-continued

```
                  1205              1210              1215

Ser Arg Gln Thr Arg Lys Asp Lys Gln Ser Gly Asp Gly Ser Arg His
          1220              1225              1230

Ser Gly Ser Arg His His Glu Ala Ala Ser Trp Ala Asp Ser Ser Arg
          1235              1240              1245

His Ser Gln Val Gly Gln Glu Gln Ser Ser Gly Ser Arg Thr Ser Arg
      1250              1255              1260

His Gln Gly Ser Ser Val Ser Gln Asp Ser Asp Ser Glu Arg His Ser
  1265              1270              1275              1280

Asp Asp Ser Glu Arg Leu Ser Gly Ser Ala Ser Arg Asn His His Gly
              1285              1290              1295

Ser Ser Arg Glu Gln Ser Arg Asp Gly Ser Arg His Pro Gly Phe His
          1300              1305              1310

Gln Glu Asp Arg Ala Ser His Gly His Ser Ala Asp Ser Ser Arg Gln
          1315              1320              1325

Ser Gly Thr His His Thr Glu Ser Ser Ser His Gly Gln Ala Val Ser
      1330              1335              1340

Ser His Glu Gln Ala Arg Ser Ser Pro Gly Glu Arg His Gly Ser Arg
  1345              1350              1355              1360

His Gln Gln Ser Ala Asp Ser Ser Arg His Ser Gly Ile Gly His Arg
              1365              1370              1375

Gln Ala Ser Ser Ala Val Arg Asp Ser Gly His Arg Gly Ser Ser Gly
          1380              1385              1390

Ser Gln Val Thr Asn Ser Glu Gly His Ser Glu Asp Ser Asp Thr Gln
      1395              1400              1405

Ser Val Ser Ala His Gly Gln Ala Gly Pro His Gln Gln Ser His Lys
  1410              1415              1420

Glu Ser Ala Arg Gly Gln Ser Gly Glu Ser Ser Gly Arg Ser Arg Ser
  1425              1430              1435              1440

Phe Leu Tyr Gln Val Ser Ser His Glu Gln Ser Glu Ser Thr His Gly
          1445              1450              1455

Gln Thr Ala Pro Ser Thr Gly Gly Arg Gln Gly Ser Arg His Glu Gln
          1460              1465              1470

Ala Arg Asn Ser Ser Arg His Ser Ala Ser Gln Asp Gly Gln Asp Thr
          1475              1480              1485

Ile Arg Gly His Pro Gly Ser Ser Arg Gly Gly Arg Gln Gly Ser Tyr
      1490              1495              1500

His Glu Gln Ser Val Asp Arg Ser Gly His Ser Gly Tyr His His Ser
  1505              1510              1515              1520

His Thr Thr Pro Gln Gly Arg Ser Asp Ala Ser His Gly Gln Ser Gly
          1525              1530              1535

Pro Arg Ser Ala Ser Arg Gln Thr Arg Asn Glu Glu Gln Ser Gly Asp
          1540              1545              1550

Gly Ser Arg His Ser Gly Ser Arg His His Glu Pro Ser Thr Arg Ala
      1555              1560              1565

Gly Ser Ser Arg His Ser Gln Val Gly Gln Gly Glu Ser Ala Gly Ser
      1570              1575              1580

Lys Thr Ser Arg Arg Gln Gly Ser Ser Val Ser Gln Asp Arg Asp Ser
  1585              1590              1595              1600

Glu Gly His Ser Glu Asp Ser Glu Arg Arg Ser Glu Ser Ala Ser Arg
              1605              1610              1615

Asn His Tyr Gly Ser Ala Arg Glu Gln Ser Arg His Gly Ser Arg Asn
          1620              1625              1630
```

Pro Arg Ser His Gln Glu Asp Arg Ala Ser His Gly His Ser Ala Glu
        1635                1640                1645

Ser Ser Arg Gln Ser Gly Thr Arg His Ala Glu Thr Ser Ser Gly Gly
    1650                1655                1660

Gln Ala Ala Ser Ser Gln Glu Gln Ala Arg Ser Ser Pro Gly Glu Arg
1665                1670                1675                1680

His Gly Ser Arg His Gln Gln Ser Ala Asp Ser Ser Thr Asp Ser Gly
            1685                1690                1695

Thr Gly Arg Arg Gln Asp Ser Ser Val Val Gly Asp Ser Gly Asn Arg
        1700                1705                1710

Gly Ser Ser Gly Ser Gln Ala Ser Asp Ser Glu Gly His Ser Glu Glu
        1715                1720                1725

Ser Asp Thr Gln Ser Val Ser Ala His Gly Gln Ala Gly Pro His Gln
        1730                1735                1740

Gln Ser His Gln Glu Ser Thr Arg Gly Gln Ser Gly Glu Arg Ser Gly
1745                1750                1755                1760

Arg Ser Gly Ser Phe Leu Tyr Gln Val Ser Thr His Glu Gln Ser Glu
            1765                1770                1775

Ser Ala His Gly Arg Thr Gly Pro Ser Thr Gly Gly Arg Gln Arg Ser
            1780                1785                1790

Arg His Glu Gln Ala Arg Asp Ser Ser Arg His Ser Ala Ser Gln Glu
        1795                1800                1805

Gly Gln Asp Thr Ile Arg Gly His Pro Gly Ser Ser Arg Gly Gly Arg
        1810                1815                1820

Gln Gly Ser His Tyr Glu Gln Ser Val Asp Ser Ser Gly His Ser Gly
1825                1830                1835                1840

Ser His His Ser His Thr Thr Ser Gln Glu Arg Ser Asp Val Ser Arg
            1845                1850                1855

Gly Gln Ser Gly Ser Arg Ser Val Ser Arg Gln Thr Arg Asn Glu Lys
            1860                1865                1870

Gln Ser Gly Asp Gly Ser Arg His Ser Gly Ser Arg His His Glu Ala
        1875                1880                1885

Ser Ser Arg Ala Asp Ser Ser Arg His Ser Gln Val Gly Gln Gly Gln
    1890                1895                1900

Ser Ser Gly Pro Arg Thr Ser Arg Asn Gln Gly Ser Ser Val Ser Gln
1905                1910                1915                1920

Asp Ser Asp Ser Gln Gly His Ser Glu Asp Ser Glu Arg Trp Ser Gly
            1925                1930                1935

Ser Ala Ser Arg Asn His Leu Gly Ser Ala Trp Glu Gln Ser Arg Asp
        1940                1945                1950

Gly Ser Arg His Pro Gly Ser His His Glu Asp Arg Ala Gly His Gly
        1955                1960                1965

His Ser Ala Asp Ser Ser Arg Gln Ser Gly Thr Arg His Thr Glu Ser
    1970                1975                1980

Ser Ser Arg Gly Gln Ala Ala Ser Ser His Glu Gln Ala Arg Ser Ser
1985                1990                1995                2000

Ala Gly Glu Arg His Gly Ser His His Gln Leu Gln Ser Ala Asp Ser
            2005                2010                2015

Ser Arg His Ser Gly Ile Gly His Gly Gln Ala Ser Ser Ala Val Arg
            2020                2025                2030

Asp Ser Gly His Arg Gly Tyr Ser Gly Ser Gln Ala Ser Asp Ser Glu
        2035                2040                2045

```
Gly His Ser Glu Asp Ser Asp Thr Gln Ser Val Ser Ala Gln Gly Lys
    2050                2055                2060

Ala Gly Pro His Gln Gln Ser His Lys Glu Ser Ala Arg Gly Gln Ser
2065                2070                2075                2080

Gly Glu Ser Ser Gly Arg Ser Gly Ser Phe Leu Tyr Gln Val Ser Thr
                2085                2090                2095

His Glu Gln Ser Glu Ser Thr His Gly Gln Ser Ala Pro Ser Thr Gly
            2100                2105                2110

Gly Arg Gln Gly Ser His Tyr Asp Gln Ala Gln Asp Ser Ser Arg His
        2115                2120                2125

Ser Ala Ser Gln Glu Gly Gln Asp Thr Ile Arg Gly His Pro Gly Pro
    2130                2135                2140

Ser Arg Gly Gly Arg Gln Gly Ser His Gln Glu Gln Ser Val Asp Arg
2145                2150                2155                2160

Ser Gly His Ser Gly Ser His His Ser His Thr Thr Ser Gln Gly Arg
                2165                2170                2175

Ser Asp Ala Ser Arg Gly Gln Ser Gly Ser Arg Ser Ala Ser Arg Lys
            2180                2185                2190

Thr Tyr Asp Lys Glu Gln Ser Gly Asp Gly Ser Arg His Ser Gly Ser
        2195                2200                2205

His His His Glu Ala Ser Ser Trp Ala Asp Ser Ser Arg His Ser Leu
    2210                2215                2220

Val Gly Gln Gly Gln Ser Ser Gly Pro Arg Thr Ser Arg Pro Arg Gly
2225                2230                2235                2240

Ser Ser Val Ser Gln Asp Ser Asp Ser Glu Gly His Ser Glu Asp Ser
                2245                2250                2255

Glu Arg Arg Ser Gly Ser Ala Ser Arg Asn His His Gly Ser Ala Gln
            2260                2265                2270

Glu Gln Ser Arg Asp Gly Ser Arg His Pro Arg Ser His His Glu Asp
        2275                2280                2285

Arg Ala Gly His Gly His Ser Ala Glu Ser Ser Arg Gln Ser Gly Thr
    2290                2295                2300

His His Ala Glu Asn Ser Ser Gly Gly Gln Ala Ala Ser Ser His Glu
2305                2310                2315                2320

Gln Ala Arg Ser Ser Ala Gly Glu Arg His Gly Ser His His Gln Gln
                2325                2330                2335

Ser Ala Asp Ser Ser Arg His Ser Gly Ile Gly His Gly Gln Ala Ser
            2340                2345                2350

Ser Ala Val Arg Asp Ser Gly His Arg Gly Ser Ser Gly Ser Gln Ala
        2355                2360                2365

Ser Asp Ser Glu Gly His Ser Glu Asp Ser Asp Thr Gln Ser Val Ser
    2370                2375                2380

Ala His Gly Gln Ala Gly Pro His Gln Gln Ser His Gln Glu Ser Thr
2385                2390                2395                2400

Arg Gly Arg Ser Ala Gly Arg Ser Gly Arg Ser Gly Ser Phe Leu Tyr
                2405                2410                2415

Gln Val Ser Thr His Glu Gln Ser Glu Ser Ala His Gly Arg Thr Gly
            2420                2425                2430

Thr Ser Thr Gly Gly Arg Gln Gly Ser His His Lys Gln Ala Arg Asp
        2435                2440                2445

Ser Ser Arg His Ser Thr Ser Gln Glu Gly Gln Asp Thr Ile His Gly
    2450                2455                2460

His Pro Gly Ser Ser Ser Gly Gly Arg Gln Gly Ser His Tyr Glu Gln
```

```
2465            2470            2475            2480

Leu Val Asp Arg Ser Gly His Ser Gly Ser His His Ser His Thr Thr
            2485            2490            2495

Ser Gln Gly Arg Ser Asp Ala Ser His Gly His Ser Gly Ser Arg Ser
            2500            2505            2510

Ala Ser Arg Gln Thr Arg Asn Asp Glu Gln Ser Gly Asp Gly Ser Arg
            2515            2520            2525

His Ser Gly Ser Arg His His Glu Ala Ser Ser Arg Ala Asp Ser Ser
            2530            2535            2540

Gly His Ser Gln Val Gly Gln Gly Gln Ser Glu Gly Pro Arg Thr Ser
2545            2550            2555            2560

Arg Asn Trp Gly Ser Ser Phe Ser Gln Asp Ser Asp Ser Gln Gly His
            2565            2570            2575

Ser Glu Asp Ser Glu Arg Trp Ser Gly Ser Ala Ser Arg Asn His His
            2580            2585            2590

Gly Ser Ala Gln Glu Gln Leu Arg Asp Gly Ser Arg His Pro Arg Ser
            2595            2600            2605

His Gln Glu Asp Arg Ala Gly His Gly His Ser Ala Asp Ser Ser Arg
            2610            2615            2620

Gln Ser Gly Thr Arg His Thr Gln Thr Ser Ser Gly Gly Gln Ala Ala
2625            2630            2635            2640

Ser Ser His Glu Gln Ala Arg Ser Ser Ala Gly Glu Arg His Gly Ser
            2645            2650            2655

His His Gln Gln Ser Ala Asp Ser Ser Arg His Ser Gly Ile Gly His
            2660            2665            2670

Gly Gln Ala Ser Ser Ala Val Arg Asp Ser Gly His Arg Gly Tyr Ser
            2675            2680            2685

Gly Ser Gln Ala Ser Asp Asn Glu Gly His Ser Glu Asp Ser Asp Thr
            2690            2695            2700

Gln Ser Val Ser Ala His Gly Gln Ala Gly Ser His Gln Gln Ser His
2705            2710            2715            2720

Gln Glu Ser Ala Arg Gly Arg Ser Gly Glu Thr Ser Gly His Ser Gly
            2725            2730            2735

Ser Phe Leu Tyr Gln Val Ser Thr His Glu Gln Ser Glu Ser Ser His
            2740            2745            2750

Gly Trp Thr Gly Pro Ser Thr Arg Gly Arg Gln Gly Ser Arg His Glu
            2755            2760            2765

Gln Ala Gln Asp Ser Ser Arg His Ser Ala Ser Gln Asp Gly Gln Asp
            2770            2775            2780

Thr Ile Arg Gly His Pro Gly Ser Ser Arg Gly Gly Arg Gln Gly Tyr
2785            2790            2795            2800

His His Glu His Ser Val Asp Ser Ser Gly His Ser Gly Ser His His
            2805            2810            2815

Ser His Thr Thr Ser Gln Gly Arg Ser Asp Ala Ser Arg Gly Gln Ser
            2820            2825            2830

Gly Ser Arg Ser Ala Ser Arg Thr Thr Arg Asn Glu Glu Gln Ser Gly
            2835            2840            2845

Asp Gly Ser Arg His Ser Gly Ser Arg His His Glu Ala Ser Thr His
            2850            2855            2860

Ala Asp Ile Ser Arg His Ser Gln Ala Val Gln Gly Gln Ser Glu Gly
2865            2870            2875            2880

Ser Arg Arg Ser Arg Arg Gln Gly Ser Ser Val Ser Gln Asp Ser Asp
            2885            2890            2895
```

```
Ser Glu Gly His Ser Glu Asp Ser Glu Arg Trp Ser Gly Ser Ala Ser
        2900              2905              2910

Arg Asn His His Gly Ser Ala Gln Glu Gln Leu Arg Asp Gly Ser Arg
        2915              2920              2925

His Pro Arg Ser His Gln Glu Asp Arg Ala Gly His Gly His Ser Ala
        2930              2935              2940

Asp Ser Ser Arg Gln Ser Gly Thr Arg His Thr Gln Thr Ser Ser Gly
2945              2950              2955              2960

Gly Gln Ala Ala Ser Ser His Glu Gln Ala Arg Ser Ser Ala Gly Glu
            2965              2970              2975

Arg His Gly Ser His His Gln Gln Ser Ala Asp Ser Ser Arg His Ser
            2980              2985              2990

Gly Ile Gly His Gly Gln Ala Ser Ser Ala Val Arg Asp Ser Gly His
            2995              3000              3005

Arg Gly Tyr Ser Gly Ser Gln Ala Ser Asp Asn Glu Gly His Ser Glu
        3010              3015              3020

Asp Ser Asp Thr Gln Ser Val Ser Ala His Gly Gln Ala Gly Ser His
3025              3030              3035              3040

Gln Gln Ser His Gln Glu Ser Ala Arg Gly Arg Ser Gly Glu Thr Ser
            3045              3050              3055

Gly His Ser Gly Ser Phe Leu Tyr Gln Val Ser Thr His Glu Gln Ser
            3060              3065              3070

Glu Ser Ser His Gly Trp Thr Gly Pro Ser Thr Arg Gly Arg Gln Gly
        3075              3080              3085

Ser Arg His Glu Gln Ala Gln Asp Ser Ser Arg His Ser Ala Ser Gln
        3090              3095              3100

Tyr Gly Gln Asp Thr Ile Arg Gly His Pro Gly Ser Ser Arg Gly Gly
3105              3110              3115              3120

Arg Gln Gly Tyr His His Glu His Ser Val Asp Ser Ser Gly His Ser
            3125              3130              3135

Gly Ser His His Ser His Thr Thr Ser Gln Gly Arg Ser Asp Ala Ser
            3140              3145              3150

Arg Gly Gln Ser Gly Ser Arg Ser Ala Ser Arg Thr Thr Arg Asn Glu
        3155              3160              3165

Glu Gln Ser Gly Asp Ser Ser Arg His Ser Val Ser Arg His His Glu
        3170              3175              3180

Ala Ser Thr His Ala Asp Ile Ser Arg His Ser Gln Ala Val Gln Gly
3185              3190              3195              3200

Gln Ser Glu Gly Ser Arg Arg Ser Arg Arg Gln Gly Ser Ser Val Ser
            3205              3210              3215

Gln Asp Ser Asp Ser Glu Gly His Ser Glu Asp Ser Glu Arg Trp Ser
            3220              3225              3230

Gly Ser Ala Ser Arg Asn His Arg Gly Ser Val Gln Glu Gln Ser Arg
            3235              3240              3245

His Gly Ser Arg His Pro Arg Ser His His Glu Asp Arg Ala Gly His
        3250              3255              3260

Gly His Ser Ala Asp Arg Ser Arg Gln Ser Gly Thr Arg His Ala Glu
3265              3270              3275              3280

Thr Ser Ser Gly Gly Gln Ala Ala Ser Ser His Glu Gln Ala Arg Ser
            3285              3290              3295

Ser Pro Gly Glu Arg His Gly Ser Arg His Gln Gln Ser Ala Asp Ser
        3300              3305              3310
```

```
Ser Arg His Ser Gly Ile Pro Arg Gly Gln Ala Ser Ser Ala Val Arg
    3315            3320            3325

Asp Ser Arg His Trp Gly Ser Ser Gly Ser Gln Ala Ser Asp Ser Glu
    3330            3335            3340

Gly His Ser Glu Glu Ser Asp Thr Gln Ser Val Ser Gly His Gly Gln
3345            3350            3355            3360

Ala Gly Pro His Gln Gln Ser His Gln Glu Ser Ala Arg Asp Arg Ser
            3365            3370            3375

Gly Gly Arg Ser Gly Arg Ser Gly Ser Phe Leu Tyr Gln Val Ser Thr
        3380            3385            3390

His Glu Gln Ser Glu Ser Ala His Gly Arg Thr Arg Thr Ser Thr Gly
        3395            3400            3405

Arg Arg Gln Gly Ser His His Glu Gln Ala Arg Asp Ser Ser Arg His
    3410            3415            3420

Ser Ala Ser Gln Glu Gly Gln Asp Thr Ile Arg Gly His Pro Gly Ser
3425            3430            3435            3440

Ser Arg Arg Gly Arg Gln Gly Ser His Tyr Glu Gln Ser Val Asp Arg
            3445            3450            3455

Ser Gly His Ser Gly Ser His His Ser His Thr Thr Ser Gln Gly Arg
        3460            3465            3470

Ser Asp Ala Ser Arg Gly Gln Ser Gly Ser Arg Ser Ala Ser Arg Gln
    3475            3480            3485

Thr Arg Asn Asp Glu Gln Ser Gly Asp Gly Ser Arg His Ser Trp Ser
    3490            3495            3500

His His His Glu Ala Ser Thr Gln Ala Asp Ser Ser Arg His Ser Gln
3505            3510            3515            3520

Ser Gly Gln Gly Gln Ser Ala Gly Pro Arg Thr Ser Arg Asn Gln Gly
        3525            3530            3535

Ser Ser Val Ser Gln Asp Ser Asp Ser Gln Gly His Ser Glu Asp Ser
        3540            3545            3550

Glu Arg Trp Ser Gly Ser Ala Ser Arg Asn His Arg Gly Ser Ala Gln
    3555            3560            3565

Glu Gln Ser Arg Asp Gly Ser Arg His Pro Thr Ser His His Glu Asp
    3570            3575            3580

Arg Ala Gly His Gly His Ser Ala Glu Ser Ser Arg Gln Ser Gly Thr
3585            3590            3595            3600

His His Ala Glu Asn Ser Ser Gly Gly Gln Ala Ala Ser Ser His Glu
            3605            3610            3615

Gln Ala Arg Ser Ser Ala Gly Glu Arg His Gly Ser His His Gln Gln
            3620            3625            3630

Ser Ala Asp Ser Ser Arg His Ser Gly Ile Gly His Gly Gln Ala Ser
        3635            3640            3645

Ser Ala Val Arg Asp Ser Gly His Arg Gly Ser Ser Gly Ser Gln Ala
    3650            3655            3660

Ser Asp Ser Glu Gly His Ser Glu Asp Ser Asp Thr Gln Ser Val Ser
3665            3670            3675            3680

Ala His Gly Gln Ala Gly Pro His Gln Gln Ser His Gln Glu Ser Thr
            3685            3690            3695

Arg Gly Arg Ser Ala Gly Arg Ser Gly Arg Ser Gly Ser Phe Leu Tyr
        3700            3705            3710

Gln Val Ser Thr His Glu Gln Ser Glu Ser Ala His Gly Arg Ala Gly
        3715            3720            3725

Pro Ser Thr Gly Gly Arg Gln Gly Ser Arg His Glu Gln Ala Arg Asp
```

```
              3730              3735              3740

Ser Ser Arg His Ser Ala Ser Gln Glu Gly Gln Asp Thr Ile Arg Gly
3745              3750              3755              3760

His Pro Gly Ser Arg Arg Gly Gly Arg Gln Gly Ser Tyr His Glu Gln
                 3765              3770              3775

Ser Val Asp Arg Ser Gly His Ser Gly Ser His His Ser His Thr Thr
                 3780              3785              3790

Ser Gln Gly Arg Ser Asp Ala Ser His Gly Gln Ser Gly Ser Arg Ser
           3795              3800              3805

Ala Ser Arg Glu Thr Arg Asn Glu Glu Gln Ser Gly Asp Gly Ser Arg
3810              3815              3820

His Ser Gly Ser Arg His His Glu Ala Ser Thr Gln Ala Asp Ser Ser
3825              3830              3835              3840

Arg His Ser Gln Ser Gly Gln Gly Glu Ser Ala Gly Ser Arg Arg Ser
                 3845              3850              3855

Arg Arg Gln Gly Ser Ser Val Ser Gln Asp Ser Asp Ser Glu Ala Tyr
                 3860              3865              3870

Pro Glu Asp Ser Glu Arg Arg Ser Glu Ser Ala Ser Arg Asn His His
                 3875              3880              3885

Gly Ser Ser Arg Glu Gln Ser Arg Asp Gly Ser Arg His Pro Gly Ser
     3890              3895              3900

Ser His Arg Asp Thr Ala Ser His Val Gln Ser Ser Pro Val Gln Ser
3905              3910              3915              3920

Asp Ser Ser Thr Ala Lys Glu His Gly His Phe Ser Ser Leu Ser Gln
                 3925              3930              3935

Asp Ser Ala Tyr His Ser Gly Ile Gln Ser Arg Gly Ser Pro His Ser
                 3940              3945              3950

Ser Ser Ser Tyr His Tyr Gln Ser Glu Gly Thr Glu Arg Gln Lys Gly
                 3955              3960              3965

Gln Ser Gly Leu Val Trp Arg His Gly Ser Tyr Gly Ser Ala Asp Tyr
3970              3975              3980

Asp Tyr Gly Glu Ser Gly Phe Arg His Ser Gln His Gly Ser Val Ser
3985              3990              3995              4000

Tyr Asn Ser Asn Pro Val Val Phe Lys Glu Arg Ser Asp Ile Cys Lys
                 4005              4010              4015

Ala Ser Ala Phe Gly Lys Asp His Pro Arg Tyr Tyr Ala Thr Tyr Ile
                 4020              4025              4030

Asn Lys Asp Pro Gly Leu Cys Gly His Ser Ser Asp Ile Ser Lys Gln
                 4035              4040              4045

Leu Gly Phe Ser Gln Ser Gln Arg Tyr Tyr Tyr Tyr Glu
     4050              4055              4060

<210> SEQ ID NO 40
<211> LENGTH: 325
<212> TYPE: PRT
<213> ORGANISM: Artificial Sequence
<220> FEATURE:
<223> OTHER INFORMATION: Synthetic Construct

<400> SEQUENCE: 40

Gln Val Ser Thr His Glu Gln Pro Asp Ser Ala His Gly Arg Thr Gly
1               5                  10                 15

Thr Ser Thr Gly Gly Arg Gln Gly Ser His His Glu Gln Ala Arg Asp
          20                 25                 30

Ser Ser Arg His Ser Ala Ser Gln Glu Gly Gln Asp Thr Ile Arg Gly
```

```
            35                  40                  45

His Pro Gly Ser Ser Arg Gly Gly Arg Gln Gly Ser His His Glu Gln
    50                  55                  60

Ser Val Asn Arg Ser Gly His Ser Gly Ser His His Ser His Thr Thr
65                  70                  75                  80

Ser Gln Gly Arg Ser Asp Ala Ser His Gly Gln Ser Gly Ser Arg Ser
                85                  90                  95

Ala Ser Arg Gln Thr Arg Asn Glu Glu Gln Ser Gly Asp Gly Thr Arg
            100                 105                 110

His Ser Gly Ser Arg His His Glu Ala Ser Ser Gln Ala Asp Ser Ser
            115                 120                 125

Arg His Ser Gln Val Gly Gln Gly Gln Ser Ser Gly Pro Arg Thr Ser
    130                 135                 140

Arg Asn Gln Gly Ser Ser Val Ser Gln Asp Ser Asp Ser Gln Gly His
145                 150                 155                 160

Ser Glu Asp Ser Glu Arg Trp Ser Gly Ser Ala Ser Arg Asn His His
            165                 170                 175

Gly Ser Ala Gln Glu Gln Ser Arg Asp Gly Ser Arg His Pro Arg Ser
            180                 185                 190

His His Glu Asp Arg Ala Gly His Gly His Ser Ala Asp Ser Ser Arg
            195                 200                 205

Lys Ser Gly Thr Arg His Thr Gln Asn Ser Ser Ser Gly Gln Ala Ala
    210                 215                 220

Ser Ser His Glu Gln Ala Arg Ser Ser Ala Gly Glu Arg His Gly Ser
225                 230                 235                 240

Arg His Gln Leu Gln Ser Ala Asp Ser Ser Arg His Ser Gly Thr Gly
            245                 250                 255

His Gly Gln Ala Ser Ser Ala Val Arg Asp Ser Gly His Arg Gly Ser
            260                 265                 270

Ser Gly Ser Gln Ala Thr Asp Ser Glu Gly His Ser Glu Asp Ser Asp
            275                 280                 285

Thr Gln Ser Val Ser Gly His Gly Gln Ala Gly His His Gln Gln Ser
    290                 295                 300

His Gln Glu Ser Ala Arg Asp Arg Ser Gly Glu Arg Ser Arg Arg Ser
305                 310                 315                 320

Gly Ser Phe Leu Tyr
                325

<210> SEQ ID NO 41
<211> LENGTH: 324
<212> TYPE: PRT
<213> ORGANISM: Artificial Sequence
<220> FEATURE:
<223> OTHER INFORMATION: Synthetic Construct

<400> SEQUENCE: 41

Gln Val Ser Thr His Lys Gln Ser Glu Ser Ser His Gly Trp Thr Gly
1               5                   10                  15

Pro Ser Thr Gly Val Arg Gln Gly Ser His His Glu Gln Ala Arg Asp
                20                  25                  30

Asn Ser Arg His Ser Ala Ser Gln Asp Gly Gln Asp Thr Ile Arg Gly
            35                  40                  45

His Pro Gly Ser Ser Arg Arg Gly Arg Gln Gly Ser His His Glu Gln
    50                  55                  60

Ser Val Asp Arg Ser Gly His Ser Gly Ser His His Ser His Thr Thr
```

-continued

```
            65                  70                  75                  80

Ser Gln Gly Arg Ser Asp Ala Ser Arg Gly Gln Ser Gly Ser Arg Ser
                    85                  90                  95

Ala Ser Arg Thr Thr Arg Asn Glu Glu Gln Ser Arg Asp Gly Ser Arg
                   100                 105                 110

His Ser Gly Ser Arg His His Glu Ala Ser Ser His Ala Asp Ile Ser
               115                 120                 125

Arg His Ser Gln Ala Gly Gln Gly Gln Ser Glu Gly Ser Arg Thr Ser
           130                 135                 140

Arg Arg Gln Gly Ser Ser Val Ser Gln Asp Ser Asp Ser Glu Gly His
145                 150                 155                 160

Ser Glu Asp Ser Glu Arg Trp Ser Gly Ser Ala Ser Arg Asn His Arg
                   165                 170                 175

Gly Ser Ala Gln Glu Gln Ser Arg His Gly Ser Arg His Pro Arg Ser
               180                 185                 190

His His Glu Asp Arg Ala Gly His Gly His Ser Ala Asp Ser Ser Arg
               195                 200                 205

Gln Ser Gly Thr Pro His Ala Glu Thr Ser Ser Gly Gly Gln Ala Ala
           210                 215                 220

Ser Ser His Glu Gln Ala Arg Ser Ser Pro Gly Glu Arg His Gly Ser
225                 230                 235                 240

Arg His Gln Gln Ser Ala Asp Ser Ser Arg His Ser Gly Ile Pro Arg
                   245                 250                 255

Arg Gln Ala Ser Ser Ala Val Arg Asp Ser Gly His Trp Gly Ser Ser
               260                 265                 270

Gly Ser Gln Ala Ser Asp Ser Glu Gly His Ser Glu Glu Ser Asp Thr
           275                 280                 285

Gln Ser Val Ser Gly His Gly Gln Asp Gly Pro His Gln Gln Ser His
           290                 295                 300

Gln Glu Ser Ala Arg Asp Trp Ser Gly Gly Arg Ser Gly Arg Ser Gly
305                 310                 315                 320

Ser Phe Ile Tyr
```

```
<210> SEQ ID NO 42
<211> LENGTH: 324
<212> TYPE: PRT
<213> ORGANISM: Artificial Sequence
<220> FEATURE:
<223> OTHER INFORMATION: Synthetic Construct

<400> SEQUENCE: 42

Gln Val Ser Thr His Glu Gln Ser Glu Ser Ala His Gly Arg Thr Arg
1               5                   10                  15

Thr Ser Thr Gly Arg Arg Gln Gly Ser His His Glu Gln Ala Arg Asp
               20                  25                  30

Ser Ser Arg His Ser Ala Ser Gln Glu Gly Gln Asp Thr Ile Arg Ala
           35                  40                  45

His Pro Gly Ser Arg Arg Gly Gly Arg Gln Gly Ser His His Glu Gln
       50                  55                  60

Ser Val Asp Arg Ser Gly His Ser Gly Ser His His Ser His Thr Thr
65                  70                  75                  80

Ser Gln Gly Arg Ser Asp Ala Ser His Gly Gln Ser Gly Ser Arg Ser
                   85                  90                  95

Ala Ser Arg Gln Thr Arg Lys Asp Lys Gln Ser Gly Asp Gly Ser Arg
               100                 105                 110
```

```
His Ser Gly Ser Arg His His Glu Ala Ala Ser Trp Ala Asp Ser Ser
        115                 120                 125

Arg His Ser Gln Val Gly Gln Glu Gln Ser Ser Gly Ser Arg Thr Ser
    130                 135                 140

Arg His Gln Gly Ser Ser Val Ser Gln Asp Ser Asp Ser Glu Arg His
145                 150                 155                 160

Ser Asp Asp Ser Glu Arg Leu Ser Gly Ser Ala Ser Arg Asn His His
                165                 170                 175

Gly Ser Ser Arg Glu Gln Ser Arg Asp Gly Ser Arg His Pro Gly Phe
                180                 185                 190

His Gln Glu Asp Arg Ala Ser His Gly His Ser Ala Asp Ser Ser Arg
        195                 200                 205

Gln Ser Gly Thr His His Thr Glu Ser Ser Ser His Gly Gln Ala Val
    210                 215                 220

Ser Ser His Glu Gln Ala Arg Ser Ser Pro Gly Glu Arg His Gly Ser
225                 230                 235                 240

Arg His Gln Gln Ser Ala Asp Ser Ser Arg His Ser Gly Ile Gly His
                245                 250                 255

Arg Gln Ala Ser Ser Ala Val Arg Asp Ser Gly His Arg Gly Ser Ser
        260                 265                 270

Gly Ser Gln Val Thr Asn Ser Glu Gly His Ser Glu Asp Ser Asp Thr
        275                 280                 285

Gln Ser Val Ser Ala His Gly Gln Ala Gly Pro His Gln Gln Ser His
    290                 295                 300

Lys Glu Ser Ala Arg Gly Gln Ser Gly Glu Ser Ser Gly Arg Ser Arg
305                 310                 315                 320

Ser Phe Leu Tyr

<210> SEQ ID NO 43
<211> LENGTH: 324
<212> TYPE: PRT
<213> ORGANISM: Artificial Sequence
<220> FEATURE:
<223> OTHER INFORMATION: Synthetic Construct

<400> SEQUENCE: 43

Gln Val Ser Ser His Glu Gln Ser Glu Ser Thr His Gly Gln Thr Ala
1               5                   10                  15

Pro Ser Thr Gly Gly Arg Gln Gly Ser Arg His Glu Gln Ala Arg Asn
            20                  25                  30

Ser Ser Arg His Ser Ala Ser Gln Asp Gly Gln Asp Thr Ile Arg Gly
        35                  40                  45

His Pro Gly Ser Ser Arg Gly Gly Arg Gln Gly Ser Tyr His Glu Gln
    50                  55                  60

Ser Val Asp Arg Ser Gly His Ser Gly Tyr His His Ser His Thr Thr
65                  70                  75                  80

Pro Gln Gly Arg Ser Asp Ala Ser His Gly Gln Ser Gly Pro Arg Ser
            85                  90                  95

Ala Ser Arg Gln Thr Arg Asn Glu Glu Gln Ser Gly Asp Gly Ser Arg
            100                 105                 110

His Ser Gly Ser Arg His His Glu Pro Ser Thr Arg Ala Gly Ser Ser
        115                 120                 125

Arg His Ser Gln Val Gly Gln Gly Glu Ser Ala Gly Ser Lys Thr Ser
    130                 135                 140
```

-continued

```
Arg Arg Gln Gly Ser Ser Val Ser Gln Asp Arg Asp Ser Glu Gly His
145             150                 155                 160

Ser Glu Asp Ser Glu Arg Arg Ser Glu Ser Ala Ser Arg Asn His Tyr
                165                 170                 175

Gly Ser Ala Arg Glu Gln Ser Arg His Gly Ser Arg Asn Pro Arg Ser
            180                 185                 190

His Gln Glu Asp Arg Ala Ser His Gly His Ser Ala Glu Ser Ser Arg
            195                 200                 205

Gln Ser Gly Thr Arg His Ala Glu Thr Ser Ser Gly Gly Gln Ala Ala
    210                 215                 220

Ser Ser Gln Glu Gln Ala Arg Ser Ser Pro Gly Glu Arg His Gly Ser
225                 230                 235                 240

Arg His Gln Gln Ser Ala Asp Ser Ser Thr Asp Ser Gly Thr Gly Arg
                245                 250                 255

Arg Gln Asp Ser Ser Val Val Gly Asp Ser Gly Asn Arg Gly Ser Ser
            260                 265                 270

Gly Ser Gln Ala Ser Asp Ser Glu Gly His Ser Glu Glu Ser Asp Thr
    275                 280                 285

Gln Ser Val Ser Ala His Gly Gln Ala Gly Pro His Gln Gln Ser His
    290                 295                 300

Gln Glu Ser Thr Arg Gly Gln Ser Gly Glu Arg Ser Gly Arg Ser Gly
305                 310                 315                 320

Ser Phe Leu Tyr

<210> SEQ ID NO 44
<211> LENGTH: 325
<212> TYPE: PRT
<213> ORGANISM: Artificial Sequence
<220> FEATURE:
<223> OTHER INFORMATION: Synthetic Construct

<400> SEQUENCE: 44

Gln Val Ser Thr His Glu Gln Ser Glu Ser Ala His Gly Arg Thr Gly
1               5                   10                  15

Pro Ser Thr Gly Gly Arg Gln Arg Ser Arg His Glu Gln Ala Arg Asp
            20                  25                  30

Ser Ser Arg His Ser Ala Ser Gln Glu Gly Gln Asp Thr Ile Arg Gly
        35                  40                  45

His Pro Gly Ser Ser Arg Gly Gly Arg Gln Gly Ser His Tyr Glu Gln
    50                  55                  60

Ser Val Asp Ser Ser Gly His Ser Gly Ser His His Ser His Thr Thr
65                  70                  75                  80

Ser Gln Glu Arg Ser Asp Val Ser Arg Gly Gln Ser Gly Ser Arg Ser
                85                  90                  95

Val Ser Arg Gln Thr Arg Asn Glu Lys Gln Ser Gly Asp Gly Ser Arg
            100                 105                 110

His Ser Gly Ser Arg His His Glu Ala Ser Ser Arg Ala Asp Ser Ser
        115                 120                 125

Arg His Ser Gln Val Gly Gln Gly Gln Ser Ser Gly Pro Arg Thr Ser
    130                 135                 140

Arg Asn Gln Gly Ser Ser Val Ser Gln Asp Ser Asp Ser Gln Gly His
145                 150                 155                 160

Ser Glu Asp Ser Glu Arg Trp Ser Gly Ser Ala Ser Arg Asn His Leu
                165                 170                 175

Gly Ser Ala Trp Glu Gln Ser Arg Asp Gly Ser Arg His Pro Gly Ser
```

-continued

```
                 180                 185                 190

His His Glu Asp Arg Ala Gly His Gly His Ser Ala Asp Ser Ser Arg
        195                 200                 205

Gln Ser Gly Thr Arg His Thr Glu Ser Ser Ser Arg Gly Gln Ala Ala
        210                 215                 220

Ser Ser His Glu Gln Ala Arg Ser Ser Ala Gly Glu Arg His Gly Ser
225                 230                 235                 240

His His Gln Leu Gln Ser Ala Asp Ser Ser Arg His Ser Gly Ile Gly
                245                 250                 255

His Gly Gln Ala Ser Ser Ala Val Arg Asp Ser Gly His Arg Gly Tyr
                260                 265                 270

Ser Gly Ser Gln Ala Ser Asp Ser Glu Gly His Ser Glu Asp Ser Asp
                275                 280                 285

Thr Gln Ser Val Ser Ala Gln Gly Lys Ala Gly Pro His Gln Gln Ser
        290                 295                 300

His Lys Glu Ser Ala Arg Gly Gln Ser Gly Glu Ser Ser Gly Arg Ser
305                 310                 315                 320

Gly Ser Phe Leu Tyr
                325

<210> SEQ ID NO 45
<211> LENGTH: 324
<212> TYPE: PRT
<213> ORGANISM: Artificial Sequence
<220> FEATURE:
<223> OTHER INFORMATION: Synthetic Construct

<400> SEQUENCE: 45

Gln Val Ser Thr His Glu Gln Ser Glu Ser Thr His Gly Gln Ser Ala
1               5                   10                  15

Pro Ser Thr Gly Gly Arg Gln Gly Ser His Tyr Asp Gln Ala Gln Asp
                20                  25                  30

Ser Ser Arg His Ser Ala Ser Gln Glu Gly Gln Asp Thr Ile Arg Gly
        35                  40                  45

His Pro Gly Pro Ser Arg Gly Gly Arg Gln Gly Ser His Gln Glu Gln
        50                  55                  60

Ser Val Asp Arg Ser Gly His Ser Gly Ser His His Ser His Thr Thr
65                  70                  75                  80

Ser Gln Gly Arg Ser Asp Ala Ser Arg Gly Gln Ser Gly Ser Arg Ser
                85                  90                  95

Ala Ser Arg Lys Thr Tyr Asp Lys Glu Gln Ser Gly Asp Gly Ser Arg
                100                 105                 110

His Ser Gly Ser His His His Glu Ala Ser Ser Trp Ala Asp Ser Ser
        115                 120                 125

Arg His Ser Leu Val Gly Gln Gly Gln Ser Ser Gly Pro Arg Thr Ser
        130                 135                 140

Arg Pro Arg Gly Ser Ser Val Ser Gln Asp Ser Asp Ser Glu Gly His
145                 150                 155                 160

Ser Glu Asp Ser Glu Arg Arg Ser Gly Ser Ala Ser Arg Asn His His
                165                 170                 175

Gly Ser Ala Gln Glu Gln Ser Arg Asp Gly Ser Arg His Pro Arg Ser
                180                 185                 190

His His Glu Asp Arg Ala Gly His Gly His Ser Ala Glu Ser Ser Arg
        195                 200                 205

Gln Ser Gly Thr His His Ala Glu Asn Ser Ser Gly Gly Gln Ala Ala
```

```
          210                 215                 220

Ser Ser His Glu Gln Ala Arg Ser Ser Ala Gly Glu Arg His Gly Ser
225                 230                 235                 240

His His Gln Gln Ser Ala Asp Ser Ser Arg His Ser Gly Ile Gly His
                245                 250                 255

Gly Gln Ala Ser Ser Ala Val Arg Asp Ser Gly His Arg Gly Ser Ser
                260                 265                 270

Gly Ser Gln Ala Ser Asp Ser Glu Gly His Ser Glu Asp Ser Asp Thr
            275                 280                 285

Gln Ser Val Ser Ala His Gly Gln Ala Gly Pro His Gln Gln Ser His
        290                 295                 300

Gln Glu Ser Thr Arg Gly Arg Ser Ala Gly Arg Ser Gly Arg Ser Gly
305                 310                 315                 320

Ser Phe Leu Tyr

<210> SEQ ID NO 46
<211> LENGTH: 324
<212> TYPE: PRT
<213> ORGANISM: Artificial Sequence
<220> FEATURE:
<223> OTHER INFORMATION: Synthetic Construct

<400> SEQUENCE: 46

Gln Val Ser Thr His Glu Gln Ser Glu Ser Ala His Gly Arg Thr Gly
1               5                   10                  15

Thr Ser Thr Gly Gly Arg Gln Gly Ser His His Lys Gln Ala Arg Asp
                20                  25                  30

Ser Ser Arg His Ser Thr Ser Gln Glu Gly Gln Asp Thr Ile His Gly
        35                  40                  45

His Pro Gly Ser Ser Ser Gly Gly Arg Gln Gly Ser His Tyr Glu Gln
    50                  55                  60

Leu Val Asp Arg Ser Gly His Ser Gly Ser His His Ser His Thr Thr
65                  70                  75                  80

Ser Gln Gly Arg Ser Asp Ala Ser His Gly His Ser Gly Ser Arg Ser
                85                  90                  95

Ala Ser Arg Gln Thr Arg Asn Asp Glu Gln Ser Gly Asp Gly Ser Arg
            100                 105                 110

His Ser Gly Ser Arg His His Glu Ala Ser Ser Arg Ala Asp Ser Ser
        115                 120                 125

Gly His Ser Gln Val Gly Gln Gly Gln Ser Glu Gly Pro Arg Thr Ser
    130                 135                 140

Arg Asn Trp Gly Ser Ser Phe Ser Gln Asp Ser Asp Ser Gln Gly His
145                 150                 155                 160

Ser Glu Asp Ser Glu Arg Trp Ser Gly Ser Ala Ser Arg Asn His His
                165                 170                 175

Gly Ser Ala Gln Glu Gln Leu Arg Asp Gly Ser Arg His Pro Arg Ser
            180                 185                 190

His Gln Glu Asp Arg Ala Gly His Gly His Ser Ala Asp Ser Ser Arg
        195                 200                 205

Gln Ser Gly Thr Arg His Thr Gln Thr Ser Ser Gly Gly Gln Ala Ala
    210                 215                 220

Ser Ser His Glu Gln Ala Arg Ser Ser Ala Gly Glu Arg His Gly Ser
225                 230                 235                 240

His His Gln Gln Ser Ala Asp Ser Ser Arg His Ser Gly Ile Gly His
                245                 250                 255
```

```
Gly Gln Ala Ser Ser Ala Val Arg Asp Ser Gly His Arg Gly Tyr Ser
        260                 265                 270

Gly Ser Gln Ala Ser Asp Asn Glu Gly His Ser Glu Asp Ser Asp Thr
        275                 280                 285

Gln Ser Val Ser Ala His Gly Gln Ala Gly Ser His Gln Gln Ser His
        290                 295                 300

Gln Glu Ser Ala Arg Gly Arg Ser Gly Glu Thr Ser Gly His Ser Gly
305                 310                 315                 320

Ser Phe Leu Tyr

<210> SEQ ID NO 47
<211> LENGTH: 324
<212> TYPE: PRT
<213> ORGANISM: Artificial Sequence
<220> FEATURE:
<223> OTHER INFORMATION: Synthetic Construct

<400> SEQUENCE: 47

Gln Val Ser Thr His Glu Gln Ser Glu Ser Ser His Gly Trp Thr Gly
1                5                  10                  15

Pro Ser Thr Arg Gly Arg Gln Gly Ser Arg His Glu Gln Ala Gln Asp
        20                  25                  30

Ser Ser Arg His Ser Ala Ser Gln Asp Gly Gln Asp Thr Ile Arg Gly
        35                  40                  45

His Pro Gly Ser Ser Arg Gly Gly Arg Gln Gly Tyr His His Glu His
        50                  55                  60

Ser Val Asp Ser Ser Gly His Ser Gly Ser His His Ser His Thr Thr
65                  70                  75                  80

Ser Gln Gly Arg Ser Asp Ala Ser Arg Gly Gln Ser Gly Ser Arg Ser
                85                  90                  95

Ala Ser Arg Thr Thr Arg Asn Glu Glu Gln Ser Gly Asp Gly Ser Arg
        100                 105                 110

His Ser Gly Ser Arg His His Glu Ala Ser Thr His Ala Asp Ile Ser
        115                 120                 125

Arg His Ser Gln Ala Val Gln Gly Gln Ser Glu Gly Ser Arg Arg Ser
        130                 135                 140

Arg Arg Gln Gly Ser Ser Val Ser Gln Asp Ser Asp Ser Glu Gly His
145                 150                 155                 160

Ser Glu Asp Ser Glu Arg Trp Ser Gly Ser Ala Ser Arg Asn His His
                165                 170                 175

Gly Ser Ala Gln Glu Gln Leu Arg Asp Gly Ser Arg His Pro Arg Ser
        180                 185                 190

His Gln Glu Asp Arg Ala Gly His Gly His Ser Ala Asp Ser Ser Arg
        195                 200                 205

Gln Ser Gly Thr Arg His Thr Gln Thr Ser Ser Gly Gly Gln Ala Ala
        210                 215                 220

Ser Ser His Glu Gln Ala Arg Ser Ser Ala Gly Glu Arg His Gly Ser
225                 230                 235                 240

His His Gln Gln Ser Ala Asp Ser Ser Arg His Ser Gly Ile Gly His
                245                 250                 255

Gly Gln Ala Ser Ser Ala Val Arg Asp Ser Gly His Arg Gly Tyr Ser
        260                 265                 270

Gly Ser Gln Ala Ser Asp Asn Glu Gly His Ser Glu Asp Ser Asp Thr
        275                 280                 285
```

```
Gln Ser Val Ser Ala His Gly Gln Ala Gly Ser His Gln Gln Ser His
    290                 295                 300

Gln Glu Ser Ala Arg Gly Arg Ser Gly Glu Thr Ser Gly His Ser Gly
305                 310                 315                 320

Ser Phe Leu Tyr

<210> SEQ ID NO 48
<211> LENGTH: 324
<212> TYPE: PRT
<213> ORGANISM: Artificial Sequence
<220> FEATURE:
<223> OTHER INFORMATION: Synthetic Construct

<400> SEQUENCE: 48

Gln Val Ser Thr His Glu Gln Ser Glu Ser Ser His Gly Trp Thr Gly
1               5                   10                  15

Pro Ser Thr Arg Gly Arg Gln Gly Ser Arg His Glu Gln Ala Gln Asp
                20                  25                  30

Ser Ser Arg His Ser Ala Ser Gln Tyr Gly Gln Asp Thr Ile Arg Gly
            35                  40                  45

His Pro Gly Ser Ser Arg Gly Gly Arg Gln Gly Tyr His His Glu His
        50                  55                  60

Ser Val Asp Ser Ser Gly His Ser Gly Ser His His Ser His Thr Thr
65                  70                  75                  80

Ser Gln Gly Arg Ser Asp Ala Ser Arg Gly Gln Ser Gly Ser Arg Ser
                85                  90                  95

Ala Ser Arg Thr Thr Arg Asn Glu Glu Gln Ser Gly Asp Ser Ser Arg
            100                 105                 110

His Ser Val Ser Arg His His Glu Ala Ser Thr His Ala Asp Ile Ser
        115                 120                 125

Arg His Ser Gln Ala Val Gln Gly Gln Ser Glu Gly Ser Arg Arg Ser
    130                 135                 140

Arg Arg Gln Gly Ser Ser Val Ser Gln Asp Ser Asp Ser Glu Gly His
145                 150                 155                 160

Ser Glu Asp Ser Glu Arg Trp Ser Gly Ser Ala Ser Arg Asn His Arg
                165                 170                 175

Gly Ser Val Gln Glu Gln Ser Arg His Gly Ser Arg His Pro Arg Ser
            180                 185                 190

His His Glu Asp Arg Ala Gly His Gly His Ser Ala Asp Arg Ser Arg
        195                 200                 205

Gln Ser Gly Thr Arg His Ala Glu Thr Ser Ser Gly Gly Gln Ala Ala
    210                 215                 220

Ser Ser His Glu Gln Ala Arg Ser Ser Pro Gly Glu Arg His Gly Ser
225                 230                 235                 240

Arg His Gln Gln Ser Ala Asp Ser Ser Arg His Ser Gly Ile Pro Arg
                245                 250                 255

Gly Gln Ala Ser Ser Ala Val Arg Asp Ser Arg His Trp Gly Ser Ser
            260                 265                 270

Gly Ser Gln Ala Ser Asp Ser Glu Gly His Ser Glu Glu Ser Asp Thr
        275                 280                 285

Gln Ser Val Ser Gly His Gly Gln Ala Gly Pro His Gln Gln Ser His
    290                 295                 300

Gln Glu Ser Ala Arg Asp Arg Ser Gly Gly Arg Ser Gly Arg Ser Gly
305                 310                 315                 320

Ser Phe Leu Tyr
```

<210> SEQ ID NO 49
<211> LENGTH: 324
<212> TYPE: PRT
<213> ORGANISM: Artificial Sequence
<220> FEATURE:
<223> OTHER INFORMATION: Synthetic Construct

<400> SEQUENCE: 49

Gln Val Ser Thr His Glu Gln Ser Glu Ser Ala His Gly Arg Thr Arg
1               5                   10                  15

Thr Ser Thr Gly Arg Arg Gln Gly Ser His His Glu Gln Ala Arg Asp
            20                  25                  30

Ser Ser Arg His Ser Ala Ser Gln Glu Gly Gln Asp Thr Ile Arg Gly
        35                  40                  45

His Pro Gly Ser Ser Arg Arg Gly Arg Gln Gly Ser His Tyr Glu Gln
    50                  55                  60

Ser Val Asp Arg Ser Gly His Ser Gly Ser His His Ser His Thr Thr
65                  70                  75                  80

Ser Gln Gly Arg Ser Asp Ala Ser Arg Gly Gln Ser Gly Ser Arg Ser
                85                  90                  95

Ala Ser Arg Gln Thr Arg Asn Asp Glu Gln Ser Gly Asp Gly Ser Arg
            100                 105                 110

His Ser Trp Ser His His His Glu Ala Ser Thr Gln Ala Asp Ser Ser
        115                 120                 125

Arg His Ser Gln Ser Gly Gln Gly Gln Ser Ala Gly Pro Arg Thr Ser
    130                 135                 140

Arg Asn Gln Gly Ser Ser Val Ser Gln Asp Ser Asp Ser Gln Gly His
145                 150                 155                 160

Ser Glu Asp Ser Glu Arg Trp Ser Gly Ser Ala Ser Arg Asn His Arg
                165                 170                 175

Gly Ser Ala Gln Glu Gln Ser Arg Asp Gly Ser Arg His Pro Thr Ser
            180                 185                 190

His His Glu Asp Arg Ala Gly His Gly His Ser Ala Glu Ser Ser Arg
        195                 200                 205

Gln Ser Gly Thr His His Ala Glu Asn Ser Ser Gly Gly Gln Ala Ala
    210                 215                 220

Ser Ser His Glu Gln Ala Arg Ser Ser Ala Gly Glu Arg His Gly Ser
225                 230                 235                 240

His His Gln Gln Ser Ala Asp Ser Ser Arg His Ser Gly Ile Gly His
            245                 250                 255

Gly Gln Ala Ser Ser Ala Val Arg Asp Ser Gly His Arg Gly Ser Ser
            260                 265                 270

Gly Ser Gln Ala Ser Asp Ser Glu Gly His Ser Glu Asp Ser Asp Thr
        275                 280                 285

Gln Ser Val Ser Ala His Gly Gln Ala Gly Pro His Gln Gln Ser His
    290                 295                 300

Gln Glu Ser Thr Arg Gly Arg Ser Ala Gly Arg Ser Gly Arg Ser Gly
305                 310                 315                 320

Ser Phe Leu Tyr

<210> SEQ ID NO 50
<211> LENGTH: 2391
<212> TYPE: PRT
<213> ORGANISM: Homo sapiens -continued

```
<400> SEQUENCE: 50

Met Thr Asp Leu Leu Arg Ser Val Val Thr Val Ile Asp Val Phe Tyr
1               5                   10                  15

Lys Tyr Thr Lys Gln Asp Gly Glu Cys Gly Thr Leu Ser Lys Gly Glu
            20                  25                  30

Leu Lys Glu Leu Leu Glu Lys Glu Leu His Pro Val Leu Lys Asn Pro
        35                  40                  45

Asp Asp Pro Asp Thr Val Asp Val Ile Met His Met Leu Asp Arg Asp
    50                  55                  60

His Asp Arg Arg Leu Asp Phe Thr Glu Phe Leu Leu Met Ile Phe Lys
65                  70                  75                  80

Leu Thr Met Ala Cys Asn Lys Val Leu Ser Lys Glu Tyr Cys Lys Ala
                85                  90                  95

Ser Gly Ser Lys Lys His Arg Arg Gly His Arg His Gln Glu Glu Glu
            100                 105                 110

Ser Glu Thr Glu Glu Asp Glu Glu Asp Thr Pro Gly His Lys Ser Gly
            115                 120                 125

Tyr Arg His Ser Ser Trp Ser Glu Gly Glu Glu His Gly Tyr Ser Ser
    130                 135                 140

Gly His Ser Arg Gly Thr Val Lys Cys Arg His Gly Ser Asn Ser Arg
145                 150                 155                 160

Arg Leu Gly Arg Gln Gly Asn Leu Ser Ser Ser Gly Asn Gln Glu Gly
            165                 170                 175

Ser Gln Lys Arg Tyr His Arg Ser Ser Cys Gly His Ser Trp Ser Gly
            180                 185                 190

Gly Lys Asp Arg His Gly Ser Ser Ser Val Glu Leu Arg Glu Arg Ile
            195                 200                 205

Asn Lys Ser His Ile Ser Pro Ser Arg Glu Ser Gly Glu Glu Tyr Glu
    210                 215                 220

Ser Gly Ser Gly Ser Asn Ser Trp Glu Arg Lys Gly His Gly Gly Leu
225                 230                 235                 240

Ser Cys Gly Leu Glu Thr Ser Gly His Glu Ser Asn Ser Thr Gln Ser
            245                 250                 255

Arg Ile Arg Glu Gln Lys Leu Gly Ser Ser Cys Ser Gly Ser Gly Asp
            260                 265                 270

Ser Gly Arg Arg Ser His Ala Cys Gly Tyr Ser Asn Ser Ser Gly Cys
            275                 280                 285

Gly Arg Pro Gln Asn Ala Ser Ser Ser Cys Gln Ser His Arg Phe Gly
    290                 295                 300

Gly Gln Gly Asn Gln Phe Ser Tyr Ile Gln Ser Gly Cys Gln Ser Gly
305                 310                 315                 320

Ile Lys Gly Gly Gln Gly His Gly Cys Val Ser Gly Gly Gln Pro Ser
            325                 330                 335

Gly Cys Gly Gln Pro Glu Ser Asn Pro Cys Ser Gln Ser Tyr Ser Gln
            340                 345                 350

Arg Gly Tyr Gly Ala Arg Glu Asn Gly Gln Pro Gln Asn Cys Gly Gly
            355                 360                 365

Gln Trp Arg Thr Gly Ser Ser Gln Ser Ser Cys Cys Gly Gln Tyr Gly
    370                 375                 380

Ser Gly Gly Ser Gln Ser Cys Ser Asn Gly Gln His Glu Tyr Gly Ser
385                 390                 395                 400

Cys Gly Arg Phe Ser Asn Ser Ser Ser Ser Asn Glu Phe Ser Lys Cys
            405                 410                 415
```

```
Asp Gln Tyr Gly Ser Gly Ser Ser Gln Ser Thr Ser Phe Glu Gln His
        420                 425             430

Gly Thr Gly Leu Ser Gln Ser Ser Gly Phe Glu Gln His Val Cys Gly
        435                 440             445

Ser Gly Gln Thr Cys Gly Gln His Glu Ser Thr Ser Ser Gln Ser Leu
        450                 455             460

Gly Tyr Asp Gln His Gly Ser Ser Ser Gly Lys Thr Ser Gly Phe Gly
465                 470             475                 480

Gln His Gly Ser Gly Ser Gly Gln Ser Ser Gly Phe Gly Gln Cys Gly
            485                 490             495

Ser Gly Ser Gly Gln Ser Ser Gly Phe Gly Gln His Gly Ser Val Ser
            500                 505             510

Gly Gln Ser Ser Gly Phe Gly Gln His Gly Ser Val Ser Gly Gln Ser
        515                 520             525

Ser Gly Phe Gly Gln His Glu Ser Arg Ser Arg Gln Ser Ser Tyr Gly
        530                 535             540

Gln His Gly Ser Gly Ser Ser Gln Ser Ser Gly Tyr Gly Gln Tyr Gly
545                 550             555                 560

Ser Arg Glu Thr Ser Gly Phe Gly Gln His Gly Leu Gly Ser Gly Gln
            565                 570             575

Ser Thr Gly Phe Gly Gln Tyr Gly Ser Gly Ser Gly Gln Ser Ser Gly
            580                 585             590

Phe Gly Gln His Gly Ser Gly Ser Gly Gln Ser Ser Gly Phe Gly Gln
        595                 600             605

His Glu Ser Arg Ser Gly Gln Ser Ser Tyr Gly Gln His Ser Ser Gly
        610                 615             620

Ser Ser Gln Ser Ser Gly Tyr Gly Gln His Gly Ser Arg Gln Thr Ser
625                 630             635                 640

Gly Phe Gly Gln His Gly Ser Gly Ser Ser Gln Ser Thr Gly Phe Gly
            645                 650             655

Gln Tyr Gly Ser Gly Ser Gly Gln Ser Ser Gly Phe Gly Gln His Val
            660                 665             670

Ser Gly Ser Gly Gln Ser Ser Gly Phe Gly Gln His Glu Ser Arg Ser
            675                 680             685

Gly His Ser Ser Tyr Gly Gln His Gly Phe Gly Ser Ser Gln Ser Ser
        690                 695             700

Gly Tyr Gly Gln His Gly Ser Ser Ser Gly Gln Thr Ser Gly Phe Gly
705                 710             715                 720

Gln His Glu Leu Ser Ser Gly Gln Ser Ser Ser Phe Gly Gln His Gly
            725                 730             735

Ser Gly Ser Gly Gln Ser Ser Gly Phe Gly Gln His Gly Ser Gly Ser
            740                 745             750

Gly Gln Ser Ser Gly Phe Gly Gln His Glu Ser Arg Ser Gly Gln Ser
        755                 760             765

Ser Tyr Gly Gln His Ser Ser Gly Ser Ser Gln Ser Ser Gly Tyr Gly
        770                 775             780

Gln His Gly Ser Arg Gln Thr Ser Gly Phe Gly Gln His Gly Ser Gly
785                 790             795                 800

Ser Ser Gln Ser Thr Gly Phe Gly Gln Tyr Gly Ser Gly Ser Gly Gln
            805                 810             815

Ser Ala Gly Phe Gly Gln His Gly Ser Gly Ser Gly Gln Ser Ser Gly
        820                 825             830
```

```
Phe Gly Gln His Glu Ser Arg Ser His Gln Ser Ser Tyr Gly Gln His
        835                 840                 845

Gly Ser Gly Ser Ser Gln Ser Ser Gly Tyr Gly Gln His Gly Ser Ser
    850                 855                 860

Ser Gly Gln Thr Ser Gly Phe Gly Gln His Arg Ser Ser Ser Gly Gln
865                 870                 875                 880

Tyr Ser Gly Phe Gly Gln His Gly Ser Gly Ser Gly Gln Ser Ser Gly
                885                 890                 895

Phe Gly Gln His Gly Thr Gly Ser Gly Gln Tyr Ser Gly Phe Gly Gln
            900                 905                 910

His Glu Ser Arg Ser His Gln Ser Ser Tyr Gly Gln His Gly Ser Gly
        915                 920                 925

Ser Ser Gln Ser Ser Gly Tyr Gly Gln His Gly Ser Ser Ser Gly Gln
    930                 935                 940

Thr Phe Gly Phe Gly Gln His Arg Ser Gly Ser Gly Gln Ser Ser Gly
945                 950                 955                 960

Phe Gly Gln His Gly Ser Gly Ser Gly Gln Ser Ser Gly Phe Gly Gln
                965                 970                 975

His Glu Ser Gly Ser Gly Lys Ser Ser Gly Phe Gly Gln His Glu Ser
            980                 985                 990

Arg Ser Ser Gln Ser Asn Tyr Gly Gln His Gly Ser Gly Ser Ser Gln
        995                1000                1005

Ser Ser Gly Tyr Gly Gln His Gly Ser Ser Ser Gly Gln Thr Thr Gly
    1010                1015                1020

Phe Gly Gln His Arg Ser Ser Ser Gly Gln Tyr Ser Gly Phe Gly Gln
1025                1030                1035                1040

His Gly Ser Gly Ser Asp Gln Ser Ser Gly Phe Gly Gln His Gly Thr
                1045                1050                1055

Gly Ser Gly Gln Ser Ser Gly Phe Gly Gln Tyr Glu Ser Arg Ser Arg
            1060                1065                1070

Gln Ser Ser Tyr Gly Gln His Gly Ser Gly Ser Ser Gln Ser Ser Gly
        1075                1080                1085

Tyr Gly Gln His Gly Ser Asn Ser Gly Gln Thr Ser Gly Phe Gly Gln
    1090                1095                1100

His Arg Pro Gly Ser Gly Gln Ser Ser Gly Phe Gly Gln Tyr Gly Ser
1105                1110                1115                1120

Gly Ser Gly Gln Ser Ser Gly Phe Gly Gln His Gly Ser Gly Thr Gly
                1125                1130                1135

Lys Ser Ser Gly Phe Ala Gln His Glu Tyr Arg Ser Gly Gln Ser Ser
            1140                1145                1150

Tyr Gly Gln His Gly Thr Gly Ser Ser Gln Ser Ser Gly Cys Gly Gln
        1155                1160                1165

His Glu Ser Gly Ser Gly Pro Thr Thr Ser Phe Gly Gln His Val Ser
    1170                1175                1180

Gly Ser Asp Asn Phe Ser Ser Ser Gly Gln His Ile Ser Asp Ser Gly
1185                1190                1195                1200

Gln Ser Thr Gly Phe Gly Gln Tyr Gly Ser Gly Ser Gly Gln Ser Thr
                1205                1210                1215

Gly Leu Gly Gln Gly Glu Ser Gln Gln Val Glu Ser Gly Ser Thr Val
            1220                1225                1230

His Gly Arg Gln Glu Thr Thr His Gly Gln Thr Ile Asn Thr Thr Arg
        1235                1240                1245

His Ser Gln Ser Gly Gln Gly Gln Ser Thr Gln Thr Gly Ser Arg Val
```

```
          1250              1255              1260

Thr Arg Arg Arg Arg Ser Ser Gln Ser Glu Asn Ser Asp Ser Glu Val
1265              1270              1275              1280

His Ser Lys Val Ser His Arg His Ser Glu His Ile His Thr Gln Ala
                  1285              1290              1295

Gly Ser His Tyr Pro Lys Ser Gly Ser Thr Val Arg Arg Arg Gln Gly
                  1300              1305              1310

Thr Thr His Gly Gln Arg Gly Asp Thr Thr Arg His Gly His Ser Gly
              1315              1320              1325

His Gly Gln Ser Thr Gln Thr Gly Ser Arg Thr Ser Gly Arg Gln Arg
          1330              1335              1340

Phe Ser His Ser Asp Ala Thr Asp Ser Glu Val His Ser Gly Val Ser
1345              1350              1355              1360

His Arg Pro His Ser Gln Glu Gln Thr His Ser Gln Ala Gly Ser Gln
                  1365              1370              1375

His Gly Glu Ser Glu Ser Thr Val His Glu Arg His Glu Thr Thr Tyr
              1380              1385              1390

Gly Gln Thr Gly Glu Ala Thr Gly His Gly His Ser Gly His Gly Gln
              1395              1400              1405

Ser Thr Gln Arg Gly Ser Arg Thr Thr Gly Arg Arg Gly Ser Gly His
      1410              1415              1420

Ser Glu Ser Ser Asp Ser Glu Val His Ser Gly Gly Ser His Arg Pro
1425              1430              1435              1440

Gln Ser Gln Glu Gln Thr His Gly Gln Ala Gly Ser Gln His Gly Glu
                  1445              1450              1455

Ser Gly Ser Thr Val His Gly Arg His Gly Thr Thr His Gly Gln Thr
              1460              1465              1470

Gly Asp Thr Thr Arg His Ala His Tyr His His Gly Lys Ser Thr Gln
              1475              1480              1485

Arg Gly Ser Ser Thr Thr Gly Arg Arg Gly Ser Gly His Ser Glu Ser
      1490              1495              1500

Ser Asp Ser Glu Val His Ser Gly Gly Ser His Thr His Ser Gly His
1505              1510              1515              1520

Thr His Gly Gln Ser Gly Ser Gln His Gly Glu Ser Glu Ser Ile Ile
                  1525              1530              1535

His Asp Arg His Arg Ile Thr His Gly Gln Thr Gly Asp Thr Thr Arg
              1540              1545              1550

His Ser Tyr Ser Gly His Glu Gln Thr Thr Gln Thr Gly Ser Arg Thr
          1555              1560              1565

Thr Gly Arg Gln Arg Thr Ser His Ser Glu Ser Thr Asp Ser Glu Val
      1570              1575              1580

His Ser Gly Gly Ser His Arg Pro His Ser Arg Glu His Thr Tyr Gly
1585              1590              1595              1600

Gln Ala Gly Ser Gln His Glu Glu Pro Glu Phe Thr Val His Glu Arg
                  1605              1610              1615

His Gly Thr Thr His Gly Gln Ile Gly Asp Thr Thr Gly His Ser His
              1620              1625              1630

Ser Gly His Gly Gln Ser Thr Gln Arg Gly Ser Arg Thr Thr Gly Arg
          1635              1640              1645

Gln Arg Ser Ser His Ser Glu Ser Ser Asp Ser Glu Val His Ser Gly
      1650              1655              1660

Val Ser His Thr His Thr Gly His Thr His Gly Gln Ala Gly Ser Gln
1665              1670              1675              1680
```

```
His Gly Gln Ser Glu Ser Ile Val Pro Glu Arg His Gly Thr Thr His
            1685                1690                1695

Gly Gln Thr Gly Asp Thr Thr Arg His Ala His Tyr His His Gly Leu
            1700                1705                1710

Thr Thr Gln Thr Gly Ser Arg Thr Thr Gly Arg Arg Gly Ser Gly His
        1715                1720                1725

Ser Glu Tyr Ser Asp Ser Glu Gly Tyr Ser Gly Val Ser His Thr His
    1730                1735                1740

Ser Gly His Thr His Gly Gln Ala Arg Ser Gln His Gly Glu Ser Glu
1745                1750                1755                1760

Ser Ile Val His Glu Arg His Gly Thr Ile His Gly Gln Thr Gly Asp
            1765                1770                1775

Thr Thr Arg His Ala His Ser Gly His Gly Gln Ser Thr Gln Thr Gly
        1780                1785                1790

Ser Arg Thr Thr Gly Arg Arg Ser Ser Gly His Ser Glu Tyr Ser Asp
    1795                1800                1805

Ser Glu Gly His Ser Gly Phe Ser Gln Arg Pro His Ser Arg Gly His
    1810                1815                1820

Thr His Gly Gln Ala Gly Ser Gln His Gly Glu Ser Glu Ser Ile Val
1825                1830                1835                1840

Asp Glu Arg His Gly Thr Thr His Gly Gln Thr Gly Asp Thr Ser Gly
            1845                1850                1855

His Ser Gln Ser Gly His Gly Gln Ser Thr Gln Ser Gly Ser Ser Thr
            1860                1865                1870

Thr Gly Arg Arg Arg Ser Gly His Ser Glu Ser Ser Asp Ser Glu Val
        1875                1880                1885

His Ser Gly Gly Ser His Thr His Ser Gly His Thr His Ser Gln Ala
    1890                1895                1900

Arg Ser Gln His Gly Glu Ser Glu Ser Thr Val His Lys Arg His Gln
1905                1910                1915                1920

Thr Thr His Gly Gln Thr Gly Asp Thr Thr Glu His Gly His Pro Ser
            1925                1930                1935

His Gly Gln Thr Ile Gln Thr Gly Ser Arg Thr Thr Gly Arg Arg Gly
        1940                1945                1950

Ser Gly His Ser Glu Tyr Ser Asp Ser Glu Gly Pro Ser Gly Val Ser
        1955                1960                1965

His Thr His Ser Gly His Thr His Gly Gln Ala Gly Ser His Tyr Pro
    1970                1975                1980

Glu Ser Gly Ser Ser Val His Glu Arg His Gly Thr Thr His Gly Gln
1985                1990                1995                2000

Thr Ala Asp Thr Thr Arg His Gly His Ser Gly His Gly Gln Ser Thr
            2005                2010                2015

Gln Arg Gly Ser Arg Thr Thr Gly Arg Arg Ala Ser Gly His Ser Glu
            2020                2025                2030

Tyr Ser Asp Ser Glu Gly His Ser Gly Val Ser His Thr His Ser Gly
        2035                2040                2045

His Ala His Gly Gln Ala Gly Ser Gln His Gly Glu Ser Gly Ser Ser
    2050                2055                2060

Val His Glu Arg His Gly Thr Thr His Gly Gln Thr Gly Asp Thr Thr
2065                2070                2075                2080

Arg His Ala His Ser Gly His Gly Gln Ser Thr Gln Arg Gly Ser Arg
            2085                2090                2095
```

-continued

```
Thr Ala Gly Arg Arg Gly Ser Gly His Ser Glu Ser Ser Asp Ser Glu
            2100            2105            2110

Val His Ser Gly Val Ser His Thr His Ser Gly His Thr Tyr Gly Gln
        2115            2120            2125

Ala Arg Ser Gln His Gly Glu Ser Gly Ser Ala Ile His Gly Arg Gln
    2130            2135            2140

Gly Thr Ile His Gly Gln Thr Gly Asp Thr Thr Arg His Gly Gln Ser
2145            2150            2155            2160

Gly His Gly Gln Ser Thr Gln Thr Gly Ser Arg Thr Thr Gly Arg Gln
            2165            2170            2175

Arg Ser Ser His Ser Glu Ser Ser Asp Ser Glu Val His Ser Glu Ala
            2180            2185            2190

Ser Pro Thr His Ser Gly His Thr His Ser Gln Ala Gly Ser Arg His
        2195            2200            2205

Gly Gln Ser Gly Ser Ser Gly His Gly Arg Gln Gly Thr Thr His Gly
    2210            2215            2220

Gln Thr Gly Asp Thr Thr Arg His Ala His Tyr Gly Tyr Gly Gln Ser
2225            2230            2235            2240

Thr Gln Arg Gly Ser Arg Thr Thr Gly Arg Arg Gly Ser Gly His Ser
            2245            2250            2255

Glu Ser Ser Asp Ser Glu Val His Ser Trp Gly Ser His Thr His Ser
            2260            2265            2270

Gly His Ile Gln Gly Gln Ala Gly Ser Gln Gln Arg Gln Pro Gly Ser
        2275            2280            2285

Thr Val His Gly Arg Leu Glu Thr Thr His Gly Gln Thr Gly Asp Thr
    2290            2295            2300

Thr Arg His Gly His Ser Gly Tyr Gly Gln Ser Thr Gln Thr Gly Ser
2305            2310            2315            2320

Arg Ser Ser Arg Ala Ser His Phe Gln Ser His Ser Ser Glu Arg Gln
            2325            2330            2335

Arg His Gly Ser Ser Gln Val Trp Lys His Gly Ser Tyr Gly Pro Ala
        2340            2345            2350

Glu Tyr Asp Tyr Gly His Thr Gly Tyr Gly Pro Ser Gly Gly Ser Arg
        2355            2360            2365

Lys Ser Ile Ser Asn Ser His Leu Ser Trp Ser Thr Asp Ser Thr Ala
    2370            2375            2380

Asn Lys Gln Leu Ser Arg His
2385            2390
```

COMPOSITIONS AND METHODS FOR THE TREATMENT OF SKIN DISEASES

CROSS REFERENCE TO RELATED APPLICATIONS

This application is a national stage application under 35 U.S.C. § 371 of International Application No. PCT/US2019/053005, filed internationally on Sep. 25, 2019, which claims the priority benefit of U.S. Provisional Application Ser. No. 62/737,009, filed Sep. 26, 2018, and U.S. Provisional Application Ser. No. 62/744,531, filed Oct. 11, 2018, each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761342000900SeqList.txt, date recorded: Mar. 24, 2021, size: 372 KB).

FIELD OF THE INVENTION

The present disclosure relates, in part, to recombinant nucleic acids comprising one or more polynucleotides encoding a laminin polypeptide (e.g., a human laminin polypeptide) and/or a filaggrin polypeptide (e.g., a human filaggrin polypeptide), viruses comprising the same, pharmaceutical compositions, formulations, and medicaments thereof, and methods of their use (e.g., for the treatment of Junctional Epidermolysis Bullosa).

BACKGROUND

Junctional Epidermolysis Bullosa (JEB) is one of the major forms of epidermolysis bullosa, a group of genetic conditions that cause the skin to be very fragile. In individuals affected with JEB, the skin and mucous membranes blister and erode in response to minor injury or friction. This disease is typically classified into two main types: Junctional Herlitz Epidermolysis Bullosa (JEB-H) and Junctional non-Herlitz Epidermolysis Bullosa (JEB-nH). JEB-H is the more severe form of JEB, often leading to death in infancy due to overwhelming infection, malnutrition, electrolyte imbalance, or complications resulting from blistering in the respiratory, gastrointestinal, or genitourinary tract. JEB-nH is less severe, characterized by generalized blistering and mucosal involvement that may be evident at birth or soon after. Although the types differ in severity, their features overlap significantly, and can be caused by underlying mutations in the same gene(s).

Laminins are large molecular weight glycoproteins constituted by the assembly of three disulfide-linked polypeptides, the α, β, and γ chains. The human genome encodes 11 genetically distinct laminin chains, and the various members of the laminin family have both common and unique functions. In particular, laminins are indispensable building blocks for extracellular polymers determining the architecture and physiology of basement membranes, as well as playing a central role in cellular networks by physically bridging the intracellular and extracellular compartments and relaying signals critical for cellular behavior.

JEB results from mutations in the human laminin genes LAMA3, LAMB3, or LAMC2; however, LAMB3 mutations are the most common, causing >80% of all JEB cases. The gene products of LAMA3, LAMB3, and LAMC2 are each a subunit of a protein macromolecule called laminin 332, which plays an important role in strengthening and stabilizing the skin by helping attach the top layer of the skin (epidermis) to the underlying layers. A mutation in any of the three genes encoding a subunit of laminin 332 leads to the production of a defective or non-functional variant of this protein macromolecule, leading to cells in the epidermis being fragile and easily damaged, causing the skin layers to separate after friction or other minor trauma.

The management of JEB is a life-long endeavor. Unfortunately, there are no available, FDA-approved therapies targeting the molecular causes of JEB, and treatment options for JEB patients are limited. Disease management is generally supportive, including providing medication to control pain and itching, administering antibiotics to stave off infections resulting from open wounds on the skin and mucosa, and surgical strategies to address scarring and deformities. Thus, there exists a clear need for novel, minimally invasive or non-invasive treatment options for JEB that can address the deficiencies in laminin proteins observed in this sensitive patient population.

All references cited herein, including patent applications, patent publications, non-patent literature, and NCBI/UniProtKB/Swiss-Prot accession numbers are herein incorporated by reference in their entirety, as if each individual reference were specifically and individually indicated to be incorporated by reference.

BRIEF SUMMARY

In some embodiments, in order to meet these and other needs, provided herein are recombinant nucleic acids (e.g., recombinant herpes simplex virus genomes) encoding laminin polypeptides (e.g., human laminin polypeptides) for use in viruses (e.g., herpes viruses), pharmaceutical compositions and formulations, medicaments, and/or methods useful for remedying laminin deficiencies in a subject in need thereof and/or for treating an individual having, or at risk of developing, a laminin-associated disorder (e.g., providing prophylactic, palliative, or therapeutic relief of a wound, disorder, or disease of the skin in a subject having, or at risk of developing, one or more signs or symptoms of JEB).

The present inventors have shown that the recombinant viruses described herein were capable of effectively transducing mammalian cells (including human skin cells) and successfully expressing their encoded exogenous human laminins (mRNA and protein) (see e.g., Example 1). Moreover, the present inventors have shown that multiple different laminin proteins, as both wild-type and codon-optimized variants, can be delivered by the viruses described herein (see e.g., Example 1). Furthermore, the present inventors have shown that the viruses described herein can be successfully engineered to express human laminins in vivo in a relevant laminin-deficient animal model, where the laminin protein localizes to the appropriate region of the skin (see e.g., Example 2). Without wishing to be bound by theory, it is believed that increasing, augmenting, and/or supplementing the levels of human laminins in one or more cells of a subject in need thereof by administering one or more of the recombinant nucleic acids, viruses, compositions, and/or medicaments described herein will allow for increased production of functional laminins in the subject. In addition, without wishing to be bound by theory, it is further believed that increasing, augmenting, and/or supplementing the levels of human laminins in one or more cells of an individual by administering one or more of the recombinant nucleic acids, viruses, compositions, and/or medicaments described herein will lead to increased cell adhesion, a reduction in the separation of the lamina lucida, and stabilization of the basement membrane in the skin of the treated individual. Without wishing to be bound by theory, it is believed that the recombinant nucleic acids, viruses, compositions, medicaments, and methods described herein will help to treat existing skin abnormalities in individuals suffering from a laminin deficiency (e.g., JEB), as well as prevent or delay reformation of wounds or other skin or mucosal abnormalities in treated subjects.

Accordingly, certain aspects of the present disclosure relate to a recombinant herpes virus genome comprising one or more polynucleotides encoding a laminin polypeptide. In some embodiments, the recombinant herpes virus genome comprises two or more polynucleotides encoding a laminin polypeptide. In some embodiments, the recombinant herpes virus genome is replication competent. In some embodiments, the recombinant herpes virus genome is replication defective. In some embodiments that may be combined with any of the preceding embodiments, the recombinant herpes virus genome comprises the one or more polynucleotides encoding a laminin polypeptide within one or more viral gene loci. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or derivatives thereof.

In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof. In some embodiments, the recombinant herpes simplex virus genome is a recombinant HSV-1 genome.

In some embodiments that may be combined with any of the preceding embodiments, the recombinant herpes simplex virus genome comprises an inactivating mutation. In some embodiments, the inactivating mutation is in a herpes simplex virus gene. In some embodiments, the inactivating mutation is a deletion of the coding sequence of the herpes simplex virus gene. In some embodiments, the herpes simplex virus gene is selected from Infected Cell Protein (ICP) 0 (one or both copies), ICP4 (one or both copies), ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome comprises an inactivating mutation in the Joint region. In some embodiments, the recombinant herpes simplex virus genome comprises a deletion of the Joint region.

In some embodiments that may be combined with any of the preceding embodiments, the recombinant herpes simplex virus genome comprises the one or more polynucleotides encoding the laminin polypeptide within one or more viral gene loci. In some embodiments that may be combined with any of the preceding embodiments, the recombinant herpes simplex virus genome comprises the one or more polynucleotides encoding the laminin polypeptide within one or both of the ICP4 viral gene loci. In some embodiments that may be combined with any of the preceding embodiments, the recombinant herpes simplex virus genome comprises the one or more polynucleotides encoding the laminin polypeptide within the ICP22 viral gene locus. In some embodiments that may be combined with any of the preceding embodiments, the recombinant herpes simplex virus genome comprises the one or more polynucleotides encoding the laminin polypeptide within the UL41 viral gene locus.

In some embodiments that may be combined with any of the preceding embodiments, the laminin polypeptide is a human laminin polypeptide. In some embodiments, the human laminin (Lam) polypeptide is selected from a human LamA1 polypeptide, a human LamA2 polypeptide, a human LamA3 polypeptide, a human LamA4 polypeptide, a human LamA5 polypeptide, a human LamB1 polypeptide, a human LamB2 polypeptide, a human LamB3 polypeptide, a human LamC1 polypeptide, a human LamC2 polypeptide, a human LamC3 polypeptide, and any chimeric polypeptides thereof. In some embodiments, the human laminin (Lam) polypeptide is selected from a human LamA3 polypeptide, a human LamB3 polypeptide, and a human LamC2 polypeptide. In some embodiments that may be combined with any of the preceding embodiments, the laminin polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-9 or 32-35. In some embodiments that may be combined with any of the preceding embodiments, the laminin polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-9.

In some embodiments that may be combined with any of the preceding embodiments, the recombinant herpes virus genome has reduced cytotoxicity when introduced into a target cell as compared to a corresponding wild-type herpes virus genome. In some embodiments, the target cell is a human cell. In some embodiments, the target cell is a cell of the epidermis and/or dermis. In some embodiments, the target cell is a keratinocyte or fibroblast.

Other aspects of the present disclosure relate to a herpes virus comprising any of the recombinant herpes virus genomes described herein. In some embodiments, the herpes virus is replication competent. In some embodiments, the herpes virus is replication defective. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, a Kaposi's sarcoma-associated herpesvirus, and any combinations or derivatives thereof. In some embodiments that may be combined with any of the preceding embodiments, the herpes virus is a herpes simplex virus. In some embodiments, the herpes simplex virus is an HSV-1, an HSV-2, or any derivatives thereof. In some embodiments, the herpes simplex virus is an HSV-1.

Other aspects of the present disclosure relate to a pharmaceutical composition comprising any of the recombinant herpes virus genomes described herein and/or any of the herpes viruses described herein and a pharmaceutically acceptable excipient. In some embodiments, the pharmaceutical composition is suitable for topical, transdermal, subcutaneous, intradermal, oral, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, epicutaneous administration, or any combinations thereof. In some embodiments that may be combined with any of the preceding embodiments, the pharmaceutical composition is suitable for topical, transdermal, subcutaneous, intradermal, or transmucosal administration. In some embodiments, the pharmaceutical composition is suitable for topical, transdermal, and/or intradermal administration. In some embodiments, the pharmaceutical composition is suitable for topical administration. In some embodiments, the pharmaceutical composition is suitable for intradermal administration. In some embodiments, the pharmaceutical composition is suitable for oral or inhaled administration. In some embodiments that may be combined with any of the preceding embodiments, the pharmaceutical composition comprises a methylcellulose gel (e.g., a carboxy methylcellulose gel, a hydroxypropyl methylcellulose gel, etc.). In some embodiments that may be combined with any of the preceding embodiments, the pharmaceutical composition comprises a phosphate buffer. In some embodiments that may be combined with any of the preceding embodiments, the pharmaceutical composition comprises glycerol. In some embodiments that may be combined with any of the preceding embodiments, the pharmaceutical composition comprises a lipid carrier. In some embodiments that may be combined with any of the preceding embodiments, the pharmaceutical composition comprises a nanoparticle carrier.

Other aspects of the present disclosure relate to the use of any of the recombinant nucleic acids, herpes viruses, and/or pharmaceutical compositions described herein as a medicament, Other aspects of the present disclosure relate to the use of any of the recombinant nucleic acids, herpes viruses, and/or pharmaceutical compositions described herein in a therapy.

Other aspects of the present disclosure relate to the use of any of the recombinant nucleic acids, herpes viruses, and/or pharmaceutical compositions described herein in the production or manufacture of a medicament for treating one or more signs or symptoms of a laminin deficiency (e.g., in a JEB patient).

Other aspects of the present disclosure relate to a method of enhancing, increasing, augmenting, and/or supplementing the levels of a laminin polypeptide in one or more cells of a subject comprising administering to the subject an effective amount of any of the herpes viruses described herein and/or any of the pharmaceutical compositions described herein. In some embodiments, the subject is a human. In some embodiments that may be combined with any of the preceding embodiments, the subject's genome comprises a loss-of-function mutation in a laminin gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments, the virus and/or pharmaceutical composition is administered topically, transdermally, subcutaneously, intradermally, or transmucosally to the subject. In some embodiments, the virus and/or pharmaceutical composition is administered topically, transdermally, subcutaneously, or intradermally to the subject. In some embodiments, the virus and/or pharmaceutical composition is administered topically, transdermally, or intradermally to the subject. In some embodiments, the virus and/or pharmaceutical composition is administered topically to the subject. In some embodiments, the virus and/or pharmaceutical composition is administered intradermally to the subject. In some embodiments that may be combined with any of the preceding embodiments, the skin of the subject is abraded prior to administration. In some embodiments, the virus and/or pharmaceutical composition is administered orally or via inhalation. In some embodiments that may be combined with any of the preceding embodiments, the virus and/or pharmaceutical composition is administered one, two, three, four, five or more times per day. In some embodiments that may be combined with any of the preceding embodiments, the virus and/or pharmaceutical composition is administered to one or more affected and/or unaffected areas of the subject. In some embodiments, the subject suffers from Junctional Herlitz Epidermolysis Bullosa (JEB-H). In some embodiments, the subject suffers from Junctional non-Herlitz Epidermolysis Bullosa (JEB-nH).

Other aspects of the present disclosure relate to a method of enhancing, increasing, augmenting, and/or supplementing cell adhesion of one or more cells in the skin of a subject comprising administering to the subject an effective amount of any of the herpes viruses described herein and/or any of the pharmaceutical compositions described herein. In some embodiments, the cell adhesion is integrin-mediated cell adhesion. In some embodiments that may be combined with any of the preceding embodiments, the subject is a human. In some embodiments that may be combined with any of the preceding embodiments, the subject's genome comprises a loss-of-function mutation in a laminin gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments, the virus and/or pharmaceutical composition is administered topically, transdermally, subcutaneously, intradermally, or transmucosally to the subject. In some embodiments, the virus and/or pharmaceutical composition is administered topically, transdermally, subcutaneously, or intradermally to the subject. In some embodiments, the virus and/or pharmaceutical composition is administered topically, transdermally, or intradermally to the subject. In some embodiments, the virus and/or pharmaceutical composition is administered topically to the subject. In some embodiments, the virus and/or pharmaceutical composition is administered intradermally to the subject. In some embodiments that may be combined with any of the preceding embodiments, the skin of the subject is abraded prior to administration. In some embodiments, the virus and/or pharmaceutical composition is administered orally or via inhalation. In some embodiments that may be combined with any of the preceding embodiments, the virus and/or pharmaceutical composition is administered one, two, three, four, five or more times per day. In some embodiments that may be combined with any of the preceding embodiments, the virus and/or pharmaceutical composition is administered to one or more affected and/or unaffected areas of the subject. In some embodiments, the subject suffers from Junctional Herlitz Epidermolysis Bullosa (JEB-H). In some embodiments, the subject suffers from Junctional non-Herlitz Epidermolysis Bullosa (JEB-nH).

Other aspects of the present disclosure relate to a method of enhancing, increasing, augmenting, and/or supplementing the lamina lucida of a subject comprising administering to the subject an effective amount of any of the herpes viruses described herein and/or any of the pharmaceutical compositions described herein. In some embodiments, the subject is a human. In some embodiments that may be combined with any of the preceding embodiments, the subject's genome comprises a loss-of-function mutation in a laminin gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments, the virus and/or pharmaceutical composition is administered topically, transdermally, subcutaneously, intradermally, or transmucosally to the subject. In some embodiments, the virus and/or pharmaceutical composition is administered topically, transdermally, subcutaneously, or intradermally to the subject. In some embodiments, the virus and/or pharmaceutical composition is administered topically, transdermally, or intradermally to the subject. In some embodiments, the virus and/or pharmaceutical composition is administered topically to the subject. In some embodiments, the virus and/or pharmaceutical composition is administered intradermally to the subject. In some embodiments that may be combined with any of the preceding embodiments, the skin of the subject is abraded prior to administration. In some embodiments, the virus and/or pharmaceutical composition is administered orally or via inhalation. In some embodiments that may be combined with any of the preceding embodiments, the virus and/or pharmaceutical composition is administered one, two, three, four, five or more times per day. In some embodiments that may be combined with any of the preceding embodiments, the virus and/or pharmaceutical composition is administered to one or more affected and/or unaffected areas of the subject. In some embodiments, the subject suffers from Junctional Herlitz Epidermolysis Bullosa (JEB-H). In some embodiments, the subject suffers from Junctional non-Herlitz Epidermolysis Bullosa (JEB-nH).

Other aspects of the present disclosure relate to a method of enhancing, increasing, augmenting, and/or supplementing epithelial basement membrane assembly, epithelial basement membrane organization, and/or epithelial basement adherence of a subject comprising administering to the subject an effective amount of any of the herpes viruses described herein and/or any of the pharmaceutical compositions described herein. In some embodiments, the subject is a human. In some embodiments that may be combined with any of the preceding embodiments, the subject's genome comprises a loss-of-function mutation in a laminin gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments, the virus and/or pharmaceutical composition is administered topically, transdermally, subcutaneously, intradermally, or transmucosally to the subject. In some embodiments, the virus and/or pharmaceutical composition is administered topically, transdermally, subcutaneously, or intradermally to the subject. In some embodiments, the virus and/or pharmaceutical composition is administered topically, transdermally, or intradermally to the subject. In some embodiments, the virus and/or pharmaceutical composition is administered topically to the subject. In some embodiments, the virus and/or pharmaceutical composition is administered intradermally to the subject. In some embodiments that may be combined with any of the preceding embodiments, the skin of the subject is abraded prior to administration. In some embodiments, the virus and/or pharmaceutical composition is administered orally or via inhalation. In some embodiments that may be combined with any of the preceding embodiments, the virus and/or pharmaceutical composition is administered one, two, three, four, five or more times per day. In some embodiments that may be combined with any of the preceding embodiments, the virus and/or pharmaceutical composition is administered to one or more affected and/or unaffected areas of the subject. In some embodiments, the subject suffers from Junctional Herlitz Epidermolysis Bullosa (JEB-H). In some embodiments, the subject suffers from Junctional non-Herlitz Epidermolysis Bullosa (JEB-nH).

Other aspects of the present disclosure relate to a method of providing prophylactic, palliative, or therapeutic relief to one or more signs or symptoms of Junctional Epidermolysis Bullosa (JEB) in a subject in need thereof comprising administering to the subject an effective amount of any of the herpes viruses described herein and/or any of the pharmaceutical compositions described herein. In some embodiments, the one or more signs or symptoms of JEB are selected from: blistering, wounding, and/or scarring of the skin; granulation tissue; skin erosion; deformity of the fingernails and/or toenails; fusion of the fingers and/or toes; tightening and/or thinning of the skin; contractures; blistering and/or scarring of the mucosa; difficulty breathing; horse cry; increased susceptibility to infection; dehydration; fluid loss; electrolyte imbalance; blistering and/or scarring of the gastrointestinal and/or gastrourinary tract; dental caries and/or enamel hypoplasia; hair loss; malnutrition; growth retardation; anemia; and any combinations thereof. In some embodiments that may be combined with any of the preceding embodiments, the subject is a human. In some embodiments that may be combined with any of the preceding embodiments, the subject's genome comprises a loss-of-function mutation in a laminin gene. In some embodiments that may be combined with any of the preceding embodiments, the herpes virus and/or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments, the virus and/or pharmaceutical composition is administered topically, transdermally, subcutaneously, intradermally, or transmucosally to the subject. In some embodiments, the virus and/or pharmaceutical composition is administered topically, transdermally, subcutaneously, or intradermally to the subject. In some embodiments, the virus and/or pharmaceutical composition is administered topically, transdermally, or intradermally to the subject. In some embodiments, the virus and/or pharmaceutical composition is administered topically to the subject. In some embodiments, the virus and/or pharmaceutical composition is administered intradermally to the subject. In some embodiments that may be combined with any of the preceding embodiments, the skin of the subject is abraded prior to administration. In some embodiments, the virus and/or pharmaceutical composition is administered orally or via inhalation. In some embodiments that may be combined with any of the preceding embodiments, the virus and/or pharmaceutical composition is administered one, two, three, four, five or more times per day. In some embodiments that may be combined with any of the preceding embodiments, the virus and/or pharmaceutical composition is administered to one or more affected and/or unaffected areas of the subject. In some embodiments, the subject suffers from Junctional Herlitz Epidermolysis Bullosa (JEB-H). In some embodiments, the subject suffers from Junctional non-Herlitz Epidermolysis Bullosa (JEB-nH).

Other aspects of the present disclosure relate to an article of manufacture or kit comprising any of the recombinant nucleic acids, viruses, medicaments, and/or pharmaceutical compositions or formulations described herein and instructions for administration thereof.

BRIEF DESCRIPTION OF THE DRAWINGS

FIGS. 1A-E show schematics of wild-type and modified herpes simplex virus genomes. FIG. 1A shows a wild-type herpes simplex virus genome. FIG. 1B shows a modified herpes simplex virus genome comprising deletions of the coding sequences of ICP4 (both copies) and ICP22, with an expression cassette containing a wild-type coding sequence of human LAMB3 integrated at each of the ICP4 loci. FIG. 1C shows a modified herpes simplex virus genome comprising deletions of the coding sequences of ICP4 (both copies) and ICP22, with an expression cassette containing a codon-optimized coding sequence of human LAMB3 integrated at each of the ICP4 loci. FIG. 1D shows a modified herpes simplex virus genome comprising deletions of the coding sequences of ICP4 (both copies) and ICP22, with an expression cassette containing a wild-type coding sequence of human LAMC2 integrated at each of the ICP4 loci. FIG. 1E shows a modified herpes simplex virus genome comprising deletions of the coding sequences of ICP4 (both copies) and ICP22, with an expression cassette containing a codon-optimized coding sequence of human LAMC2 integrated at each of the ICP4 loci.

FIGS. 2A-B show expression of wild-type (WT) human LamB3 in Vero cells infected with the indicated viral isolates. FIG. 2A shows expression of wild-type human LAMB3 in infected Vero cells, as assessed by qRT-PCR analysis. FIG. 2B shows expression of wild-type human LamB3 protein in infected Vero cells, as assessed by western blot.

FIG. 5A shows expression of wild-type human LAMC2 in infected Vero cells, as assessed by qRT-PCR analysis. FIG. 5B shows expression of codon-optimized human LAMC2 in infected Vero cells, as assessed by qRT-PCR analysis. FIG. 5C shows expression of wild-type and codon-optimized human LamC2 protein in infected Vero cells, as assessed by western blot. Uninfected Vero cells were used as a negative control. The viral isolate "LGA" expressing codon-optimized LamC2 was selected for additional experimentation.

FIG. 6A shows the viral genome copy number in primary immortalized human keratinocytes after infection with viral isolate "LGA" at the indicated MOIs, as assessed by qPCR analysis. FIG. 6B shows the transcript levels of codon-optimized LAMC2 expressed in primary immortalized human keratinocytes after infection with viral isolate "LGA" at the indicated MOIs, as assessed by qRT-PCR analysis. For qPCR and qRT-PCR analyses, data is presented as the average of two replicates±SEM. FIG. 6C shows expression of human LamC2 protein in primary immortalized human keratinocytes after infection with viral isolate "LGA" at the indicated MOIs, as assessed by western blot. GAPDH was used as a loading control. For each analysis, uninfected primary keratinocytes, as well as primary keratinocytes infected with an mCherry-encoding HSV vector (mCherry), were used as negative controls.

FIGS. 7A-D show LamC2 nucleic acid and protein analysis in skin biopsies harvested 72 hours after intradermal injection of HSV isolate "LGA" or vehicle control to LAMC2$^{-/-}$-hLAMC2$^{tet-on}$ mice (15 days off doxycycline (doxy-)). FIG. 7A shows a schematic of the intradermal injection sites on the treated animals. FIG. 7B shows the levels of human LAMC2 DNA present in skin biopsies after intradermal administration of LGA or vehicle control, as assessed by qPCR analysis. FIG. 7C shows the levels of human LAMC2 transcripts present in skin biopsies after intradermal administration of LGA or vehicle control, as assessed by qRT-PCR analysis. For each condition in the qPCR and qRT-PCR analysis, data is presented as the average of two replicates±SEM. FIG. 7D shows representative immunofluorescence images of human LamC2 protein expression in skin biopsies after intradermal administration of LGA or vehicle control. DAPI staining was used to visualize nuclei; pKa1 staining was used to visualize mouse laminin-332.

FIGS. 8A-F show schematics of wild-type and modified herpes simplex virus genomes. FIG. 8A shows a wild-type herpes simplex virus genome. FIG. 8B shows a modified herpes simplex virus genome comprising deletions of the coding sequence of ICP4 (both copies), with an expression cassette containing a nucleic acid encoding a human filaggrin polypeptide integrated at each of the ICP4 loci. FIG. 8C shows a modified herpes simplex virus genome comprising deletions of the coding sequences of ICP4 (both copies) and ICP22, with an expression cassette containing a nucleic acid encoding a human filaggrin polypeptide integrated at each of the ICP4 loci. FIG. 8D shows a modified herpes simplex virus genome comprising deletions of the coding sequences of ICP4 (both copies) and ICP22, with an expression cassette containing a nucleic acid encoding a human filaggrin polypeptide integrated at the ICP22 locus. FIG. 8E shows a modified herpes simplex virus genome comprising deletions of the coding sequences of ICP4 (both copies) and UL41, with an expression cassette containing a nucleic acid encoding a human filaggrin polypeptide integrated at the UL41 locus. FIG. 8F shows a modified herpes simplex virus genome comprising deletions of the coding sequences of ICP4 (both copies), ICP22, and UL41, with an expression cassette containing a nucleic acid encoding a human filaggrin polypeptide integrated at the UL41 locus.

DETAILED DESCRIPTION

Figure 1A:
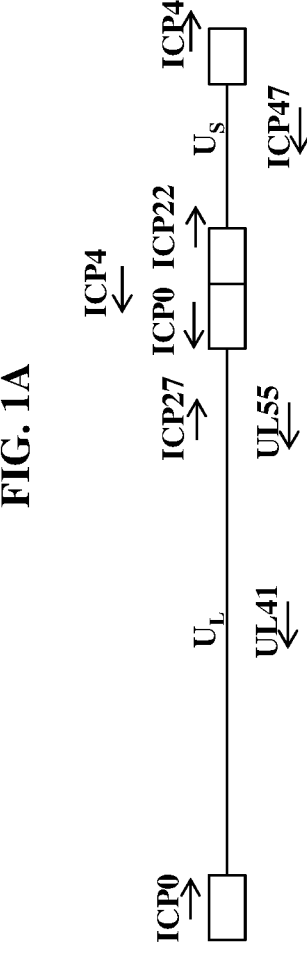

In some embodiments, the present disclosure relates to recombinant nucleic acids (e.g., recombinant herpes viral genomes) comprising one or more polynucleotides encoding a laminin polypeptide (e.g., a human laminin polypeptide), and/or use of the recombinant nucleic acids in virus (e.g., herpes viruses), compositions, formulations, medicaments, and/or methods in order to supplement laminin protein levels and/or treat laminin gene deficiencies (e.g., in a subject whose genome harbors a loss-of-function mutation and/or pathogenic variant of a laminin gene), and/or provide medical intervention to a subject in need thereof (e.g., to provide prophylactic, palliative, and/or therapeutic relief to one or more diseases or disorders arising from a laminin deficiency (e.g., JEB). Without wishing to be bound by theory, it is believed that the recombinant nucleic acids, viruses, compositions, formulations, medicaments, and/or methods described herein will help to treat the existing skin and/or mucosal abnormalities in individuals suffering from a laminin deficiency (e.g., JEB patients), as well as prevent or delay the reformation of such skin and/or mucosal abnormalities in treated subjects.

In some embodiments, the present disclosure relates to recombinant nucleic acids (e.g., recombinant herpes viral genomes) comprising one or more polynucleotides encoding a filaggrin polypeptide (e.g., a human filaggrin polypeptide), and/or use of the recombinant nucleic acids in virus (e.g., herpes viruses), compositions, formulations, medicaments, and/or methods in order to supplement filaggrin protein levels and/or treat filaggrin gene deficiencies (e.g., in a subject whose genome harbors a loss-of-function mutation and/or pathogenic variant of an FLG and/or FLG2 gene), and/or provide medical intervention to a subject in need thereof (e.g., to provide prophylactic, palliative, and/or therapeutic relief to one or more diseases or disorders arising from a filaggrin deficiency (e.g., atopic dermatitis, ichthyosis vulgaris, etc.). Without wishing to be bound by theory, it is believed that the recombinant nucleic acids, viruses, compositions, formulations, medicaments, and/or methods described herein will help to treat the existing skin abnormalities in individuals suffering from a filaggrin deficiency (e.g., atopic dermatitis and/or ichthyosis vulgaris patients), as well as prevent or delay the reformation of such skin abnormalities in treated subjects.

The following description sets forth exemplary methods, parameters, and the like. It should be recognized, however, that such a description is not intended as a limitation on the scope of the present disclosure but is instead provided as a description of exemplary embodiments.

I. GENERAL TECHNIQUES

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. DEFINITIONS

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operatively linked" or "operably linked" means that the DNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a contiguous stretch of nucleic acids, either DNA or RNA, that encode a protein or polypeptide. Typically, the nucleic acid comprises a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some embodiments, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject mammal to provide an effective dose of the active ingredient(s) employed.

As used herein, an "effective amount" is at least the minimum amount required to affect a measurable improvement or prevention of one or more symptoms of a particular disorder. An "effective amount" may vary according to factors such as the disease state, age, sex, and weight of the patient. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications used to treat symptoms of the disease, delaying the progression of the disease, and/or prolonging survival. An effective amount can be administered in one or more administrations. For purposes of the present disclosure, an effective amount of a recombinant nucleic acid, virus, and/or pharmaceutical composition is an amount sufficient to accomplish prophylactic or therapeutic treatment either directly or indirectly. As is understood in the clinical context, an effective amount of a recombinant nucleic acid, virus, and/or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" refers to clinical intervention designed to alter the natural course of the individual or cell being treated during the course of clinical pathology. Desirable effects of treatment include decreasing the rate of disease/disorder/defect progression, ameliorating or palliating the disease/disorder/defect state, and remission or improved prognosis. For example, an individual is successfully "treated" if one or more symptoms associated with JEB are mitigated or eliminated, including the reduction or elimination of one or more wounds on the skin or mucosa.

As used herein, the term "delaying progression of" a disease/disorder/defect refers to deferring, hindering, slowing, retarding, stabilizing, and/or postponing development of the disease/disorder/defect. This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease.

III. RECOMBINANT NUCLEIC ACIDS

Certain aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding a laminin polypeptide (e.g., a human laminin polypeptide). In some embodiments, the recombinant nucleic acid comprises one polynucleotide encoding a laminin polypeptide. In some embodiments, the recombinant nucleic acid comprises two polynucleotides encoding a laminin polypeptide. In some embodiments, the laminin polypeptide is a human laminin polypeptide. In some embodiments, the laminin polypeptide is a Laminin subunit alpha-3 (LamA3) polypeptide, a Laminin subunit beta-3 (LamB3) polypeptide, or a Laminin subunit gamma-2 (LamC2) polypeptide. In some embodiments, the laminin polypeptide is a human LamA3 polypeptide, a human LamB3 polypeptide, or a human LamC2 polypeptide.

Other aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding a filaggrin polypeptide (e.g., a human filaggrin polypeptide). In some embodiments, the recombinant nucleic acid comprises one polynucleotide encoding a filaggrin polypeptide. In some embodiments, the recombinant nucleic acid comprises two polynucleotides encoding a filaggrin polypeptide. In some embodiments, the recombinant nucleic acid comprises three polynucleotides encoding a filaggrin polypeptide. In some embodiments, the filaggrin polypeptide is a full-length pro-filaggrin polypeptide. In some embodiments, the filaggrin polypeptide is a filaggrin monomer (e.g., a filaggrin monomer resulting from proteolytic cleavage (e.g., via serine protease cleavage) of a full-length pro-filaggrin polypeptide).

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant nucleic acid is a recombinant herpes simplex virus genome. In some embodiments, the recombinant nucleic acid is a recombinant herpes simplex virus type 1 (HSV-1) genome.

Polynucleotides Encoding Laminin Polypeptides

In some embodiments, the present disclosure relates to a recombinant nucleic acid comprising one or more polynucleotides comprising the coding sequence of a laminin gene (e.g., a human laminin gene), or portions thereof. Any suitable laminin gene (including any isoform thereof) known in the art may be encoded by a polynucleotide of the present disclosure, including, for example, a LAMA1 gene (see e.g., NCBI Gene ID: 284217), a LAMA2 gene (see e.g., NCBI Gene ID: 3908), a LAMA3 gene (see e.g., NCBI Gene ID: 3909), a LAMA4 gene (see e.g., NCBI Gene ID: 3910), a LAMA5 gene (see e.g., NCBI Gene ID: 3911), a LAMB1 gene (see e.g., NCBI Gene ID: 3912), a LAMB2 gene (see e.g., NCBI Gene ID: 3913), a LAMB3 gene (see e.g., NCBI Gene ID: 3914), a LAMC1 gene (see e.g., NCBI Gene ID: 3915), a LAMC2 gene (see e.g., NCBI Gene ID: 3918), a LAMC3 gene (see e.g., NCBI Gene ID: 10319), etc. In some embodiments, the one or more polynucleotides do not encode a LAMB3 gene. Examples of non-human laminin genes include, for example, mouse laminins (see e.g., NCBI Gene IDs: 16774, 16780, and 16782), rat laminins (see e.g., NCBI Gene IDs: 307582, 305078, and 192362), chimpanzee laminins (see e.g., NCBI Gene IDs: 455339, 469668, and 457571), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the coding sequence of any of the laminin genes (and/or coding sequences thereof) described herein or known in the art. Methods of identifying laminin gene homologs/orthologs from additional species are known to one of ordinary skill in the art, including, for example, using a nucleic acid sequence alignment program such as the BLAST® blastn suite. In some embodiments, one or more polynucleotides of the present disclosure comprises the coding sequence of a human laminin gene.

In some embodiments, a polynucleotide of the present disclosure comprises a codon-optimized variant of any of the laminin genes described herein or known in the art. In some embodiments, use of a codon-optimized variant of a laminin gene (e.g., a codon-optimized variant of a human laminin gene) increases stability and/or yield of heterologous expression (RNA and/or protein) of the encoded laminin in a target cell (e.g., a target human cell such as a human keratinocyte or fibroblast), as compared to the stability and/or yield of heterologous expression of a corresponding non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, one or more polynucleotides of the present disclosure comprises the coding sequence of a human LAMA3 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from SEQ ID NOS: 1-2 or 24-29. In some embodiments, a polynucleotide of the present disclosure comprises a sequence selected from SEQ ID NOS: 1-2 or 24-29. In some embodiments, a polynucleotide of the present disclosure comprises a sequence selected from SEQ ID NOS: 2, 25, 27, or 29. In some embodiments, a polynucleotide of the present disclosure comprises the sequence of SEQ ID NO: 1. In some embodiments, a polynucleotide of the present disclosure comprises the sequence of SEQ ID NO: 2.

In some embodiments, a polynucleotide of the present disclosure comprises a 5' truncation, a 3' truncation, or a fragment of the sequence of SEQ ID NO: 1 or SEQ ID NO: 2. In some embodiments, the 5' truncation, 3' truncation, or fragment of the sequence of SEQ ID NO: 1 or SEQ ID NO: 2 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1500, at least 2000, at least 2500, at least 3000, at least 3500, at least 4000, at least 4500, or at least 5000, but fewer than 5175, consecutive nucleotides of SEQ ID NO: 1 or SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-5172 of SEQ ID NO: 1 or SEQ ID NO: 2. In some embodiments, a polynucleotide of the present disclosure comprises the sequence of nucleic acids 1-5172 of SEQ ID NO: 1 or SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 82-5172 of SEQ ID NO: 1 or SEQ ID NO: 2. In some embodiments, a polynucleotide of the present disclosure comprises the sequence of nucleic acids 82-5172 of SEQ ID NO: 1 or SEQ ID NO: 2.

In some embodiments, a polynucleotide of the present disclosure comprises a 5' truncation, a 3' truncation, or a fragment of the sequence of SEQ ID NO: 24 or SEQ ID NO: 25. In some embodiments, the 5' truncation, 3' truncation, or fragment of the sequence of SEQ ID NO: 24 or SEQ ID NO: 25 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1500, at least 2000, at least 2500, at least 3000, at least 3500, at least 4000, at least 4500, at least 5000, at least 5500, at least 6000, at least 6500, at least 7000, at least 7500, at least 8000, at least 8500, at least 9000, at least 9500, at least 10000, but fewer than 10002, consecutive nucleotides of SEQ ID NO: 24 or SEQ ID NO: 25. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-9999 of SEQ ID NO: 24 or SEQ ID NO: 25. In some embodiments, a polynucleotide of the present disclosure comprises the sequence of nucleic acids 1-9999 of SEQ ID NO: 24 or SEQ ID NO: 25.

In some embodiments, a polynucleotide of the present disclosure comprises a 5' truncation, a 3' truncation, or a fragment of the sequence of SEQ ID NO: 26 or SEQ ID NO: 27. In some embodiments, the 5' truncation, 3' truncation, or fragment of the sequence of SEQ ID NO: 26 or SEQ ID NO: 27 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1500, at least 2000, at least 2500, at least 3000, at least 3500, at least 4000, at least 4500, at least 5000, at least 5500, at least 6000, at least 6500, at least 7000, at least 7500, at least 8000, at least 8500, at least 9000, at least 9500, but fewer than 9834, consecutive nucleotides of SEQ ID NO: 26 or SEQ ID NO: 27. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-9831 of SEQ ID NO: 26 or SEQ ID NO: 27. In some embodiments, a polynucleotide of the present disclosure comprises the sequence of nucleic acids 1-9831 of SEQ ID NO: 26 or SEQ ID NO: 27.

In some embodiments, a polynucleotide of the present disclosure comprises a 5' truncation, a 3' truncation, or a fragment of the sequence of SEQ ID NO: 28 or SEQ ID NO:

29. In some embodiments, the 5' truncation, 3' truncation, or fragment of the sequence of SEQ ID NO: 28 or SEQ ID NO: 29 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1500, at least 2000, at least 2500, at least 3000, at least 3500, at least 4000, at least 4500, at least 5000, but fewer than 5007, consecutive nucleotides of SEQ ID NO: 28 or SEQ ID NO: 29. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-5004 of SEQ ID NO: 28 or SEQ ID NO: 29. In some embodiments, a polynucleotide of the present disclosure comprises the sequence of nucleic acids 1-5004 of SEQ ID NO: 28 or SEQ ID NO: 29.

In some embodiments, one or more polynucleotides of the present disclosure comprises the coding sequence of the human LAMB3 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 3 or SEQ ID NO: 4. In some embodiments, a polynucleotide of the present disclosure comprises the sequence of SEQ ID NO: 3 or SEQ ID NO: 4.

In some embodiments, a polynucleotide of the present disclosure comprises a 5' truncation, a 3' truncation, or a fragment of the sequence of SEQ ID NO: 3 or SEQ ID NO: 4. In some embodiments, the 5' truncation, 3' truncation, or fragment of the sequence of SEQ ID NO: 3 or SEQ ID NO: 4 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, at least 3500, but fewer than 3519, consecutive nucleotides of SEQ ID NO: 3 or SEQ ID NO: 4. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3516 of SEQ ID NO: 3 or SEQ ID NO: 4. In some embodiments, a polynucleotide of the present disclosure comprises the sequence of nucleic acids 1-3516 of SEQ ID NO: 3 or SEQ ID NO: 4. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 55-3516 of SEQ ID NO: 3 or SEQ ID NO: 4. In some embodiments, a polynucleotide of the present disclosure comprises the sequence of nucleic acids 55-3516 of SEQ ID NO: 3 or SEQ ID NO: 4.

In some embodiments, one or more polynucleotides of the present disclosure comprises the coding sequence of the human LAMC2 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from SEQ ID NOS: 5-6 or 30-31. In some embodiments, a polynucleotide of the present disclosure comprises a sequence selected from SEQ ID NOS: 5-6 or 30-31. In some embodiments, a polynucleotide of the present disclosure comprises the sequence of SEQ ID NO: 5 or SEQ ID NO: 6. In some embodiments, a polynucleotide of the present disclosure comprises the sequence of SEQ ID NO: 6 or SEQ ID NO: 31.

In some embodiments, a polynucleotide of the present disclosure comprises a 5' truncation, a 3' truncation, or a fragment of the sequence of SEQ ID NO: 5 or SEQ ID NO: 6. In some embodiments, the 5' truncation, 3' truncation, or fragment of the sequence of SEQ ID NO: 5 or SEQ ID NO: 6 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, at least 3500, but fewer than 3582, consecutive nucleotides of SEQ ID NO: 5 or SEQ ID NO: 6. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3579 of SEQ ID NO: 5 or SEQ ID NO: 6. In some embodiments, a polynucleotide of the present disclosure comprises the sequence of nucleic acids 1-3579 of SEQ ID NO: 5 or SEQ ID NO: 6. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 67-3579 of SEQ ID NO: 5 or SEQ ID NO: 6. In some embodiments, a polynucleotide of the present disclosure comprises the sequence of nucleic acids 67-3579 of SEQ ID NO: 5 or SEQ ID NO: 6.

In some embodiments, a polynucleotide of the present disclosure comprises a 5' truncation, a 3' truncation, or a fragment of the sequence of SEQ ID NO: 30 or SEQ ID NO: 31. In some embodiments, the 5' truncation, 3' truncation, or fragment of the sequence of SEQ ID NO: 30 or SEQ ID NO: 31 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, but fewer than 3336, consecutive nucleotides of SEQ ID NO: 30 or SEQ ID NO: 31. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3333 of SEQ ID NO: 30 or SEQ ID NO: 31. In some embodiments, a polynucleotide of the present disclosure comprises the sequence of nucleic acids 1-3333 of SEQ ID NO: 30 or SEQ ID NO: 31.

Polynucleotides Encoding Filaggrin Polypeptides

In some embodiments, the present disclosure relates to a recombinant nucleic acid comprising one or more polynucleotides comprising the coding sequence of a filaggrin gene (e.g., the coding sequence of a pro-filaggrin polypeptide), or portions thereof (e.g., the coding sequence corresponding to one or more filaggrin monomers resulting from proteolytic cleavage (e.g., via serine protease cleavage) of a pro-filaggrin polypeptide). Any suitable filaggrin gene (including any isoform thereof) known in the art may be encoded by a polynucleotide of the present disclosure, including, for example, a human FLG gene (see e.g., NCBI Gene ID: 2312), a human FLG2 gene (see e.g., NCBI Gene ID: 388698), a chimpanzee FLG gene (see e.g., NCBI Gene ID: 104002779), a chimpanzee FLG2 gene (see e.g., NCBI Gene ID: 100614947), a mouse FLG gene (see e.g., NCBI Gene ID: 14246), a mouse FLG2 gene (see e.g., NCBI Gene ID: 229574), a rat FLG gene (see e.g., NCBI Gene ID: 24641), a rat FLG2 gene (see e.g., NCBI Gene ID: 310586), a dog FLG gene (see e.g., NCBI Gene ID: 102157111), a dog FLG2 gene (see e.g., NCBI Gene ID: 483211), a rabbit FLG gene (see e.g., NCBI Gene ID: 100351762), a rabbit FLG2 gene (see e.g., NCBI Gene ID: 100344953), a cow FLG gene (see e.g., NCBI Gene ID: 788551), a cow FLG2 gene (see e.g., NCBI Gene ID: 101909133), a rhesus monkey FLG gene (see e.g., NCBI Gene ID: 102138001; NCBI Gene ID: 712658), a rhesus monkey FLG2 gene (see e.g., NCBI Gene ID: 102140950; NCBI Gene ID: 714566), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the filaggrin genes (e.g., an FLG gene, an FLG2 gene) described herein or known in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the coding sequence corresponding to one or more filaggrin monomers resulting from proteolytic cleavage (e.g., via serine protease cleavage) of a filaggrin gene (e.g., an FLG gene, an FLG2 gene) product described herein or known in the art. Methods of identifying filaggrin gene homologs/orthologs from additional species are known to one of ordinary skill in the art, including, for example, using a nucleic acid sequence alignment program such as the BLAST® blastn suite.

In some embodiments, a polynucleotide of the present disclosure comprises a codon-optimized variant of any of the filaggrin genes described herein or known in the art. In some embodiments, use of a codon-optimized variant of a filaggrin gene increases stability and/or yield of heterologous expression (RNA and/or protein) of the encoded filaggrin polypeptide in a target cell (e.g., a target human cell such as a human keratinocyte or fibroblast), as compared to the stability and/or yield of heterologous expression of a corresponding non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, one or more polynucleotides of the present disclosure comprises the coding sequence of a human filaggrin gene. In some embodiments, the human filaggrin gene is a human FLG gene, a human FLG2 gene, or any derivatives thereof. In some embodiments, one or more polynucleotides of the present disclosure comprises the coding sequence of one or more filaggrin monomers resulting from proteolytic cleavage (e.g., via serine protease cleavage) of a human filaggrin gene. In some embodiments, the one or more filaggrin monomers is a monomer derived from a human FLG gene and/or a human FLG2 gene.

In some embodiments, a polynucleotide of the present disclosure comprises the coding sequence of the human FLG gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 36 or SEQ ID NO: 37. In some embodiments, a polynucleotide of the present disclosure comprises the sequence of SEQ ID NO: 36 or SEQ ID NO: 37.

In some embodiments, a polynucleotide of the present disclosure comprises a 5' truncation, a 3' truncation, or a fragment of the sequence of SEQ ID NO: 36 or SEQ ID NO: 37. In some embodiments, the 5' truncation, 3' truncation, or fragment of the sequence of SEQ ID NO: 36 or SEQ ID NO: 37 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 2000, at least 3000, at least 4000, at least 5000, at least 6000, at least 7000, at least 8000, at least 9000, at least 10000, at least 11000, at least 12000, but fewer than 12186 consecutive nucleotides of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-12183 of SEQ ID NO: 36 or SEQ ID NO: 37. In some embodiments, a polynucleotide of the present disclosure comprises the sequence of nucleic acids 1-12183 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1411-2385 of SEQ ID NO: 36 or SEQ ID NO: 37. In some embodiments, a polynucleotide of the present disclosure comprises the sequence of nucleic acids 1411-2385 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1441-2385 of SEQ ID NO: 36 or SEQ ID NO: 37. In some embodiments, a polynucleotide of the present disclosure comprises the sequence of nucleic acids 1441-2385 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 2386-3357 of SEQ ID NO: 36 or SEQ ID NO: 37. In some embodiments, a polynucleotide of the present disclosure comprises the sequence of nucleic acids 2386-3357 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 2416-3357 of SEQ ID NO: 36 or SEQ ID NO: 37. In some embodiments, a polynucleotide of the present disclosure comprises the sequence of nucleic acids 2416-3357 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 3358-4329 of SEQ ID NO: 36 or SEQ ID NO: 37. In some embodiments, a polynucleotide of the present disclosure comprises the sequence of nucleic acids 3358-4329 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 3388-4329 of SEQ ID NO: 36 or SEQ ID NO: 37. In some embodiments, a polynucleotide of the present disclosure comprises the sequence of nucleic acids 3388-4329 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 4330-5301 of SEQ ID NO: 36 or SEQ ID NO: 37. In some embodiments, a polynucleotide of the present disclosure comprises the sequence of nucleic acids 4330-5301 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 4360-5301 of SEQ ID NO: 36 or SEQ ID NO: 37. In some embodiments, a polynucleotide of the present disclosure comprises the sequence of nucleic acids 4360-5301 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 5302-6276 of SEQ ID NO: 36 or SEQ ID NO: 37. In some embodiments, a polynucleotide of the present disclosure comprises the sequence of nucleic acids 5302-6276 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 5332-6276 of SEQ ID NO: 36 or SEQ ID NO: 37. In some embodiments, a polynucleotide of the present disclosure comprises the sequence of nucleic acids 5332-6276 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 6277-7248 of SEQ ID NO: 36 or SEQ ID NO: 37. In some embodiments, a polynucleotide of the present disclosure comprises the sequence of nucleic acids 6277-7248 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 6307-7248 of SEQ ID NO: 36 or SEQ ID NO: 37. In some embodiments, a polynucleotide of the present disclosure comprises the sequence of nucleic acids 6307-7248 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 7249-8220 of SEQ ID NO: 36 or SEQ ID NO: 37. In some embodiments, a polynucleotide of the present disclosure comprises the sequence of nucleic acids 7249-8220 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 7279-8220 of SEQ ID NO: 36 or SEQ ID NO: 37. In some embodiments, a polynucleotide of the present disclosure comprises the sequence of nucleic acids 7279-8220 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 8221-9192 of SEQ ID NO: 36 or SEQ ID NO: 37. In some embodiments, a polynucleotide of the present disclosure comprises the sequence of nucleic acids 8221-9192 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 8251-9192 of SEQ ID NO: 36 or SEQ ID NO: 37. In some embodiments, a polynucleotide of the present disclosure comprises the sequence of nucleic acids 8251-9192 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 9193-10164 of SEQ ID NO: 36 or SEQ ID NO: 37. In some embodiments, a polynucleotide of the present disclosure comprises the sequence of nucleic acids 9193-10164 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 9223-10164 of SEQ ID NO: 36 or SEQ ID NO: 37. In some embodiments, a polynucleotide of the present disclosure comprises the sequence of nucleic acids 9223-10164 of SEQ ID NO: 36 or SEQ ID NO: 37.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 10165-11136 of SEQ ID NO: 36 or SEQ ID NO: 37. In some embodiments, a polynucleotide of the present disclosure comprises the sequence of nucleic acids 10165-11136 of SEQ ID NO: 36 or SEQ ID NO: 37. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 10195-11136 of SEQ ID NO: 36 or SEQ ID NO: 37. In some embodiments, a polynucleotide of the present disclosure comprises the sequence of nucleic acids 10195-11136 of SEQ ID NO: 36 or SEQ ID NO: 37.

In some embodiments, a polynucleotide of the present disclosure comprises the coding sequence of the human FLG2 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 38. In some embodiments, a polynucleotide of the present disclosure comprises the sequence of SEQ ID NO: 38.

In some embodiments, a polynucleotide of the present disclosure comprises a 5' truncation, a 3' truncation, or a fragment of the sequence of SEQ ID NO: 38. In some embodiments, the 5' truncation, 3' truncation, or fragment of the sequence of SEQ ID NO: 38 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 2000, at least 3000, at least 4000, at least 5000, at least 6000, at least 7000, but fewer than 7176 consecutive nucleotides of SEQ ID NO: 38. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-7173 of SEQ ID NO: 38.

A polynucleotide of the present disclosure (e.g., encoding a laminin polypeptide) may further encode additional coding and non-coding sequences. Examples of additional coding and non-coding sequences may include, but are not limited to, sequences encoding additional polypeptide tags (e.g., encoded in-frame with the laminin or filaggrin polypeptide in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited, to any combination of purification tags, such as his-tags, flag-tags, maltose binding protein and gluta-thione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucle-otides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance effector protein expression in specific cell types (such as human keratinocytes and/or fibroblasts).

In some embodiments, a polynucleotide of the present disclosure encodes a leader, signal, and/or secretory sequence (in-frame) at the N-terminus of an encoded protein (e.g., an encoded laminin polypeptide). Any leader, signal, and/or secretory sequence known in the art may be encoded by a polynucleotide of the present disclosure, including, for example, a native laminin signal sequence, a native filaggrin signal sequence, or a heterologous or synthetic signal sequence (see e.g., von Heijne G. (1983) Patterns of amino acids near signal-sequence cleavage sites. Eur J Biochem 133 (1) 17-21; Martoglio B. and Dobberstein B. (1998) Signal sequences: More than just greasy peptides. Trends Cell Biol 8 (10), 410-5; Hegde R. S. and Bernstein H. D. (2006) The surprising complexity of signal sequences. Trends Biochem Sci 31(10), 563-71; and Kapp K., Schrempf S., Lemberg M. K. and Dobberstein B. (2009) Post-Target-ing Functions of Signal Peptides. Chapter in: Protein Trans-port into the Endoplasmic Reticulum, Landes Bioscience.

In some embodiments, a polynucleotide of the present disclosure is operably linked to one or more (e.g., one or more, two or more, three or more, four or more, five or more, ten or more, etc.) regulatory sequences. The term "regula-tory sequence" may include enhancers, insulators, promot-ers, and other expression control elements (e.g., polyade-nylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cyto-megalovirus early promoter enhancer, the polyoma enhancer on the late side of the replication origin, adenovirus enhanc-ers, and the like), and any combinations thereof. Any suit-able insulator(s) known in the art may be used, including, for example, herpes simplex virus (HSV) chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suit-able for transcription in mammalian host cells) known in the art may be used, including, for example, promoters obtained from the genomes of viruses (such as polyoma virus, fowl-pox virus, adenovirus (such as Adenovirus 2), bovine pap-illoma virus, avian sarcoma virus, cytomegalovirus, a ret-rovirus, hepatitis-B virus, Simian Virus 40 (SV40), and the like), promoters from heterologous mammalian genes (such as the actin promoter (e.g., the β-actin promoter), a ubiquitin promoter (e.g., a ubiquitin C (UbC) promoter), a phospho-glycerate kinase (PGK) promoter, an immunoglobulin pro-moter, from heat-shock protein promoters, and the like), promoters from native and/or homologous mammalian genes (e.g., human laminin gene promoters, human filaggrin gene promoters), synthetic promoters (such as the CAGG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure is operably linked to one or more heterologous promoters. In some embodiments, the one or more heter-ologous promoters are one or more of constitutive promot-ers, tissue-specific promoters, temporal promoters, spatial promoters, inducible promoters and repressible promoters. In some embodiments, the one or more heterologous pro-moters are one or more of the human cytomegalovirus (HCMV) immediate early promoter, the human elongation factor-1 (EF1) promoter, the human β-actin promoter, the human UbC promoter, the human PGK promoter, the syn-thetic CAGG promoter, and any combinations thereof. In some embodiments, a polynucleotide of the present disclo-sure is operably linked to an HCMV promoter.

In some embodiments, a recombinant nucleic acid of the present disclosure comprises multiple expression cassettes, where each expression cassette comprises a polynucleotide encoding a polypeptide (e.g., a laminin polypeptide). In some embodiments, a recombinant nucleic acid of the pres-ent disclosure comprises two or more polynucleotides encoding polypeptides (e.g., laminin polypeptides) linked by a nucleic acid encoding an internal ribosomal entry site (IRES). In some embodiments, a recombinant nucleic acid of the present disclosure comprises two or more polynucle-otides encoding polypeptides (e.g., laminin polypeptides) linked by a nucleic acid encoding a linker polypeptide (e.g., a cleavable linker polypeptide).

Recombinant Nucleic Acids Comprising Multiple Expression Cassettes

In some embodiments, a recombinant nucleic acid of the present disclosure comprises two or more (e.g., two or more, three or more, etc.) expression cassettes, where each expression cassette comprises a polynucleotide encoding polypeptide of the present disclosure (e.g., any of the laminin polypeptides described herein). In some embodiments, each of the expression cassettes comprise their own independent regulatory sequences (e.g., promoters, enhancers, polyadenylation signals, etc.).

In some embodiments, the recombinant nucleic acid comprises two expression cassettes each comprising a polynucleotide encoding a laminin polypeptide. In some embodiments, the two expression cassettes comprise polynucleotides encoding identical laminin polypeptides. In some embodiments, each expression cassette comprises a polynucleotide encoding a LamA3 polypeptide. In some embodiments, each expression cassette comprises a polynucleotide encoding a LamB3 polypeptide. In some embodiments, each expression cassette comprises a polynucleotide encoding a LamC2 polypeptide. In some embodiments, the two expression cassettes comprise polynucleotides encoding different laminin polypeptides (e.g., a first expression cassette comprising a polynucleotide encoding a first laminin polypeptide, and a second expression cassette comprising a polynucleotide encoding a second laminin polypeptide). In some embodiments, the first expression cassette comprises a polynucleotide encoding a LamA3 polypeptide, and the second expression cassette comprises a polynucleotide encoding a LamB3 polypeptide. In some embodiments, the first expression cassette comprises a polynucleotide encoding a LamA3 polypeptide, and the second expression cassette comprises a polynucleotide encoding a LamC2 polypeptide. In some embodiments, the first expression cassette comprises a polynucleotide encoding a LamB3 polypeptide, and the second expression cassette comprises a polynucleotide encoding a LamC2 polypeptide.

In some embodiments, the first and second expression cassettes are in the same orientation in the DNA. In some embodiments, the first and second expression cassettes are in opposite orientations to one another in the DNA. Without wishing to be bound by theory, incorporating two expression cassettes in an antisense orientation (opposite strands of DNA) may help to avoid read-through and ensure proper expression of each cassette.

In some embodiments, the recombinant nucleic acid comprises three expression cassettes each comprising a polynucleotide encoding a laminin polypeptide (e.g., any of the laminin polypeptides described herein). In some embodiments, the three expression cassettes comprise polynucleotides encoding identical laminin polypeptides. In some embodiments, each expression cassette comprises a polynucleotide encoding a LamA3 polypeptide. In some embodiments, each expression cassette comprises a polynucleotide encoding a LamB3 polypeptide. In some embodiments, each expression cassette comprises a polynucleotide encoding a LamC2 polypeptide. In some embodiments, the first and second expression cassettes each comprise polynucleotides encoding identical laminin polypeptides, and the third expression cassette comprises a polynucleotide encoding a different laminin polypeptide. In some embodiments, the first and second expression cassettes each comprise a polynucleotide encoding a LamA3 polypeptide, and the third expression cassette comprises a polynucleotide encoding a LamB3 polypeptide. In some embodiments, the first and second expression cassettes each comprise a polynucleotide encoding a LamA3 polypeptide, and the third expression cassette comprises a polynucleotide encoding a LamC2 polypeptide. In some embodiments, the first and second expression cassettes comprise polynucleotides encoding a LamB3 polypeptide, and the third expression cassette comprises a polynucleotide encoding a LamA3 polypeptide. In some embodiments, the first and second expression cassettes each comprise a polynucleotide encoding a LamB3 polypeptide, and the third expression cassette comprises a polynucleotide encoding a LamC2 polypeptide. In some embodiments, the first and second expression cassettes each comprise a polynucleotide encoding a LamC2 polypeptide, and the third expression cassette comprises a polynucleotide encoding a LamA3 polypeptide. In some embodiments, the first and second expression cassettes each comprise a polynucleotide encoding a LamC2 polypeptide, and the third expression cassette comprises a polynucleotide encoding a LamB3 polypeptide. In some embodiments, the three expression cassettes comprise polynucleotides encoding different laminin polypeptides (e.g., a first expression cassette comprising a first polynucleotide encoding a first laminin polypeptide, a second expression cassette comprising a second polynucleotide encoding a second laminin polypeptide, and a third expression cassette comprising a third polynucleotide encoding a third laminin polypeptide). In some embodiments, the first expression cassette comprises a first polynucleotide encoding a LamA3 polypeptide, the second expression cassette comprises a second polynucleotide encoding a LamB3 polypeptide, and the third expression cassette comprises a third polynucleotide encoding a LamC2 polypeptide.

In some embodiments, the first and second expression cassettes are in the same orientation in the DNA. In some embodiments, the first and second expression cassettes are in opposite orientations to one another in the DNA. In some embodiments, the first and third expression cassettes are in the same orientation in the DNA. In some embodiments, the first and third expression cassettes are in opposite orientations to one another in the DNA. In some embodiments, the second and third expression cassettes are in the same orientation in the DNA. In some embodiments, the second and third expression cassettes are in opposite orientations to one another in the DNA.

Recombinant Nucleic Acids Encoding Polycistronic mRNAs

In some embodiments, a recombinant nucleic acid of the present disclosure comprises two or more (e.g., two or more, three or more, etc.) polynucleotides encoding polypeptides of the present disclosure (e.g., any of the laminin polypeptides described herein) linked by a nucleic acid encoding an IRES (i.e., a recombinant nucleic acid encoding at least one polycistronic mRNA).

In some embodiments, the recombinant nucleic acid comprises: (a) a first polynucleotide encoding a first polypeptide (e.g., a first laminin polypeptide), (b) a second polynucleotide encoding a second polypeptide (e.g., a second laminin polypeptide), and (c) a nucleic acid encoding an IRES linking (a) to (b). In some embodiments, the first and second polypeptides are identical (e.g., the first and second laminin polypeptides are LamA3 polypeptides). In some embodiments, the first and second polypeptides are different (e.g., the first laminin polypeptide is a LamA3 polypeptide and the second laminin polypeptide is a LamB3 polypeptide).

In some embodiments, the recombinant nucleic acid comprises: (a) a first polynucleotide encoding a first polypeptide (e.g., a first laminin polypeptide), (b) a second polynucleotide encoding a second polypeptide (e.g., a second laminin polypeptide), (c) a third polynucleotide encoding a third polypeptide (e.g., a third laminin polypeptide), (d) a first nucleic acid encoding a first IRES linking (a) to (b), and (e) a second nucleic acid encoding a second IRES linking (b) to (c). In some embodiments, the first, second, and third polypeptides are identical (e.g., the first, second, and third laminin polypeptides are LamA3 polypeptides). In some embodiments, the first and second polypeptides are identical (e.g., the first and second laminin polypeptides are LamA3 polypeptides), and the third polypeptide is different (e.g., the third laminin polypeptide is a LamB3 polypeptide). In some embodiments, the first and third polypeptides are identical (e.g., the first and third laminin polypeptides are LamA3 polypeptides), and the second polypeptide is different (e.g., the second laminin polypeptide is a LamB3 polypeptide). In some embodiments, the second and third polypeptides are identical (e.g., the second and third laminin polypeptides are LamA3 polypeptide), and the first polypeptide is different (e.g., the first laminin polypeptide is a LamB3 polypeptide). In some embodiments, the first, second, and third polypeptides are different (e.g., the first laminin polypeptide is a LamA3 polypeptide, the second laminin polypeptide is a LamB3 polypeptide, and the third laminin polypeptide is a LamC2 polypeptide). In some embodiments, the first and second IRESs are the same. In some embodiments, the first and second IRESs are different.

Any suitable IRES known in the art may be used in the polycistronic mRNAs of the present disclosure, including, for example, a virally-derived IRES (e.g. an IRES derived from a poliovirus, rhinovirus, encephalomyocarditis virus (EMCV), foot-and-mouth disease virus, hepatitis C virus, classic swine fever virus, rous sarcoma virus, human immunodeficiency virus, cricket paralysis virus, Kaposi's sarcoma-associated herpesvirus, etc.), a cellular mRNA-derived IRES (e.g. an IRES derived from growth factor mRNAs, such as fibroblast growth factor 2, platelet-derived growth factor B, and vascular endothelial growth factor; an IRES derived from transcription factor mRNAs, such as antennapedia, ultrabithorax, and NF-κB repressing factor; an IRES derived from oncogene mRNAs, such as c-myc, pim-1, and protein kinase $p58^{PITSLRE}$, etc.), a synthetic IRES (e.g., a CP148 IRES), and others (see e.g., Mokrejs et al. (2007) A Bioinformatical Approach to the Analysis of Viral and Cellular Internal Ribosome Entry Sites. Columbus F editors. New Messenger RNA Research Communications. Hauppauge, NY: Nova Science Publishers; pp. 133-166; see also Mokrejs et al. (2006) Nucleic Acids Res 1; 34(Database issue): D125-30).

In some embodiments, the IRES is a CP148 IRES. An exemplary nucleic acid sequence encoding a CP148 IRES is provided as SEQ ID NO: 10. In some embodiments, the IRES is an EMCV IRES. An exemplary nucleic acid sequence encoding an EMCV IRES is provided as SEQ ID NO: 11.

In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 10 or SEQ ID NO: 11. In some embodiments, the nucleic acid sequence encoding the IRES has the sequence of SEQ ID NO: 10 or SEQ ID NO: 11.

An exemplary nucleic acid sequence encoding a polycistronic mRNA comprising, from 5' to 3', 1) a first polynucleotide encoding a first laminin polypeptide, 2) an IRES, and 3) a second polynucleotide encoding a second laminin polypeptide is provided as SEQ ID NO: 12. An exemplary nucleic acid sequence encoding a polycistronic mRNA comprising, from 5' to 3', 1) a first polynucleotide encoding a first laminin polypeptide, 2) a first IRES, 3) a second polynucleotide encoding a second laminin polypeptide, 4) a second IRES, and 5) a third polynucleotide encoding a third laminin polypeptide is provided as SEQ ID NO: 13.

Recombinant Nucleic Acids Encoding Chimeric Polypeptides

In some embodiments, a recombinant nucleic acid of the present disclosure comprises two or more polynucleotides encoding polypeptides of the present disclosure (e.g., any of the laminin polypeptide described herein) linked by a nucleic acid encoding a linker polypeptide (i.e., a recombinant nucleic acid encoding a chimeric polypeptide). In some embodiments, the linker polypeptide is a cleavable linker polypeptide.

In some embodiments, the recombinant nucleic acid comprises: (a) a first polynucleotide encoding a first polypeptide (e.g., a first laminin polypeptide), (b) a second polynucleotide encoding a second polypeptide (e.g., a second laminin polypeptide), and (c) a nucleic acid encoding a linker polypeptide linking (a) to (b). In some embodiments, the first and second polypeptides are identical (e.g., the first and second laminin polypeptides are LamA3 polypeptides). In some embodiments, the first and second polypeptides are different (e.g., the first laminin polypeptide is a LamA3 polypeptide and the second laminin polypeptide is a LamB3 polypeptide). In some embodiments, the linker polypeptide is a cleavable linker polypeptide.

In some embodiments, the recombinant nucleic acid comprises: (a) a first polynucleotide encoding a first polypeptide (e.g., a first laminin polypeptide), (b) a second polynucleotide encoding a second polypeptide (e.g., a second laminin polypeptide), (c) a third polynucleotide encoding a third polypeptide (e.g., a third laminin polypeptide), (d) a first nucleic acid encoding a first linker polypeptide linking (a) to (b), and (e) a second nucleic acid encoding a second linker polypeptide linking (b) to (c). In some embodiments, the first, second, and third polypeptides are identical (e.g., the first, second, and third laminin polypeptides are LamA3 polypeptides). In some embodiments, the first and second polypeptides are identical (e.g., the first and second laminin polypeptides are LamA3 polypeptides), and the third polypeptide is different (e.g., the third laminin polypeptide is a LamB3 polypeptide). In some embodiments, the first and third polypeptides are identical (e.g., the first and third laminin polypeptides are LamA3 polypeptides), and the second polypeptide is different (e.g., the second laminin polypeptide is a LamB3 polypeptide). In some embodiments, the second and third polypeptides are identical (e.g., the second and third laminin polypeptides are LamA3 polypeptides), and the first polypeptide is different (e.g., the first laminin polypeptide is a LamB3 polypeptide). In some embodiments, the first, second, and third polypeptides are different (e.g., the first laminin polypeptide is a LamA3 polypeptide, the second laminin polypeptide is a LamB3 polypeptide, and the third laminin polypeptide is a LamC2 polypeptide). In some embodiments, the first and second linker polypeptides are the same. In some embodiments, the first and second linker polypeptides are different.

Any linker polypeptide known in the art may be used in the chimeric polypeptides of the present disclosure, including, for example, cleavable linker polypeptides such as a T2A linker, a P2A linker, an E2A linker, an F2A linker, etc. An exemplary nucleic acid sequence encoding a T2A linker polypeptide is provided as SEQ ID NO: 14. An exemplary amino acid sequence of a T2A linker polypeptide is provided as SEQ ID NO: 18. In some embodiments, the linker polypeptide is a P2A linker polypeptide. An exemplary nucleic acid sequence encoding a P2A linker polypeptide is provided as SEQ ID NO: 15. An exemplary amino acid sequence of a P2A linker polypeptide is provided as SEQ ID NO: 19. In some embodiments, the linker polypeptide is an E2A linker polypeptide. An exemplary nucleic acid sequence encoding an E2A linker polypeptide is provided as SEQ ID NO: 16. An exemplary amino acid sequence of an E2A linker polypeptide is provided as SEQ ID NO: 20. In some embodiments, the linker polypeptide is an F2A linker polypeptide. An exemplary nucleic acid sequence encoding an F2A linker polypeptide is provided as SEQ ID NO: 17. An exemplary amino acid sequence of an F2A linker polypeptide is provided as SEQ ID NO: 21.

In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 18-21. In some embodiments, the linker polypeptide comprises a sequence selected from SEQ ID NOS: 18-21.

An exemplary nucleic acid sequence (encoding a chimeric polypeptide) comprising, from 5' to 3', 1) a first polynucleotide encoding a first laminin polypeptide, 2) a nucleic acid encoding a linker polypeptide, and 3) a second polynucleotide encoding a second laminin polypeptide is provided as SEQ ID NO: 22. An exemplary nucleic acid sequence (encoding a chimeric polypeptide) comprising, from 5' to 3', 1) a first polynucleotide encoding a first laminin polypeptide, 2) a first nucleic acid encoding a first linker polypeptide, 3) a second polynucleotide encoding a second laminin polypeptide, 4) a second nucleic acid encoding a second linker polypeptide, and 5) a third polynucleotide encoding a third laminin polypeptide is provided as SEQ ID NO: 23.

In some embodiments, a recombinant nucleic acid of the present disclosure does not comprise a polynucleotide comprising the coding sequence of (e.g., a transgene encoding) a Collagen alpha-1 (VII) chain polypeptide (COL7). In some embodiments, a recombinant nucleic acid of the present disclosure does not comprise a polynucleotide comprising the coding sequence of (e.g., a transgene encoding) a Lysyl hydroxylase 3 polypeptide (LH3). In some embodiments, a recombinant nucleic acid of the present disclosure does not comprise a polynucleotide comprising the coding sequence of (e.g., a transgene encoding) a Keratin type I cytoskeletal 17 polypeptide (KRT17). In some embodiments, a recombinant nucleic acid of the present disclosure does not comprise a polynucleotide comprising the coding sequence of (e.g., a transgene encoding) a transglutaminase (TGM) polypeptide (e.g., a human transglutaminase polypeptide such as a human TGM1 polypeptide). In some embodiments, a recombinant nucleic acid of the present disclosure does not comprise a polynucleotide comprising the coding sequence of (e.g., a transgene encoding) cosmetic proteins, collagen proteins, fibronectins, elastins, lumicans, vitronectins/vitronectin receptors, neuromodulators, fibrillins, additional dermal extracellular matrix proteins, etc. In some embodiments, a recombinant nucleic acid of the present disclosure does not comprise a polynucleotide comprising the coding sequence of (e.g., a transgene encoding) an antibody (e.g., a full-length antibody, an antibody fragments, etc.). In some embodiments, a recombinant nucleic acid of the present disclosure does not comprise a polynucleotide comprising the coding sequence of (e.g., a transgene encoding) a filaggrin polypeptide. In some embodiments, a recombinant nucleic acid of the present disclosure does not comprise a polynucleotide comprising the coding sequence of (e.g., a transgene encoding) a serine protease inhibitor kazal-type (SPINK) polypeptide (e.g., a human SPINK polypeptide such as a human SPINK5 polypeptide). In some embodiments, a recombinant nucleic acid of the present disclosure does not comprise a polynucleotide comprising the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a recombinant nucleic acid of the present disclosure does not comprise a polynucleotide comprising the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide, an antibody, a SPINK polypeptide, and/or any chimeric polypeptides thereof.

Laminin Polypeptides

In some embodiments, the present disclosure relates to one or more polynucleotides encoding a laminin (Lam) polypeptide (e.g., a human laminin polypeptide), or any portions thereof. Any suitable laminin polypeptide known in the art may be encoded by a polynucleotide of the present disclosure, including, for example, a Laminin subunit alpha-1 (LamA1) polypeptide (see e.g., UniProt accession number P25391), a Laminin subunit alpha-2 (LamA2) polypeptide (see e.g., UniProt accession number P24043), a Laminin subunit alpha-3 (LamA3) polypeptide (see e.g., UniProt accession number Q16787), a Laminin subunit alpha-4 (LamA4) polypeptide (see e.g., UniProt accession number Q16363), a Laminin subunit alpha-5 (LamA5) polypeptide (see e.g., UniProt accession number O15230), a Laminin subunit beta-1 (LamB1) polypeptide (see e.g., UniProt accession number P07942), a Laminin subunit beta-2 (LamB2) polypeptide (see e.g., UniProt accession number P55268), a Laminin subunit beta-3 (LamB3) polypeptide (see e.g., UniProt accession number Q13751), a Laminin subunit gamma-1 (LamC1) polypeptide (see e.g., UniProt accession number P11047), a Laminin subunit gamma-2 (LamC2) polypeptide (see e.g., UniProt accession number Q13753), a Laminin subunit gamma-3 (LamC3) polypeptide (see e.g., UniProt accession number Q9Y6N6), etc. In some embodiments, the laminin polypeptide is not a LamB3 polypeptide. Examples of non-human laminin polypeptides include, for example, mouse laminins (see e.g., UniProt accession numbers Q61789, Q61087, and Q61092), rat laminins (see e.g., UniProt accession numbers D3ZN05, F1LPI5, and F1LRH4), chimpanzee laminins (see e.g., UniProt accession numbers H2QEC7, H2R041, and H2Q0R2), etc. In some embodiments, a laminin polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of any laminin polypeptides described herein or known in the art. Methods of identifying laminin polypeptide homologs/orthologs from additional species are known to one of ordinary skill in the art, including, for example, using an amino acid sequence alignment program such as the BLAST® blastp suite or OrthoDB.

In some embodiments, a laminin polypeptide of the present disclosure comprises, consists essentially of, or consists of a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 7-9 or 32-35. In some embodiments, a laminin polypeptide of the present disclosure comprises, consists essentially of, or consists of a sequence selected from SEQ ID NOS: 7-9 or 32-35.

In some embodiments, the laminin polypeptide is a human laminin polypeptide. In some embodiments, a polynucleotide encoding a human laminin polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from SEQ ID NOS: 7-9 or 32-35. In some embodiments, a polynucleotide encoding a human laminin polypeptide is a polynucleotide that encodes a polypeptide comprising an amino acid sequence selected from SEQ ID NOS: 7-9 or 32-35.

In some embodiments, the human laminin polypeptide is a human LamA3 polypeptide (e.g., SEQ ID NO: 7), a human LamB3 polypeptide (e.g., SEQ ID NO: 8), a human LamC2 polypeptide (e.g., SEQ ID NO: 9), or any derivatives thereof.

In some embodiments, a polynucleotide of the present disclosure encodes a human LamA3 polypeptide. In some embodiments, a polynucleotide encoding a LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from SEQ ID NOS: 7 or 32-34. In some embodiments, a polynucleotide encoding a human LamA3 polypeptide is a polynucleotide that encodes a polypeptide comprising an amino acid sequence selected from SEQ ID NOS: 7 or 32-34.

In some embodiments, a polynucleotide encoding a LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence or SEQ ID NO: 7. In some embodiments, a polynucleotide encoding a human LamA3 polypeptide is a polynucleotide that encodes a polypeptide comprising the amino acid sequence of SEQ ID NO: 7.

In some embodiments, a polynucleotide encoding a LamA3 polypeptide is a polynucleotide that encodes an N-terminal truncation, a C-terminal truncation, or a fragment of the amino acid sequence of SEQ ID NO: 7. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, but fewer than 1724, consecutive amino acids of SEQ ID NO: 7. In some embodiments, a polynucleotide encoding a LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of amino acids 28-1724 of SEQ ID NO: 7. In some embodiments, a polynucleotide encoding a human LamA3 polypeptide is a polynucleotide that encodes a polypeptide comprising amino acids 28-1724 of SEQ ID NO: 7.

In some embodiments, a polynucleotide encoding a LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence or SEQ ID NO: 32. In some embodiments, a polynucleotide encoding a human LamA3 polypeptide is a polynucleotide that encodes a polypeptide comprising the amino acid sequence of SEQ ID NO: 32.

In some embodiments, a polynucleotide encoding a LamA3 polypeptide is a polynucleotide that encodes an N-terminal truncation, a C-terminal truncation, or a fragment of the amino acid sequence of SEQ ID NO: 32. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, at least 3000, at least 3250, but fewer than 3333, consecutive amino acids of SEQ ID NO: 32.

In some embodiments, a polynucleotide encoding a LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence or SEQ ID NO: 33. In some embodiments, a polynucleotide encoding a human LamA3 polypeptide is a polynucleotide that encodes a polypeptide comprising the amino acid sequence of SEQ ID NO: 33.

In some embodiments, a polynucleotide encoding a LamA3 polypeptide is a polynucleotide that encodes an N-terminal truncation, a C-terminal truncation, or a fragment of the amino acid sequence of SEQ ID NO: 33. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, at least 3000, at least 3250, but fewer than 3277, consecutive amino acids of SEQ ID NO: 33.

In some embodiments, a polynucleotide encoding a LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence or SEQ ID NO: 34. In some embodiments, a polynucleotide encoding a human LamA3 polypeptide is a polynucleotide that encodes a polypeptide comprising the amino acid sequence of SEQ ID NO: 34.

In some embodiments, a polynucleotide encoding a LamA3 polypeptide is a polynucleotide that encodes an N-terminal truncation, a C-terminal truncation, or a fragment of the amino acid sequence of SEQ ID NO: 34. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, but fewer than 1668, consecutive amino acids of SEQ ID NO: 34.

In some embodiments, a polynucleotide of the present disclosure encodes a human LamB3 polypeptide. In some embodiments, a polynucleotide encoding a LamB3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 8. In some embodiments, a polynucleotide encoding a human LamB3 polypeptide is a polynucleotide that encodes a polypeptide comprising the amino acid sequence of SEQ ID NO: 8.

In some embodiments, a polynucleotide encoding a LamB3 polypeptide is a polynucleotide that encodes an N-terminal truncation, a C-terminal truncation, or a fragment of the amino acid sequence of SEQ ID NO: 8. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1172, consecutive amino acids of SEQ ID NO: 8. In some embodiments, a polynucleotide encoding a LamB3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of amino acids 18-1172 of SEQ ID NO: 8. In some embodiments, a polynucleotide encoding a human LamB3 polypeptide is a polynucleotide that encodes a polypeptide comprising amino acids 18-1172 of SEQ ID NO: 8.

In some embodiments, a polynucleotide of the present disclosure encodes a human LamC2 polypeptide. In some embodiments, a polynucleotide encoding a LamC2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 9 or SEQ ID NO: 35. In some embodiments, a polynucleotide encoding a human LamC2 polypeptide is a polynucleotide that encodes a polypeptide comprising the amino acid sequence of SEQ ID NO: 9 or SEQ ID NO: 35.

In some embodiments, a polynucleotide encoding a LamC2 polypeptide is a polynucleotide that encodes an N-terminal truncation, a C-terminal truncation, or a fragment of the amino acid sequence of SEQ ID NO: 9. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1193, consecutive amino acids of SEQ ID NO: 9. In some embodiments, a polynucleotide encoding a LamC2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of amino acids 22-1193 of SEQ ID NO: 9. In some embodiments, a polynucleotide encoding a human LamC2 polypeptide is a polynucleotide that encodes a polypeptide comprising amino acids 22-1193 of SEQ ID NO: 9.

In some embodiments, a polynucleotide encoding a LamC2 polypeptide is a polynucleotide that encodes an N-terminal truncation, a C-terminal truncation, or a fragment of the amino acid sequence of SEQ ID NO: 35. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1111, consecutive amino acids of SEQ ID NO: 35.

In some embodiments, a polynucleotide of the present disclosure encoding a laminin polypeptide (e.g., a human laminin polypeptide) expresses the laminin polypeptide when the polynucleotide is delivered into one or more target cells of a subject (e.g., one or more skin and/or mucosal cells). In some embodiments, the laminin polypeptide enhances, increases, augments, and/or supplements the levels, function, and/or activity of a laminin polypeptide in one or more target cells of a subject (e.g., as compared to prior to expression of the exogenous laminin polypeptide). In some embodiments, expression of the laminin polypeptide enhances, increases, augments, and/or supplements cell adhesion of one or more cells in the skin and/or mucosa of a subject. In some embodiments, expression of the laminin polypeptide enhances, increases, augments, and/or supplements the lamina lucida of a subject. In some embodiments, expression of the laminin polypeptide enhances, increases, augments, and/or supplements epithelial basement membrane assembly, organization, and/or adherence in a subject.

Filaggrin Polypeptides

In some embodiments, the present disclosure relates to one or more polynucleotides encoding a filaggrin polypeptide (e.g., a full-length pro-filaggrin polypeptide), or portions thereof (e.g., the amino acid sequence of one or more filaggrin monomers resulting from proteolytic cleavage (e.g., via serine protease cleavage) of a full-length pro-filaggrin polypeptide). Any suitable filaggrin polypeptide known in the art may be encoded by a polynucleotide of the present disclosure, including, for example, a human filaggrin polypeptide (see e.g., UniProt accession number P20930), a human fillagrin-2 polypeptide (see e.g., UniProt accession number Q5D862), a chimpanzee filaggrin polypeptide (see e.g., UniProt accession number H2R8N0; UniProt accession number A0A2J8JJv8), a chimpanzee filaggrin-2 polypeptide (see e.g., UniProt accession number H2Q003), a mouse filaggrin polypeptide (see e.g., UniProt accession number P11088), a mouse filaggrin-2 polypeptide (see e.g., UniProt accession number Q2VIS4), a rat filaggrin polypeptide (see e.g., UniProt accession number Q8CIU0), a rat filaggrin-2 polypeptide (see e.g., UniProt accession number M0RBW0), a rabbit filaggrin-2 polypeptide (see e.g., UniProt accession number G1T229), a rhesus monkey filaggrin polypeptide (see e.g., UniProt accession number A0A0U4MFE5), a rhesus monkey filaggrin-2 polypeptide (see e.g., UniProt accession number F6Q6L1; UniProt accession number A0A2K5W550), etc. In some embodiments, a filaggrin polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of any of the filaggrin polypeptides described herein or known in the art. In some embodiments, a filaggrin polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence corresponding to one or more filaggrin monomers resulting from proteolytic cleavage (e.g., via serine protease cleavage) of any of the full-length filaggrin polypeptides described herein or known in the art. Methods of identifying filaggrin polypeptide homologs/orthologs from additional species are known to one of ordinary skill in the art, including, for example, using an amino acid sequence alignment program such as the BLAST® blastp suite or OrthoDB.

In some embodiments, a filaggrin polypeptide of the present disclosure is a human filaggrin polypeptide. In some embodiments, the human filaggrin polypeptide is a human filaggrin polypeptide (e.g., SEQ ID NO: 39), a human filaggrin-2 polypeptide (e.g., SEQ ID NO: 50), or any derivatives thereof.

In some embodiments, a polynucleotide of the present disclosure encodes a human filaggrin polypeptide. In some embodiments, a polynucleotide encoding a filaggrin polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 39. In some embodiments, a polynucleotide encoding a human filaggrin polypeptide is a polynucleotide that encodes a polypeptide comprising the amino acid sequence of SEQ ID NO: 39.

In some embodiments, a polynucleotide encoding a human filaggrin polypeptide is a polynucleotide that encodes an N-terminal truncation, a C-terminal truncation, or a fragment of the amino acid sequence of SEQ ID NO: 39. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 1000, at least 2000, at least 3000, at least 4000, but fewer than 4061, consecutive amino acids of SEQ ID NO: 39.

In some embodiments, a polynucleotide of the present disclosure encodes a human filaggrin-2 polypeptide. In some embodiments, a polynucleotide encoding a filaggrin-2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 50. In some embodiments, a polynucleotide encoding a human filaggrin-2 polypeptide is a polynucleotide that encodes a polypeptide comprising the amino acid sequence of SEQ ID NO: 50.

In some embodiments, a polynucleotide encoding a human filaggrin-2 polypeptide is a polynucleotide that encodes an N-terminal truncation, a C-terminal truncation, or a fragment of the amino acid sequence of SEQ ID NO: 50. N-terminal truncations, C-terminal truncations, or fragments may at least 10, at least 12, at least 14, at least 16, at least 18, at least 20, at least 30, at least 40, at least 50, at least 75, at least 100, at least 200, at least 300, at least 400, at least 500, at least 1000, at least 1500, at least 2000, at least 2100, at least 2200, at least 2300, but fewer than 2391, consecutive amino acids of SEQ ID NO: 50.

In some embodiments, a filaggrin polypeptide of the present disclosure comprises, consists essentially of, or consists of the amino acid sequence of one or more filaggrin monomers resulting from proteolytic cleavage (e.g., via serine protease cleavage) of a full-length human filaggrin polypeptide. In some embodiments, the one or more filaggrin monomers is a monomer derived from a full-length human filaggrin polypeptide (e.g., SEQ ID NO: 39) or a full-length human filaggrin-2 polypeptide (e.g., SEQ ID NO: 50).

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 40. In some embodiments, a polynucleotide encoding a filaggrin monomer is a polynucleotide that encodes a polypeptide comprising or consisting of the amino acid sequence of SEQ ID NO: 40. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-325 of SEQ ID NO: 40. In some embodiments, a polynucleotide encoding a filaggrin monomer is a polynucleotide that encodes a polypeptide comprising or consisting of amino acids 11-325 of SEQ ID NO: 40.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 41. In some embodiments, a polynucleotide encoding a filaggrin monomer is a polynucleotide that encodes a polypeptide comprising or consisting of the amino acid sequence of SEQ ID NO: 41. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 41. In some embodiments, a polynucleotide encoding a filaggrin monomer is a polynucleotide that encodes a polypeptide comprising or consisting of amino acids 11-324 of SEQ ID NO: 41.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 42. In some embodiments, a polynucleotide encoding a filaggrin monomer is a polynucleotide that encodes a polypeptide comprising or consisting of the amino acid sequence of SEQ ID NO: 42. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 42. In some embodiments, a polynucleotide encoding a filaggrin monomer is a polynucleotide that encodes a polypeptide comprising or consisting of amino acids 11-324 of SEQ ID NO: 42.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 43. In some embodiments, a polynucleotide encoding a filaggrin monomer is a polynucleotide that encodes a polypeptide comprising or consisting of the amino acid sequence of SEQ ID NO: 43. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 43. In some embodiments, a polynucleotide encoding a filaggrin monomer is a polynucleotide that encodes a polypeptide comprising or consisting of amino acids 11-324 of SEQ ID NO: 43.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 44. In some embodiments, a polynucleotide encoding a filaggrin monomer is a polynucleotide that encodes a polypeptide comprising or consisting of the amino acid sequence of SEQ ID NO: 44. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-325 of SEQ ID NO: 44. In some embodiments, a polynucleotide encoding a filaggrin monomer is a polynucleotide that encodes a polypeptide comprising or consisting of amino acids 11-325 of SEQ ID NO: 44.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 45. In some embodiments, a polynucleotide encoding a filaggrin monomer is a polynucleotide that encodes a polypeptide comprising or consisting of the amino acid sequence of SEQ ID NO: 45. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 45. In some embodiments, a polynucleotide encoding a filaggrin monomer is a polynucleotide that encodes a polypeptide comprising or consisting of amino acids 11-324 of SEQ ID NO: 45.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 46. In some embodiments, a polynucleotide encoding a filaggrin monomer comprising or consisting of the amino acid sequence of SEQ ID NO: 46. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 46. In some embodiments, a polynucleotide encoding a filaggrin monomer is a polynucleotide that encodes a polypeptide comprising or consisting of amino acids 11-324 of SEQ ID NO: 46.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 47. In some embodiments, a polynucleotide encoding a filaggrin monomer is a polynucleotide that encodes a polypeptide comprising or consisting of the amino acid sequence of SEQ ID NO: 47. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 47. In some embodiments, a polynucleotide encoding a filaggrin monomer is a polynucleotide that encodes a polypeptide comprising or consisting of amino acids 11-324 of SEQ ID NO: 47.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 48. In some embodiments, a polynucleotide encoding a filaggrin monomer is a polynucleotide that encodes a polypeptide comprising or consisting of the amino acid sequence of SEQ ID NO: 48. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 48. In some embodiments, a polynucleotide encoding a filaggrin monomer is a polynucleotide that encodes a polypeptide comprising or consisting of amino acids 11-324 of SEQ ID NO: 48.

In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 49. In some embodiments, a polynucleotide encoding a filaggrin monomer is a polynucleotide that encodes a polypeptide comprising or consisting of the amino acid sequence of SEQ ID NO: 49. In some embodiments, a polynucleotide encoding a filaggrin monomer is a polynucleotide that encodes a polypeptide comprising or consisting of an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to amino acids 11-324 of SEQ ID NO: 49. In some embodiments, a polynucleotide encoding a filaggrin monomer is a polynucleotide that encodes a polypeptide comprising or consisting of amino acids 11-324 of SEQ ID NO: 49.

In some embodiments, a polynucleotide of the present disclosure encoding a filaggrin polypeptide is a polynucleotide that encodes a polypeptide comprising, consisting essentially of, or consisting of a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 39-50. In some embodiments, a polynucleotide of the present disclosure encoding a filaggrin polypeptide is a polynucleotide that encodes a polypeptide comprising, consisting essentially of, or consisting of a sequence selected from SEQ ID NOS: 39-50.

In some embodiments, a polynucleotide of the present disclosure encoding a filaggrin polypeptide (e.g., a human filaggrin polypeptide) expresses the filaggrin polypeptide when the polynucleotide is delivered into one or more target cells of a subject. In some embodiments, expression of the filaggrin polypeptide (e.g., a human filaggrin polypeptide) enhances, increases, augments, and/or supplements the levels, function, and/or activity of a filaggrin polypeptide in one or more target cells of a subject (e.g., as compared to prior to expression of the filaggrin polypeptide). In some embodiments, expression of the filaggrin polypeptide (e.g., a human filaggrin polypeptide) enhances production of and/or stabilizes the stratum corneum layer of the skin of a subject (e.g., as compared to prior to expression of the filaggrin polypeptide). In some embodiments, expression of the filaggrin polypeptide (e.g., a human filaggrin polypeptide) reduces or treats a skin barrier function defect (e.g., TEWL) in a subject (e.g., as compared to prior to expression of the filaggrin polypeptide). In some embodiments, expression of the filaggrin polypeptide (e.g., a human filaggrin polypeptide) reduces or inhibits percutaneous transfer of allergens in a subject (e.g., as compared to prior to expression of the filaggrin polypeptide). In some embodiments, expression of the filaggrin polypeptide (e.g., a human filaggrin polypeptide) provides prophylactic, palliative, or therapeutic relief of a skin disorder (e.g., atopic dermatitis) in a subject (e.g., as compared to prior to expression of the filaggrin polypeptide).

Recombinant Nucleic Acids

In some embodiments, the present disclosure relates to recombinant nucleic acids comprising any one or more of the polynucleotides described herein. In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". *Viruses* 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding wild-type herpes virus genome). In some embodiments, the recombinant herpes virus genome is replication competent. In some embodiments, the recombinant herpes virus genome is replication defective.

In some embodiments, the recombinant nucleic acid is a recombinant herpes simplex virus (HSV) genome. In some embodiments, the recombinant herpes simplex virus genome is a recombinant herpes simplex virus type-1 (HSV-1) genome, a recombinant herpes simplex virus type-2 (HSV-2) genome, or any derivatives thereof. In some embodiments, the recombinant herpes simplex virus genome is a recombinant HSV-1 genome. In some embodiments, the recombinant HSV-1 genome may be from any HSV-1 strain known in the art, including, for example, strains 17, Ty25, R62, S25, Ku86, S23, R11, Ty148, Ku47, H166syn, 1319-2005, F-13, M-12, 90237, F-17, KOS, 3083-2008, F12g, L2, CD38, H193, M-15, India 2011, 0116209, F-11I, 66-207, 2762, 369-2007, 3355, MacIntyre, McKrae, 7862, 7-hse, HF10, 1394, 2005, 270-2007, OD4, SC16, M-19, 4J1037, 5J1060, J1060, KOS79, 132-1988, 160-1982, H166, 2158-2007, RE, 78326, F18g, F11, 172-2010, H129, F, E4, CJ994, F14g, E03, E22, E10, E06, E11, E25, E23, E35, E15, E07, E12, E14, E08, E19, E13, ATCC 2011, etc. (see e.g., Bowen et al. J Virol. 2019 Apr. 3; 93(8)). In some embodiments, the recombinant HSV-1 genome is from the KOS strain. In some embodiments, the recombinant HSV-1 genome is not from the McKrae strain. In some embodiments, the recombinant herpes simplex virus genome is attenuated. In some embodiments, the recombinant herpes simplex virus genome is replication competent. In some embodiments, the recombinant herpes simplex virus genome is replication defective. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 (one or both copies) and/or ICP47 herpes simplex virus genes (e.g., to avoid production of an immune-stimulating virus). In some embodiments, the recombinant herpes simplex virus genome does not comprise an inactivating mutation in the ICP34.5 (one or both copies) herpes simplex virus gene. In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an inactivating mutation in the ICP4 (one or both copies), ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP4 gene (one or both copies), and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0 (one or both copies), ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long ($IR_L$) and internal repeat short ($IR_S$) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 (one or both copies) and/or UL41 genes.

In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0 (one or both copies), ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and/or UL55 herpes simplex viral gene loci. In some embodiments, a recombinant herpes simplex virus genome comprises one or more polynucleotides of the present disclosure within one or both of the viral ICP4 gene loci (e.g., a recombinant virus comprising a polynucleotide encoding a laminin polypeptide in one or both of the ICP4 loci; a recombinant virus comprising a nucleic acid encoding a polycistronic mRNA in one or both of the ICP4 loci; a recombinant virus comprising a nucleic encoding a chimeric polypeptide in one or both of the ICP4 loci; etc.). In some embodiments, a recombinant herpes simplex virus genome comprises one or more polynucleotides of the present disclosure within the viral ICP22 gene locus (e.g., a recombinant virus comprising a polynucleotide encoding a laminin polypeptide in the ICP22 locus; a recombinant virus comprising a nucleic acid encoding a polycistronic mRNA in the ICP22 locus; a recombinant virus comprising a nucleic acid encoding a chimeric polypeptide in the ICP22 locus; etc.). In some embodiments, a recombinant herpes simplex virus genome comprises one or more polynucleotides of the present disclosure within the viral UL41 gene locus (e.g., a recombinant virus comprising a polynucleotide encoding a laminin polypeptide in the UL41 locus; a recombinant virus comprising a nucleic acid encoding a polycistronic mRNA in the UL41 locus; a recombinant virus comprising a nucleic acid encoding a chimeric polypeptide in the UL41 locus; etc.). In some embodiments, a recombinant herpes simplex virus genome comprises one or more polynucleotides of the present disclosure within the viral ICP27 gene locus (e.g., a recombinant virus comprising a polynucleotide encoding a laminin polypeptide in the ICP27 locus; a recombinant virus comprising a nucleic acid encoding a polycistronic mRNA in the ICP27 locus; a recombinant virus comprising a nucleic acid encoding a chimeric polypeptide in the ICP27 locus; etc.). In some embodiments, a recombinant herpes simplex virus genome comprises one or more polynucleotides of the present disclosure within the viral ICP47 gene locus (e.g., a recombinant virus comprising a polynucleotide encoding a laminin polypeptide in the ICP47 locus; a recombinant virus comprising a nucleic acid encoding a polycistronic mRNA in the ICP47 locus; a recombinant virus comprising a nucleic acid encoding a chimeric polypeptide in the ICP47 locus; etc.).

In some embodiments, a recombinant herpes simplex virus genome comprises one or more polynucleotides of the present disclosure within one or both of the viral ICP4 gene loci, and one or more polynucleotides of the present disclosure within the viral ICP22 gene locus (e.g., a recombinant virus comprising a polynucleotide encoding a first laminin polypeptide in one or both of the ICP4 loci, and a polynucleotide encoding a second laminin polypeptide in the ICP22 locus; etc.). In some embodiments, a recombinant herpes simplex virus genome comprises one or more polynucleotides of the present disclosure within one or both of the viral ICP4 gene loci, and one or more polynucleotides of the present disclosure within the viral UL41 gene locus (e.g., a recombinant virus comprising a polynucleotide encoding a first laminin polypeptide in one or both of the ICP4 loci, and a polynucleotide encoding a second laminin polypeptide in the UL41 locus etc.). In some embodiments, a recombinant herpes simplex virus genome comprises one or more polynucleotides of the present disclosure within the viral UL41 gene locus, and one or more polynucleotides of the present disclosure within the viral ICP22 gene locus (e.g., a recombinant virus comprising a polynucleotide encoding a first laminin polypeptide in the UL41 locus, and a polynucleotide encoding second laminin polypeptide in the ICP22 locus; etc.). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, and one or more polynucleotides of the present disclosure within the viral UL41 gene locus (e.g., a recombinant virus comprising a polynucleotide encoding a first laminin polypeptide in one or both of the ICP4 loci, a polynucleotide encoding a second laminin polypeptide in the ICP22 locus, and a polynucleotide encoding a third laminin polypeptide in the UL41 locus; etc.)

In some embodiments, the recombinant herpes virus genome (e.g., a recombinant herpes simplex virus genome) has been engineered to decrease or eliminate expression of one or more herpes virus genes (e.g., one or more toxic herpes virus genes), such as one or both copies of the HSV ICP0 gene, one or both copies of the HSV ICP4 gene, the HSV ICP22 gene, the HSV UL41 gene, the HSV ICP27 gene, etc. In some embodiments, the recombinant herpes virus genome (e.g., recombinant herpes simplex virus genome) has been engineered to reduce cytotoxicity of the recombinant genome (e.g., when introduced into a target cell) as compared to a corresponding wild-type herpes virus genome (e.g., a wild-type herpes simplex virus genome). In some embodiments, the target cell is a human cell. In some embodiments, the target cell is a cell of the epidermis and/or dermis (e.g., a cell of the human epidermis and/or dermis). In some embodiments, the target cell is a keratinocyte or fibroblast (e.g., a human keratinocyte or human fibroblast). In some embodiments, the target cell is a cell of the mucosa. In some embodiments, cytotoxicity (e.g., in human keratinocytes and/or fibroblast cells) of the recombinant herpes virus genome (e.g., a recombinant herpes simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). In some embodiments, cytotoxicity (e.g., in human keratinocytes and/or fibroblast cells) of the recombinant herpes virus genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant herpes virus genome (e.g., a recombinant herpes simplex virus genome) has been engineered to reduce its impact on host cell proliferation after exposure of a target cell to the recombinant genome, as compared to a corresponding wild-type herpes virus genome (e.g., a wild-type herpes simplex virus genome). In some embodiments, the target cell is a human cell. In some embodiments, the target cell is a cell of the epidermis and/or dermis (e.g., a cell of the human epidermis and/or dermis). In some embodiments, the target cell is a keratinocyte or fibroblast (e.g., a human keratinocyte or human fibroblast). In some embodiments, host cell proliferation (e.g., of human keratinocytes and/or fibroblasts) after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). In some embodiments, host cell proliferation (e.g., of human keratinocytes and/or fibroblasts) after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). Methods of measuring cellular proliferation are known to one of ordinary skill in the art, including, for example, through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, a recombinant nucleic acid (e.g., a recombinant herpes virus genome, such as a recombinant herpes simplex virus genome) of the present disclosure comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide.

In some embodiments, the present disclosure relates to one or more heterologous polynucleotides (e.g., a bacterial artificial chromosome (BAC)) comprising any of the recombinant nucleic acids described herein.

IV. VIRUSES

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human). In some embodiments, the present disclosure relates to one or more viral particles comprising any of the polynucleotides and/or recombinant nucleic acids described herein. In some embodiments, the one or more target cells are one or more human cells. In some embodiments, the one or more target cells are one or more cells with a laminin deficiency (e.g., one or more cells comprising a loss-of-function mutation in, or a pathogenic variant of, a native laminin gene such as a LAMA3, LAMB3, or LAMC2 gene). In some embodiments, the one or more target cells are one or more cells with a filaggrin deficiency (e.g., one or more cells comprising a loss-of-function mutation in, or a pathogenic variant of, a native FLG or FLG2 gene). In some embodiments, the one or more target cells are one or more cells of the mucosa. In some embodiments, the one or more target cells are one or more cells of the skin (e.g., one or more cells of the epidermis, dermis, and/or subcutis). In some embodiments, the one or more target cells are cells of the epidermis and/or dermis (e.g., cells of the human epidermis and/or dermis). In some embodiments, the one or more target cells are selected from keratinocytes, melanocytes, Langerhans cells, Merkel cells, mast cells, fibroblasts, and/or adipocytes. In some embodiments, the one or more target cells are keratinocytes. In some embodiments, the one or more target cells reside in the stratum corneum, stratum granulosum, stratum spinulosum, stratum basale, and/or basement membrane. In some embodiments, the one or more target cells are one or more epidermal cells. In some embodiments, the one or more target cells are one or more dermal cells.

Any suitable virus known in the art may be used, including, for example, adenovirus, adeno-associated virus, retrovirus, lentivirus, sendai virus, papillomavirus, herpes virus (e.g., a herpes simplex virus), vaccinia virus, and/or any hybrid or derivative viruses thereof. In some embodiments, the virus is attenuated. In some embodiments, the virus is replication defective. In some embodiments, the virus is replication competent. In some embodiments, the virus has been modified to alter its tissue tropism relative to the tissue tropism of a corresponding unmodified, wild-type virus. In some embodiments, the virus has reduced cytotoxicity as compared to a corresponding wild-type virus. Methods of producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, and a Kaposi's sarcoma-associated herpesvirus, etc. In some embodiments, the herpes virus is attenuated. In some embodiments, the herpes virus is replication competent. In some embodiments, the herpes virus is replication defective. In some embodiments, the herpes virus has reduced cytotoxicity as compared to a corresponding wild-type herpes virus. In some embodiments, the herpes virus is not oncolytic.

In some embodiments, the herpes virus is a herpes simplex virus. Herpes simplex viruses comprising recombinant nucleic acids may be produced by a process disclosed, for example, in WO2015/009952 and/or WO2017/176336. In some embodiments, the herpes simplex virus is attenuated. In some embodiments, the herpes simplex virus is replication competent. In some embodiments, the herpes simplex virus is replication defective. In some embodiments, the herpes simplex virus is a type 1 herpes simplex virus (HSV-1), a type 2 herpes simplex virus (HSV-2), of any derivatives thereof. In some embodiments, the herpes simplex virus is a type 1 herpes simplex virus (HSV-1). In some embodiments, the HSV-1 is attenuated. In some embodiments, the HSV-1 is replication competent. In some embodiments, the HSV-1 is replication defective. In some embodiments, the herpes simplex virus (e.g., the HSV-1) has reduced cytotoxicity as compared to a corresponding wild-type herpes simplex virus (e.g., a wild-type HSV-1). In some embodiments, the herpes simplex virus (e.g., the HSV-1) is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus such as a herpes simplex virus) for one or more target cells (e.g., one or more human keratinocytes and/or fibroblasts) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more human keratinocytes and/or fibroblasts) is about 85% to about 100%. In some embodiments, the virus is a herpes simplex virus and the transduction efficiency of the virus for one or more target cells (e.g., one or more human keratinocytes) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

V. PHARMACEUTICAL COMPOSITIONS AND FORMULATIONS

Certain aspects of the present disclosure relate to compositions and formulations (e.g., pharmaceutical compositions or formulations) comprising any of the recombinant nucleic acids (e.g., recombinant herpes virus genomes) and/or viruses (e.g., herpes viruses comprising the recombinant genomes) described herein (such as a herpes simplex virus comprising a recombinant herpes simplex virus genome), and an excipient or carrier (e.g., a pharmaceutically acceptable excipient or carrier).

In some embodiments, the pharmaceutical composition or formulation comprises any one or more of the viruses (e.g., herpes viruses) described herein. In some embodiments, the pharmaceutical composition or formulation comprises from about $10^4$ to about $10^{12}$ plaque forming units (PFU)/mL of the virus. For example, the pharmaceutical composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about $10^8$, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the pharmaceutical composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Pharmaceutical compositions and formulations can be prepared by mixing the active ingredient(s) (such as a recombinant nucleic acid and/or a virus) having the desired degree of purity with one or more pharmaceutically acceptable carriers or excipients. Pharmaceutically acceptable carriers or excipients are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 1%, 2%, 3%, 4%, 5%, 6%, 7%, 8%, 9%, 10%, 11%, 12%, 13%, 14%, 15%, etc. glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); and/or non-ionic surfactants (such as polyethylene glycol (PEG)). A thorough discussion of pharmaceutically acceptable carriers is available in REMINGTON'S PHARMACEUTICAL SCIENCES (Mack Pub. Co., N.J. 1991).

In some embodiments, the pharmaceutical composition or formulation comprises one or more lipid (e.g., cationic lipid) carriers. In some embodiments, the pharmaceutical composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics) for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly(glycolic acid), PLGA, PLA, PGA, and any combinations thereof (see e.g., Vauthier et al. Adv Drug Del Rev. (2003) 55: 519-48; US2007/0148074; US2007/0092575; US2006/0246139; U.S. Pat. Nos. 5,753,234; 7,081,483; and WO2006/052285).

In some embodiments, the pharmaceutically acceptable carrier or excipient may be adapted for or suitable for any administration route known in the art, including, for example, intravenous, intramuscular, subcutaneous, cutaneous, oral, nasal, intratracheal, sublingual, buccal, topical, transdermal, intradermal, intraperitoneal, intraorbital, subretinal, intravitreal, transmucosal, intraarticular, by implantation, by inhalation, intratheal, intraventricular, and/or intranasal administration. In some embodiments, the pharmaceutical composition or formulation is adapted for or suitable for any administration route known in the art, including, for example, intravenous, intramuscular, subcutaneous, cutaneous, oral, nasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutically acceptable carrier or excipient is adapted for or suitable for topical, transdermal, subcutaneous, intradermal, and/or transmucosal administration. In some embodiments, the pharmaceutical composition or formulation is adapted for or suitable for topical, transdermal, subcutaneous, intradermal, and/or transmucosal administration. In some embodiments, the pharmaceutically acceptable carrier or excipient is adapted for or suitable for topical, transdermal, subcutaneous, and/or intradermal administration. In some embodiments, the pharmaceutical composition or formulation is adapted for or suitable for topical, transdermal, subcutaneous, and/or intradermal administration. In some embodiments, the pharmaceutically acceptable carrier or excipient is adapted for or suitable for topical, transdermal, and/or intradermal administration. In some embodiments, the pharmaceutical composition or formulation is adapted for or suitable for topical, transdermal, and/or intradermal administration. In some embodiments, the pharmaceutically acceptable carrier or excipient is adapted for or suitable for topical administration. In some embodiments, the pharmaceutical composition or formulation is adapted for or suitable for topical administration. In some embodiments, the pharmaceutically acceptable carrier or excipient is adapted for or suitable for oral, sublingual, nasal, or buccal administration, or administration via inhalation. In some embodiments, the pharmaceutical composition or formulation is adapted for or suitable for oral, sublingual, nasal, or buccal administration, or administration via inhalation. In some embodiments, the pharmaceutically acceptable carrier or excipient is adapted for or suitable for topical (to the eye), intravitreal, subretinal or intraorbital administration. In some embodiments, the pharmaceutical composition or formulation is adapted for or suitable for topical (to the eye), intravitreal, subretinal, or intraorbital administration.

Examples of carriers or excipients adapted for or suitable for use in pharmaceutical compositions or formulations of the present disclosure may include, but are not limited to, ointments, oils, pastes, creams, aerosols, suspensions, emulsions, fatty ointments, gels (e.g., methylcellulose gels, such as carboxy methylcellulose, hydroxypropyl methylcellulose, etc.), powders, liquids, lotions, solutions, sprays, patches (e.g., transdermal patches or microneedle patches), adhesive strips, a microneedle or microneedle arrays, and inhalants. In some embodiments, the carrier or excipient (e.g., the pharmaceutically acceptable carrier or excipient) comprises one or more (e.g., one or more, two or more, three or more, four or more, five or more, etc.) of an ointment, oil, paste, cream, aerosol, suspension, emulsion, fatty ointment, gel, powder, liquid, lotion, solution, spray, patch, adhesive strip, and an inhalant. In some embodiments, the carrier comprises a patch (e.g. a patch that adheres to the skin), such as a transdermal patch or microneedle patch. In some embodiments, the carrier comprises a microneedle or microneedle array. Methods for making and using microneedle arrays suitable for composition delivery are generally known in the art (see e.g., Kim Y. et al. "Microneedles for drug and vaccine delivery". *Advanced Drug Delivery Reviews* 2012, 64 (14): 1547-68).

In some embodiments, the pharmaceutical composition or formulation further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; methylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the pharmaceutical composition or formulation comprises a methylcellulose gel, such as a carboxy methylcellulose gel, a hydroxypropyl methylcellulose gel, etc. (e.g., at about 0.5%, at about 1%, at about 1.5%, at about 2%, at about 2.5%, at about 3%, at about 3.5%, at about 4%, at about 4.5%, at about 5%, at about 5.5%, at about 6%, at about 6.5%, at about 7%, at about 7.5%, at about 8%, at about 8.5%, at about 9%, at about 9.5%, at about 10%, at about 10.5%, at about 11%, at about 11.5%, at about 12%, etc.). In some embodiments, the pharmaceutical composition or formulation comprises a phosphate buffer. In some embodiments, the pharmaceutical composition or formulation comprises glycerol (e.g., at about 1%, about 2%, about 3%, about 4%, about 5%, about 6%, about 7%, about 8%, about 9%, about 10%, about 11%, about 12%, about 13%, about 14%, about 15%, etc.). In some embodiments, the pharmaceutical composition or formulation comprises a methylcellulose gel (a carboxy methylcellulose gel, a hydroxypropyl methylcellulose gel, etc.), a phosphate buffer, and/or glycerol.

Compositions and formulations (e.g., pharmaceutical compositions and formulations) to be used for in vivo administration are generally sterile. Sterility may be readily accomplished, e.g., by filtration through sterile filtration membranes.

In some embodiments, any of the recombinant nucleic acids, viruses, and/or pharmaceutical compositions or formulations described herein may be used to deliver one or more polynucleotides encoding a laminin polypeptide into one or more cells of a subject (e.g., one or more laminin-deficient cells, one or more cells harboring a laminin gene mutation, etc.). In some embodiments, any of the recombinant nucleic acids, viruses, and/or pharmaceutical compositions or formulations may be used in a therapy. In some embodiments, any of the recombinant nucleic acids, viruses, and/or pharmaceutical compositions or formulations described herein may be used in the treatment of a disease or condition that would benefit from the expression of a laminin polypeptide (e.g., a disease/disorder/defect associated with a laminin deficiency and/or a disease associated with a laminin gene mutation (such as JEB)). In some embodiments, any of the recombinant nucleic acids, viruses, and/or pharmaceutical compositions or formulations described herein may be used in the treatment of one or more signs or symptoms of a laminin deficiency. Signs and symptoms of laminin deficiencies include, but are not limited to: blistering, wounding, and/or scarring of the skin; granulation tissue; skin erosion; deformity of the fingernails and/or toenails; fusion of the fingers and/or toes; tightening and/or thinning of the skin; contractures; blistering and/or scarring of the mucosa; difficulty breathing; horse cry; increased susceptibility to infection; dehydration; fluid loss; electrolyte imbalance; blistering and/or scarring of the gastrointestinal and/or gastrourinary tract; dental caries, enamel hypoplasia, and/or other oral or dental defects; hair loss; malnutrition; growth retardation; anemia; and any combinations thereof. In some embodiments, any of the recombinant nucleic acids, viruses, and/or pharmaceutical compositions or formulations described herein may be used for providing prophylactic, palliative, or therapeutic relief to one or more signs or symptoms of Junctional Epidermolysis Bullosa.

In some embodiments, any of the recombinant nucleic acids, viruses, and/or pharmaceutical compositions or formulations described herein may be used in the preparation or manufacture of a medicament. In some embodiments, any of the recombinant nucleic acids, viruses, and/or pharmaceutical compositions or formulations described herein may be used in the preparation or manufacture of a medicament useful for delivering one or more polynucleotides encoding a laminin polypeptide into one or more cells of a subject (e.g., one or more laminin-deficient cells, one or more cells harboring a laminin gene mutation, etc.). In some embodiments, any of the recombinant nucleic acids, viruses, and/or pharmaceutical compositions or formulations described herein may be used in the preparation or manufacture of a medicament useful for the treatment of a disease or condition that would benefit from the expression of a laminin polypeptide (e.g., a disease/disorder/defect associated with a laminin deficiency and/or a disease associated with a laminin gene mutation (such as JEB)). In some embodiments, any of the recombinant nucleic acids, viruses, and/or pharmaceutical compositions or formulations described herein may be used in the preparation or manufacture of a medicament useful for the treatment of one or more signs or symptoms of a laminin deficiency. Signs and symptoms of laminin deficiencies include, but are not limited to: blistering, wounding, and/or scarring of the skin; granulation tissue; skin erosion; deformity of the fingernails and/or toenails; fusion of the fingers and/or toes; tightening and/or thinning of the skin; contractures; blistering and/or scarring of the mucosa; difficulty breathing; horse cry; increased susceptibility to infection; dehydration; fluid loss; electrolyte imbalance; blistering and/or scarring of the gastrointestinal and/or gastrourinary tract; dental caries, enamel hypoplasia, and/or other oral or dental defects; hair loss; malnutrition; growth retardation; anemia; and any combinations thereof. In some embodiments, any of the recombinant nucleic acids, viruses, and/or pharmaceutical compositions or formulations described herein may be used in the preparation or manufacture of a medicament useful for the treatment of Junctional Epidermolysis Bullosa.

In some embodiments, any of the recombinant nucleic acids, viruses, and/or pharmaceutical compositions or formulations described herein may be used to deliver one or more polynucleotides encoding a filaggrin polypeptide into one or more cells of a subject (e.g., one or more filaggrin-deficient cells, one or more cells harboring an FLG or FLG2 gene mutation, etc.). In some embodiments, any of the recombinant nucleic acids, viruses, and/or pharmaceutical compositions or formulations may be used in a therapy. In some embodiments, any of the recombinant nucleic acids, viruses, and/or pharmaceutical compositions or formulations described herein may be used in the treatment of a disease or condition that would benefit from the expression of a filaggrin polypeptide (e.g., a disease/disorder/defect associated with a filaggrin deficiency and/or a disease associated with an FLG or FLG2 gene mutation (such as atopic dermatitis, ichthyosis, a peeling skin syndrome, etc.)). In some embodiments, any of the recombinant nucleic acids, viruses, and/or pharmaceutical compositions or formulations described herein may be used in the treatment of one or more signs or symptoms of a filaggrin deficiency. Signs and symptoms of filaggrin deficiencies include, but are not limited to: dry skin; itching, which may be severe, especially at night; red to brownish-gray patches, especially on the hands, feet, ankles, wrists, neck, upper chest, eyelids, inside the bend of the elbows and knees, and in infants, the face and scalp; small, raised bumps on the skin which may be weeping; skin infections; eyelid dermatitis; cataracts; increased IgE levels; thickened, cracked, or scaly skin; raw, sensitive, swollen skin from scratching; and any combinations thereof. In some embodiments, any of the recombinant nucleic acids, viruses, and/or pharmaceutical compositions or formulations described herein may be used for providing prophylactic, palliative, or therapeutic relief to one or more signs or symptoms of atopic dermatitis.

In some embodiments, any of the recombinant nucleic acids, viruses, and/or pharmaceutical compositions or formulations described herein may be used in the preparation or manufacture of a medicament. In some embodiments, any of the recombinant nucleic acids, viruses, and/or pharmaceutical compositions or formulations described herein may be used in the preparation or manufacture of a medicament useful for delivering one or more polynucleotides encoding a filaggrin polypeptide into one or more cells of a subject (e.g., one or more filaggrin-deficient cells, one or more cells harboring an FLG or FLG2 gene mutation, etc.). In some embodiments, any of the recombinant nucleic acids, viruses, and/or pharmaceutical compositions or formulations described herein may be used in the preparation or manufacture of a medicament useful for the treatment of a disease or condition that would benefit from the expression of a filaggrin polypeptide (e.g., a disease/disorder/defect associated with a filaggrin deficiency and/or a disease associated with an FLG or FLG2 gene mutation (such as atopic dermatitis, ichthyosis vulgaris, a peeling skin syndrome, etc.)). In some embodiments, any of the recombinant nucleic acids, viruses, and/or pharmaceutical compositions or formulations described herein may be used in the preparation or manufacture of a medicament useful for the treatment of one or more signs or symptoms of a filaggrin deficiency. Signs and symptoms of filaggrin deficiencies include, but are not limited to: dry skin; itching, which may be severe, especially at night; red to brownish-gray patches, especially on the hands, feet, ankles, wrists, neck, upper chest, eyelids, inside the bend of the elbows and knees, and in infants, the face and scalp; small, raised bumps on the skin which may be weeping; skin infections; eyelid dermatitis; cataracts; increased IgE levels; thickened, cracked, or scaly skin; raw, sensitive, swollen skin from scratching; and any combinations thereof. In some embodiments, any of the recombinant nucleic acids, viruses, and/or pharmaceutical compositions or formulations described herein may be used in the preparation or manufacture of a medicament useful for the treatment of atopic dermatitis.

VI. METHODS

Certain aspects of the present disclosure relate to enhancing, increasing, augmenting, and/or supplementing the levels of one or more laminin polypeptides (e.g., one or more human laminin polypeptides) in one or more cells and/or in the extracellular matrix of a subject comprising administering to the subject an effective amount of any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation, a pathogenic variant) in an endogenous laminin gene (e.g., a LAMA3, LAMB3, and/or LAMC2 gene). In some embodiments, the subject suffers from Junctional Epidermolysis Bullosa (JEB). In some embodiments, the JEB is Herlitz-type JEB (JEB-H). In some embodiments, the JEB is non-Herlitz-type JEB.

In some embodiments, administration of the recombinant nucleic acid, virus, medicament, and/or pharmaceutical composition or formulation to the subject increases laminin levels (transcript or protein levels) by at least about 25% in one or more contacted or treated cells of the subject, as compared to the endogenous levels of the laminin in one or more corresponding untreated cells of the subject. In some embodiments, administration of the recombinant nucleic acid, virus, medicament, and/or pharmaceutical composition or formulation to the subject increases laminin levels (transcript or protein levels) by at least about 25%, at least about 30%, at least about 40%, at least about 50%, at least about 50%, at least about 60%, at least about 70%, at least about 80%, at least about 90%, at least about 95%, at least about 99%, or more in one or more contacted or treated cells of the subject, as compared to the endogenous levels of the laminin in one or more corresponding untreated cells of the subject. In some embodiments, administration of the recombinant nucleic acid, virus, medicament, and/or pharmaceutical composition or formulation to the subject increases laminin levels (transcript or protein levels) by at least about 2-fold in one or more contacted or treated cells of the subject, as compared to the endogenous levels of the laminin in one or more corresponding untreated cells of the subject. For example, administration of the recombinant nucleic acid, virus, medicament, and/or pharmaceutical composition or formulation may increase laminin levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of the laminin in one or more corresponding untreated cells of the subject. In some embodiments, the one or more contacted or treated cells are one or more cells of the epidermis, dermis, and/or mucosa. Methods of measuring transcript or protein levels from a sample are well known to one of ordinary skill in the art, including, for example, by qPCR, western blot, mass spectrometry, etc.

Other aspects of the present disclosure relate to enhancing, increasing, augmenting, and/or supplementing cell adhesion of one or more cells of a subject comprising administering to the subject any of the recombinant nucleic acids, viruses, medicaments, and/or pharmaceutical compositions or formulations described herein. In some embodiments, the enhanced, increased, augmented, or supplemented cell adhesion is in comparison to the levels of cell adhesion of a corresponding cell that has not been contacted with or administered the recombinant nucleic acids, viruses, medicaments, and/or pharmaceutical compositions described herein. In some embodiments, the one or more cells are one or more epidermal, dermal, and/or mucosal cells. In some embodiments, the one or more cells are one or more cells of the skin of the subject. In some embodiments, the cell adhesion is integrin-mediated cell adhesion. Methods of measuring cell adhesion are known to one of ordinary skill in the art (see e.g., Boettiger D. Methods Enzymol. 2007; 426:1-25). In some embodiments, the subject is a human. In some embodiments, the subject's genome comprises a mutation (e.g., a loss-of-function mutation, a pathogenic variant) in an endogenous laminin gene (e.g., a LAMA3, LAMB3, and/or LAMC2 gene). In some embodiments, the subject suffers from Junctional Epidermolysis Bullosa (JEB). In some embodiments, the JEB is Herlitz-type JEB (JEB-H). In some embodiments, the JEB is non-Herlitz-type JEB.

Other aspects of the present disclosure relate to: 1) enhancing, increasing, augmenting, and/or supplementing the lamina lucida of a subject; 2) stabilizing the lamina lucida of a subject; 3) inhibiting, slowing, preventing, and/or ameliorating the formation of blisters within the lamina lucida of a subject; and/or 4) preventing skin separation in the lamina lucida of a subject, comprising administering to the subject any of the recombinant nucleic acids, viruses, medicaments, and/or pharmaceutical compositions or formulations described herein. In some embodiments, the one or more beneficial effects on the structure or stability of the lamina lucida are in comparison to the structure and/or stability of the lamina lucida in the subject prior to administration of the recombinant nucleic acids, viruses, medicaments, and/or pharmaceutical compositions described herein (or in comparison to the structure and/or stability of the lamina lucida in an untreated region of the subject). Methods of monitoring changes/improvements in the structure and/or stability of the lamina lucida are known in the art, including, for example, by microscopic evaluation. In some embodiments, the subject is a human. In some embodiments, the subject's genome comprises a mutation (e.g., a loss-of-function mutation, a pathogenic variant) in an endogenous laminin gene (e.g., a LAMA3, LAMB3, and/or LAMC2 gene). In some embodiments, the subject suffers from Junctional Epidermolysis Bullosa (JEB). In some embodiments, the JEB is Herlitz-type JEB (JEB-H). In some embodiments, the JEB is non-Herlitz-type JEB.

Other aspects of the present disclosure relate to enhancing, increasing, augmenting, and/or supplementing epithelial basement membrane assembly, epithelial basement membrane organization, epithelial basement membrane adherence, and/or dermoepidermal junction integrity in a subject, comprising administering to the subject any of the recombinant nucleic acids, viruses, medicaments, and/or pharmaceutical compositions or formulations described herein. In some embodiments, the one or more beneficial effects on the assembly, organization, adherence, and/or integrity of the epithelial basement membrane and/or dermoepidermal junction are in comparison to the assembly, organization, adherence, and/or integrity of the basement membrane and/or dermoepidermal junction in the subject prior to administration of the recombinant nucleic acids, viruses, medicaments, and/or pharmaceutical compositions described herein (or in comparison to the assembly, organization, adherence, and/or integrity of the basement membrane and/or dermoepidermal junction in an untreated region of the subject). Methods of monitoring changes/improvements in the assembly, organization, adherence, and/or integrity of the basement membrane and/or dermoepidermal junction are known in the art, including, for example, by microscopic evaluation. In some embodiments, the subject is a human. In some embodiments, the subject's genome comprises a mutation (e.g., a loss-of-function mutation, a pathogenic variant) in an endogenous laminin gene (e.g., a LAMA3, LAMB3, and/or LAMC2 gene). In some embodiments, the subject suffers from Junctional Epidermolysis Bullosa (JEB). In some embodiments, the JEB is Herlitz-type JEB (JEB-H). In some embodiments, the JEB is non-Herlitz-type JEB.

Other aspects of the present disclosure relate to providing prophylactic, palliative, or therapeutic relief to one or more signs or symptoms of Junctional Epidermolysis Bullosa (JEB) in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation, a pathogenic variant) in an endogenous laminin gene (e.g., a LAMA3, LAMB3, and/or LAMC2 gene). In some embodiments, the subject has JEB or is at risk of developing JEB. In some embodiments, the JEB is Herlitz-type JEB (JEB-H). In some embodiments, the JEB is non-Herlitz-type JEB. Signs and/or symptoms of JEB may include, but are not limited to, blistering, wounding, and/or scarring of the skin, the presence or development of granulation tissue, skin erosion, deformity of the fingernails and/or toenails, fusion of the fingers and/or toes, tightening and/or thinning of the skin, contractures, blistering and/or scarring of the mucosa, difficulty breathing, horse cry, increased susceptibility to infection, dehydration, fluid loss, electrolyte imbalance, blistering and/or scarring of the gastrointestinal and/or gastrourinary tract, dental caries and/or enamel hypoplasia, hair loss, alopecia, malnutrition, growth retardation, anemia, and any combinations thereof.

In some embodiments, the recombinant nucleic acid expresses the encoded laminin protein(s) (e.g., human LamA3, LamB3, and/or LamC2 proteins) when the recombinant nucleic acid is delivered into one or more target cells of a subject. In some embodiments, expression of the laminin protein(s) (e.g., human LamA3, LamB3, and/or LamC2 proteins) enhances, increases, augments, and/or supplements the levels of laminins in one or more target cells. In some embodiments, expression of the laminin protein(s) (e.g., human LamA3, LamB3, and/or LamC2 proteins) enhances, increases, augments, and/or supplements the levels of laminins secreted by one or more target cells. In some embodiments, expression of the laminin protein(s) (e.g., human LamA3, LamB3, and/or LamC2 proteins) enhances, increases, augments, and/or supplements the stability of the extracellular matrix in the subject. In some embodiments, expression of the laminin protein(s) (e.g., human LamA3, LamB3, and/or LamC2 proteins) enhances, augments, and/or supplements the lamina lucida, basement membrane, and/or dermoepidermal junction in the subject. In some embodiments, expression of the laminin protein(s) (e.g., human LamA3, LamB3, and/or LamC2 proteins) treats a laminin deficiency in a JEB patient. In some embodiments, expression of the laminin protein(s) (e.g., human LamA3, LamB3, and/or LamC2 proteins) provides prophylactic, palliative, or therapeutic relief of one or more signs or symptoms (e.g., blistering) in a JEB patient.

Other aspects of the present disclosure relate to enhancing, increasing, augmenting, and/or supplementing the levels of a filaggrin polypeptide in one or more cells of a subject comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, the subject suffers from a skin disease, including, for example, atopic dermatitis, ichthyosis vulgaris, a skin peeling syndrome, etc. In some embodiments, the subject suffers from atopic dermatitis. In some embodiments, one or more portions of the skin of the subject is abraded or made more permeable prior to treatment.

In some embodiments, administration of the recombinant nucleic acid, virus, medicament, and/or pharmaceutical composition or formulation to the subject increases filaggrin levels (transcript or protein levels) by at least about 2-fold in one or more contacted or treated cells of the subject, as compared to the endogenous levels of the filaggrin in one or more corresponding untreated cells in the subject. For example, administration of the recombinant nucleic acid, virus, medicament, and/or pharmaceutical composition or formulation may increase filaggrin levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of filaggrin in one or more corresponding untreated cells in the subject. In some embodiments, the one or more contacted or treated cells are one or more cells of the epidermis and/or dermis (e.g., a keratinocyte or fibroblast). Methods of measuring transcript or protein levels from a sample are well known to one of ordinary skill in the art, including, for example, by qPCR, western blot, mass spectrometry, etc.

Other aspects of the present disclosure relate to a method of enhancing production of and/or stabilizing the stratum corneum layer of the skin of a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, the subject suffers from a skin disease, including, for example, atopic dermatitis, ichthyosis vulgaris, a skin peeling syndrome, etc. In some embodiments, the subject suffers from atopic dermatitis. In some embodiments, one or more portions of the skin of the subject is abraded or made more permeable prior to treatment. Methods of monitoring changes/improvements in the production and/or stabilization of the stratum corneum are known to one of ordinary skill in the art, including, for example, by microscopic evaluation.

Other aspects of the present disclosure relate to a method of reducing or treating a skin barrier function defect in a subject in need thereof comprising administering to the subject any of the recombinant nucleic acids, viruses, medicaments, and/or pharmaceutical compositions or formulations described herein. In some embodiments, the barrier function defect is transepidermal water loss (TEWL). In some embodiments, the methods of the present disclosure reduce transepidermal water loss in a subject in need thereof.

In some embodiments, the subject is a human. In some embodiments, the subject's genome comprises a mutation (e.g., a loss-of-function mutation) in an endogenous FLG and/or FLG2 genes. In some embodiments, the subject suffers from a skin disease, including, for example, atopic dermatitis, ichthyosis vulgaris, a skin peeling syndrome, etc. In some embodiments, the subject suffers from atopic dermatitis. In some embodiments, one or more portions of the skin of the subject is abraded or made more permeable prior to treatment. Methods of measuring barrier function, including TEWL, are well known to one of ordinary skill in the art, including, for example, by any of the methods described by Antonov et al. (Curr Probl Dermatol. 2016; 49:61-70).

Other aspects of the present disclosure relate to a method of reducing or inhibiting percutaneous transfer of allergens in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, the subject suffers from a skin disease, including, for example, atopic dermatitis, ichthyosis vulgaris, a skin peeling syndrome, etc. In some embodiments, the subject suffers from atopic dermatitis. In some embodiments, one or more portions of the skin of the subject is abraded or made more permeable prior to treatment. Methods of measuring percutaneous allergen transfer are well known to one of ordinary skill in the art, including, for example, by the methods described by Shtessel et al. (Ann Allergy Asthma Immunol. 2018 January; 120(1):80-83).

Other aspects of the present disclosure relate to a method of providing prophylactic, palliative, or therapeutic relief of one or more signs or symptoms of a skin disease in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, the skin disease is selected from atopic dermatitis, ichthyosis vulgaris, and a skin peeling syndrome (e.g., a noninflammatory type A skin peeling syndrome, an inflammatory type B skin peeling syndrome, acral peeling skin syndrome, etc.). In some embodiments, the subject suffers from atopic dermatitis. In some embodiments, one or more portions of the skin of the subject is abraded or made more permeable prior to treatment. In some embodiments, the recombinant nucleic acid, virus, medicament, and/or pharmaceutical composition or formulation is administered to one or more affected and/or unaffected areas of the subject.

Other aspects of the present disclosure relate to a method of providing prophylactic, palliative, or therapeutic relief of one or more signs or symptoms of atopic dermatitis in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, one or more portions of the skin of the subject is abraded or made more permeable prior to treatment. In some embodiments, the recombinant nucleic acid, virus, medicament, and/or pharmaceutical composition or formulation is administered to one or more affected and/or unaffected areas of the subject.

Signs and symptoms of atopic dermatitis may include, without limitation: dry skin; itching, which may be severe, especially at night; red to brownish-gray patches, especially on the hands, feet, ankles, wrists, neck, upper chest, eyelids, inside the bend of the elbows and knees, and in infants, the face and scalp; small, raised bumps on the skin which may be weeping; skin infections; eyelid dermatitis; cataracts; increased IgE levels; thickened, cracked, or scaly skin; and raw, sensitive, swollen skin from scratching.

Other aspects of the present disclosure relate to a method of providing prophylactic, palliative, or therapeutic relief of one or more signs or symptoms of ichthyosis vulgaris in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, one or more portions of the skin of the subject is abraded or made more permeable prior to treatment. In some embodiments, the recombinant nucleic acid, virus, and/or pharmaceutical composition is administered to one or more affected and/or unaffected areas of the subject.

Signs and symptoms of ichthyosis vulgaris may include, without limitation: flaky scalp; itchy skin; polygon-shaped or tile-like scales on the skin; scales that are brown, grey, or white; severely dry skin; painful cracks in the skin; and thickened skin.

Other aspects of the present disclosure relate to a method of providing prophylactic, palliative, or therapeutic relief of one or more signs or symptoms of a skin peeling syndrome (e.g., a noninflammatory type A skin peeling syndrome, an inflammatory type B skin peeling syndrome, acral peeling skin syndrome, etc.) in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous FLG and/or FLG2 genes. In some embodiments, one or more portions of the skin of the subject is abraded or made more permeable prior to treatment. In some embodiments, the recombinant nucleic acid, virus, medicament, and/or pharmaceutical composition or formulation is administered to one or more affected and/or unaffected areas of the subject.

Signs and symptoms of a skin peeling syndrome may include, without limitation: abnormal blistering of the skin; aminoaciduria; dry skin; ichthyosis; multiple café-au-lait spots; brittle hair; erythema; increased IgE levels; onycholysis; and scaling skin.

The recombinant nucleic acids, viruses, medicaments, and/or pharmaceutical compositions or formulations described herein may be administered by any suitable method or route known in the art, including, without limitation, by oral administration, sublingual administration, buccal administration, topical administration, rectal administration, via inhalation, transdermal administration, subcutaneous injection, intradermal injection, intravenous injection, intra-arterial injection, intramuscular injection, intracardiac injection, intraosseous injection, intraperitoneal injection, transmucosal administration, vaginal administration, intravitreal administration, intraorbital administration, subretinal administration, subconjunctival administration (e.g., the use of subconjunctival depots), suprachoroidal administration, intra-articular administration, peri-articular administration, local administration, epicutaneous administration, or any combinations thereof. The present disclosure thus encompasses methods of delivering any of the recombinant nucleic acids, viruses, medicaments, and/or pharmaceutical compositions or formulations described herein to an individual (or a specific site or tissue thereof).

In some embodiments, the recombinant nucleic acid, virus, medicaments, and/or pharmaceutical composition or formulation used in the methods of the present disclosure is administered cutaneously, topically, transdermally, subcutaneously, intradermally, transmucosally, sublingually, nasally, buccally, intravitreally, subretinally, subconjunctivally, suprachoroidally, intraarticularly, or via inhalation to the subject. In some embodiments, the recombinant nucleic acid, virus, medicament, and/or pharmaceutical composition or formulation is administered topically, transdermally, subcutaneously, intradermally or transmucosally to the subject. In some embodiments, the recombinant nucleic acid, virus, medicament, and/or pharmaceutical composition or formulation is administered topically, transdermally, or intradermally to the subject. In some embodiments, the recombinant nucleic acid, virus, medicament, and/or pharmaceutical composition or formulation is administered topically to the subject. In some embodiments, the recombinant nucleic acid, virus, medicament, and/or pharmaceutical composition or formulation is administered intradermally to the subject. In some embodiments, the recombinant nucleic acid, virus, medicament, and/or pharmaceutical composition or formulation is administered orally, sublingually, buccally, nasally, or via inhalation to the subject. In some embodiments, the recombinant nucleic acid, virus, medicament, and/or pharmaceutical composition or formulation is administered orally or via inhalation to the subject. In some embodiments, the recombinant nucleic acid, virus, medicament, and/or pharmaceutical composition or formulation is administered intraorbitally, intravitreally, subretinally, subconjunctivally, suprachoroidally, or topically (to the eye) of the subject.

In some embodiments, the recombinant nucleic acid, virus, medicament, and/or pharmaceutical composition or formulation is administered once to the subject. In some embodiments, the recombinant nucleic acid, virus, medicament, and/or pharmaceutical composition or formulation is administered at least twice (e.g., at least 2 times, at least 3 times, at least 4 times, at least 5 times, at least 10 times, etc.) to the subject. In some embodiments, at least about 1 hour (e.g., at least about 1 hour, at least about 6 hours, at least about 12 hours, at least about 18 hours, at least about 1 day, at least about 2 days, at least about 3 days, at least about 4 days, at least about 5 days, at least about 6 days, at least about 7 days, at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.). In some embodiments, the recombinant nucleic acid, virus, medicament, and/or pharmaceutical composition or formulation is administered one, two, three, four, five or more times per day to the subject. In some embodiments, the recombinant nucleic acid, virus, medicament, and/or pharmaceutical composition or formulation is administered to one or more affected (e.g., one or more regions displaying one or more signs or symptoms of JEB) and/or unaffected areas of the subject.

In some embodiments, one or more portions of the skin of the subject is abraded or made more permeable prior to treatment with a recombinant nucleic acid, virus, medicament, and/or pharmaceutical composition or formulation described herein. Any suitable method of abrading the skin or increasing skin permeability known in the art may be used, including, for example, use of a dermal roller, repeated use of adhesive strips to remove layers of skin cells (tape stripping), scraping with a scalpel or blade, use of sandpaper, use of chemical permeation enhancers or electrical energy, use of sonic or ultrasonic energy, use of light (e.g., laser) energy, use of micron-sized needles or blades with a length suitable to pierce but not completely pass through the epidermis, etc.

VII. HOST CELLS

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), *Serratia* (e.g., *S. marcescans*), and *Shigella*, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NS0 and Sp2/0. In some embodiments, the host cell is a human or non-human primate cell. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1 hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in WO2015/009952 and/or WO2017/176336.

VIII. ARTICLES OF MANUFACTURE OR KITS

Certain aspects of the present disclosure relate to an article of manufacture or a kit comprising any of the recombinant nucleic acids, viruses, medicaments, and/or pharmaceutical compositions or formulations described herein. In some embodiments, the article of manufacture or kit comprises a package insert comprising instructions for administering the recombinant nucleic acid, virus, medicament, and/or pharmaceutical composition or formulation to treat a laminin deficiency (e.g., in a subject harboring a laminin gene mutation such as a LAMA3, LAMB3, and/or LAMC2 gene mutation) and/or to provide prophylactic, palliative, or therapeutic relief of one or more signs or symptoms of a disease or disorder associated with a laminin deficiency (such as JEB) in a subject in need thereof. In some embodiments, the article of manufacture or kit comprises a package insert comprising instructions for administering the recombinant nucleic acid, virus, medicament, and/or pharmaceutical composition or formulation to treat a filaggrin deficiency (e.g., in a subject harboring an FLG or FLG2 gene mutation) and/or to provide prophylactic, palliative, or therapeutic relief of one or more signs or symptoms of a disease or disorder associated with a filaggrin deficiency (such as atopic dermatitis, ichthyosis vulgaris, a peeling skin syndrome, etc.) in a subject in need thereof.

Suitable containers for the recombinant nucleic acids, viruses, medicaments, and/or pharmaceutical compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, needles, syringes, package inserts, and the like.

IX. ENUMERATED EMBODIMENTS

Embodiment 1: a recombinant herpes virus genome comprising one or more polynucleotides encoding a laminin polypeptide.

Embodiment 2: the recombinant herpes virus genome of embodiment 1, wherein the recombinant herpes virus genome is replication competent.

Embodiment 3: the recombinant herpes virus genome of embodiment 1, wherein the recombinant herpes virus genome is replication defective.

Embodiment 4: the recombinant herpes virus genome of any one of embodiments 1-3, wherein the recombinant herpes virus genome comprises the one or more poly-nucleotides encoding a laminin polypeptide within one or more viral gene loci.

Embodiment 5: the recombinant herpes virus genome of any one of embodiments 1-4, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

Embodiment 6: the recombinant herpes virus genome of any one of embodiments 1-5, wherein the laminin polypeptide is a human laminin (Lam) polypeptide.

Embodiment 7: the recombinant herpes virus genome of embodiment 6, wherein the human laminin (Lam) polypeptide is selected from the group consisting of a human LamA1 polypeptide, a human LamA2 polypeptide, a human LamA3 polypeptide, a human LamA4 polypeptide, a human LamA5 polypeptide, a human LamB1 polypeptide, a human LamB2 polypeptide, a human LamB3 polypeptide, a human LamC1 polypeptide, a human LamC2 polypeptide, a human LamC3 polypeptide, and any chimeric polypeptides thereof.

Embodiment 8: the recombinant herpes virus genome of embodiment 6 or 7, wherein the human laminin (Lam) polypeptide is selected from the group consisting of a human LamA3 polypeptide, a human LamB3 polypeptide, and a human LamC2 polypeptide.

Embodiment 9: the recombinant herpes virus genome of any one of embodiments 1-8, wherein the laminin polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 7-9.

Embodiment 10: the recombinant herpes virus genome of any one of embodiments 1-9, wherein the recombinant herpes virus genome is a recombinant herpes simplex virus genome.

Embodiment 11: the recombinant herpes virus genome of embodiment 10, wherein the recombinant herpes simplex virus genome is a recombinant type 1 herpes simplex virus (HSV-1) genome, a recombinant type 2 herpes simplex virus (HSV-2) genome, or any derivatives thereof.

Embodiment 12: the recombinant herpes virus genome of embodiment 10 or 11, wherein the recombinant herpes simplex virus genome comprises an inactivating mutation.

Embodiment 13: the recombinant herpes virus genome of embodiment 12, wherein the inactivating mutation is in a herpes simplex virus gene.

Embodiment 14: the recombinant herpes virus genome of embodiment 13, wherein the inactivating mutation is a deletion of the coding sequence of the herpes simplex virus gene.

Embodiment 15: the recombinant herpes virus genome of embodiment 13 or 14, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 16: the recombinant herpes virus genome of embodiment 15, wherein the recombinant herpes simplex virus genome comprises an inactivating mutation in one or both copies of the ICP4 gene.

Embodiment 17: the recombinant herpes virus genome of embodiment 15 or 16, wherein the recombinant herpes simplex virus genome comprises an inactivating mutation in the ICP22 gene.

Embodiment 18: the recombinant herpes virus genome of any one of embodiments 15-17, wherein the recombinant herpes simplex virus genome comprises an inactivating mutation in the UL41 gene.

Embodiment 19: the recombinant herpes virus genome of any one of embodiments 15-18, wherein the recombinant herpes simplex virus genome comprises an inactivating mutation in one or both copies of the ICP0 gene.

Embodiment 20: the recombinant herpes virus genome of any one of embodiments 15-19, wherein the recombinant herpes simplex virus genome comprises an inactivating mutation in the ICP27 gene.

Embodiment 21: the recombinant herpes virus genome of any one of embodiments 10-20, wherein the recombinant herpes simplex virus genome comprises the one or more polynucleotides encoding the laminin polypeptide within one or both of the ICP4 viral gene loci.

Embodiment 22: the recombinant herpes virus genome of any one of embodiments 10-21, wherein the recombinant herpes simplex virus genome comprises the one or more polynucleotides encoding the laminin polypeptide within the ICP22 viral gene locus.

Embodiment 23: the recombinant herpes virus genome of any one of embodiments 10-22, wherein the recombinant herpes simplex virus genome comprises the one or more polynucleotides encoding the laminin polypeptide within the UL41 viral gene locus.

Embodiment 24: the recombinant herpes virus genome of any one of embodiments 1-23, wherein the recombinant herpes virus genome has reduced cytotoxicity when introduced into a target cell as compared to a corresponding wild-type herpes virus genome.

Embodiment 25: the recombinant herpes virus genome of embodiment 24, wherein the target cell is a human cell.

Embodiment 26: the recombinant herpes virus genome of embodiment 24 or 25, wherein the target cell is a cell of the epidermis and/or dermis.

Embodiment 27: the recombinant herpes virus genome of any one of embodiments 24-26, wherein the target cell is a keratinocyte or fibroblast.

Embodiment 28: a herpes virus comprising the recombinant herpes virus genome of any one of embodiments 1-27.

Embodiment 29: the herpes virus of embodiment 28, wherein the herpes virus is replication competent.

Embodiment 30: the herpes virus of embodiment 28, wherein the herpes virus is replication defective.

Embodiment 31: the herpes virus of any one of embodiments 28-30, wherein the herpes virus has reduced cytotoxicity as compared to a corresponding wild-type herpes virus.

Embodiment 32: the herpes virus of any one of embodiments 28-31, wherein the herpes virus is selected from the group consisting of a herpes simplex virus, a varicella zoster virus, a human cytomegalovirus, a herpesvirus 6A, a herpesvirus 6B, a herpesvirus 7, a Kaposi's sarcoma-associated herpesvirus, and any derivatives thereof.

Embodiment 33: the herpes virus of any one of embodiments 28-32, wherein the herpes virus is a herpes simplex virus.

Embodiment 34: the herpes virus of embodiment 32 or 33, wherein the herpes simplex virus is a type 1 herpes simplex virus (HSV-1), a type 2 herpes simplex virus (HSV-2), or any derivatives thereof.

Embodiment 35: a pharmaceutical composition comprising the recombinant herpes virus genome of any one of embodiments 1-27 or the herpes virus of any one of embodiments 28-34 and a pharmaceutically acceptable excipient.

Embodiment 36: the pharmaceutical composition of embodiment 35, wherein the pharmaceutical composition is suitable for topical, transdermal, subcutaneous, intradermal, oral, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 37: the pharmaceutical composition of embodiment 35 or 36, wherein the pharmaceutical composition is suitable for topical, transdermal, subcutaneous, intradermal, or transmucosal administration.

Embodiment 38: the pharmaceutical composition of any one of embodiments 35-37, wherein the pharmaceutical composition is suitable for topical administration.

Embodiment 39: the pharmaceutical composition of embodiment 35 or 36, wherein the pharmaceutical composition is suitable for oral or inhaled administration.

Embodiment 40: the pharmaceutical composition of any one of embodiments 35-39, wherein the pharmaceutical composition comprises a hydroxypropyl methylcellulose gel.

Embodiment 41: the pharmaceutical composition of any one of embodiments 35-40, wherein the pharmaceutical composition comprises a phosphate buffer.

Embodiment 42: the pharmaceutical composition of any one of embodiments 35-41, wherein the pharmaceutical composition comprises glycerol.

Embodiment 43: the pharmaceutical composition of any one of embodiments 35-42, wherein the pharmaceutical composition comprises a lipid carrier.

Embodiment 44: the pharmaceutical composition of any one of embodiments 35-43, wherein the pharmaceutical composition comprises a nanoparticle carrier.

Embodiment 45: a method of enhancing, increase, augmenting, and/or supplementing the levels of a laminin polypeptide in one or more cells of a subject, the method comprising administering to the subject an effective amount of the herpes virus of any one of embodiments 28-34 or the pharmaceutical composition of any one of embodiments 35-44.

Embodiment 46: a method of enhancing, increasing, augmenting, and/or supplementing cell adhesion of one or more cells in the skin of a subject, the method comprising administering to the subject an effective amount of the herpes virus of any one of embodiments 28-34 or the pharmaceutical composition of any one of embodiments 35-44.

Embodiment 47: the method of embodiment 46, wherein the cell adhesion is integrin-mediated cell adhesion.

Embodiment 48: a method of enhancing, increasing, augmenting, and/or supplementing the lamina lucida of a subject, the method comprising administering to the subject an effective amount of the herpes virus of any one of embodiments 28-34 or the pharmaceutical composition of any one of embodiments 35-44.

Embodiment 49: a method of enhancing, increasing, augmenting, and/or supplementing epithelial basement membrane assembly, epithelial basement membrane organization, and/or epithelial basement adherence of a subject, the method comprising administering to the subject an effective amount of the herpes virus of any one of embodiments 28-34 or the pharmaceutical composition of any one of embodiments 35-44.

Embodiment 50: a method of providing prophylactic, palliative, or therapeutic relief to one or more signs or symptoms of Junctional Epidermolysis Bullosa (JEB) in a subject in need thereof, the method comprising administering to the subject an effective amount of the herpes virus of any one of embodiments 28-34 or the pharmaceutical composition of any one of embodiments 35-44.

Embodiment 51: the method of any one of embodiments 45-50, wherein the subject is a human.

Embodiment 52: the method of any one of embodiments 45-51, wherein the subject's genome comprises a loss-of-function mutation in a laminin gene.

Embodiment 53: the method of any one of embodiments 45-52, wherein the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject.

Embodiment 54: the method of any one of embodiments 45-53, wherein the herpes virus or pharmaceutical composition is administered topically, transdermally, subcutaneously, or intradermally to the subject.

Embodiment 55: the method of any one of embodiments 45-54, wherein the herpes virus or pharmaceutical composition is administered topically to the subject.

Embodiment 56: the method of any one of embodiments 45-54, wherein the herpes virus or pharmaceutical composition is administered intradermally to the subject.

Embodiment 57: the method of any one of embodiments 45-56, wherein the skin of the subject is abraded prior to administration.

Embodiment 58: the method of any one of embodiments 45-53, wherein the herpes virus or pharmaceutical composition is administered orally or via inhalation.

Embodiment 59: the method of any one of embodiments 45-58, wherein the herpes virus or pharmaceutical composition is administered one, two, three, four, five or more times per day.

Embodiment 60: the method of any one of embodiments 45-59, wherein the herpes virus or pharmaceutical composition is administered to one or more affected and/or unaffected areas of the subject.

Embodiment 61: the method of any one of embodiments 50-60, wherein the one or more signs or symptoms of JEB are selected from blistering, wounding, and/or scarring of the skin, granulation tissue, skin erosion, deformity of the fingernails and/or toenails, fusion of the fingers and/or toes, tightening and/or thinning of the skin, contractures, blistering and/or scarring of the mucosa, difficulty breathing, horse cry, increased susceptibility to infection, dehydration, fluid loss, electrolyte imbalance, blistering and/or scarring of the gastrointestinal and/or gastrourinary tract, dental caries and/or enamel hypoplasia, hair loss, malnutrition, growth retardation, anemia, and any combinations thereof.

Embodiment 62: the method of any one of embodiments 50-61, wherein the subject suffers from Junctional Herlitz Epidermolysis Bullosa (JEB-H).

Embodiment 63: the method of any one of embodiments 50-61, wherein the subject suffers from Junctional non-Herlitz Epidermolysis Bullosa (JEB-nH).

Embodiment 64: a recombinant herpes virus genome comprising one or more polynucleotides encoding a filaggrin polypeptide.

Embodiment 65: the recombinant herpes virus genome of embodiment 64, wherein the recombinant herpes virus genome is replication competent.

Embodiment 66: the recombinant herpes virus genome of embodiment 64, wherein the recombinant herpes virus genome is replication defective.

Embodiment 67: the recombinant herpes virus genome of any one of embodiments 64-66, wherein the recombinant herpes virus genome comprises the one or more polynucleotides encoding the filaggrin polypeptide within one or more viral gene loci.

Embodiment 68: the recombinant herpes virus genome of any one of embodiments 64-67, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

Embodiment 69: the recombinant herpes virus genome of any one of embodiments 64-68, wherein the filaggrin polypeptide is a human filaggrin polypeptide or a human filaggrin-2 polypeptide.

Embodiment 70: the recombinant herpes virus genome of any one of embodiments 64-69, wherein the filaggrin polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 39-50.

Embodiment 71: the recombinant herpes virus genome of any one of embodiments 64-70, wherein the filaggrin polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 39.

Embodiment 72: the recombinant herpes virus genome of any one of embodiments 64-71, wherein the recombinant herpes virus genome is a recombinant herpes simplex virus genome.

Embodiment 73: the recombinant herpes virus genome of embodiment 72, wherein the recombinant herpes simplex virus genome is a recombinant HSV-1 genome, a recombinant HSV-2 genome, or any derivatives thereof.

Embodiment 74: the recombinant herpes virus of embodiment 72 or 73, wherein the recombinant herpes simplex virus genome comprises an inactivating mutation.

Embodiment 75: the recombinant herpes virus of embodiment 74, wherein the inactivating mutation is in a herpes simplex virus gene.

Embodiment 76: the recombinant herpes virus genome of embodiment 75, wherein the inactivating mutation is a deletion of the coding sequence of the herpes simplex virus gene.

Embodiment 77: the recombinant herpes virus genome of embodiment 75 or 76, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 78: the recombinant herpes virus genome of embodiment 77, wherein the recombinant herpes simplex virus genome comprises an inactivating mutation in one or both copies of the ICP4 gene.

Embodiment 79: the recombinant herpes virus genome of embodiment 77 or 78, wherein the recombinant herpes simplex virus genome comprises an inactivating mutation in the ICP22 gene.

Embodiment 80: the recombinant herpes virus genome of any one of embodiments 77-79, wherein the recombinant herpes simplex virus genome comprises an inactivating mutation in the UL41 gene.

Embodiment 81: the recombinant herpes virus genome of any one of embodiments 77-80, wherein the recombinant herpes simplex virus genome comprises an inactivating mutation in one or both copies of the ICP0 gene.

Embodiment 82: the recombinant herpes virus genome of any one of embodiments 77-81, wherein the recombinant herpes simplex virus genome comprises an inactivating mutation in the ICP27 gene.

Embodiment 83: the recombinant herpes virus genome of any one of embodiments 72-82, wherein the recombinant herpes simplex virus genome comprises the one or more polynucleotides encoding the filaggrin polypeptide within one or both of the ICP4 viral gene loci.

Embodiment 84: the recombinant herpes virus genome of any one of embodiments 72-83, wherein the recombinant herpes simplex virus genome comprises the one or more polynucleotides encoding the filaggrin polypeptide within the ICP22 viral gene locus.

Embodiment 85: the recombinant herpes virus genome of any one of embodiments 72-84, wherein the recombinant herpes simplex virus genome comprises the one or more polynucleotides encoding the filaggrin polypeptide within the UL41 viral gene locus.

Embodiment 86: the recombinant herpes virus genome of any one of embodiments 64-85, wherein the recombinant herpes virus genome has reduced cytotoxicity when introduced into a target cell as compared to a corresponding wild-type herpes virus genome.

Embodiment 87: the recombinant herpes virus genome of embodiment 86, wherein the target cell is a human cell.

Embodiment 88: the recombinant herpes virus genome of embodiment 86 or 87, wherein the target cell is a cell of the epidermis and/or dermis.

Embodiment 89: the recombinant herpes virus genome of any one of embodiments 86-88, wherein the target cell is a keratinocyte or fibroblast.

Embodiment 90: a herpes virus comprising the recombinant herpes virus genome of any one of embodiments 64-89.

Embodiment 91: the herpes virus of embodiments 90, wherein the herpes virus is replication competent.

Embodiment 92: the herpes virus of embodiment 90, wherein the herpes virus is replication defective.

Embodiment 93: the herpes virus of any one of embodiments 90-92, wherein the herpes virus has reduced cytotoxicity as compared to a corresponding wild-type herpes virus.

Embodiment 94: the herpes virus of any one of embodiments 90-93, wherein the herpes virus is selected from the group consisting of a herpes simplex virus, a varicella zoster virus, a human cytomegalovirus, a herpesvirus 6A, a herpesvirus 6B, a herpesvirus 7, and a Kaposi's sarcoma-associated herpesvirus.

Embodiment 95: the herpes virus of any one of embodiments 90-94, wherein the herpes virus is a herpes simplex virus.

Embodiment 96: the herpes virus of embodiment 94 or 95, wherein the herpes simplex virus is a herpes simplex type 1 virus (HSV-1), a herpes simplex type 2 virus (HSV-2), or any derivatives thereof.

Embodiment 97: a pharmaceutical composition comprising the recombinant herpes virus genome of any one of embodiments 64-89 or the herpes virus of any one of embodiments 90-96 and a pharmaceutically acceptable excipient.

Embodiment 98: the pharmaceutical composition of embodiment 97, wherein the pharmaceutical composition is suitable for topical, transdermal, subcutaneous, intradermal, oral, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 99: the pharmaceutical composition of embodiment 97 or 98, wherein the pharmaceutical composition is suitable for topical, transdermal, subcutaneous, intradermal, or transmucosal administration.

Embodiment 100: the pharmaceutical composition of any one of embodiments 97-99, wherein the pharmaceutical composition is suitable for topical administration.

Embodiment 101: the pharmaceutical composition of any one of embodiments 97-100, wherein the pharmaceutical composition comprises a hydroxypropyl methylcellulose gel.

Embodiment 102: the pharmaceutical composition of any one of embodiments 97-101, wherein the pharmaceutical composition comprises a phosphate buffer.

Embodiment 103: the pharmaceutical composition of any one of embodiments 97-102, wherein the pharmaceutical composition comprises glycerol.

Embodiment 104: the pharmaceutical composition of any one of embodiments 97-103, wherein the pharmaceutical composition comprises a lipid carrier.

Embodiment 105: the pharmaceutical composition of any one of embodiments 97-104, wherein the pharmaceutical composition comprises a nanoparticle carrier.

Embodiment 106: a method of enhancing, increasing, augmenting, and/or supplementing the levels of a filaggrin polypeptide in one or more cells of a subject, the method comprising administering to the subject an effective amount of the herpes virus of any one of embodiments 90-96 or the pharmaceutical composition of any one of embodiments 97-105.

Embodiment 107: a method of enhancing production of and/or stabilizing the stratum corneum layer of the skin of a subject in need thereof, the method comprising administering to the subject an effective amount of the herpes virus of any one of embodiments 90-96 or the pharmaceutical composition of any one of embodiments 97-105.

Embodiment 108: a method of reducing or treating a skin barrier function defect in a subject in need thereof, the method comprising administering to the subject an effective amount of the herpes virus of any one of embodiments 90-96 or the pharmaceutical composition of any one of embodiments 97-105.

Embodiment 109: the method of embodiment 108, wherein the skin barrier defect is transepithelial water loss (TEWL).

Embodiment 110: a method of reducing or inhibiting percutaneous transfer of allergens in a subject in need thereof, the method comprising administering to the subject an effective amount of the herpes virus of any one of embodiments 90-96 or the pharmaceutical composition of any one of embodiments 97-105.

Embodiment 111: a method of providing prophylactic, palliative, or therapeutic relief of one or more signs or symptoms of a skin disease in a subject in need thereof, the method comprising administering to the subject an effective amount of the herpes virus of any one of embodiments 90-96 or the pharmaceutical composition of any one of embodiments 97-105.

Embodiment 112: the method of embodiment 111, wherein the skin disease is selected from the group consisting of atopic dermatitis, ichthyosis vulgaris, and a peeling skin syndrome.

Embodiment 113: a method of providing prophylactic, palliative, or therapeutic relief of one or more signs or symptoms of atopic dermatitis in a subject in need thereof, the method comprising administering to the subject an effective amount of the herpes virus of any one of embodiments 90-96 or the pharmaceutical composition of any one of embodiments 97-105.

Embodiment 114: the method of embodiment 113, wherein the one or more signs or symptoms of atopic dermatitis are selected from the group consisting of itchy skin, dry skin, red to brownish-grey patches on the skin, small raised bumps on the skin, thickened skin, cracked skin, scaly skin, swollen skin, weeping sores, skin infections, eyelid dermatitis, cataracts, and any combinations thereof.

Embodiment 115: a method of providing prophylactic, palliative, or therapeutic relief of one or more signs or symptoms of ichthyosis vulgaris in a subject in need thereof, the method comprising administering to the subject an effective amount of the herpes virus of any one of embodiments 90-96 or the pharmaceutical composition of any one of embodiments 97-105.

Embodiment 116: the method of embodiment 115, wherein the one or more signs or symptoms of ichthyosis vulgaris are selected from the group consisting of flaky scalp, itchy skin, polygon-shaped or tile-like scales on the skin, scales that are brown, grey, or white, severely dry skin, painful cracks in the skin, thickened skin, and any combinations thereof.

Embodiment 117: the method of any one of embodiments 106-116, wherein the subject is a human Embodiment 118: the method of any one of embodiments 106-117, wherein the subject's genome comprises a loss-of-function mutation in an FLG gene and/or an FLG2 gene.

Embodiment 119: the method of any one of embodiments 106-118, wherein the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject.

Embodiment 120: the method of any one of embodiments 106-119, wherein the herpes virus or pharmaceutical composition is administered topically, transdermally, subcutaneously, intradermally, or transmucosally to the subject.

Embodiment 121: the method of any one of embodiments 106-120, wherein the herpes virus or pharmaceutical composition is administered topically to the subject.

Embodiment 122: the method of any one of embodiments 106-121, wherein the skin of the subject is abraded prior to administration.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art, and are to be included within the spirit and purview of this application and scope of the appended claims.

Example 1

Generation of Modified Herpes Simplex Virus Vectors Encoding Human Laminins

The following example describes the construction of recombinant herpes simplex type-1 viruses modified to express human laminin proteins.

Figures 1B, 1C:
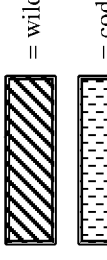

Wild-type herpes simplex virus genomes (FIG. 1A) were first modified by deleting the coding sequence of both copies of the viral ICP4 gene as well as the single copy ICP22 gene (4/22). The 4/22 viral genome was also engineered to contain an mCherry expression cassette in each of the ICP4 loci. The viral genome was then further modified to encode wild-type or codon-optimized human LAMB3 or LAMC2. Briefly, plasmids containing wild-type or codon-optimized human LAMB3 or LAMC2 (under control of the hCMV promoter) and flanked by the upstream (US) and downstream (DS) regions of ICP4 were transfected into Vero cells modified to express the herpes virus ICP4 gene. These transfected cells were then infected with the modified mCherry-expressing viruses described above. The US and DS ICP4 regions flanking the laminin genes allowed for a double crossover and replacement of each of the mCherry loci. Visual screening for the absence of mCherry fluorescence was then used to identify cells containing recombined virus. Four variants of these attenuated recombinant viral constructs were created with this method: 1) a recombinant ΔICP4/ΔICP22-modified HSV-1 genome comprising expression cassettes containing wild-type human LAMB3 (SEQ ID NO: 3) under the control of a heterologous promoter integrated at each ICP4 locus (FIG. 1B); 2) a recombinant ΔICP4/ΔICP22-modified HSV-1 genome comprising expression cassettes containing codon-optimized human LAMB3 (SEQ ID NO: 4) under the control of a heterologous promoter integrated at each ICP4 locus (FIG. 1C); 3) a recombinant ΔICP4/ΔICP22-modified HSV-1 genome comprising expression cassettes containing wild-type human LAMC2 (SEQ ID NO: 5) under the control of a heterologous promoter integrated at each ICP4 locus (FIG. 1D); and 4) a recombinant ΔICP4/ΔICP22-modified HSV-1 genome comprising expression cassettes containing codon-optimized human LAMC2 (SEQ ID NO: 6) under the control of a heterologous promoter integrated at each ICP4 locus (FIG. 1E). Multiple isolates of each of the modified viruses were collected for further validation.

Figures 2A, 2B:
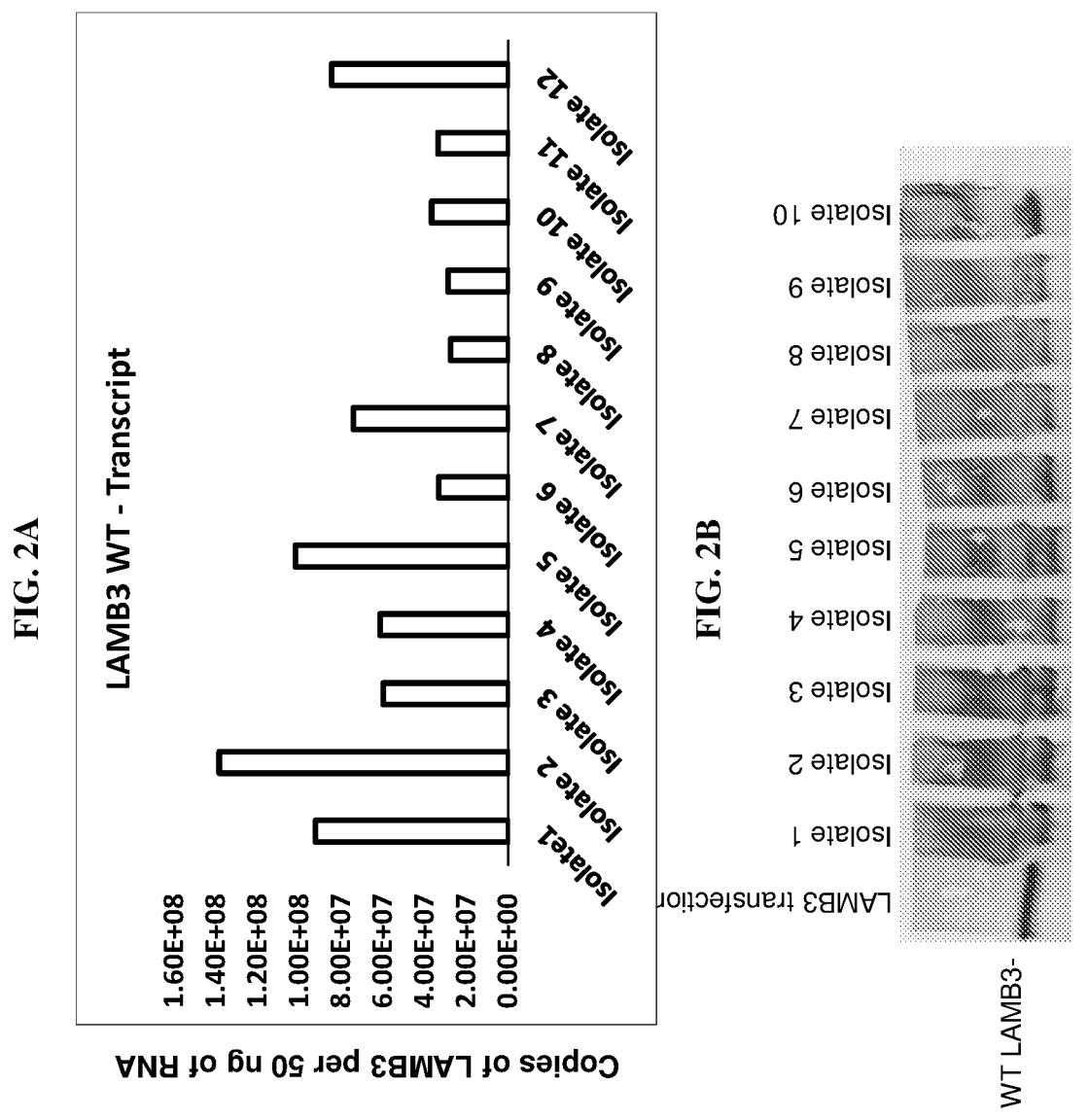

To test whether these isolates were capable of expressing the encoded wild-type human LamB3 protein, ICP4-complementing Vero cells were plated in 6-well plates and were infected with 12 untitered viral isolates of wild-type LamB3-encoding viruses until completion of infection. After infection, RNA was harvested, cDNA was generated, and expression of wild-type LAMB3 from each isolate was determined by qRT-PCR (FIG. 2A). All 12 isolates were capable of expressing wild-type human LAMB3 in the transduced Vero cells at varying levels. The ability of 10 of these isolates to express human LamB3 was also tested by western blot. ICP4-complementing Vero cells were plated in 6-well plates and were infected with 10 untitered viral isolates of wild-type LamB3 expressing viruses until completion of infection. A well of Vero cells was transfected with a LamB3 expression plasmid as a positive control. After infection, the cells were collected by gentle scraping, centrifuged to collect cell pellets, culture medium was aspirated, and the cell pellets were washed once with PBS. Following washing, each cell pellet was resuspended in 200 µL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. After electrophoresis, the protein was transferred to a PVDF membrane, and the membrane was blocked for 30 minutes in 5% milk/TBS. Primary rabbit anti-LamB3 antibody (Abcam, cat. No. ab128864) was then added to the PVDF membrane at 1:1000 dilution in 5% milk/TBS and incubated overnight at RT° C. (~16 hours). The blots were then washed 3× for 5 minutes each with TBS, and then stained with an AP-conjugated goat anti-rabbit IgG antibody (Sigma, cat. No. A3687) in 5% milk/TBS for 1 hour at RT° C. The membranes were then washed 3× for 5 minutes each with TBS, BCIP/NBT was added, and the blots were developed for ~10 minutes at RT° C. In agreement with the qRT-PCR data, all 10 viral isolates were capable of expressing the encoded wild-type human LamB3 protein at varying levels (FIG. 2B).

Figure 3:
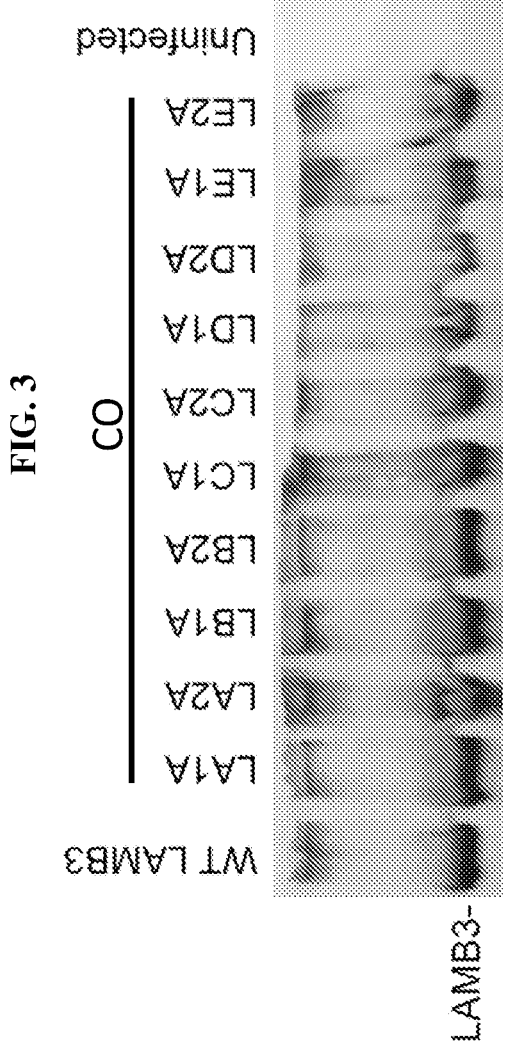
FIG. 3 shows expression of wild-type (WT) or codon-optimized (CO) human LamB3 protein in Vero cells infected with the indicated viral isolates, as assessed by western blot. Uninfected Vero cells were used as a negative control.

Viruses encoding codon-optimized variants of human LamB3 were also tested for their ability to express their cargo in Vero cells by western blot analysis. Briefly, 10 untitered viral isolates of codon-optimized (CO) LamB3-encoding viruses were used to infect Vero cells, cell pellets were collected, each pellet was resuspended in RIPA buffer containing protease inhibitors, and western blots were conducted using these cell lysates, as described above. All 10 viral isolates were capable of expressing the encoded codon-optimized human LamB3 in Vero cells (FIG. 3).

Figure 4:
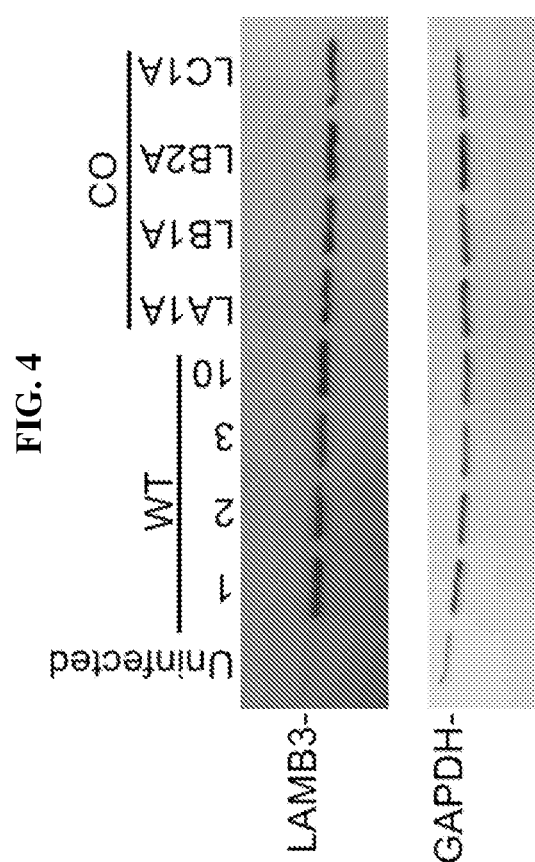
FIG. 4 shows expression of wild-type (WT) or codon-optimized (CO) human LamB3 protein in primary human keratinocytes infected with the indicated viral isolates, as assessed by western blot. Uninfected primary keratinocytes were used as a negative control; GAPDH was used as a loading control.

Next, four viral isolates encoding either wild-type or codon-optimized LAMB3 were tested for their capacity to transduce primary human cells and express their cargo. Immortalized primary normal keratinocytes were infected at a multiplicity of infection (MOI) of 1.0 for 48 hours. Uninfected cells were used as a negative control. Expression of LamB3 in the infected human keratinocytes was then examined by western blot. Western blots were carried out as described above using a primary rabbit anti-LamB3 antibody (Abcam, cat. No. ab 128864). In line with the data generated using Vero cells, the viral isolates expressing either wild-type and codon-optimized LamB3 were confirmed to effectively transduce primary human keratinocytes and express their encoded construct at suitable levels (FIG. 4).

To test whether LamC2-containing isolates were capable of expressing the encoded wild-type or codon-optimized human LAMC2, ICP4-complementing Vero cells were plated in 6-well plates and were infected with a number of untitered wild-type or codon-optimized LAMC2-expressing viral isolates until completion of infection. After infection, RNA was harvested, cDNA was generated, and expression of wild-type LAMC2 (FIG. 5A) or codon-optimized LAMC2 (FIG. 5B) from each isolate was determined by qRT-PCR. 8/12 isolates were capable of expressing wild-type human LAMC2 in the transduced Vero cells at varying levels, while 3/7 isolates were capable of expressing codon-optimized human LAMC2.

Figures 5A, 5B, 5C:
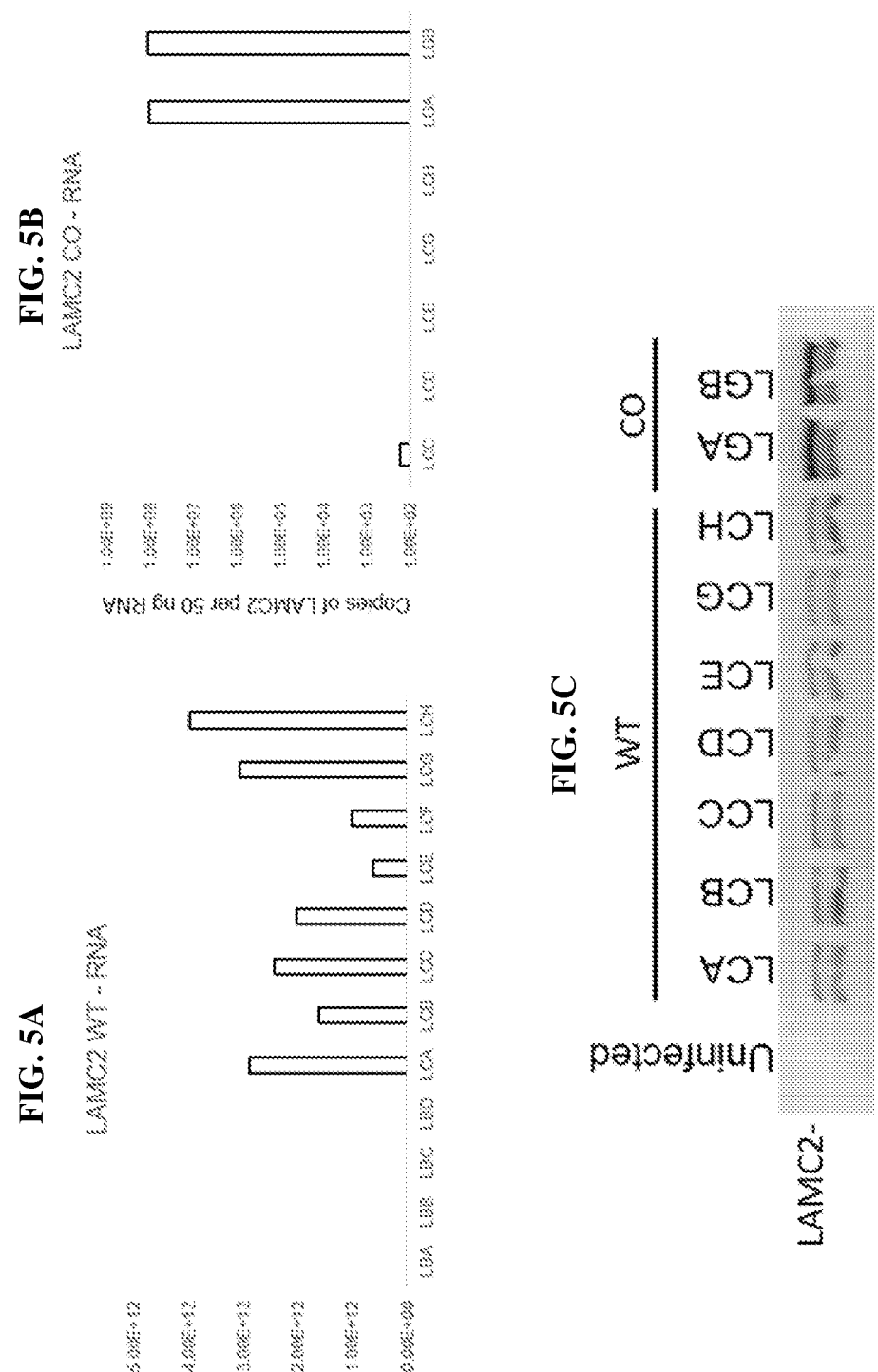
FIGS. 5A-C show expression of wild-type (WT) and codon-optimized (CO) human LamC2 in Vero cells infected with the indicated viral isolates.

The ability of certain wild-type and codon-optimized isolates to express human LamC2 protein was next tested by western blot. ICP4-complementing Vero cells were plated in 6-well plates and were infected with untitered viral isolates until completion of infection. A well of Vero cells was left uninfected as a negative control. After infection, the cells were collected by gentle scraping, centrifuged to collect cell pellets, culture medium was aspirated, and the cell pellets were washed once with PBS. Following washing, each cell pellet was resuspended in 200 µL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. After electrophoresis, the protein was transferred to a PVDF membrane, and the membrane was blocked for 30 minutes in 5% milk/TBS. Primary rabbit anti-LamC2 antibody (Abcam, cat. No. ab96327) was then added to the PVDF membrane at 1:1000 dilution in 5% milk/TB S and incubated overnight at RT° C. (~16 hours). The blots were then washed 3× for 5 minutes each with TBS, and then stained with an AP-conjugated goat anti-rabbit IgG antibody (Sigma, cat. No. A3687) in 5% milk/TBS for 1 hour at RT° C. The membranes were then washed 3× for 5 minutes each with TBS, BCIP/NBT was added, and the blots were developed for ~10 minutes at RT° C. In agreement with the qRT-PCR data, all 9 of the tested viral isolates were also able to express the encoded human LamC2 (FIG. 5C).

Figures 6A, 6B:
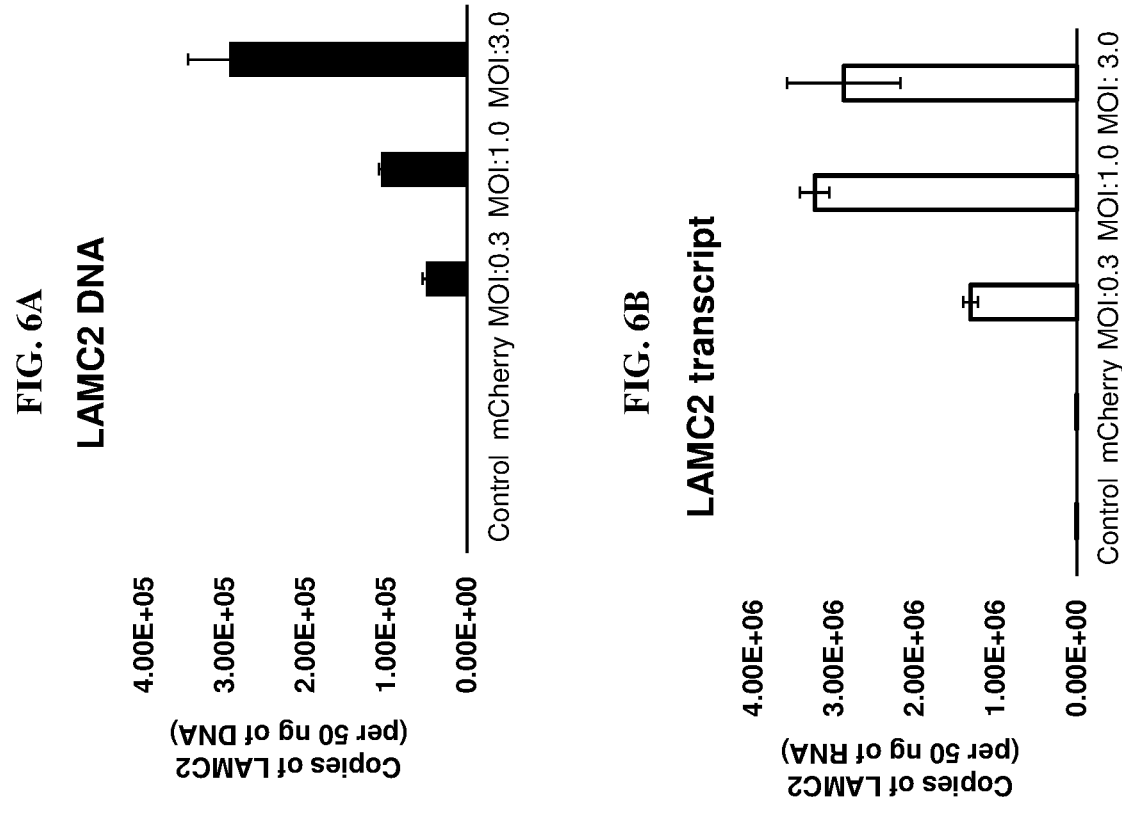
FIGS. 6A-C show human LAMC2 expressed from viral isolate "LGA" in immortalized primary human keratinocytes infected at the indicated multiplicities of infection (MOIs).
Figure 6C:
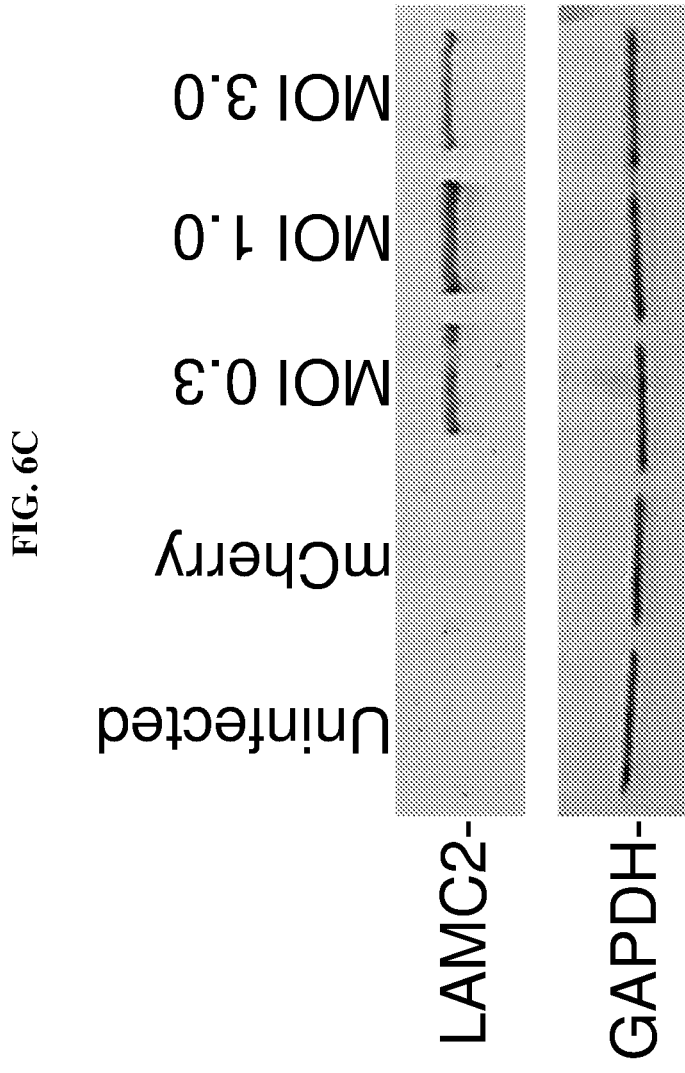

The codon-optimized LamC2-expressing viral isolate "LGA" was selected for further testing in human cells Immortalized primary normal keratinocytes were infected with the LGA isolate at a multiplicity of infection (MOI) of 0.3, 1.0, or 3.0 for 48 hours. Uninfected (control) and mCherry-expressing virus infected cells were used as a negative control. DNA and RNA were extracted from the immortalized keratinocytes after 48 hours of infection, and qPCR/qRT-PCR was performed (FIGS. 6A-B). A good dose-response was observed for the LGA isolate in the immortalized keratinocytes, as assessed by viral genome copies detected per 50 ng of DNA (FIG. 6A). Interestingly, while a dose response was observed at the transcript level when increasing the MOI from 0.3 to 1.0, no additional increase in transcript levels were observed when increasing from an MOI of 1.0 to 3.0 (FIG. 6B). Expression of LamC2 protein in the infected human keratinocytes were also examined by western blot. Western blots were carried out as described above (primary rabbit anti-LamC2 antibody (Abcam, cat. No. ab96327) was used). In line with the transcript analysis, a dose response was observed at the protein level when increasing MOI from 0.3 to 1.0, but not from 1.0 to 3.0 (FIG. 6C).

Taken together, the data suggests that multiple human laminin proteins (from wild-type and codon-optimized nucleic acid sequences) could be successfully expressed from the recombinant, replication-defective HSV-1 viruses.

Example 2

In Vivo Analysis of a Modified Herpes Simplex Virus Vector Encoding Human LAMC2

The use of knockout animal models to study the function of laminins is complicated by the fact that targeted deletion of laminin subunits in mice results in severe developmental defects, including neonatal death in the cases of either LAMB3 or LAMC2. As such, an in vivo study was conducted employing a transgenic immunocompetent mouse model carrying a homozygous deletion of endogenous mouse LAMC2 and a doxycycline-inducible (tet-on) wild-type human LAMC2 expression construct (LAMC2$^{-/-}$-hLAMC2$^{tet-on}$ mice). These mice were generated to prevent the neonatal lethality observed in LAMC2 knockout animals by rescuing the knockout of endogenous LAMC2 with expression of human LAMC2 in the presence of doxycycline, as the human construct was under the control of a tetracycline transactivator (hLAMC2$^{tet-on}$). Removal of doxycycline from the diet of these animals causes a slow reduction in human LamC2 protein levels with concomitant increases in symptoms associated with the loss of functional laminin-332 (as determined by losses in bodyweight and difficulties breathing). These laminin-deficient (doxy-) animals were tested for the ability of viral isolate "LGA" to restore human laminin expression.

Figure 7A:
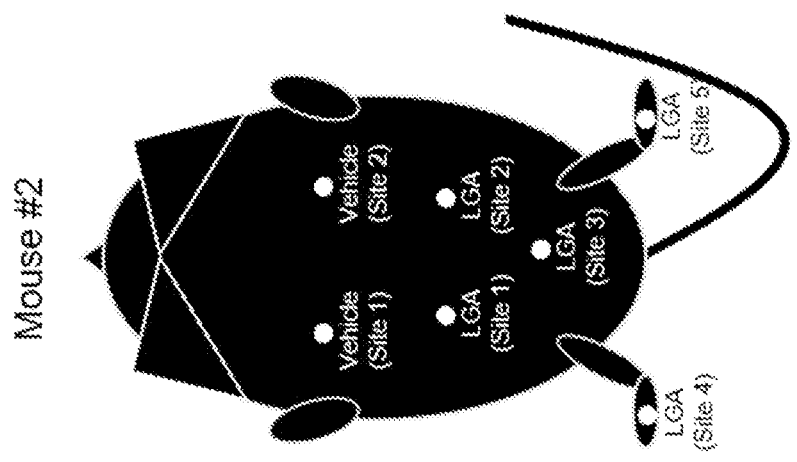
Figure 7A:
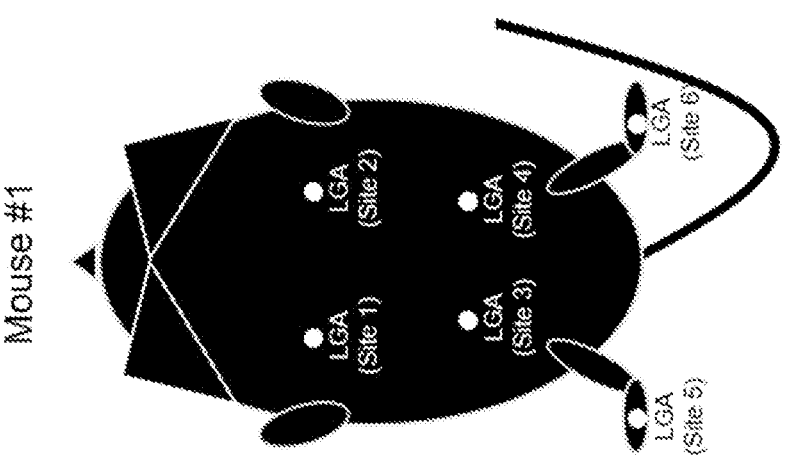

Specifically, in vivo human LAMC2 expression was assessed by qPCR, qRT-PCR, and immunofluorescence after intradermal injection of LGA. In order to induce a laminin-332 deficiency prior to test article treatment, doxycycline was withdrawn from the mice for 15 days (doxy-) prior to LGA administration. 1×10$^8$ plaque forming units (PFUs) of formulated LGA was intradermally injected into the dorsal skin and footpads of two mice. An equivalent volume of vehicle alone was intradermally administered to the dorsal skin of one mouse to act as a negative control. A schematic of the injection sites for the two animals treated in this study is provided in FIG. 7A.

72 hours post-administration, a full thickness 8 mm biopsy was taken from each treatment site and split in half. One half of each section was flash frozen in liquid nitrogen and subsequently processed for qPCR and qRT-PCR analysis in order to quantify LAMC2 DNA copy numbers and transcript levels in the dorsal skin. Exogenous LGA-encoded human LAMC2 DNA (FIG. 7B) and RNA (FIG. 7C) was detected in each LGA-treated tissue sample, indicating that the engineered vector was capable of expressing its transgene when infecting LAMC2-deficient tissue in vivo.

Figure 7D:
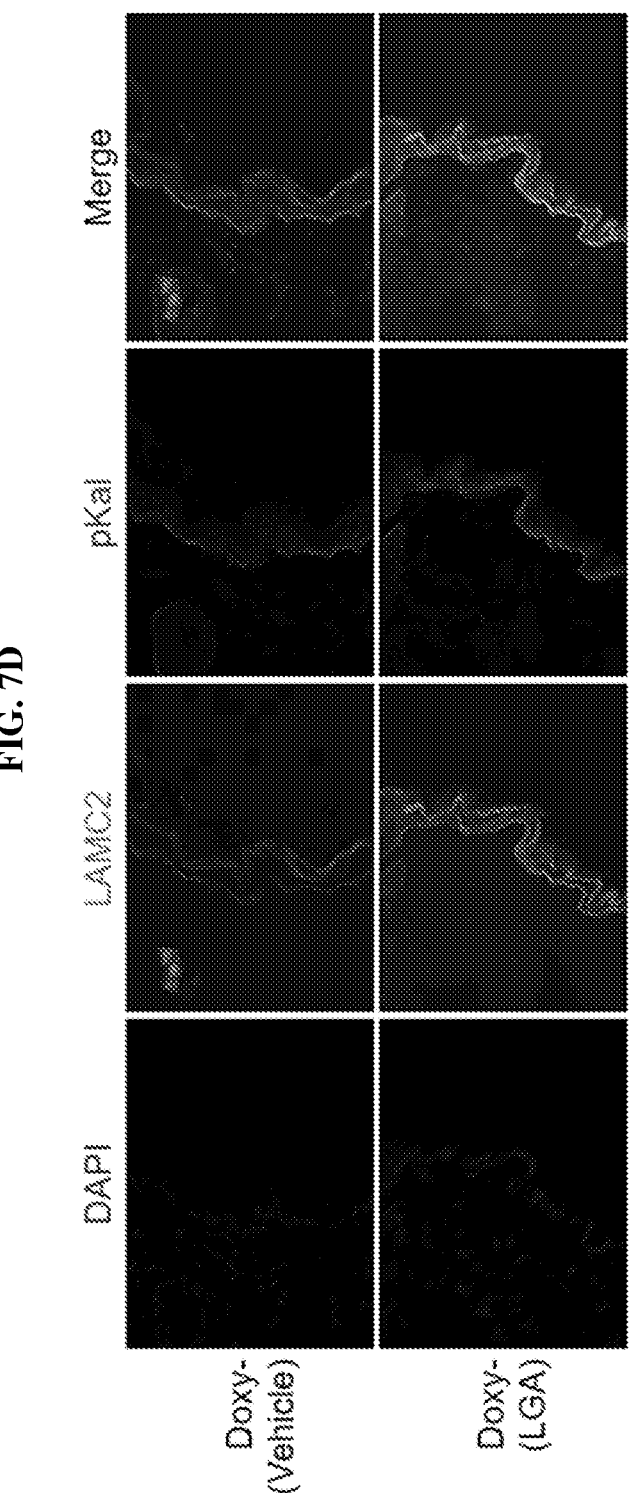

The remaining half of each biopsy was embedded in OCT for immunofluorescence (IF). LamC2 expression in cryo-sections was determined by immunofluorescent analysis using an anti-human LamC2 antibody (Abcam, cat. no. ab96327). A region of dorsal skin biopsied from a mouse continuously exposed to doxycycline (doxy+) was also examined to determine the baseline levels of human LamC2 protein expressed in the transgenic mice prior to doxycycline removal. In addition, to confirm that the human LamC2 expressed from LGA was correctly localized to the region of the skin where native laminin-332 is found, the dorsal skin samples were also counterstained for mouse laminin-332 (pKa1). Intradermal administration of LGA led to successful transduction of mouse skin, with robust expression of the encoded human transgene in the correct layer of the epidermis (FIG. 7D). Histological evaluation of the biopsies showed no inflammatory infiltration at the treated site, demonstrating the safety of this therapy.

Taken together, the data presented in this example demonstrates that (1) an HSV-based gene therapy vector could successfully deliver a human laminin-332 subunit in vivo in a relevant, immunocompetent animal model, and (2) the recombinant human laminin-332 subunit localized to the appropriate region of the epidermis of treated animals. Without wishing to be bound by theory, it is believed that these preclinical studies provide ample support for the use of engineered HSV as a convenient, safe, and efficacious gene therapy vector for direct molecular correction of laminin deficiencies (e.g., LAMB3 deficiencies in JEB patients).

Example 3

Generation of Modified Herpes Simplex Virus Vectors Encoding Human Filaggrins Filaggrin monomers are proteins originated from pro-filaggrin, produced by keratinocytes; they are the main components of keratohyalin granules. Conversion of pro-filaggrin into filaggrin monomers occurs through dephosphorylation and proteolysis by serine proteases, releasing multiple (typically 10-12) active monomers of filaggrin. Changes in skin barrier proteins, such as decreased expression of pro-filaggrin/filaggrin and/or pro-filaggrin-2/filaggrin-2 in the skin, as well as loss-of-function mutations in the filaggrin (FLG) or filaggrin-2 (FLG2) genes, have wide ranging and often devastating effects. The increased skin permeability observed in patients harboring FLG mutations results in enhanced percutaneous exposure to allergens. Moreover, FLG mutations are associated with increased IgE serum levels, decreased stratum corneum hydration, amplified trans epidermal water loss (TEWL), a higher skin pH, and increased skin inflammation. Indeed, patients with loss-of-function FLG or FLG2 mutations have a higher risk of developing skin diseases (e.g., atopic dermatitis, ichthyosis vulgaris, and peeling skin syndromes) and allergies (e.g., rhinitis, certain food allergies, and allergic asthma). Thus, there exists a clear need for novel treatment options targeting molecular correction of filaggrin or filaggrin-2 deficiencies observed in these sensitive patients.

In some embodiments, in order to meet these and other needs, provided herein are recombinant nucleic acids (e.g., recombinant herpes virus genomes) encoding one or more filaggrin polypeptides for use in viruses (e.g., herpes viruses), pharmaceutical compositions and formulations, medicaments, and/or methods useful for treating filaggrin deficiencies in a subject in need thereof. Without wishing to be bound by theory, it is believed that increasing, augmenting, and/or supplementing the levels of filaggrins in one or more cells of an individual in need thereof by administering one or more of the recombinant nucleic acids, viruses, and/or compositions described herein will: 1) stabilize the stratum corneum and/or enhance its production; 2) reduce TEWL; 3) inhibit percutaneous transfer of allergens; 4) reduce or treat skin barrier defects; and/or 5) provide prophylactic, palliative, or therapeutic relief of one or more signs or symptoms of a skin disease (e.g., atopic dermatitis, ichthyosis vulgaris, a peeling skin syndrome, etc.).

Figures 8C, 8D:
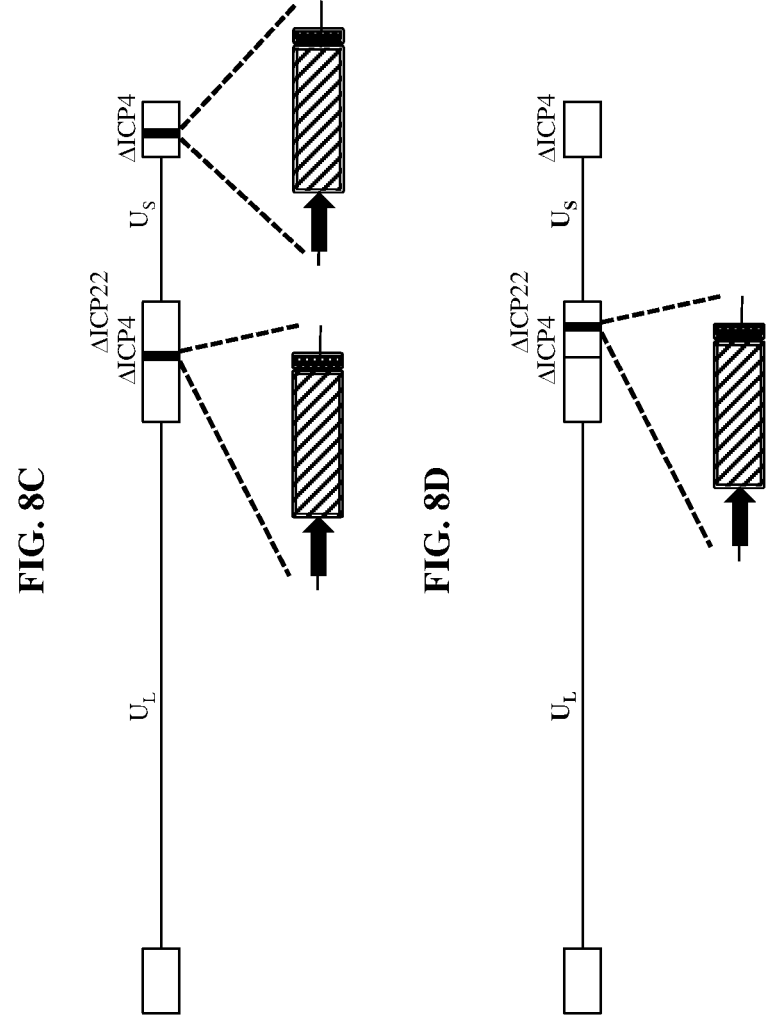

To make modified herpes simplex virus genome vectors capable of expressing filaggrin polypeptides in a target mammalian cell (such as a human keratinocyte or fibroblast), a herpes simplex virus genome (FIG. 8A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding the desired filaggrin polypeptide. These variants include: 1) a recombinant ΔICP4-modified HSV-1 genome comprising expression cassettes containing the coding sequence (SEQ ID NO: 37) of a human filaggrin polypeptide (SEQ ID NO: 39) under the control of a heterologous promoter integrated at each ICP4 locus (FIG. 8B); 2) a recombinant ΔICP4/ΔICP22-modified HSV-1 genome comprising expression cassettes containing the coding sequence (SEQ ID NO: 37) of a human filaggrin polypeptide (SEQ ID NO: 39) under the control of a heterologous promoter integrated at each ICP4 locus (FIG. 8C); 3) a recombinant ΔICP4/ΔICP22-modified HSV-1 genome comprising an expression cassette containing the coding sequence (SEQ ID NO: 37) of a human filaggrin polypeptide (SEQ ID NO: 39) under the control of a heterologous promoter integrated at the ICP22 locus (FIG. 8D); 4) a recombinant ΔICP4/AUL41-modified HSV-1 genome comprising an expression cassette containing the coding sequence (SEQ ID NO: 37) of a human filaggrin polypeptide (SEQ ID NO: 39) under the control of a heterologous promoter integrated at the UL41 locus (FIG. 8E); and 5) a recombinant ΔICP4/ΔICP22/ΔUL41-modified HSV-1 genome comprising expression cassettes containing the coding sequence (SEQ ID NO: 37) of a human filaggrin polypeptide (SEQ ID NO: 39) under the control of a heterologous promoter integrated at the UL41 locus (FIG. 8F).

These modified herpes simplex virus genome vectors are transfected into engineered Vero cells that are modified to express one or more herpes virus genes. These engineered Vero cells secrete into the supernatant of the cell culture a replication-defective herpes simplex virus with the modified genomes packaged therein. The supernatant is then collected, concentrated, and sterile filtered through a 5 μm filter.

What is claimed is:

1. A pharmaceutical composition useful for delivery of one or more polynucleotides encoding a human filaggrin polypeptide to the skin of a subject having a skin disease, the pharmaceutical composition comprising:

a) a herpes simplex virus comprising a recombinant herpes simplex virus genome, wherein the recombinant herpes simplex virus genome comprises the one or more polynucleotides encoding the human filaggrin polypeptide; and b) a pharmaceutically acceptable excipient, wherein the skin disease is selected from the group consisting of atopic dermatitis, ichthyosis vulgaris, and a peeling skin syndrome, wherein the one or more polynucleotides encoding the human filaggrin polypeptide does not comprise a ribonucleic acid (RNA), and wherein the recombinant herpes simplex virus genome does not comprise a polynucleotide encoding a collagen polypeptide, a fibronectin polypeptide, an elastin polypeptide, a lumican polypeptide, a vitronectin polypeptide, a vitronectin receptor polypeptide, a neuromodulator polypeptide, a fibrillin polypeptide, a laminin polypeptide, or a transglutaminase polypeptide.

2. The pharmaceutical composition of claim 1, wherein the herpes simplex virus is replication defective.

3. The pharmaceutical composition of claim 1, wherein the pharmaceutical composition is suitable for topical, transdermal, subcutaneous, intradermal, oral, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

4. The pharmaceutical composition of claim 1, wherein the pharmaceutical composition is suitable for topical administration.

5. The pharmaceutical composition of claim 1, wherein the filaggrin polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 39-50.

6. A method of providing prophylactic, palliative, or therapeutic relief of one or more signs or symptoms of a skin disease in a subject in need thereof, the method comprising administering to the subject an effective amount of a pharmaceutical composition comprising;

a) a herpes simplex virus comprising a recombinant herpes simplex virus genome, wherein the recombinant herpes simplex virus genome comprises one or more polynucleotides encoding a human filaggrin polypeptide; and b) a pharmaceutically acceptable excipient, wherein the skin disease is selected from the group consisting of atopic dermatitis, ichthyosis vulgaris, and a peeling skin syndrome, wherein the one or more polynucleotides encoding the human filaggrin polypeptide does not comprise a ribonucleic acid (RNA), and wherein the recombinant herpes simplex virus genome does not comprise a polynucleotide encoding a collagen polypeptide, a fibronectin polypeptide, an elastin polypeptide, a lumican polypeptide, a vitronectin polypeptide, a vitronectin receptor polypeptide, a neuromodulator polypeptide, a fibrillin polypeptide, a laminin polypeptide, or a transglutaminase polypeptide.

7. The method of claim 6, wherein the subject is a human.

8. The method of claim 6, wherein the pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject.

9. The pharmaceutical composition of claim 1, wherein the recombinant herpes simplex virus genome is a recombinant herpes simplex virus type 1 (HSV-1) genome or a recombinant herpes simplex virus type 2 (HSV-2) genome.

10. The method of claim 6, wherein the recombinant herpes simplex virus genome is a recombinant herpes simplex virus type 1 (HSV-1) genome or a recombinant herpes simplex virus type 2 (HSV-2) genome.

\*   \*   \*   \*   \*